US012810964B2

(12) United States Patent
Greving et al.

(10) Patent No.: US 12,810,964 B2
(45) Date of Patent: *Nov. 24, 2026

(54) MESO-SCALE ENGINEERED PEPTIDES AND METHODS OF SELECTING

(71) Applicant: iBio, Inc., Bryan, TX (US)

(72) Inventors: Matthew P. Greving, San Carlos, CA (US); Kevin Eduard Hauser, Jupiter, FL (US); Andrew Morin, San Mateo, CA (US); Jordan R. Willis, Hayward, CA (US)

(73) Assignee: iBio, Inc., San Diego, CA (US)

( * ) Notice: Subject to any disclaimer, the term of this patent is extended or adjusted under 35 U.S.C. 154(b) by 1237 days.

This patent is subject to a terminal disclaimer.

(21) Appl. No.: 17/537,215

(22) Filed: Nov. 29, 2021

(65) Prior Publication Data

US 2022/0081472 A1 Mar. 17, 2022

Related U.S. Application Data

(63) Continuation of application No. PCT/US2020/032715, filed on May 13, 2020.

(60) Provisional application No. 62/855,767, filed on May 31, 2019.

(51) Int. Cl.

| | |
|---|---|
| ***G16B 40/20*** | (2019.01) |
| ***C07K 14/00*** | (2006.01) |
| ***G06N 5/04*** | (2023.01) |
| ***G06N 20/00*** | (2019.01) |
| ***G16B 5/00*** | (2019.01) |
| ***G16B 5/30*** | (2019.01) |

(52) U.S. Cl.

CPC ............ *G16B 40/20* (2019.02); *C07K 14/001* (2013.01); *G06N 5/04* (2013.01); *G06N 20/00* (2019.01); *G16B 5/00* (2019.02); *G16B 5/30* (2019.02)

(58) Field of Classification Search

None

See application file for complete search history.

(56) References Cited

U.S. PATENT DOCUMENTS

| | | | |
|---|---|---|---|
| 7,894,995 | B2 | 2/2011 | Jojic et al. |
| 8,050,870 | B2 | 11/2011 | Heckerman et al. |
| 8,374,828 | B1 | 2/2013 | Jacobs et al. |
| 8,734,828 | B2 | 5/2014 | Kaps et al. |
| 10,431,325 | B2 | 10/2019 | Agrawal et al. |
| 2006/0020396 | A1 | 1/2006 | Gantier et al. |
| 2007/0016380 | A1 | 1/2007 | Smythe et al. |
| 2013/0090265 | A1 | 4/2013 | Gardner |
| 2018/0009850 | A1 | 1/2018 | Raman et al. |
| 2018/0068054 | A1 | 3/2018 | Baker et al. |
| 2019/0065677 | A1 | 2/2019 | Gifford et al. |
| 2020/0279616 | A1 | 9/2020 | Rooney et al. |
| 2023/0016112 | A1* | 1/2023 | Greving .......... C07K 14/70596 |

FOREIGN PATENT DOCUMENTS

| | | | |
|---|---|---|---|
| EP | 1206494 | | 2/2001 |
| EP | 1510959 | A2 | 3/2005 |
| EP | 3417874 | A1 | 12/2018 |
| KR | 10-2018-0012747 | A | 2/2018 |
| WO | WO 2016/005969 | A1 | 1/2016 |
| WO | WO-2016/164305 | A1 | 10/2016 |
| WO | WO 2018/201020 | A1 | 11/2018 |
| WO | WO-2020/102603 | A1 | 5/2020 |
| WO | WO 2002/064734 | A2 | 8/2022 |

OTHER PUBLICATIONS

Bengio, et al., Representation Learning: A Review and New Perspectives, IEEE Transactions on Pattern Analysis and Machine Intelligence, Mar. 7, 2013, pp. 1798-1828, vol. 35, Issue 8.

Correla, et al. Computational design of epitope-scaffolds allows induction of antibodies specific for a poorly immunogenic HIV vaccine epitope, Structure, 2010, pp. 1116-1126, vol. 18.

Das, et al. Macromolecular modeling with rosetta, Annu. Rev. Biochem, 2008, pp. 363-382, vol. 77.

Elton, et al. Deep learning for molecular design—a review of the state of the art, Mol. Syst. Des. Eng., 2019, pp. 828-849, vol. 4.

Gao, W., et al., Deep Learning in Protein Structural Modeling and Design, Patterns, Dec. 11, 2020, 23 pages, vol. 1, Issue 9.

Jumper, J., et al., Highly accurate protein structure prediction with AlphaFold, Nature, Aug. 26, 2021, pp. 583-589, vol. 596, No. 7873.

Ofek, et al., Elicitation of structure-specific antibodies by epitope scaffolds, PNAS, 2010, pp. 17880-17887, vol. 107.

Sinha et al., "Dissecting the Non-specific and Specific Components of the Initial Folding Reaction of Barstar by Multi-site FRET Measurements," J. Mol. Biol. (2007) 370, 385-405 (21 pages).

Zhou, et al. Computational peptidology: a new and promising approach to therapeutic peptide design, Current Medicinaal Chemistry, 2013, pp. 1985-1996, vol. 20, No. 15.

The International Bureau of WIPO, International Search Report and Written Opinion for PCT/US2021/61289, Feb. 23, 2022, 12 pages.

The International Bureau of WIPO, International Search Report and Written Opinion for PCT/US2020/032724, Sep. 25, 2020, 12 pages.

The International Bureau of WIPO, International Search Report and Written Opinion for PCT/US2020/032715, Sep. 9, 2020, 11 pages.

United States Patent and Trademark Office, Non-Final Office Action, Jul. 12, 2021, for U.S. Appl. No. 17/108,958, 18 pages.

(Continued)

*Primary Examiner* — Christopher M Gross

(74) *Attorney, Agent, or Firm* — Edwin S. Flores; Daniel J. Chalker; Chalker Flores, LLP

(57) ABSTRACT

Provided herein engineered peptides that comprise a combination of spatially-associated topological constraints, wherein at least one constraint is derived from a reference target, and methods of selecting said engineered peptides. Further provided are methods of using the engineered peptides, including as positive and/or negative selection molecules in methods of screening a library of binding molecules.

26 Claims, 103 Drawing Sheets

Specification includes a Sequence Listing.

(56) References Cited

OTHER PUBLICATIONS

United States Patent and Trademark Office, Final Office Action, Nov. 16, 2021, for U.S. Appl. No. 17/108,958, 18 pages.
Bhardwaj, et al. "Accurate de novo design of hyperstable constrained peptides" Nature, vol. 538, No. 7625, Oct. 1, 2016 (Oct. 1, 2016), pp. 329-335, XP055528081, London, ISSN: 0028-0836, DOI: 10.1038/naturel9791.
European Patent Office, Extended European Search Report for EP Appl. No. 20813167.2 dated Jul. 14, 2023, 16 pp.
Namrata, et al. "Generative Modeling for Protein Structures" Jan. 1, 2018 (Jan. 1, 2018), XP093050633, Retrieved from the Internet: URL:https://proceedings.neurips.cc/paper_f iles/paper/2018/file/afa299a4dld8c52e75dd8a24c3ce534f-Paper.pdf.
Po-Ssu, et al., "RosettaRemodel: A generalized framework for flexible backbone protein design", PLoS ONE, Aug. 31, 2011 (Aug. 31, 2011), pp. e24109-e24109, XP093050603, United States, DOI: 10.1371/journal.pone.0024109 Retrieved from the Internet: URL:https://www.ncbi.nlm.nih.gov/pmc/artic les/PMC3166072/pdf/pone.0024109.pdf.
Yang, et al. "Improved protein structure prediction using predicted interresidue orientations" PNAS, 1496-1503, Jan. 21, 2020, vol. 117, No. 3.
Rosetta, et al. "A Generalized Framework for Flexible Backbone Protein Design" PLoS ONE | www.plosone.org, Aug. 2011, vol. 6, Issue 8, e24109.
Huang, et al. "RosettaRemodel: A Generalized Framework for Flexible Backbone Protein Design" PLoS ONE , Aug. 2011, vol. 6, Issue 8, E24109.
China Intellectual Property Office, Examination Report for Chinese Appl. No. 2020800503019 Dated Nov. 23, 2023 with translation, 23 pp.
Japan Patent Office, Examination Report for Japan Appl. No. 2021-571033 dated May 27, 2024, 9 PP.
European Patent Office, Extended European Search Report dated Jul. 14, 2023 for EP Appl No. 20813167.2, 16 pp.
Kuhlman, et al. "Design of a Novel Globular Protein Fold with Atomic-Level Accuracy", Science, vol. 302, No. 5649, Nov. 21, 2003 (Nov. 21, 2003), pp. 1364-1368, XP093061250, us ISSN: 0036-8075, DOI: 10.1126/science.1089427.
Liu, et al. "RosettaDesign server for protein design", Nucleic Acids Research, vol. 34, No. Web Server, Jul. 1, 2006 (Jul. 1, 2006), pp. W235-W238, XP055106540, ISSN: 0305-1048, DOI: 10.1093/nar/gkl163.
Tiwari, et al. "WEBnm@ v2.0: Web server and services for comparing protein flexibility", BMC Bioinformatics, Biomed Central , London, GB, vol. 15, No. 1, Dec. 30, 2014 (Dec. 30, 2014), pp. 427, XP021211166, ISSN: 1471-2105, DOI: 10.1186/S12859-014-0427-6.

* cited by examiner

Step 1: Extract Reference Interface

Step 2: Define Reference Interface Topology
Spatially constrained atomic distance
& amino acid descriptor

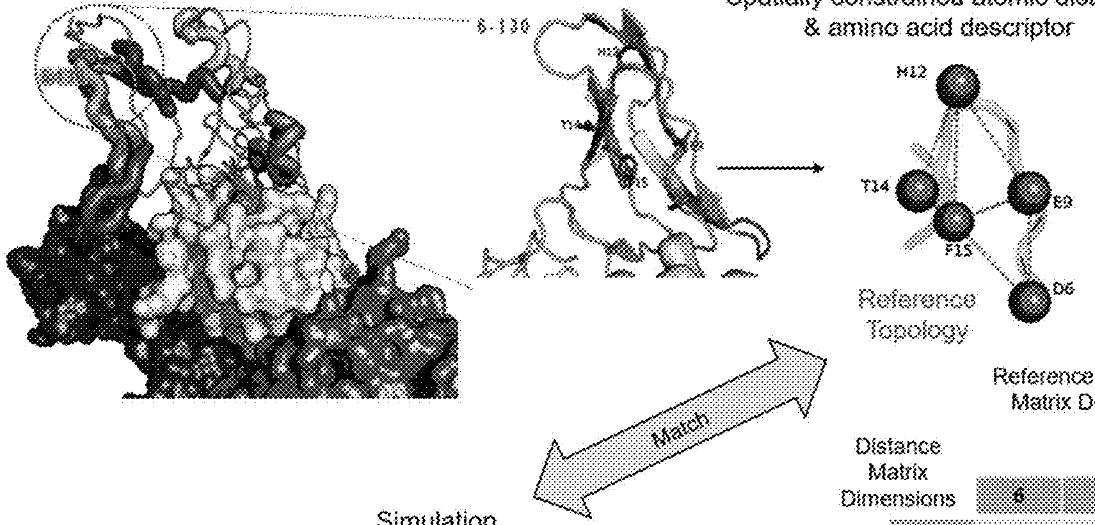

Simulation Topologies

Step 3: *In silico* screen for engineered peptides with best-matched topology vs. reference interface topology Amino Acid Matrix Dimension

| | |
|---|---|
| 6 | 19 |
| 9 | 20 |
| 12 | 18 |
| 14 | 12 |
| 15 | 10 |

Reference Topology Matrix Definition

| Distance Matrix Dimensions | 6 | 9 | 12 | 14 | 15 |
|---|---|---|---|---|---|
| 6 | | 8.8 | 17.6 | 18.3 | 16.3 |
| 9 | | | 9.3 | 10.2 | 9.3 |
| 12 | | | | 7.6 | 10.1 |
| 14 | | | | | 3.7 |
| 15 | | | | | |

Amino Acid Descriptor Lookup Table

| NUMERIC | LETTER CODE |
|---|---|
| 1 | M |
| 2 | A |
| 3 | V |
| 4 | P |
| 5 | L |
| 6 | I |
| 7 | G |
| 8 | W |
| 9 | Y |
| 10 | F |
| 11 | S |
| 12 | T |
| 13 | C |
| 14 | N |
| 15 | Q |
| 16 | K |
| 17 | R |
| 18 | H |
| 19 | D |
| 20 | E |

*FIG. 3A*

Step 1: Reference target

Step 2: Spatially constrained amino acid & Atomic distance reference topology

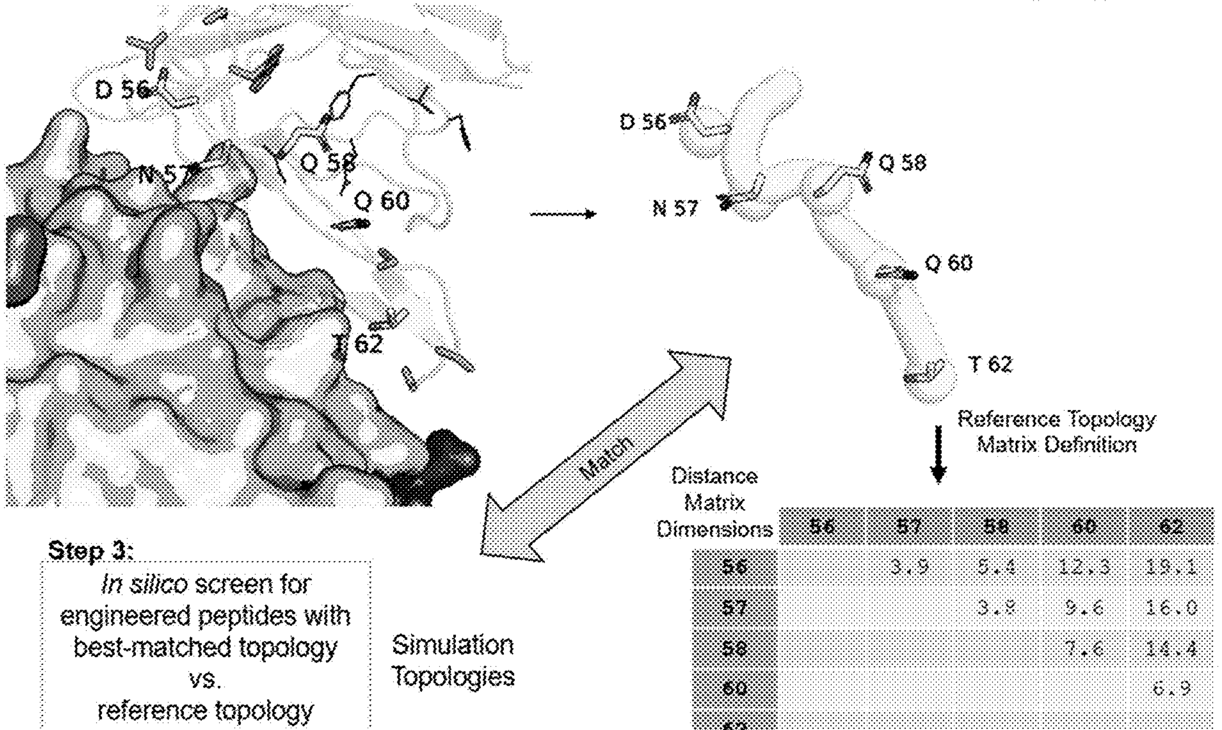

Step 3:
*In silico* screen for engineered peptides with best-matched topology vs. reference topology Simulation Topologies Distance Matrix Dimensions

| | 56 | 57 | 58 | 60 | 62 |
|---|---|---|---|---|---|
| 56 | | 3.9 | 5.4 | 12.3 | 19.1 |
| 57 | | | 3.8 | 9.6 | 16.0 |
| 58 | | | | 7.6 | 14.4 |
| 60 | | | | | 6.9 |
| 62 | | | | | |

Amino Acid Matrix Dimension

| | |
|---|---|
| 56 | 19 |
| 57 | 14 |
| 58 | 15 |
| 60 | 15 |
| 62 | 12 |

Amino Acid Descriptor Lookup Table

| NUMERIC | LETTER CODE |
|---|---|
| 1 | M |
| 2 | A |
| 3 | V |
| 4 | P |
| 5 | L |
| 6 | I |
| 7 | G |
| 8 | W |
| 9 | Y |
| 10 | F |
| 11 | S |
| 12 | T |
| 13 | C |
| 14 | N |
| 15 | Q |
| 16 | K |
| 17 | R |
| 18 | H |
| 19 | D |
| 20 | E |

*FIG. 4A*

Reference Target

Reference Target Interface

Reference Target Atomic Distance & Amino Acid Descriptor Topology

Reference Topology Matrix Definition

Distance Matrix Dimensions

| | 82 | 83 | 84 | 85 | 86 | 87 | 88 | 89 | 90 | 91 |
|---|---|---|---|---|---|---|---|---|---|---|
| 82 | | 3.8 | 6.6 | 9.4 | 12.3 | 10.4 | 8.0 | 6.2 | 5.8 | 6.5 |
| 83 | | | 3.8 | 6.0 | 6.7 | 7.9 | 5.8 | 4.4 | 7.7 | 8.8 |
| 84 | | | | 3.8 | 6.3 | 5.0 | 5.4 | 6.5 | 9.5 | 11.9 |
| 85 | | | | | 3.8 | 5.5 | 6.7 | 8.2 | 11.8 | 14.6 |
| 86 | | | | | | 3.8 | 6.4 | 9.2 | 12.9 | 16.3 |
| 87 | | | | | | | 3.8 | 7.4 | 11.0 | 14.2 |
| 88 | | | | | | | | 3.8 | 7.0 | 10.5 |
| 89 | | | | | | | | | 3.8 | 7.3 |
| 90 | | | | | | | | | | 3.8 |
| 91 | | | | | | | | | | |

Amino Acid Matrix Dimension

| | |
|---|---|
| 82 | 17 |
| 83 | 6 |
| 84 | 16 |
| 85 | 4 |
| 86 | 15 |
| 87 | 15 |
| 88 | 7 |
| 89 | 15 |
| 90 | 18 |
| 91 | 6 |

Amino Acid Descriptor Lookup Table

| NUMERIC | LETTER CODE |
|---|---|
| 1 | M |
| 2 | A |
| 3 | V |
| 4 | P |
| 5 | L |
| 6 | I |
| 7 | G |
| 8 | W |
| 9 | Y |
| 10 | F |
| 11 | S |
| 12 | T |
| 13 | C |
| 14 | N |
| 15 | Q |
| 16 | K |
| 17 | R |
| 18 | H |
| 19 | D |
| 20 | E |

Reference Target
Candidate MEM 1
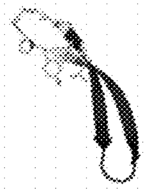
MEM
Atomic Distance &
Amino Acid Descriptor Topology
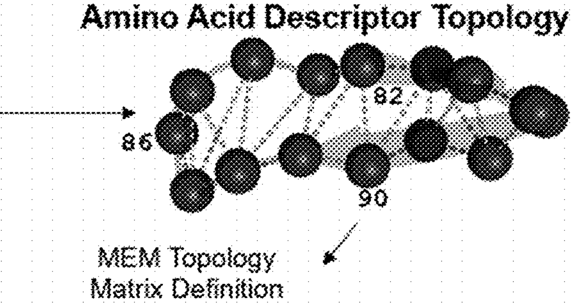
MEM Topology Matrix Definition
Distance Matrix Dimensions
| | 82 | 83 | 84 | 85 | 86 | 87 | 88 | 89 | 90 | 91 |
|---|---|---|---|---|---|---|---|---|---|---|
| 82 | | 3.8 | 6.7 | 9.8 | 12.0 | 10.2 | 8.5 | 5.8 | 5.4 | 6.3 |
| 83 | | | 3.8 | 6.3 | 8.3 | 7.0 | 5.6 | 4.5 | 5.6 | 8.4 |
| 84 | | | | 3.8 | 6.4 | 5.4 | 6.9 | 7.3 | 7.6 | 10.9 |
| 85 | | | | | 3.8 | 5.5 | 7.2 | 9.3 | 10.7 | 13.9 |
| 86 | | | | | | 3.9 | 6.1 | 9.5 | 11.3 | 15 |
| 87 | | | | | | | 3.9 | 7.1 | 8.1 | 11.8 |
| 88 | | | | | | | | 3.8 | 6.3 | 10.1 |
| 89 | | | | | | | | | 3.8 | 7.0 |
| 90 | | | | | | | | | | 3.8 |
| 91 | | | | | | | | | | |
Amino Acid Matrix Dimension
| | |
|---|---|
| 82 | 17 |
| 83 | 6 |
| 84 | 16 |
| 85 | 4 |
| 86 | 18 |
| 87 | 15 |
| 88 | 7 |
| 89 | 15 |
| 90 | 18 |
| 91 | 6 |
Amino Acid Descriptor Lookup Table
| NUMERIC | LETTER CODE |
|---|---|
| 1 | M |
| 2 | A |
| 3 | V |
| 4 | P |
| 5 | L |
| 6 | I |
| 7 | G |
| 8 | W |
| 9 | Y |
| 10 | F |
| 11 | S |
| 12 | T |
| 13 | C |
| 14 | N |
| 15 | Q |
| 16 | K |
| 17 | R |
| 18 | H |
| 19 | D |
| 20 | E |
*FIG. 6C*

Reference Target Candidate MEM 2 MEM Atomic Distance & Amino Acid Descriptor Topology

MEM Topology Matrix Definition

Distance Matrix Dimensions

| | 82 | 83 | 84 | 85 | 86 | 87 | 88 | 89 | 90 | 91 |
|---|---|---|---|---|---|---|---|---|---|---|
| 82 | | 3.8 | 6.7 | 8.8 | 12.0 | 10.2 | 8.6 | 5.9 | 5.4 | 6.2 |
| 83 | | | 3.8 | 6.3 | 8.3 | 6.8 | 5.7 | 4.6 | 5.8 | 8.5 |
| 84 | | | | 3.8 | 6.4 | 9.4 | 6.6 | 7.4 | 7.7 | 10.6 |
| 85 | | | | | 3.8 | 5.5 | 7.2 | 9.3 | 10.7 | 14.0 |
| 86 | | | | | | 3.9 | 6.1 | 9.5 | 11.3 | 15.1 |
| 87 | | | | | | | 3.9 | 7.1 | 5.2 | 11.9 |
| 88 | | | | | | | | 3.9 | 6.3 | 10.1 |
| 89 | | | | | | | | | 3.8 | 7.0 |
| 90 | | | | | | | | | | 3.8 |
| 91 | | | | | | | | | | |

Amino Acid Matrix Dimension

| | |
|---|---|
| 82 | 17 |
| 83 | 6 |
| 84 | 16 |
| 85 | 4 |
| 86 | 18 |
| 87 | 15 |
| 88 | 7 |
| 89 | 15 |
| 90 | 18 |
| 91 | 6 |

Amino Acid Descriptor Lookup Table

| NUMERIC | LETTER CODE |
|---|---|
| 1 | M |
| 2 | A |
| 3 | V |
| 4 | P |
| 5 | L |
| 6 | I |
| 7 | G |
| 8 | W |
| 9 | Y |
| 10 | F |
| 11 | S |
| 12 | T |
| 13 | C |
| 14 | N |
| 15 | Q |
| 16 | K |
| 17 | R |
| 18 | H |
| 19 | D |
| 20 | E |

Reference Target Candidate MEM 3 MEM Atomic Distance & Amino Acid Descriptor Topology

MEM Topology Matrix Definition

Distance Matrix Dimensions

| | 82 | 83 | 84 | 85 | 86 | 87 | 88 | 89 | 90 | 91 |
|---|---|---|---|---|---|---|---|---|---|---|
| 82 | | 3.8 | 6.6 | 9.7 | 11.0 | 10.3 | 8.6 | 5.7 | 5.4 | 6.2 |
| 83 | | | 3.8 | 6.2 | 8.5 | 7.4 | 9.8 | 4.6 | 6.5 | 8.9 |
| 84 | | | | 3.8 | 6.2 | 5.0 | 6.1 | 6.5 | 8.0 | 11.0 |
| 85 | | | | | 3.8 | 5.9 | 7.0 | 8.9 | 11.3 | 14.5 |
| 86 | | | | | | 3.8 | 6.2 | 9.4 | 12.1 | 15.7 |
| 87 | | | | | | | 3.8 | 6.8 | 8.9 | 12.7 |
| 88 | | | | | | | | 3.8 | 7.1 | 10.6 |
| 89 | | | | | | | | | 3.8 | 7.0 |
| 90 | | | | | | | | | | 3.8 |
| 91 | | | | | | | | | | |

Amino Acid Matrix Dimension

| | |
|---|---|
| 82 | 10 |
| 83 | 3 |
| 84 | 6 |
| 85 | 20 |
| 86 | 7 |
| 87 | 9 |
| 88 | 19 |
| 89 | 3 |
| 90 | 3 |
| 91 | 12 |

Amino Acid Descriptor Lookup Table

| NUMERIC | LETTER CODE |
|---|---|
| 1 | M |
| 2 | A |
| 3 | V |
| 4 | P |
| 5 | L |
| 6 | I |
| 7 | G |
| 8 | W |
| 9 | Y |
| 10 | F |
| 11 | S |
| 12 | T |
| 13 | C |
| 14 | N |
| 15 | Q |
| 16 | K |
| 17 | R |
| 18 | H |
| 19 | D |
| 20 | E |

| MEM Rank | MEM ID | Mean Percentage Error |
|---|---|---|
| 1 | MEM 2 | 6.00 |
| 2 | MEM 1 | 6.03 |
| 3 | MEM 3 | 22.8 |

Mean Percentage Error =

$$\frac{100\%}{n}\sum_{n}^{1}\frac{|ref_n - eng_n|}{ref_n}$$

FIG. 6F

Reference Target
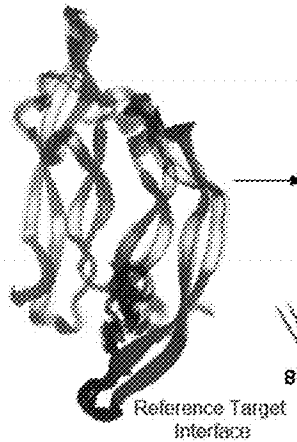
Reference Target
Atomic Fluctuation Topology → Reference Topology Matrix Definition
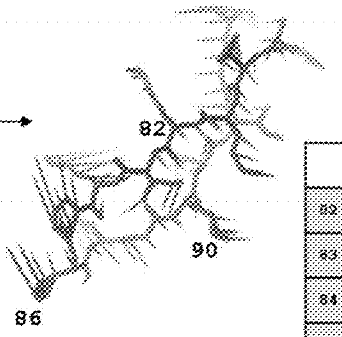
Distance Matrix Dimensions
| | 82 | 83 | 84 | 85 | 86 | 87 | 88 | 89 | 90 | 91 |
|---|---|---|---|---|---|---|---|---|---|---|
| 82 | | 3.8 | 6.8 | 8.4 | 10.3 | 10.4 | 8.0 | 6.2 | 5.8 | 6.6 |
| 83 | | | 3.8 | 6.0 | 8.7 | 7.2 | 5.8 | 6.4 | 7.7 | 8.8 |
| 84 | | | | 3.8 | 6.0 | 5.0 | 5.4 | 6.5 | 9.5 | 11.6 |
| 85 | | | | | 3.8 | 5.9 | 6.7 | 8.2 | 11.8 | 13.6 |
| 86 | | | | | | 3.8 | 6.4 | 9.2 | 12.9 | 16.3 |
| 87 | | | | | | | 3.8 | 7.4 | 11.0 | 14.2 |
| 88 | | | | | | | | 3.8 | 7.0 | 10.5 |
| 89 | | | | | | | | | 3.8 | 7.3 |
| 90 | | | | | | | | | | 3.8 |
| 91 | | | | | | | | | | |
Amino Acid Matrix Dimension
| | |
|---|---|
| 82 | 17 |
| 83 | 6 |
| 84 | 16 |
| 85 | 4 |
| 86 | 19 |
| 87 | 15 |
| 88 | 7 |
| 89 | 18 |
| 90 | 18 |
| 91 | 6 |
Atomic Fluctuation Dimensions
| | | | |
|---|---|---|---|
| 82 | 0.069 | 0.042 | -0.111 |
| 83 | 0.078 | 0.028 | -0.05 |
| 84 | -0.008 | 0.064 | 0.066 |
| 85 | -0.086 | -0.029 | 0.087 |
| 86 | -0.054 | -0.005 | 0.002 |
| 87 | 0.016 | 0.048 | -0.024 |
| 88 | 0.002 | 0.02 | -0.052 |
| 89 | 0.030 | 0.046 | -0.005 |
| 90 | -0.009 | -0.079 | 0.02 |
| 91 | -0.039 | -0.136 | 0.065 |
*FIG. 6G*

Distance Matrix Dimensions

| | 82 | 83 | 84 | 85 | 86 | 87 | 88 | 89 | 90 | 91 |
|---|---|---|---|---|---|---|---|---|---|---|
| 82 | | 3.8 | 6.7 | 9.8 | 12.0 | 10.2 | 8.5 | 5.8 | 5.4 | 6.3 |
| 83 | | | 3.5 | 6.3 | 8.3 | 7.0 | 5.6 | 4.5 | 5.6 | 8.4 |
| 84 | | | | 3.8 | 6.4 | 5.9 | 6.4 | 7.3 | 7.6 | 10.9 |
| 85 | | | | | 3.5 | 5.5 | 7.2 | 9.3 | 10.7 | 13.9 |
| 86 | | | | | | 3.9 | 6.1 | 9.6 | 11.3 | 15 |
| 87 | | | | | | | 3.8 | 7.3 | 8.1 | 11.8 |
| 88 | | | | | | | | 3.8 | 6.3 | 10.1 |
| 89 | | | | | | | | | 3.8 | 7.0 |
| 90 | | | | | | | | | | 3.8 |
| 91 | | | | | | | | | | |

Amino Acid Matrix Dimension

| | |
|---|---|
| 82 | 17 |
| 83 | 6 |
| 84 | 16 |
| 85 | 4 |
| 86 | 18 |
| 87 | 15 |
| 88 | 7 |
| 89 | 15 |
| 90 | 18 |
| 91 | 6 |

Atomic Fluctuation Dimensions

| | X | Y | Z |
|---|---|---|---|
| 82 | 1.412 | -0.727 | -0.009 |
| 83 | -1.1 | -0.897 | -0.316 |
| 84 | -0.86 | -0.956 | -0.487 |
| 85 | -0.168 | -0.154 | -0.38 |
| 86 | -0.649 | 0.341 | -0.001 |
| 87 | 0.065 | 0.419 | 0.388 |
| 88 | 0.652 | 0.806 | 0.068 |
| 89 | 0.350 | 0.511 | 0.374 |
| 90 | 0.348 | 0.002 | 0.411 |
| 91 | -0.059 | 0.375 | -0.031 |

Amino Acid Descriptor Lookup Table

| NUMERIC | LETTER CODE |
|---|---|
| 1 | M |
| 2 | A |
| 3 | V |
| 4 | P |
| 5 | L |
| 6 | I |
| 7 | G |
| 8 | W |
| 9 | Y |
| 10 | F |
| 11 | S |
| 12 | T |
| 13 | C |
| 14 | N |
| 15 | Q |
| 16 | K |
| 17 | R |
| 18 | H |
| 19 | D |
| 20 | E |

Reference Epitope
Eigenvector #1
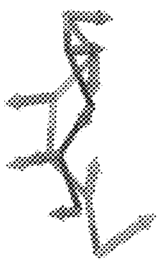
| Atom | X | Y | Z |
|---|---|---|---|
| 1 | -0.08 | -0.08 | 0.12 |
| 2 | -0.07 | -0.09 | 0.16 |
| 3 | 0.04 | -0.13 | 0.06 |
| 4 | 0.09 | 0.07 | -0.22 |
| 5 | 0.15 | 0.06 | -0.30 |
| 6 | 0.10 | -0.27 | -0.06 |
| 7 | -0.08 | -0.07 | 0.42 |
| 8 | -0.11 | -0.15 | 0.21 |
| 9 | -0.11 | 0.23 | -0.03 |
| 10 | 0.06 | 0.42 | -0.36 |
Eigenvector #1
Eigenvalue 2.61
Eigenvector #2
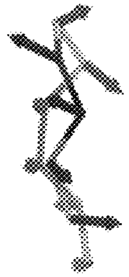
| Atom | X | Y | Z |
|---|---|---|---|
| 1 | 0.22 | 0.10 | -0.29 |
| 2 | 0.24 | 0.04 | 0.03 |
| 3 | -0.07 | 0.17 | 0.43 |
| 4 | -0.40 | -0.10 | 0.14 |
| 5 | -0.05 | 0.06 | -0.35 |
| 6 | 0.32 | -0.01 | -0.11 |
| 7 | 0.02 | 0.03 | 0.11 |
| 8 | 0.03 | 0.03 | 0.16 |
| 9 | -0.19 | -0.14 | 0.00 |
| 10 | -0.16 | -0.18 | -0.12 |
Eigenvector #2
Eigenvalue 1.40
*FIG. 7C*

Reference Epitope
Eigenvector #1
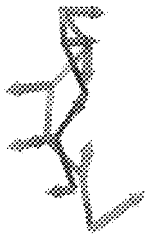
| Atom | X | Y | Z |
|---|---|---|---|
| 1 | -0.08 | -0.05 | 0.12 |
| 2 | -0.07 | -0.09 | 0.16 |
| 3 | 0.04 | -0.12 | 0.06 |
| 4 | 0.09 | 0.07 | -0.22 |
| 5 | 0.15 | 0.06 | -0.30 |
| 6 | 0.10 | -0.27 | -0.06 |
| 7 | -0.08 | -0.07 | 0.42 |
| 8 | -0.11 | -0.15 | 0.21 |
| 9 | -0.11 | 0.23 | -0.03 |
| 10 | 0.06 | 0.42 | -0.36 |
Eigenvector #1
Eigenvalue 2.61
MEM: XTR-1000-B2
Eigenvector #1
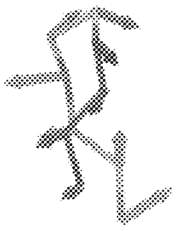
| Atom | X | Y | Z |
|---|---|---|---|
| 1 | -0.03 | -0.05 | 0.06 |
| 2 | -0.07 | -0.15 | 0.12 |
| 3 | 0.05 | -0.20 | 0.05 |
| 4 | 0.23 | -0.02 | 0.00 |
| 5 | 0.30 | 0.15 | -0.02 |
| 6 | 0.06 | 0.16 | -0.25 |
| 7 | -0.31 | -0.36 | 0.18 |
| 8 | -0.15 | -0.13 | 0.12 |
| 9 | -0.22 | 0.20 | -0.04 |
| 10 | 0.07 | 0.43 | -0.23 |
Eigenvector #1
Eigenvalue 2.37
MEM (green)
Reference Epitope (blue)
| MEM Variant | RMSIP |
|---|---|
| XTR-1000-B2 | 0.766 |
*FIG. 7D*

| Panning Programs | Panning Round 1 | | Panning Round 2 | | Panning Round 3 | | |
|---|---|---|---|---|---|---|---|
| | (+) Bait | (−) Bait | (+) Bait | (−) Bait | (+) Bait | (−) Bait | |
| Program 6 | **sMEM** | BSA | VEGF | BSA | **sMEM** | **iMEM1** | |
| Program 10 | **sMEM** | BSA | VEGF | BSA | VEGF | BSA | |
| Program 8 | VEGF | BSA | **sMEM** | **iMEM1** | VEGF | BSA | |
| Program 9 | **sMEM** | BSA | VEGF | BSA | **sMEM** | BSA | |
| Program 13 | **sMEM** | BSA | VEGF | BSA | VEGF | BSA | |
| Program 7 | **uMEM** | BSA | VEGF | BSA | **uMEM** | **iMEM2** | |
| Program 11 | **uMEM** | BSA | VEGF | BSA | VEGF | BSA | |
| Program 12 | VEGF | BSA | VEGF | BSA | VEGF | BSA | Conventional Non-Programmed Selection |

sMEM: High Topology Reference Match Bait
uMEM: Low Topology Reference Match Bait
iMEM: Zero Topology Reference Match Bait
BSA: Bovine Serum Albumin
VEGF: Tx Target Protein

*FIG. 11*

| Program | 6 | 7 | 8 | 9 | 10 | 11 | 12 | 13 |
|---|---|---|---|---|---|---|---|---|
| Min | 0.28 | 0.20 | 0.29 | 0.25 | 0.26 | 0.12 | 0.25 | 0.23 |
| Max | 83.42 | 84.51 | 70.84 | 106.50 | 70.01 | 118.10 | 71.91 | 79.68 |
| Mean | 3.34 | 1.77 | 2.80 | 2.84 | 3.34 | 3.66 | 3.96 | 2.85 |

| Program | 6 | 7 | 8 | 9 | 10 | 11 | 12 | 13 |
|---|---|---|---|---|---|---|---|---|
| Min | 0.10 | 0.08 | 0.14 | 0.10 | 0.13 | 0.02 | 0.10 | 0.09 |
| Max | 372.20 | 320.90 | 434.90 | 504.30 | 358.80 | 139.60 | 227.40 | 341.20 |
| Mean | 8.24 | 2.80 | 6.03 | 9.83 | 7.90 | 4.57 | 4.33 | 6.39 |

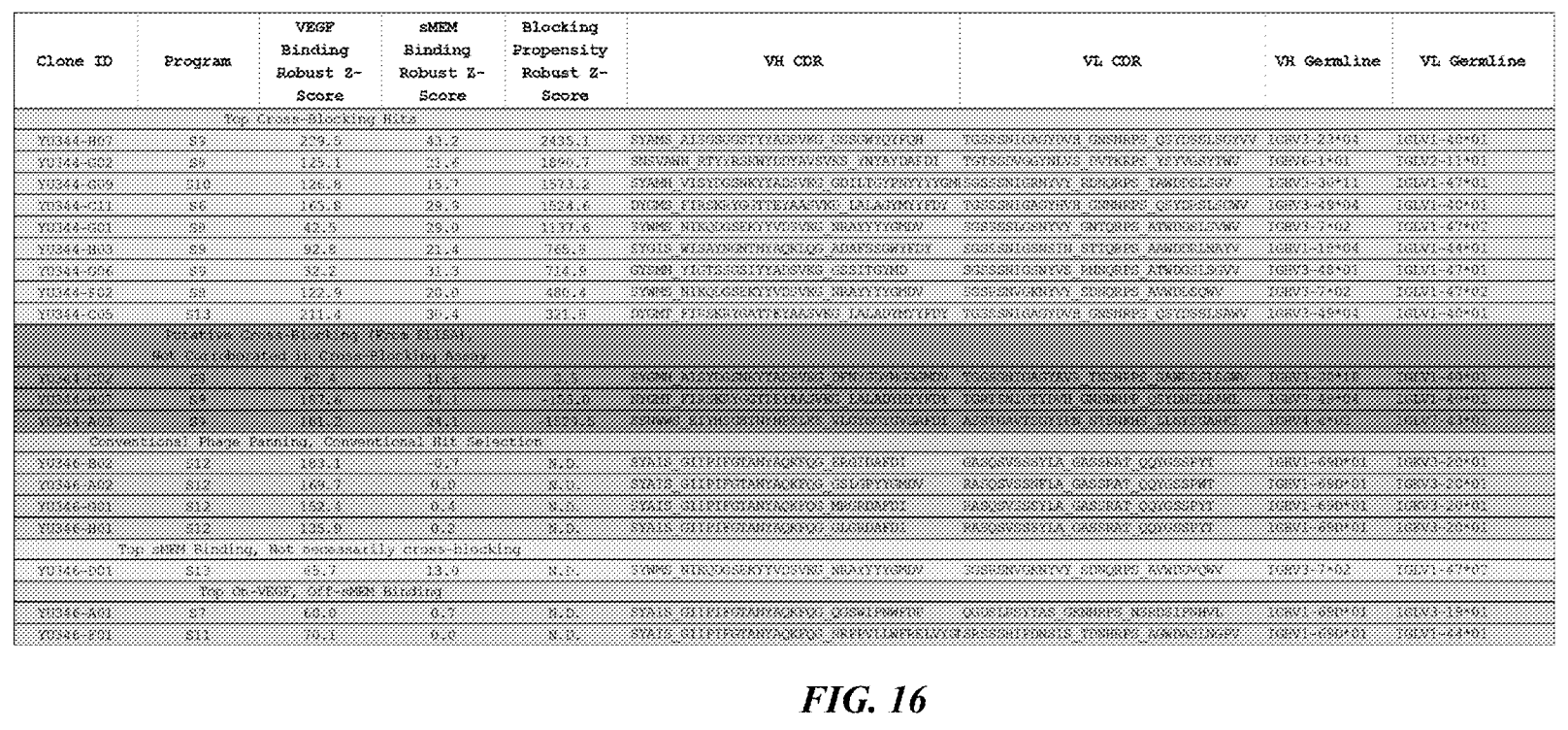

| Clone ID | Program | VEGF Binding Robust Z-Score | sMEM Binding Robust Z-Score | Blocking Propensity Robust Z-Score | VH CDR | VL CDR | VH Germline | VL Germline |
|---|---|---|---|---|---|---|---|---|
| Top Cross-Blocking Hits | | | | | | | | |
| YU344-H07 | S5 | 223.3 | 41.2 | 2435.3 | SYAMS_AISGSGGSTYYADSVKG_GSGWYQYFDH | TGSSSNIGAGYDVH_GNSNRPS_QSYDSSLSGVV | IGHV3-23*04 | IGLV1-40*01 |
| YU344-E02 | S9 | 129.1 | 31.4 | 1896.7 | SNSAAWN_RTYYRSKWYNDYAVSVKS_YNYAYDAFDI | TGTSSDVGGYNYVS_DVSKRPS_YSYAGSYTWV | IGHV6-1*01 | IGLV2-11*01 |
| YU344-G09 | S10 | 126.8 | 15.7 | 1573.2 | SYGMH_VISYDGSNKYYADSVKG_GGILDYPRYYYYGMDV | SGSSSNIGRNYVY_RNNQRPS_AAWDDSLSGV | IGHV3-30*11 | IGLV1-47*01 |
| YU344-C11 | S6 | 165.8 | 29.5 | 1524.6 | DYAMS_FIRSKAYGGTTEYAASVKG_LALAGMDYFDY | TGSSSNIGAGYDVH_GNSNRPS_QSYDSSLSGWV | IGHV3-49*04 | IGLV1-40*01 |
| YU344-E01 | S9 | 42.5 | 29.0 | 1137.6 | SYWMS_NIKQDGSEKYYVDSVKG_NRAYYYGMDV | SGSSSNIGSNYVY_RNNQRPS_ATWDDSLNWV | IGHV3-7*02 | IGLV1-47*01 |
| YU344-H03 | S9 | 92.8 | 21.4 | 765.5 | SYGIS_WISAYNGNTNYAQKLQG_ADAPSSGWYFDY | SGSSSNIGSNSVN_SNNQRPS_AAWDDRLNAYV | IGHV1-18*04 | IGLV1-44*01 |
| YU344-G06 | S5 | 32.2 | 31.3 | 714.9 | SYSMN_YISSSSSTIYYADSVKG_DSSITGMDV | SGSSSNIGSNYVS_RNNQRPS_ATWDDSLSGYV | IGHV3-48*01 | IGLV1-47*01 |
| YU344-F02 | S8 | 122.4 | 20.0 | 480.4 | SYWMS_NIKQDGSEKYYVDSVKG_NRAYYYGMDV | SGSSNVGRNYVY_SNNQRPS_AAWDDSLSGWV | IGHV3-7*02 | IGLV1-47*01 |
| YU344-C05 | S13 | 211.4 | 30.4 | 321.8 | DYAMT_FIRSKAYGGTTEYAASVKG_LALAGVDYFDY | TGSSSNIGAGYDVH_GNSNRPS_QSYDSSLSAWV | IGHV3-49*04 | IGLV1-40*01 |
| [illegible] | | | | | | | | |
| [illegible] | [illegible] | [illegible] | [illegible] | [illegible] | [illegible] | [illegible] | [illegible] | [illegible] |
| [illegible] | [illegible] | [illegible] | [illegible] | [illegible] | [illegible] | [illegible] | [illegible] | [illegible] |
| [illegible] | [illegible] | [illegible] | [illegible] | [illegible] | [illegible] | [illegible] | [illegible] | [illegible] |
| Conventional Phage Panning, Conventional Hit Selection | | | | | | | | |
| YU346-B02 | S12 | 183.1 | -0.7 | N.D. | [illegible] | [illegible] | IGHV1-69*01 | IGKV3-20*01 |
| YU346-A02 | S12 | 169.7 | 0.0 | N.D. | [illegible] | [illegible] | IGHV1-69*01 | IGKV3-20*01 |
| YU346-H01 | S12 | 152.1 | 0.4 | N.D. | [illegible] | [illegible] | IGHV1-69*01 | IGKV3-20*01 |
| YU346-H03 | S12 | 135.9 | 0.2 | N.D. | [illegible] | [illegible] | IGHV1-69*01 | IGKV3-20*01 |
| Top sMEM Binding, Not necessarily cross-blocking | | | | | | | | |
| YU346-D01 | S13 | 65.7 | 13.0 | N.D. | SYWMS_NIKQDGSEKYYVDSVKG_NRAYYYGMDV | [illegible] | IGHV3-7*02 | IGLV1-47*01 |
| Top On-VEGF, Off-sMEM Binding | | | | | | | | |
| YU346-A03 | S7 | 60.9 | 0.7 | N.D. | [illegible] | [illegible] | IGHV1-69*01 | IGLV1-19*01 |
| YU346-F01 | S11 | 70.1 | 0.0 | N.D. | [illegible] | [illegible] | IGHV1-69*01 | IGLV1-44*01 |

FIG. 16

| | Panning Round 1 | | Panning Round 2 | | Panning Round 3 | | X-Blocking Enrichment vs. Control |
|---|---|---|---|---|---|---|---|
| | (+) Bait | (-) Bait | (+) Bait | (-) Bait | (+) Bait | (-) Bait | |
| MEM Driven Panning Program Designs | sMEM | BSA | VEGF | BSA | sMEM | iMEM1 | -13.4% |
| | sMEM | BSA | VEGF | BSA | VEGF | BSA | 35.7% |
| | VEGF | BSA | sMEM | iMEM1 | VEGF | BSA | 17.5% |
| | sMEM | BSA | VEGF | BSA | sMEM | BSA | -4.3% |
| | uMEM | BSA | VEGF | BSA | uMEM | iMEM2 | 18.3% |
| | uMEM | BSA | VEGF | BSA | VEGF | BSA | 27.1% |
| Full-Length Antigen | VEGF | BSA | VEGF | BSA | VEGF | BSA | CONTROL |

*FIG. 20*

$$Clonality = \frac{S}{N}$$

$$\text{Normalized Shannon} = \frac{-\sum_{i=1}^{S} \frac{n_i}{S} \ln\left(\frac{n_i}{S}\right)}{\ln(S)}$$

$N$ = *Number of* Reads $S$ = *Total Number of Clonotypes*

$n_i$ = *Number of clonotypes i*

Naïve Hu Ig Repertoire
Round 1 Panning Germline Usage

Round 1 Panning: Sequence and Germline
Dimension-Reduction Clusters

NGS Sample Collection (after Panning Round 1) — NGS Sample Collection (after Panning Round 2) — NGS Sample Collection (after Panning Round 3)

| Panning Programs | Panning Round 1 | | Panning Round 2 | | Panning Round 3 | | |
|---|---|---|---|---|---|---|---|
| | (+) Bait | (-) Bait | (+) Bait | (-) Bait | (+) Bait | (-) Bait | |
| A1 | **sMEM #1** | BSA | PD-L1 | BSA | **sMEM #1** | BSA | High Stability MEM Bait |
| A2 | **sMEM #1** | BSA | PD-L1 | BSA | **sMEM #1** | **iMEM** | High Stability MEM Bait |
| A3 | **sMEM #1** | BSA | PD-L1 | BSA | PD-L1 | BSA | High Stability MEM Bait |
| B1 | **sMEM #5** | BSA | PD-L1 | BSA | **sMEM #5** | BSA | High Stability MEM Bait |
| B2 | **sMEM #5** | BSA | PD-L1 | BSA | PD-L1 | BSA | High Stability MEM Bait |
| C1 | PD-L1 | BSA | PD-L1 | BSA | PD-L1 | BSA | Full-Length Bait |

sMEM #1: Stable Engineered MEM
sMEM #5: Stable Naïve MEM
iMEM: Inverse MEM
BSA: Bovine Serum Albumin
PD-L1: Tx Target Protein (full length bait)

*FIG. 33*

P-value ≤ 0.05

| | Mean 1 | Mean 2 | Diff. | P-Value |
|---|---|---|---|---|
| P1 vs. P2 | 1.14 | 1.05 | 0.09 | 0.9973 |
| P1 vs. P3 | 1.14 | 1.06 | 0.08 | 0.9983 |
| P1 vs. P4 | 1.14 | 1.34 | -0.19 | 0.9176 |
| P1 vs. P5 | 1.14 | 3.27 | -2.13 | <0.0001 |
| P1 vs. P6 | 1.14 | 2.01 | -0.87 | 0.0001 |
| P2 vs. P3 | 1.05 | 1.06 | -0.01 | >0.9999 |
| P2 vs. P4 | 1.05 | 1.34 | -0.28 | 0.6867 |
| P2 vs. P5 | 1.05 | 3.27 | -2.22 | <0.0001 |
| P2 vs. P6 | 1.05 | 2.01 | -0.96 | <0.0001 |
| P3 vs. P4 | 1.06 | 1.34 | -0.28 | 0.7128 |
| P3 vs. P5 | 1.06 | 3.27 | -2.21 | <0.0001 |
| P3 vs. P6 | 1.06 | 2.01 | -0.95 | <0.0001 |
| P4 vs. P5 | 1.34 | 3.27 | -1.93 | <0.0001 |
| P4 vs. P6 | 1.34 | 2.01 | -0.68 | 0.0066 |
| P5 vs. P6 | 3.27 | 2.01 | 1.26 | <0.0001 |

| | P1 | P2 | P3 | P4 | P5 | P6 |
|---|---|---|---|---|---|---|
| Sample Size | 768 | 768 | 768 | 768 | 768 | 768 |
| | | | | | | |
| Minimum | 0.009 | 0.007 | 0.152 | 0.183 | 0.053 | 0.397 |
| Median | 0.927 | 0.927 | 0.927 | 0.915 | 1 | 1.03 |
| Maximum | 66.2 | 15.4 | 24.3 | 61.5 | 67.4 | 57.9 |
| | | | | | | |
| Mean | 1.14 | 1.05 | 1.06 | 1.34 | 3.27 | 2.01 |

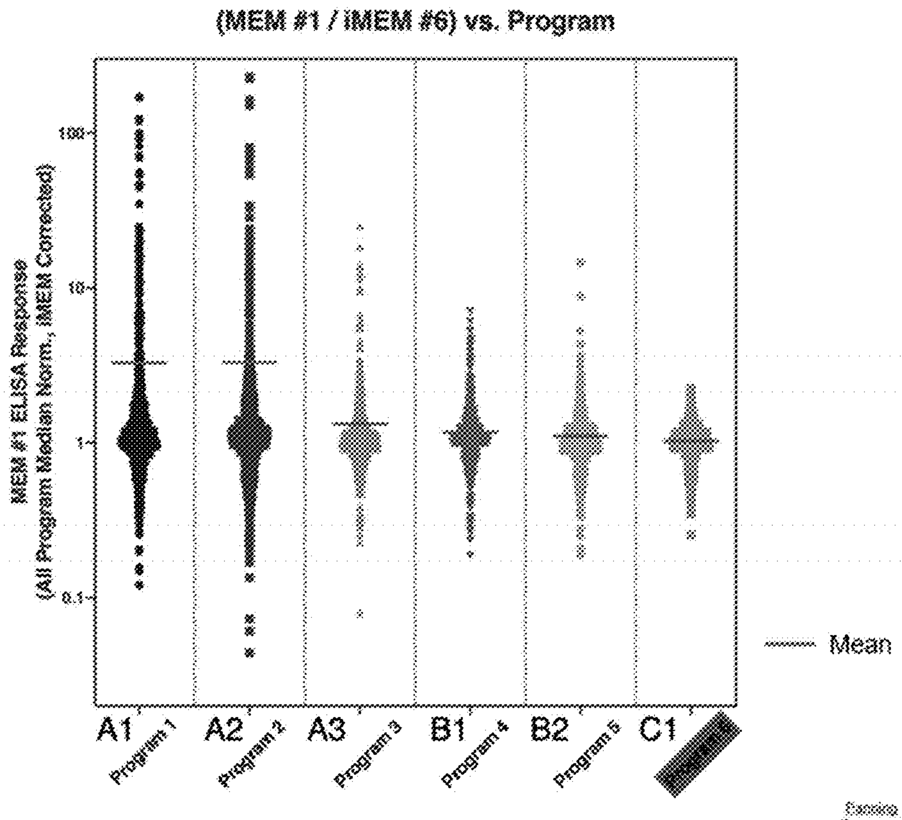

| P-value ≤ 0.05 | Mean 1 | Mean 2 | Diff. | P-Value |
|---|---|---|---|---|
| P1 vs. P2 | 3.29 | 3.31 | -0.03 | >0.9999 |
| P1 vs. P3 | 3.29 | 1.33 | 1.96 | <0.0001 |
| P1 vs. P4 | 3.29 | 1.17 | 2.12 | <0.0001 |
| P1 vs. P5 | 3.29 | 1.10 | 2.18 | <0.0001 |
| P1 vs. P6 | 3.29 | 1.03 | 2.26 | <0.0001 |
| P2 vs. P3 | 3.31 | 1.33 | 1.99 | <0.0001 |
| P2 vs. P4 | 3.31 | 1.17 | 2.15 | <0.0001 |
| P2 vs. P5 | 3.31 | 1.10 | 2.21 | <0.0001 |
| P2 vs. P6 | 3.31 | 1.03 | 2.29 | <0.0001 |
| P3 vs. P4 | 1.33 | 1.17 | 0.16 | 0.9988 |
| P3 vs. P5 | 1.33 | 1.10 | 0.22 | 0.9942 |
| P3 vs. P6 | 1.33 | 1.03 | 0.30 | 0.9774 |
| P4 vs. P5 | 1.17 | 1.10 | 0.06 | >0.9999 |
| P4 vs. P6 | 1.17 | 1.03 | 0.14 | 0.9994 |
| P5 vs. P6 | 1.10 | 1.03 | 0.08 | >0.9999 |

| | P1 | P2 | P3 | P4 | P5 | P6 |
|---|---|---|---|---|---|---|
| Sample Size | 768 | 768 | 768 | 768 | 768 | 768 |
| | | | | | | |
| Minimum | 0.121 | 0.044 | 0.08 | 0.186 | 0.19 | 0.254 |
| Median | 1.1 | 1.1 | 1.06 | 1.08 | 1.03 | 1 |
| Maximum | 170 | 230 | 25.2 | 7 | 14.7 | 2.25 |
| | | | | | | |
| Mean | 3.29 | 3.31 | 1.33 | 1.17 | 1.1 | 1.03 |

| Panning Programs | Panning Round 1 | | Panning Round 2 | | Panning Round 3 | |
|---|---|---|---|---|---|---|
| A1 | [illegible] | [illegible] | [illegible] | [illegible] | [illegible] | [illegible] |
| A2 | [illegible] | [illegible] | [illegible] | [illegible] | [illegible] | [illegible] |
| A3 | [illegible] | [illegible] | [illegible] | [illegible] | [illegible] | [illegible] |
| B1 | [illegible] | [illegible] | [illegible] | [illegible] | [illegible] | [illegible] |
| B2 | [illegible] | [illegible] | [illegible] | [illegible] | [illegible] | [illegible] |
| C1 | [illegible] | [illegible] | [illegible] | [illegible] | [illegible] | [illegible] |

*FIG. 35*

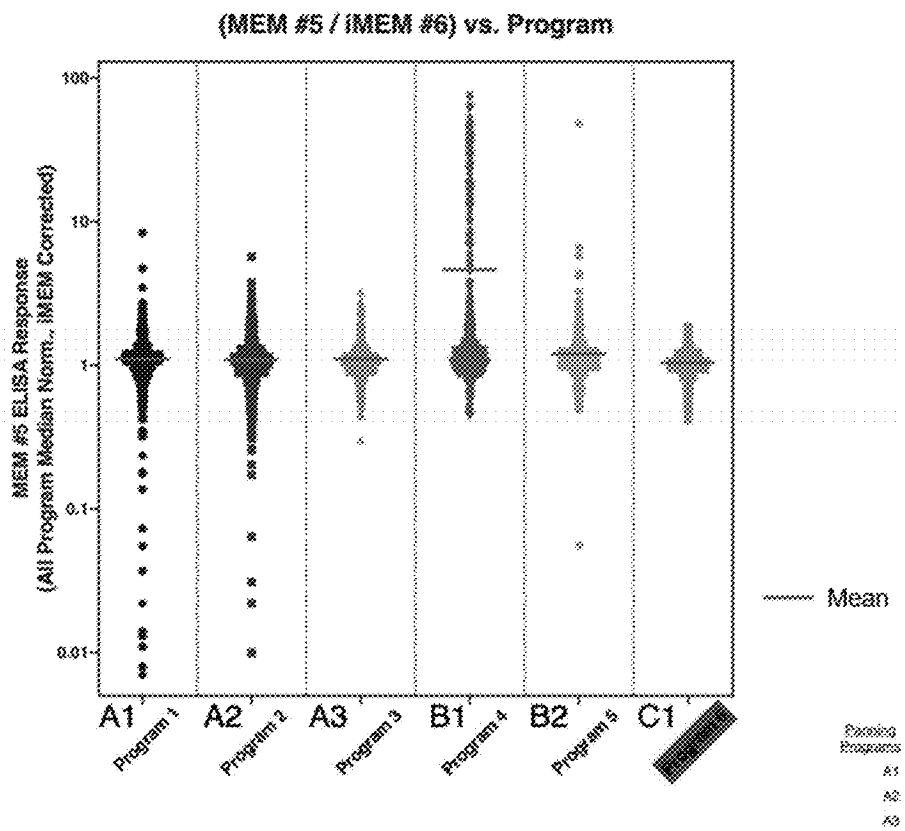

| P-value ≤ 0.05 | Mean 1 | Mean 2 | Diff. | P-Value |
|---|---|---|---|---|
| P1 vs. P2 | 1.11 | 1.09 | 0.02 | >0.9999 |
| P1 vs. P3 | 1.11 | 1.11 | 0.00 | >0.9999 |
| P1 vs. P4 | 1.11 | 4.62 | −3.51 | <0.0001 |
| P1 vs. P5 | 1.11 | 1.20 | −0.09 | 0.9984 |
| P1 vs. P6 | 1.11 | 1.04 | 0.07 | 0.9996 |
| P2 vs. P3 | 1.09 | 1.11 | −0.02 | >0.9999 |
| P2 vs. P4 | 1.09 | 4.63 | −3.53 | <0.0001 |
| P2 vs. P5 | 1.09 | 1.20 | −0.11 | 0.9959 |
| P2 vs. P6 | 1.09 | 1.04 | 0.05 | >0.9999 |
| P3 vs. P4 | 1.11 | 4.62 | −3.51 | <0.0001 |
| P3 vs. P5 | 1.11 | 1.20 | −0.09 | 0.9982 |
| P3 vs. P6 | 1.11 | 1.04 | 0.06 | 0.9997 |
| P4 vs. P5 | 4.62 | 1.20 | 3.41 | <0.0001 |
| P4 vs. P6 | 4.62 | 1.04 | 3.57 | <0.0001 |
| P5 vs. P6 | 1.20 | 1.04 | 0.16 | 0.9791 |

| | P1 | P2 | P3 | P4 | P5 | P6 |
|---|---|---|---|---|---|---|
| Sample Size | 768 | 768 | 768 | 768 | 768 | 768 |
| | | | | | | |
| Minimum | 0.007 | 0.01 | 0.302 | 0.435 | 0.056 | 0.416 |
| Median | 1.06 | 1.06 | 1.06 | 1.15 | 1.09 | 1.06 |
| Maximum | 8.36 | 5.7 | 3.24 | 74.8 | 46.1 | 1.86 |
| | | | | | | |
| Mean | 1.11 | 1.09 | 1.11 | 4.62 | 1.2 | 1.04 |

| Panning Programs | Panning Round 3 | | Panning Round 2 | | Panning Round 3 | |
|---|---|---|---|---|---|---|
| | [illegible] | [illegible] | [illegible] | [illegible] | [illegible] | [illegible] |
| A1 | [illegible] | [illegible] | [illegible] | [illegible] | [illegible] | [illegible] |
| A2 | [illegible] | [illegible] | [illegible] | [illegible] | [illegible] | [illegible] |
| A3 | [illegible] | [illegible] | [illegible] | [illegible] | [illegible] | [illegible] |
| B1 | [illegible] | [illegible] | [illegible] | [illegible] | [illegible] | [illegible] |
| B2 | [illegible] | [illegible] | [illegible] | [illegible] | [illegible] | [illegible] |
| C1 | [illegible] | [illegible] | [illegible] | [illegible] | [illegible] | [illegible] |

*FIG. 36*

P-value ≤ 0.05

| | Mean 1 | Mean 2 | Diff. | P-Value |
|---|---|---|---|---|
| P1 vs. P2 | 4.33 | 3.80 | 0.53 | 0.9572 |
| P1 vs. P3 | 4.33 | 1.66 | 2.67 | 0.0002 |
| P1 vs. P4 | 4.33 | 1.67 | 2.66 | 0.0002 |
| P1 vs. P5 | 4.33 | 3.67 | 0.66 | 0.8931 |
| P1 vs. P6 | 4.33 | 2.15 | 2.18 | 0.0054 |
| P2 vs. P3 | 3.80 | 1.66 | 2.14 | 0.0070 |
| P2 vs. P4 | 3.80 | 1.67 | 2.14 | 0.0071 |
| P2 vs. P5 | 3.80 | 3.67 | 0.13 | >0.9999 |
| P2 vs. P6 | 3.80 | 2.15 | 1.66 | 0.0784 |
| P3 vs. P4 | 1.66 | 1.67 | 0.00 | >0.9999 |
| P3 vs. P5 | 1.66 | 3.67 | -2.01 | 0.0147 |
| P3 vs. P6 | 1.66 | 2.15 | -0.48 | 0.9704 |
| P4 vs. P5 | 1.67 | 3.67 | -2.00 | 0.0149 |
| P4 vs. P6 | 1.67 | 2.15 | -0.48 | 0.9711 |
| P5 vs. P6 | 3.67 | 2.15 | 1.52 | 0.1339 |

| | P1 | P2 | P3 | P4 | P5 | P6 |
|---|---|---|---|---|---|---|
| Sample Size | 768 | 768 | 768 | 768 | 768 | 768 |
| | | | | | | |
| Minimum | 0.004 | 0.003 | 0.012 | 0.043 | 0.053 | 0.148 |
| Median | 1.05 | 1.07 | 1 | 0.973 | 1.1 | 1.12 |
| Maximum | 434 | 287 | 92.4 | 101 | 159 | 57.9 |
| | | | | | | |
| Mean | 4.33 | 3.8 | 1.66 | 1.67 | 3.67 | 2.15 |

P-value ≤ 0.05

| | Mean 1 | Mean 2 | Diff. | P Value |
|---|---|---|---|---|
| P1 vs. P2 | 1.38 | 1.21 | 0.17 | 0.9998 |
| P1 vs. P3 | 1.38 | 1.20 | 0.18 | 0.9998 |
| P1 vs. P4 | 1.38 | 6.62 | -5.24 | <0.0001 |
| P1 vs. P5 | 1.38 | 4.40 | -3.01 | <0.0001 |
| P1 vs. P6 | 1.38 | 2.15 | -0.76 | 0.0370 |
| P2 vs. P3 | 1.21 | 1.20 | 0.01 | >0.9999 |
| P2 vs. P4 | 1.21 | 6.62 | -5.41 | <0.0001 |
| P2 vs. P5 | 1.21 | 4.40 | -3.18 | <0.0001 |
| P2 vs. P6 | 1.21 | 2.15 | -0.93 | 0.6832 |
| P3 vs. P4 | 1.20 | 6.62 | -5.42 | <0.0001 |
| P3 vs. P5 | 1.20 | 4.40 | -3.19 | <0.0001 |
| P3 vs. P6 | 1.20 | 2.15 | -0.94 | 0.6763 |
| P4 vs. P5 | 6.62 | 4.40 | 2.23 | 0.0062 |
| P4 vs. P6 | 6.62 | 2.15 | 4.48 | <0.0001 |
| P5 vs. P6 | 4.40 | 2.15 | 2.25 | 0.0054 |

| | P1 | P2 | P3 | P4 | P5 | P6 |
|---|---|---|---|---|---|---|
| Sample Size | 768 | 768 | 768 | 768 | 768 | 768 |
| | | | | | | |
| Minimum | 0.0001 | 0.0001 | 0.046 | 0.109 | 0.04 | 0.287 |
| Median | 0.993 | 0.993 | 0.985 | 1.08 | 1.13 | 1.11 |
| Maximum | 106 | 12.7 | 27.6 | 297 | 522 | 61.6 |
| | | | | | | |
| Mean | 1.38 | 1.21 | 1.2 | 6.62 | 4.4 | 2.15 |

| Selection Filter # | PD-L1 | sMEM #1 / iMEM | nMEM #5 / iMEM | PD-L1 / iMEM | Program | Clone Count |
|---|---|---|---|---|---|---|
| 1 (+) | > 5-fold | > 2-fold | > 2-fold | > 1.5-fold | ALL | 23 |
| 2 (ctl) | > 5-fold | > 1.5-fold | > 1.5-fold | NONE | 6 | 3 |
| 3 (+) | > 5-fold | NONE | > 2-fold | > 2-fold | ALL | 11 |
| 4 (ctl) | > 5-fold | > 2-fold | NONE | > 2-fold | ALL | 14 |
| 5 (+) | > 3-fold | NONE | > 3-fold | > 3-fold | ALL | 4 |
| 6 (+) | > 3-fold | > 3-fold | NONE | > 3-fold | ALL | 5 |
| 7 (ctl) | > 10-fold | NONE | NONE | NONE | 6 | 27 |
| 8 (ctl) | NONE | NONE | NONE | > 25-fold | (NOT) 6 | 28 |
| 9 (ctl) | NONE | > 100-fold | NONE | > Median | ALL | 4 |
| 10 (ctl) | NONE | NONE | > 50-fold | > Median | ALL | 5 |

*FIG. 40*

| Notes | Clone ID | Panning Program | PD-L1 ELISA Response | Blocking Propensity | Germline of VH | Germline of VL | CDR of VH | CDR of VL |
|---|---|---|---|---|---|---|---|---|
| ELISA & X-Block Hit | YU349-C03 | B2 | 72.15 | 186.01 | IGHV3-23*04 | IGLV3-1*01 | SYAMS_AISGSGGSTYYADSVKG_GSSGWYQYFQH | SGDKLGDKYAS_QDKKRPS_QAWDSSTVV |
| ELISA & X-Block Hit | YU349-C02 | B2 | 66.61 | 284.00 | IGHV4-39*07 | IGLV1-47*02 | SSSYYWG_SIYYSGSTYYNPSLKS_LVLMPAYYFDY | SGSSSNIGRNYVQ_KNNQRPS_AAWDDSLYSWV |
| ELISA & X-Block Hit | YU349-F02 | B2 | 50.89 | 85.51 | IGHV4-39*07 | IGLV1-47*02 | SSSYYWG_SIYYSGSTYYNPSLKS_LSRYYYYGMDV | SGSSSNIGSNYVY_SNNQRPS_AAWDDRLSAWV |
| ELISA & X-Block Hit | YU349-E08 | C1 | 34.25 | 144.05 | IGHV4-59*04 | IGKV3-11*01 | SSSYYWG_SINYSGNTYYNPSLKS_RYNWNYVFDY | RASQNIRNTLV_DASSRAT_QQLSTLPYT |
| ELISA & X-Block Hit | YU349-H06 | C1 | 23.67 | 140.57 | IGHV3-43D*01 | IGLV6-57*02 | DYAMH_LISWDGGSTYYADSVKG_SRGRRAWSFDY | ARSSGTIASNYVQ_EDNQRPS_QSFDRRNLV |
| ELISA & X-Block Hit | YU349-D08 | C1 | 23.59 | 216.15 | IGHV4-39*07 | IGKV3-20*01 | SSSYYWG_SIYYSGTTYYNPSLKS_TRLSGTPDY | RASQSVSSSYLA_GASSRAT_QQYGSSFPT |
| ELISA & X-Block Hit | YU349-D09 | C1 | 22.39 | 51.62 | IGHV4-38-2*01 | IGKV1S22*01 | SGYYWG_SIYYSGSTYYNPSLKS_VRGDSLVDY | RASQGVSTALA_DASSLPS_QHSNSYFFT |
| ELISA & X-Block Hit | YU349-B09 | C1 | 20.42 | 54.77 | IGHV3-64D*06 | IGKV1-39*01 | SYAMH_AISSNGGSTYYADSVKG_GYYDSSGYYYADYYYYYGMDV | RASQSISSYLN_AASSLQS_QQSYSTLFT |
| ELISA & X-Block Hit | YU349-A09 | C1 | 16.73 | 561.56 | IGHV3-7*02 | IGKV1-39*01 | SYWMS_NIKQDGSEKYYVDSVKG_APLWAAYFDY | RASQSISSYLN_AASSLQS_QQSYSTPPT |
| ELISA & X-Block Hit | YU349-E05 | A3 | 11.53 | 98.93 | IGHV4-38-2*02 | IGKV1-17*01 | SGYYWG_SIYHSGSTYYNPSLKS_IRRDGYNVDY | RASQGIRNDLG_AASSLQS_LQHNSYPLT |
| ELISA & X-Block Hit | YU349-A12 | A1 | 9.36 | 202.22 | IGHV3-30*02 | IGLV7-46*01 | SYGMH_FIRYDGSNKYYADSVKG_SNDY | GSSTGPVTSGHDPY_GATNRHS_LLSYRGLWV |
| ELISA & X-Block Hit | YU349-A01 | A2 | 7.23 | 152.34 | IGHV3-48*03 | IGLV3-21*02 | SYGMH_YISSSGSTIYYADSVKG_SLTYGAPYFDY | AGNNIGSKSVH_DDSDRPS_QVWHSTSSHRRDVA |
| ELISA & X-Block Hit | YU349-F01 | A2 | 4.23 | 70.96 | IGHV3-23*04 | IGLV2-14*01 | SYAMS_TISGSGGSITYYADSVKG_ASWDGHNLFFDY | TGTSSDVGGYNYVS_DVSNRPS_SSYTSSDTVI |
| ELISA & X-Block Hit | YU349-A02 | A2 | 4.17 | 258.03 | IGHV1-2*02 | IGLV6-57*01 | GYYMH_WINPNSGGTNYAQKFQG_DLGGGYGFDY | TRSSGSIAGNYVQ_LNNQRPS_QSYDSSHRWV |
| ELISA & X-Block Hit | YU349-B01 | A2 | 4.15 | 77.35 | IGHV1-18*04 | IGLV1-40*01 | SYGIS_WISAYNGNTNYAQKLQG_DGSLRWSGYYNTPAYYYYGMDV | TGSSSNIGAGYDVH_ANSKRPS_QSYDSSLSGWV |
| ELISA & X-Block Hit | YU349-A05 | A2 | 4.11 | 74.74 | IGHV1-18*04 | IGKV1-27*01 | SYGIS_WISAYNGNTNYAQKLQG_VVPGFGYYGMDV | RASQDISDWLA_AATRLQG_QKYNSAPFS |
| ELISA & X-Block Hit | YU349-G01 | A2 | 4.10 | 170.65 | IGHV4-39*07 | IGLV10-54*01 | SSSYYWG_SIYYSGSTYYNPSLKS_QDGITAFDI | TGNSNNVGNQGAA_RNNNRPS_SAWDSSLSAWV |
| ELISA & X-Block Hit | YU349-G09 | B1 | 3.71 | 225.74 | IGHV1-2*04 | IGLV1-47*01 | SYAIS_WINPNSGGTNYAQKFQG_DRIAAAGPYYYYYGMDV | SGSSSNIGSNSVH_RNNQRPS_AAWDDSLSGRL |
| ELISA & X-Block Hit | YU349-F11 | A1 | 2.38 | 113.62 | IGHV3-30*18 | IGLV2-14*01 | SYGMH_VISYDGSDKYYADSVKG_DLSGLPYIDY | IGTSSDVGGYNYVS_EVSNRPS_SSYTSSSTLV |
| ELISA & X-Block Hit | YU349-D12 | A1 | 1.91 | 273.14 | IGHV1-18*04 | IGLV7-43*01 | SYGIS_WISAYNGNTNYAQKLQG_VLHYYGSGSYGGWFDP | ASSTGAVTSAYYPN_DTSNKHS_LLYSGGGHWV |
| ELISA & X-Block Hit | YU349-A11 | B1 | 0.66 | 143.07 | IGHV1-69D*01 | IGKV5-2*01 | SYAIS_GIIPIFGTANYAQKFQG_KYYDFWSGYFPNYYYGMDV | RASQDIDDDMN_EGSNLVP_LQHDSLPHT |
| ELISA & X-Block Hit | YU349-D01 | A2 | 0.30 | 383.38 | IGHV3-7*02 | IGLV1-40*01 | NWWMS_NINQDGSERNYVDSVKG_GPRILDY | TRSSSDIGAGYDVH_GNYHRPS_QSYDPNLKGSI |
| ELISA & X-Block Hit | YU349-A08 | C1 | -30.29 | 590.64 | IGHV1-18*04 | IGLV1-44*01 | SYGIS_WISAYNGNTNYAQKLQG_MGDYGDYTTTYYYYGMDV | SGSSSNIGSNTVS_YNNQRPS_AAWDDSLNAYV |

*FIG. 43*

| Clone ID | Strategy | Blocking Propensity |
|---|---|---|
| YU351-F09 | A1 | 326.12 |
| YU351-A09 | A1 | 207.52 |
| YU351-E09 | A1 | 148.23 |
| YU351-D09 | A1 | 44.47 |
| YU351-C09 | A1 | 37.06 |
| YU351-B09 | A1 | 37.06 |
| YU351-D08 | A1 | 37.06 |
| YU351-F08 | A1 | 29.65 |
| YU351-H08 | A1 | 14.82 |
| YU351-G08 | A1 | 7.41 |
| YU351-E08 | A1 | 7.41 |
| YU351-G09 | A1 | 0.00 |
| YU351-A01 | A2 | 103.76 |
| YU351-E02 | A2 | 74.12 |
| YU351-D02 | A2 | 44.47 |
| YU351-B03 | A2 | 37.06 |
| YU351-A03 | A2 | 29.65 |
| YU351-B01 | A2 | 22.23 |
| YU351-C01 | A2 | 22.23 |
| YU351-G02 | A2 | 14.82 |
| YU351-F02 | A2 | 7.41 |
| YU351-D03 | A2 | 7.41 |
| YU351-H02 | A2 | 0.00 |
| YU351-C03 | A2 | 0.00 |
| YU351-H03 | A3 | 59.29 |
| YU351-E04 | A3 | 44.47 |
| YU351-D04 | A3 | 37.06 |
| YU351-F03 | A3 | 29.65 |
| YU351-H06 | A3 | 22.23 |
| YU351-B04 | A3 | 22.23 |
| YU351-A04 | A3 | 22.23 |
| YU351-C04 | A3 | 7.41 |
| YU351-G03 | A3 | 0.00 |
| YU351-F06 | A3 | 0.00 |
| YU351-G06 | A3 | 0.00 |

*FIG. 45B*

| Clone ID | Strategy | Blocking Propensity |
|---|---|---|
| YU351-C08 | B1 | 59.3 |
| YU351-B08 | B1 | 22.2 |
| YU351-A07 | B1 | 14.8 |
| YU351-D07 | B1 | 14.8 |
| YU351-B07 | B1 | 7.4 |
| YU351-E07 | B1 | 7.4 |
| YU351-F07 | B1 | 7.4 |
| YU351-G07 | B1 | 0.0 |
| YU351-C07 | B1 | 0.0 |
| YU351-A08 | B1 | 0.0 |
| YU351-H07 | B1 | 0.0 |
| YU351-H04 | B2 | 259.4 |
| YU351-A02 | B2 | 200.1 |
| YU351-H01 | B2 | 96.4 |
| YU351-A05 | B2 | 88.9 |
| YU351-G04 | B2 | 74.1 |
| YU351-B02 | B2 | 74.1 |
| YU351-F04 | B2 | 74.1 |
| YU351-F01 | B2 | 74.1 |
| YU351-D01 | B2 | 66.7 |
| YU351-C02 | B2 | 37.1 |
| YU351-E01 | B2 | 29.6 |
| YU351-G01 | B2 | 29.6 |
| YU351-E05 | C1 | 407.6 |
| YU351-D05 | C1 | 163.1 |
| YU351-C06 | C1 | 118.6 |
| YU351-A06 | C1 | 81.5 |
| YU351-B06 | C1 | 66.7 |
| YU351-C05 | C1 | 37.1 |
| YU351-G05 | C1 | 29.6 |
| YU351-D06 | C1 | 29.6 |
| YU351-B05 | C1 | 14.8 |
| YU351-H05 | C1 | 0.0 |
| YU351-E06 | C1 | 0.0 |
| YU351-F05 | C1 | 0.0 |

*FIG. 45C*

| | Panning Round 1 | | Panning Round 2 | | Panning Round 3 | | X-Blocking Enrichment vs. Control |
|---|---|---|---|---|---|---|---|
| | (+) Bait | (-) Bait | (+) Bait | (-) Bait | (+) Bait | (-) Bait | |
| MEM Driven Panning Program Designs | sMEM #1 | BSA | PD-L1 | BSA | sMEM #1 | BSA | 2.3% |
| | sMEM #1 | BSA | PD-L1 | BSA | sMEM #1 | iMEM | -18.7% |
| | sMEM #1 | BSA | PD-L1 | BSA | PD-L1 | BSA | -32.5% |
| | nMEM #5 | BSA | PD-L1 | BSA | nMEM #5 | BSA | -52.1% |
| | nMEM #5 | BSA | PD-L1 | BSA | PD-L1 | BSA | 36.7% |
| Full-Length Antigen | PD-L1 | BSA | PD-L1 | BSA | PD-L1 | BSA | CONTROL |

Conventional *in Vitro* Selection Approach

*FIG. 46*

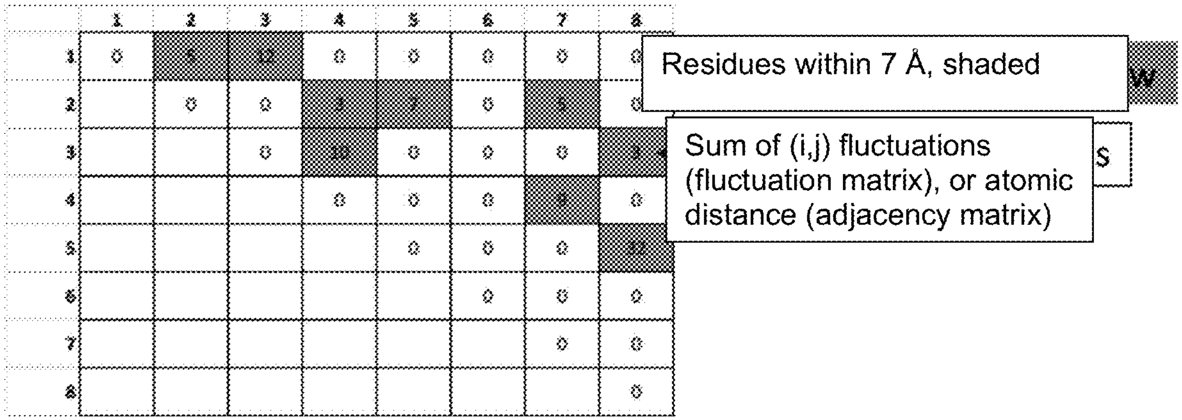

*FIG. 47*

| | 1 | 2 | 3 | 4 | 5 | 6 | 7 | 8 |
|---|---|---|---|---|---|---|---|---|
| 1 | -4 | 5 | 12 | 14 | 0 | 3 | -42 | 2 |
| 2 | 1 | 3 | 56 | -22 | -43 | -11 | 44 | 0 |
| 3 | -103 | -55 | 145 | 12 | 33 | 53 | 0 | 3 |

SEQUENCE LISTING

```
<160> NUMBER OF SEQ ID NOS: 98

<210> SEQ ID NO 1
<211> LENGTH: 31
<212> TYPE: PRT
<213> ORGANISM: Artificial Sequence
<220> FEATURE:
```

<223> OTHER INFORMATION: synthetic
<220> FEATURE:
<221> NAME/KEY: MOD_RES
<222> LOCATION: (31)..(31)
<223> OTHER INFORMATION: 5' Biotin

<400> SEQUENCE: 1

```
Lys Thr Tyr Val Leu Gln Ile Met Arg Ile Lys Pro His Gln Gly Gln
1               5                   10                  15

His Ile Gly Glu Val Glu Phe His Glu Gly Ser Gly Ser Gly Lys
            20                  25                  30
```

<210> SEQ ID NO 2
<211> LENGTH: 31
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (31)..(31)
<223> OTHER INFORMATION: 5' Biotin

<400> SEQUENCE: 2

```
Lys Thr Tyr Val Leu Leu Thr Gln Glu Asp Ile Glu Gly Tyr Asp Thr
1               5                   10                  15

Tyr Tyr Lys Leu Val Glu Phe His Glu Gly Ser Gly Ser Gly Lys
            20                  25                  30
```

<210> SEQ ID NO 3
<211> LENGTH: 31
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (31)..(31)
<223> OTHER INFORMATION: 5' Biotin

<400> SEQUENCE: 3

```
Cys Glu Ile Tyr Leu Gln Ile Met Arg Ile Lys Pro His Gln Gly Gln
1               5                   10                  15

His Ile Gly Glu Val Pro Tyr Pro Cys Gly Ser Gly Ser Gly Lys
            20                  25                  30
```

<210> SEQ ID NO 4
<211> LENGTH: 31
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (31)..(31)
<223> OTHER INFORMATION: 5' Biotin

<400> SEQUENCE: 4

```
Cys Glu Ile Tyr Leu Ser Thr Thr Phe Tyr Ile Glu Gly Tyr Asp Tyr
1               5                   10                  15

Tyr Thr Lys Met Val Pro Tyr Pro Cys Gly Ser Gly Ser Gly Lys
            20                  25                  30
```

<210> SEQ ID NO 5
<211> LENGTH: 23
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: Biotin

<400> SEQUENCE: 5

Lys Gly Ser Gly Ser Gly Cys Ile Tyr Tyr Cys Glu Ser Glu Asp Lys
1 5 10 15

Asn Leu Cys Gln Ile Val Cys
20

<210> SEQ ID NO 6
<211> LENGTH: 25
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (25)..(25)
<223> OTHER INFORMATION: 5' Biotin

<400> SEQUENCE: 6

Cys Ala Leu Ile Val Tyr Trp Glu Met Glu Asp Lys Asn Ile Ile Gln
1 5 10 15

Phe Val Cys Gly Ser Gly Ser Gly Lys
20 25

<210> SEQ ID NO 7
<211> LENGTH: 23
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (23)..(23)
<223> OTHER INFORMATION: 5' Biotin

<400> SEQUENCE: 7

Cys Glu Tyr Lys Cys Ser Ser Gly Thr Lys Leu Leu Cys Tyr Ile Val
1 5 10 15

Cys Gly Ser Gly Ser Gly Lys
20

<210> SEQ ID NO 8
<211> LENGTH: 33
<212> TYPE: PRT
<213> ORGANISM: Artificial Sequence
<220> FEATURE:
<223> OTHER INFORMATION: synthetic

<400> SEQUENCE: 8

Ser Tyr Ala Met Ser Ala Ile Ser Gly Ser Gly Gly Ser Thr Tyr Tyr
1 5 10 15

Ala Asp Ser Val Lys Gly Gly Ser Ser Gly Trp Tyr Gln Tyr Phe Gln
20 25 30

His

<210> SEQ ID NO 9
<211> LENGTH: 33
<212> TYPE: PRT
<213> ORGANISM: Artificial Sequence
<220> FEATURE:

<223> OTHER INFORMATION: synthetic

<400> SEQUENCE: 9

```
Thr Gly Ser Ser Ser Asn Ile Gly Ala Gly Tyr Asp Val His Gly Asn
1               5                   10                  15

Ser Asn Arg Pro Ser Gln Ser Tyr Asp Ser Ser Leu Ser Gly Tyr Val
            20                  25                  30

Val
```

<210> SEQ ID NO 10
<211> LENGTH: 35
<212> TYPE: PRT
<213> ORGANISM: Artificial Sequence
<220> FEATURE:
<223> OTHER INFORMATION: synthetic

<400> SEQUENCE: 10

```
Ser Asn Ser Val Ala Trp Asn Arg Thr Tyr Tyr Arg Ser Lys Trp Tyr
1               5                   10                  15

Asp Asp Tyr Ala Val Ser Val Lys Ser Tyr Asn Tyr Ala Tyr Asp Ala
            20                  25                  30

Phe Asp Ile
        35
```

<210> SEQ ID NO 11
<211> LENGTH: 31
<212> TYPE: PRT
<213> ORGANISM: Artificial Sequence
<220> FEATURE:
<223> OTHER INFORMATION: synthetic

<400> SEQUENCE: 11

```
Thr Gly Thr Ser Ser Asp Val Gly Gly Tyr Asn Leu Val Ser Asp Val
1               5                   10                  15

Thr Lys Arg Pro Ser Tyr Ser Tyr Val Gly Ser Tyr Thr Trp Val
            20                  25                  30
```

<210> SEQ ID NO 12
<211> LENGTH: 39
<212> TYPE: PRT
<213> ORGANISM: Artificial Sequence
<220> FEATURE:
<223> OTHER INFORMATION: synthetic

<400> SEQUENCE: 12

```
Ser Tyr Ala Met His Val Ile Ser Tyr Asp Gly Ser Asn Lys Tyr Tyr
1               5                   10                  15

Ala Asp Ser Val Lys Gly Gly Asp Ile Leu Thr Gly Tyr Pro Asn Tyr
            20                  25                  30

Tyr Tyr Tyr Gly Met Asp Val
        35
```

<210> SEQ ID NO 13
<211> LENGTH: 30
<212> TYPE: PRT
<213> ORGANISM: Artificial Sequence
<220> FEATURE:
<223> OTHER INFORMATION: synthetic

<400> SEQUENCE: 13

```
Ser Gly Ser Ser Ser Asn Ile Gly Arg Asn Tyr Val Tyr Arg Asp Asn
1               5                   10                  15
```

```
Gln Arg Pro Ser Thr Ala Trp Asp Asp Ser Leu Ser Gly Val
            20                  25                  30


<210> SEQ ID NO 14
<211> LENGTH: 36
<212> TYPE: PRT
<213> ORGANISM: Artificial Sequence
<220> FEATURE:
<223> OTHER INFORMATION: synthetic

<400> SEQUENCE: 14

Asp Tyr Gly Met Ser Phe Ile Arg Ser Lys Arg Tyr Gly Gly Thr Thr
1               5                   10                  15

Glu Tyr Ala Ala Ser Val Lys Asp Leu Ala Leu Ala Gly Tyr Met Tyr
            20                  25                  30

Tyr Phe Asp Tyr
        35


<210> SEQ ID NO 15
<211> LENGTH: 32
<212> TYPE: PRT
<213> ORGANISM: Artificial Sequence
<220> FEATURE:
<223> OTHER INFORMATION: synthetic

<400> SEQUENCE: 15

Thr Gly Ser Ser Ser Asn Ile Gly Ala Gly Tyr His Val His Gly Asn
1               5                   10                  15

Asn Asn Arg Pro Ser Gln Ser Tyr Asp Arg Ser Leu Ser Gly Trp Val
            20                  25                  30


<210> SEQ ID NO 16
<211> LENGTH: 33
<212> TYPE: PRT
<213> ORGANISM: Artificial Sequence
<220> FEATURE:
<223> OTHER INFORMATION: synthetic

<400> SEQUENCE: 16

Ser Tyr Trp Met Ser Asn Ile Lys Gln Asp Gly Ser Glu Lys Tyr Tyr
1               5                   10                  15

Val Asp Ser Val Lys Gly Asn Arg Ala Tyr Tyr Tyr Tyr Gly Met Asp
            20                  25                  30

Val


<210> SEQ ID NO 17
<211> LENGTH: 31
<212> TYPE: PRT
<213> ORGANISM: Artificial Sequence
<220> FEATURE:
<223> OTHER INFORMATION: synthetic

<400> SEQUENCE: 17

Ser Gly Ser Ser Ser Ser Leu Gly Ser Asn Tyr Val Tyr Gly Asn Thr
1               5                   10                  15

Gln Arg Pro Ser Ala Thr Trp Asp Asp Ser Leu Ser Val Trp Val
            20                  25                  30


<210> SEQ ID NO 18
<211> LENGTH: 34
<212> TYPE: PRT
<213> ORGANISM: Artificial Sequence
<220> FEATURE:
<223> OTHER INFORMATION: synthetic
```

<400> SEQUENCE: 18

Ser Tyr Gly Ile Ser Trp Ile Ser Ala Tyr Asn Gly Asn Thr Asn Tyr
1 5 10 15

Ala Gln Lys Leu Gln Gly Ala Asp Ala Phe Ser Ser Gly Trp Tyr Phe
20 25 30

Asp Tyr

<210> SEQ ID NO 19
<211> LENGTH: 31
<212> TYPE: PRT
<213> ORGANISM: Artificial Sequence
<220> FEATURE:
<223> OTHER INFORMATION: synthetic

<400> SEQUENCE: 19

Ser Gly Ser Ser Ser Asn Ile Gly Ser Asn Ser Ile Asn Ser Thr Thr
1 5 10 15

Gln Arg Pro Ser Ala Ala Trp Asp Asp Arg Leu Asn Ala Tyr Val
20 25 30

<210> SEQ ID NO 20
<211> LENGTH: 31
<212> TYPE: PRT
<213> ORGANISM: Artificial Sequence
<220> FEATURE:
<223> OTHER INFORMATION: synthetic

<400> SEQUENCE: 20

Gly Tyr Ser Met Asn Tyr Ile Gly Thr Ser Ser Gly Ser Ile Tyr Tyr
1 5 10 15

Ala Asp Ser Val Lys Gly Gly Ser Ser Ile Thr Gly Tyr Met Asp
20 25 30

<210> SEQ ID NO 21
<211> LENGTH: 31
<212> TYPE: PRT
<213> ORGANISM: Artificial Sequence
<220> FEATURE:
<223> OTHER INFORMATION: synthetic

<400> SEQUENCE: 21

Ser Gly Ser Ser Ser Asn Ile Gly Ser Asn Tyr Val Ser Arg Asn Asn
1 5 10 15

Gln Arg Pro Ser Ala Thr Trp Asp Gly Ser Leu Ser Gly Val Val
20 25 30

<210> SEQ ID NO 22
<211> LENGTH: 33
<212> TYPE: PRT
<213> ORGANISM: Artificial Sequence
<220> FEATURE:
<223> OTHER INFORMATION: synthetic

<400> SEQUENCE: 22

Ser Tyr Trp Met Ser Asn Ile Lys Gln Asp Gly Ser Glu Lys Tyr Tyr
1 5 10 15

Val Asp Ser Val Lys Gly Asn Arg Ala Tyr Tyr Tyr Tyr Gly Met Asp
20 25 30

Val

<210> SEQ ID NO 23

```
<211> LENGTH: 29
<212> TYPE: PRT
<213> ORGANISM: Artificial Sequence
<220> FEATURE:
<223> OTHER INFORMATION: synthetic

<400> SEQUENCE: 23

Ser Gly Ser Arg Ser Asn Val Gly Lys Asn Tyr Val Tyr Ser Asp Asn
1               5                   10                  15

Gln Arg Pro Ser Ala Val Trp Asp Asp Ser Gln Trp Val
            20                  25


<210> SEQ ID NO 24
<211> LENGTH: 36
<212> TYPE: PRT
<213> ORGANISM: Artificial Sequence
<220> FEATURE:
<223> OTHER INFORMATION: synthetic

<400> SEQUENCE: 24

Asp Tyr Gly Met Thr Phe Ile Arg Ser Lys Arg Tyr Gly Ala Thr Thr
1               5                   10                  15

Glu Tyr Ala Ala Ser Val Lys Gly Leu Ala Leu Ala Asp Tyr Met Tyr
            20                  25                  30

Tyr Phe Asp Tyr
        35


<210> SEQ ID NO 25
<211> LENGTH: 32
<212> TYPE: PRT
<213> ORGANISM: Artificial Sequence
<220> FEATURE:
<223> OTHER INFORMATION: synthetic

<400> SEQUENCE: 25

Thr Gly Ser Ser Ser Asn Ile Gly Ala Gly Tyr Asp Val His Gly Asn
1               5                   10                  15

Ser Asn Arg Pro Ser Gln Ser Tyr Asp Ser Ser Leu Ser Ala Trp Val
            20                  25                  30


<210> SEQ ID NO 26
<211> LENGTH: 36
<212> TYPE: PRT
<213> ORGANISM: Artificial Sequence
<220> FEATURE:
<223> OTHER INFORMATION: synthetic

<400> SEQUENCE: 26

Ser Tyr Gly Met His Ala Ile Ser Tyr Asp Gly Ser Asn Lys Tyr Tyr
1               5                   10                  15

Ala Asp Ser Val Lys Gly Asp Phe Asn Tyr Gly Asp Tyr Met Gly Gly
            20                  25                  30

Gly Met Asp Val
        35


<210> SEQ ID NO 27
<211> LENGTH: 32
<212> TYPE: PRT
<213> ORGANISM: Artificial Sequence
<220> FEATURE:
<223> OTHER INFORMATION: synthetic

<400> SEQUENCE: 27

Thr Gly Gly Ser Ser Asn Ile Gly Ala Gly Tyr Ala Val Arg Thr Asn
```

1 5 10 15

Ser Asn Arg Pro Ser Ser Ala Trp Asp Ser Ser Leu Ser Gly Trp Val
20 25 30

<210> SEQ ID NO 28
<211> LENGTH: 36
<212> TYPE: PRT
<213> ORGANISM: Artificial Sequence
<220> FEATURE:
<223> OTHER INFORMATION: synthetic

<400> SEQUENCE: 28

Asn Tyr Gly Met Thr Phe Ile Arg Ser Lys Arg Tyr Gly Gly Thr Thr
1 5 10 15

Glu Tyr Ala Ala Ser Val Lys Gly Leu Ala Leu Ala Asp Tyr Met Tyr
20 25 30

Tyr Phe Asp Tyr
35

<210> SEQ ID NO 29
<211> LENGTH: 31
<212> TYPE: PRT
<213> ORGANISM: Artificial Sequence
<220> FEATURE:
<223> OTHER INFORMATION: synthetic

<400> SEQUENCE: 29

Thr Gly Arg Thr Ser Asn Ile Gly Thr Tyr Asp Val His Gly Asn Asn
1 5 10 15

Asn Arg Pro Pro Gln Ser Tyr Asp Asn Ser Leu Arg Ala Trp Leu
20 25 30

<210> SEQ ID NO 30
<211> LENGTH: 36
<212> TYPE: PRT
<213> ORGANISM: Artificial Sequence
<220> FEATURE:
<223> OTHER INFORMATION: synthetic

<400> SEQUENCE: 30

Ser Ser Asn Trp Trp Ser Glu Ile Tyr His Ser Gly Ser Thr Asn Tyr
1 5 10 15

Asn Pro Ser Leu Lys Ser Val Leu Gly Tyr Ser Gly Tyr Gly Val Gly
20 25 30

Ala Phe Asp Ile
35

<210> SEQ ID NO 31
<211> LENGTH: 31
<212> TYPE: PRT
<213> ORGANISM: Artificial Sequence
<220> FEATURE:
<223> OTHER INFORMATION: synthetic

<400> SEQUENCE: 31

Ala Ser Ser Thr Gly Ala Val Thr Ser Gly Tyr Tyr Pro Asn Ser Thr
1 5 10 15

Ser Asn Lys His Ser Leu Leu Ser Tyr Ser Gly Ala Arg Lys Ile
20 25 30

<210> SEQ ID NO 32
<211> LENGTH: 31
<212> TYPE: PRT

```
<213> ORGANISM: Artificial Sequence
<220> FEATURE:
<223> OTHER INFORMATION: synthetic

<400> SEQUENCE: 32

Ser Tyr Ala Ile Ser Gly Ile Ile Pro Ile Phe Gly Thr Ala Asn Tyr
1               5                   10                  15

Ala Gln Lys Phe Gln Gly Glu Arg Gly Ile Asp Ala Phe Asp Ile
            20                  25                  30


<210> SEQ ID NO 33
<211> LENGTH: 28
<212> TYPE: PRT
<213> ORGANISM: Artificial Sequence
<220> FEATURE:
<223> OTHER INFORMATION: synthetic

<400> SEQUENCE: 33

Gly Ala Ser Gln Ser Val Ser Ser Ser Tyr Leu Ala Gly Ala Ser Ser
1               5                   10                  15

Arg Ala Thr Gln Gln Tyr Gly Ser Ser Pro Tyr Thr
            20                  25


<210> SEQ ID NO 34
<211> LENGTH: 33
<212> TYPE: PRT
<213> ORGANISM: Artificial Sequence
<220> FEATURE:
<223> OTHER INFORMATION: synthetic

<400> SEQUENCE: 34

Ser Tyr Ala Ile Ser Gly Ile Ile Pro Ile Phe Gly Thr Ala Asn Tyr
1               5                   10                  15

Ala Gln Lys Phe Gln Gly Gly Ser Leu Gly Pro Tyr Tyr Gly Met Asp
            20                  25                  30

Val


<210> SEQ ID NO 35
<211> LENGTH: 28
<212> TYPE: PRT
<213> ORGANISM: Artificial Sequence
<220> FEATURE:
<223> OTHER INFORMATION: synthetic

<400> SEQUENCE: 35

Arg Ala Ser Gln Ser Val Ser Ser Asn Phe Leu Ala Gly Ala Ser Ser
1               5                   10                  15

Arg Ala Thr Gln Gln Tyr Gly Ser Ser Pro Trp Thr
            20                  25


<210> SEQ ID NO 36
<211> LENGTH: 31
<212> TYPE: PRT
<213> ORGANISM: Artificial Sequence
<220> FEATURE:
<223> OTHER INFORMATION: synthetic

<400> SEQUENCE: 36

Ser Tyr Ala Ile Ser Gly Ile Ile Pro Ile Phe Gly Thr Ala Asn Tyr
1               5                   10                  15

Ala Gln Lys Phe Gln Gly Met Arg Gly Arg Asp Ala Phe Asp Ile
            20                  25                  30
```

<210> SEQ ID NO 37
<211> LENGTH: 28
<212> TYPE: PRT
<213> ORGANISM: Artificial Sequence
<220> FEATURE:
<223> OTHER INFORMATION: synthetic

<400> SEQUENCE: 37

Arg Ala Ser Gln Ser Val Ser Ser Ser Tyr Leu Ala Gly Ala Ser Ser
1 5 10 15

Arg Ala Thr Gln Gln Tyr Gly Ser Ser Pro Tyr Thr
20 25

<210> SEQ ID NO 38
<211> LENGTH: 31
<212> TYPE: PRT
<213> ORGANISM: Artificial Sequence
<220> FEATURE:
<223> OTHER INFORMATION: synthetic

<400> SEQUENCE: 38

Ser Tyr Ala Ile Ser Gly Ile Ile Pro Ile Phe Gly Thr Ala Asn Tyr
1 5 10 15

Ala Gln Lys Phe Gln Gly Gly Leu Gly Arg Asp Ala Phe Asp Ile
20 25 30

<210> SEQ ID NO 39
<211> LENGTH: 28
<212> TYPE: PRT
<213> ORGANISM: Artificial Sequence
<220> FEATURE:
<223> OTHER INFORMATION: synthetic

<400> SEQUENCE: 39

Arg Ala Ser Gln Ser Val Ser Ser Ser Tyr Leu Ala Gly Ala Ser Ser
1 5 10 15

Arg Ala Thr Gln Gln Tyr Gly Ser Ser Pro Tyr Thr
20 25

<210> SEQ ID NO 40
<211> LENGTH: 33
<212> TYPE: PRT
<213> ORGANISM: Artificial Sequence
<220> FEATURE:
<223> OTHER INFORMATION: synthetic

<400> SEQUENCE: 40

Ser Tyr Trp Met Ser Asn Ile Lys Gln Asp Gly Ser Glu Lys Tyr Tyr
1 5 10 15

Val Asp Ser Val Lys Gly Asn Arg Ala Tyr Tyr Tyr Tyr Gly Met Asp
20 25 30

Val

<210> SEQ ID NO 41
<211> LENGTH: 29
<212> TYPE: PRT
<213> ORGANISM: Artificial Sequence
<220> FEATURE:
<223> OTHER INFORMATION: synthetic

<400> SEQUENCE: 41

Ser Gly Ser Arg Ser Asn Val Gly Lys Asn Tyr Val Tyr Ser Asp Asn
1 5 10 15

Gln Arg Pro Ser Ala Val Trp Asp Asp Val Gln Trp Val 20 25

<210> SEQ ID NO 42
<211> LENGTH: 33
<212> TYPE: PRT
<213> ORGANISM: Artificial Sequence
<220> FEATURE:
<223> OTHER INFORMATION: synthetic

<400> SEQUENCE: 42

Ser Tyr Ala Ile Ser Gly Ile Ile Pro Ile Phe Gly Thr Ala Asn Tyr
1 5 10 15

Ala Gln Lys Phe Gln Gly Gln Gly Ser Trp Ile Pro Asn Trp Phe Asp
20 25 30

Pro

<210> SEQ ID NO 43
<211> LENGTH: 29
<212> TYPE: PRT
<213> ORGANISM: Artificial Sequence
<220> FEATURE:
<223> OTHER INFORMATION: synthetic

<400> SEQUENCE: 43

Gln Gly Asp Ser Leu Arg Ser Tyr Tyr Ala Ser Gly Lys Asn Asn Arg
1 5 10 15

Pro Ser Asn Ser Arg Asp Ser Ile Pro Asn His Val Leu
20 25

<210> SEQ ID NO 44
<211> LENGTH: 37
<212> TYPE: PRT
<213> ORGANISM: Artificial Sequence
<220> FEATURE:
<223> OTHER INFORMATION: synthetic

<400> SEQUENCE: 44

Ser Tyr Ala Ile Ser Gly Ile Ile Pro Ile Phe Gly Thr Ala Asn Tyr
1 5 10 15

Ala Gln Lys Phe Gln Gly Asn Arg Pro Pro Val Leu Leu Trp Phe Arg
20 25 30

Glu Leu Val Tyr Gly
35

<210> SEQ ID NO 45
<211> LENGTH: 31
<212> TYPE: PRT
<213> ORGANISM: Artificial Sequence
<220> FEATURE:
<223> OTHER INFORMATION: synthetic

<400> SEQUENCE: 45

Ser Arg Ser Ser Ser His Ile Pro Asp Asn Ser Ile Ser Thr Asp Asn
1 5 10 15

His Arg Pro Ser Ala Gly Trp Asp Ala Ser Leu Asn Gly Pro Val
20 25 30

<210> SEQ ID NO 46
<211> LENGTH: 27
<212> TYPE: PRT
<213> ORGANISM: Artificial Sequence
<220> FEATURE:
<223> OTHER INFORMATION: synthetic

<400> SEQUENCE: 46

Gln Gln Ile Met Cys Ile Lys Pro His Gln Gly Gln Cys Ile Gly Glu
1 5 10 15

Ala Glu Glu Ala Leu Lys Ile Thr Ala Lys Ala
20 25

<210> SEQ ID NO 47
<211> LENGTH: 27
<212> TYPE: PRT
<213> ORGANISM: Artificial Sequence
<220> FEATURE:
<223> OTHER INFORMATION: synthetic

<400> SEQUENCE: 47

Ser Gln Ile Met Cys Ile Lys Pro His Gln Gly Gln His Ile Gly Glu
1 5 10 15

Thr Ser Glu Asp Cys Asp Lys Ala Ala Lys Ser
20 25

<210> SEQ ID NO 48
<211> LENGTH: 27
<212> TYPE: PRT
<213> ORGANISM: Artificial Sequence
<220> FEATURE:
<223> OTHER INFORMATION: synthetic

<400> SEQUENCE: 48

Ser Gln Ile Cys Arg Ile Lys Pro His Gln Gly Gln His Cys Gly Glu
1 5 10 15

Thr Ser Glu Asp Ala Asp Lys Ala Ala Lys Ser
20 25

<210> SEQ ID NO 49
<211> LENGTH: 27
<212> TYPE: PRT
<213> ORGANISM: Artificial Sequence
<220> FEATURE:
<223> OTHER INFORMATION: synthetic

<400> SEQUENCE: 49

Gln Gln Ile Met Cys Ile Lys Pro His Gln Gly Gln Cys Ile Gly Glu
1 5 10 15

Ala Glu Glu Val Tyr Lys Lys Arg Lys Lys Ser
20 25

<210> SEQ ID NO 50
<211> LENGTH: 27
<212> TYPE: PRT
<213> ORGANISM: Artificial Sequence
<220> FEATURE:
<223> OTHER INFORMATION: synthetic

<400> SEQUENCE: 50

Gln Gln Ile Met Cys Ile Lys Pro His Gln Gly Gln Cys Ile Gly Glu
1 5 10 15

Ala Glu Glu Tyr Tyr Thr Lys Ala Lys Arg Ser
20 25

<210> SEQ ID NO 51
<211> LENGTH: 32
<212> TYPE: PRT
<213> ORGANISM: Artificial Sequence
<220> FEATURE:
<223> OTHER INFORMATION: synthetic

<400> SEQUENCE: 51

Gly Tyr Thr Phe Thr Asn Tyr Gly Ile Asn Thr Tyr Thr Gly Glu Pro
1 5 10 15

Ala Lys Tyr Pro His Tyr Tyr Gly Ser Ser His Trp Tyr Phe Asp Val
20 25 30

<210> SEQ ID NO 52
<211> LENGTH: 32
<212> TYPE: PRT
<213> ORGANISM: Artificial Sequence
<220> FEATURE:
<223> OTHER INFORMATION: synthetic

<400> SEQUENCE: 52

Gly Tyr Asp Phe Thr His Tyr Gly Ile Asn Thr Tyr Thr Gly Glu Pro
1 5 10 15

Ala Lys Tyr Pro Tyr Tyr Tyr Gly Thr Ser His Trp Tyr Phe Asp Val
20 25 30

<210> SEQ ID NO 53
<211> LENGTH: 18
<212> TYPE: PRT
<213> ORGANISM: Artificial Sequence
<220> FEATURE:
<223> OTHER INFORMATION: synthetic

<400> SEQUENCE: 53

Gln Asp Ile Ser Asn Tyr Phe Thr Ser Gln Gln Tyr Ser Thr Val Pro
1 5 10 15

Trp Thr

<210> SEQ ID NO 54
<211> LENGTH: 27
<212> TYPE: PRT
<213> ORGANISM: Artificial Sequence
<220> FEATURE:
<223> OTHER INFORMATION: synthetic

<400> SEQUENCE: 54

Ser Gly Asp Lys Leu Gly Asp Lys Tyr Ala Ser Gln Asp Arg Lys Arg
1 5 10 15

Pro Ser Gln Ala Trp Asp Ser Ser Thr Val Val
20 25

<210> SEQ ID NO 55
<211> LENGTH: 34
<212> TYPE: PRT
<213> ORGANISM: Artificial Sequence
<220> FEATURE:
<223> OTHER INFORMATION: synthetic

<400> SEQUENCE: 55

Ser Ser Ser Tyr Tyr Trp Gly Ser Ile Tyr Tyr Ser Gly Ser Thr Tyr
1 5 10 15

Tyr Asn Pro Ser Leu Lys Ser Leu Val Leu Met Pro Ala Tyr Tyr Phe
20 25 30

Asp Tyr

<210> SEQ ID NO 56
<211> LENGTH: 31
<212> TYPE: PRT
<213> ORGANISM: Artificial Sequence
<220> FEATURE:
<223> OTHER INFORMATION: synthetic

<400> SEQUENCE: 56

Ser Gly Ser Ser Ser Asn Ile Gly Arg Asn Tyr Val Gln Lys Asn Asn
1               5                   10                  15

Gln Arg Pro Ser Ala Ala Trp Asp Asp Ser Leu Tyr Ser Trp Val
            20                  25                  30

<210> SEQ ID NO 57
<211> LENGTH: 34
<212> TYPE: PRT
<213> ORGANISM: Artificial Sequence
<220> FEATURE:
<223> OTHER INFORMATION: synthetic

<400> SEQUENCE: 57

Ser Ser Ser Tyr Tyr Trp Gly Ser Ile Tyr Tyr Ser Gly Ser Thr Tyr
1               5                   10                  15

Tyr Asn Pro Ser Leu Lys Ser Leu Ser Arg Tyr Tyr Tyr Tyr Gly Met
            20                  25                  30

Asp Val

<210> SEQ ID NO 58
<211> LENGTH: 31
<212> TYPE: PRT
<213> ORGANISM: Artificial Sequence
<220> FEATURE:
<223> OTHER INFORMATION: synthetic

<400> SEQUENCE: 58

Ser Gly Ser Ser Ser Asn Ile Gly Ser Asn Tyr Val Tyr Ser Asn Asn
1               5                   10                  15

Gln Arg Pro Ser Ala Ala Trp Asp Asp Arg Leu Ser Ala Trp Val
            20                  25                  30

<210> SEQ ID NO 59
<211> LENGTH: 33
<212> TYPE: PRT
<213> ORGANISM: Artificial Sequence
<220> FEATURE:
<223> OTHER INFORMATION: synthetic

<400> SEQUENCE: 59

Ser Ser Ser Tyr Tyr Trp Gly Ser Ile Asn Tyr Ser Gly Asn Thr Tyr
1               5                   10                  15

Tyr Asn Pro Ser Leu Lys Ser Arg Tyr Asn Trp Asn Tyr Val Phe Asp
            20                  25                  30

Tyr

<210> SEQ ID NO 60
<211> LENGTH: 27
<212> TYPE: PRT
<213> ORGANISM: Artificial Sequence
<220> FEATURE:
<223> OTHER INFORMATION: synthetic

<400> SEQUENCE: 60

Arg Ala Ser Gln Asn Ile Arg Asn Thr Leu Val Asp Ala Ser Ser Arg
1               5                   10                  15

Ala Thr Gln Gln Leu Ser Thr Leu Pro Tyr Thr
            20                  25

<210> SEQ ID NO 61
<211> LENGTH: 33
<212> TYPE: PRT
<213> ORGANISM: Artificial Sequence
<220> FEATURE:
<223> OTHER INFORMATION: synthetic

<400> SEQUENCE: 61

```
Asp Tyr Ala Met His Leu Ile Ser Trp Asp Gly Gly Ser Thr Tyr Tyr
1               5                   10                  15

Ala Asp Ser Val Lys Gly Ser Arg Gly Arg Arg Ala Trp Ser Phe Asp
            20                  25                  30

Tyr
```

<210> SEQ ID NO 62
<211> LENGTH: 29
<212> TYPE: PRT
<213> ORGANISM: Artificial Sequence
<220> FEATURE:
<223> OTHER INFORMATION: synthetic

<400> SEQUENCE: 62

```
Ala Arg Ser Ser Gly Thr Ile Ala Ser Asn Tyr Val Gln Glu Asp Asn
1               5                   10                  15

Gln Arg Pro Ser Gln Ser Phe Asp Arg Arg Asn Leu Val
            20                  25
```

<210> SEQ ID NO 63
<211> LENGTH: 32
<212> TYPE: PRT
<213> ORGANISM: Artificial Sequence
<220> FEATURE:
<223> OTHER INFORMATION: synthetic

<400> SEQUENCE: 63

```
Ser Ser Ser Tyr Tyr Trp Gly Ser Ile Tyr Tyr Ser Gly Thr Thr Tyr
1               5                   10                  15

Tyr Asn Pro Ser Leu Lys Ser Ile Arg Leu Ser Gly Thr Pro Asp Tyr
            20                  25                  30
```

<210> SEQ ID NO 64
<211> LENGTH: 28
<212> TYPE: PRT
<213> ORGANISM: Artificial Sequence
<220> FEATURE:
<223> OTHER INFORMATION: synthetic

<400> SEQUENCE: 64

```
Arg Ala Ser Gln Ser Val Ser Ser Ser Tyr Leu Ala Gly Ala Ser Ser
1               5                   10                  15

Arg Ala Thr Gln Gln Tyr Gly Ser Ser Pro Pro Thr
            20                  25
```

<210> SEQ ID NO 65
<211> LENGTH: 31
<212> TYPE: PRT
<213> ORGANISM: Artificial Sequence
<220> FEATURE:
<223> OTHER INFORMATION: synthetic

<400> SEQUENCE: 65

```
Ser Gly Tyr Tyr Trp Gly Ser Ile Tyr Tyr Ser Gly Ser Thr Tyr Tyr
1               5                   10                  15
```

```
Asn Pro Ser Leu Lys Ser Val Arg Gly Asp Ser Leu Val Asp Tyr
            20                  25                  30


<210> SEQ ID NO 66
<211> LENGTH: 27
<212> TYPE: PRT
<213> ORGANISM: Artificial Sequence
<220> FEATURE:
<223> OTHER INFORMATION: synthetic

<400> SEQUENCE: 66

Arg Ala Ser Gln Gly Val Ser Thr Ala Leu Ala Asp Ala Ser Ser Leu
1               5                   10                  15

Pro Ser Gln His Ser Asn Ser Tyr Pro Phe Thr
            20                  25


<210> SEQ ID NO 67
<211> LENGTH: 43
<212> TYPE: PRT
<213> ORGANISM: Artificial Sequence
<220> FEATURE:
<223> OTHER INFORMATION: synthetic

<400> SEQUENCE: 67

Ser Tyr Ala Met His Ala Ile Ser Ser Asn Gly Gly Ser Thr Tyr Tyr
1               5                   10                  15

Ala Asp Ser Val Lys Gly Gly Tyr Tyr Asp Ser Ser Gly Tyr Tyr Tyr
            20                  25                  30

Ala Asp Tyr Tyr Tyr Tyr Tyr Gly Met Asp Val
        35                  40


<210> SEQ ID NO 68
<211> LENGTH: 27
<212> TYPE: PRT
<213> ORGANISM: Artificial Sequence
<220> FEATURE:
<223> OTHER INFORMATION: synthetic

<400> SEQUENCE: 68

Arg Ala Ser Gln Ser Ile Ser Ser Tyr Leu Asn Ala Ala Ser Ser Leu
1               5                   10                  15

Gln Ser Gln Gln Ser Tyr Ser Thr Leu Phe Thr
            20                  25


<210> SEQ ID NO 69
<211> LENGTH: 32
<212> TYPE: PRT
<213> ORGANISM: Artificial Sequence
<220> FEATURE:
<223> OTHER INFORMATION: synthetic

<400> SEQUENCE: 69

Ser Tyr Trp Met Ser Asn Ile Lys Gln Asp Gly Ser Glu Lys Tyr Tyr
1               5                   10                  15

Val Asp Ser Val Lys Gly Ala Pro Leu Trp Ala Ala Tyr Phe Asp Tyr
            20                  25                  30


<210> SEQ ID NO 70
<211> LENGTH: 27
<212> TYPE: PRT
<213> ORGANISM: Artificial Sequence
<220> FEATURE:
<223> OTHER INFORMATION: synthetic

<400> SEQUENCE: 70
```

```
Arg Ala Ser Gln Ser Ile Ser Ser Tyr Leu Asn Ala Ala Ser Ser Leu
1               5                   10                  15

Gln Ser Gln Gln Ser Tyr Ser Thr Pro Pro Thr
            20                  25


<210> SEQ ID NO 71
<211> LENGTH: 32
<212> TYPE: PRT
<213> ORGANISM: Artificial Sequence
<220> FEATURE:
<223> OTHER INFORMATION: synthetic

<400> SEQUENCE: 71

Ser Gly Tyr Tyr Trp Gly Ser Ile Tyr His Ser Gly Ser Thr Tyr Tyr
1               5                   10                  15

Asn Pro Ser Leu Lys Ser Ile Arg Arg Asp Gly Tyr Asn Val Asp Tyr
            20                  25                  30


<210> SEQ ID NO 72
<211> LENGTH: 27
<212> TYPE: PRT
<213> ORGANISM: Artificial Sequence
<220> FEATURE:
<223> OTHER INFORMATION: synthetic

<400> SEQUENCE: 72

Arg Ala Ser Gln Gly Ile Arg Asn Asp Leu Gly Ala Ala Ser Ser Leu
1               5                   10                  15

Gln Ser Leu Gln His Asn Ser Tyr Pro Leu Thr
            20                  25


<210> SEQ ID NO 73
<211> LENGTH: 26
<212> TYPE: PRT
<213> ORGANISM: Artificial Sequence
<220> FEATURE:
<223> OTHER INFORMATION: synthetic

<400> SEQUENCE: 73

Ser Tyr Gly Met His Phe Ile Arg Tyr Asp Gly Ser Asn Lys Tyr Tyr
1               5                   10                  15

Ala Asp Ser Val Lys Gly Ser Asn Asp Tyr
            20                  25


<210> SEQ ID NO 74
<211> LENGTH: 30
<212> TYPE: PRT
<213> ORGANISM: Artificial Sequence
<220> FEATURE:
<223> OTHER INFORMATION: synthetic

<400> SEQUENCE: 74

Gly Ser Ser Thr Gly Pro Val Thr Ser Gly His Asp Pro Tyr Gly Ala
1               5                   10                  15

Thr Asn Arg His Ser Leu Leu Ser Tyr Arg Gly Leu Trp Val
            20                  25                  30


<210> SEQ ID NO 75
<211> LENGTH: 33
<212> TYPE: PRT
<213> ORGANISM: Artificial Sequence
<220> FEATURE:
<223> OTHER INFORMATION: synthetic
```

<400> SEQUENCE: 75

Ser Tyr Gly Met His Tyr Ile Ser Ser Ser Gly Ser Thr Ile Tyr Tyr
1 5 10 15

Ala Asp Ser Val Lys Gly Ser Leu Thr Tyr Gly Ala Pro Tyr Phe Asp
20 25 30

Tyr

<210> SEQ ID NO 76
<211> LENGTH: 32
<212> TYPE: PRT
<213> ORGANISM: Artificial Sequence
<220> FEATURE:
<223> OTHER INFORMATION: synthetic

<400> SEQUENCE: 76

Ala Gly Asn Asn Ile Gly Ser Lys Ser Val His Asp Asp Ser Asp Arg
1 5 10 15

Pro Ser Gln Val Trp His Ser Thr Ser Ser His Arg Arg Asp Val Ala
20 25 30

<210> SEQ ID NO 77
<211> LENGTH: 34
<212> TYPE: PRT
<213> ORGANISM: Artificial Sequence
<220> FEATURE:
<223> OTHER INFORMATION: synthetic

<400> SEQUENCE: 77

Ser Tyr Ala Met Ser Thr Ile Ser Gly Ser Gly Ser Ile Thr Tyr Tyr
1 5 10 15

Ala Asp Ser Val Lys Gly Ala Ser Trp Asp Gly His Asn Leu Phe Phe
20 25 30

Asp Tyr

<210> SEQ ID NO 78
<211> LENGTH: 30
<212> TYPE: PRT
<213> ORGANISM: Artificial Sequence
<220> FEATURE:
<223> OTHER INFORMATION: synthetic

<400> SEQUENCE: 78

Thr Gly Thr Ser Ser Asp Val Gly Gly Asn Tyr Val Ser Asp Val Ser
1 5 10 15

Asn Arg Pro Ser Ser Ser Tyr Thr Ser Ser Asp Thr Val Ile
20 25 30

<210> SEQ ID NO 79
<211> LENGTH: 32
<212> TYPE: PRT
<213> ORGANISM: Artificial Sequence
<220> FEATURE:
<223> OTHER INFORMATION: synthetic

<400> SEQUENCE: 79

Gly Tyr Tyr Met His Trp Ile Asn Pro Asn Ser Gly Gly Thr Asn Tyr
1 5 10 15

Ala Gln Lys Phe Gln Gly Asp Leu Gly Gly Gly Tyr Gly Phe Asp Tyr
20 25 30

<210> SEQ ID NO 80
<211> LENGTH: 30

<212> TYPE: PRT
<213> ORGANISM: Artificial Sequence
<220> FEATURE:
<223> OTHER INFORMATION: synthetic

<400> SEQUENCE: 80

Thr Arg Ser Ser Gly Ser Ile Ala Gly Asn Tyr Val Gln Leu Asn Asn
1               5                   10                  15

Gln Arg Pro Ser Gln Ser Tyr Asp Ser Ser His Arg Trp Val
            20                  25                  30

<210> SEQ ID NO 81
<211> LENGTH: 44
<212> TYPE: PRT
<213> ORGANISM: Artificial Sequence
<220> FEATURE:
<223> OTHER INFORMATION: synthetic

<400> SEQUENCE: 81

Ser Tyr Gly Ile Ser Trp Ile Ser Ala Tyr Asn Gly Asn Thr Asn Tyr
1               5                   10                  15

Ala Gln Lys Leu Gln Gly Asp Gly Ser Leu Arg Trp Ser Gly Tyr Tyr
            20                  25                  30

Asn Thr Pro Ala Tyr Tyr Tyr Tyr Gly Met Asp Val
        35                  40

<210> SEQ ID NO 82
<211> LENGTH: 32
<212> TYPE: PRT
<213> ORGANISM: Artificial Sequence
<220> FEATURE:
<223> OTHER INFORMATION: synthetic

<400> SEQUENCE: 82

Thr Gly Ser Ser Ser Asn Ile Gly Ala Gly Tyr Asp Val His Ala Asn
1               5                   10                  15

Ser Lys Arg Pro Ser Gln Ser Tyr Asp Ser Ser Leu Ser Gly Trp Asn
            20                  25                  30

<210> SEQ ID NO 83
<211> LENGTH: 33
<212> TYPE: PRT
<213> ORGANISM: Artificial Sequence
<220> FEATURE:
<223> OTHER INFORMATION: synthetic

<400> SEQUENCE: 83

Ser Tyr Gly Ile Ser Trp Ile Ser Ala Tyr Asn Gly Asn Thr Asn Tyr
1               5                   10                  15

Ala Gln Lys Leu Gln Gly Trp Pro Gly Phe Gly Tyr Tyr Gly Met Asp
            20                  25                  30

Val

<210> SEQ ID NO 84
<211> LENGTH: 27
<212> TYPE: PRT
<213> ORGANISM: Artificial Sequence
<220> FEATURE:
<223> OTHER INFORMATION: synthetic

<400> SEQUENCE: 84

Arg Ala Ser Gln Asp Ile Ser Asp Trp Leu Ala Ala Ala Thr Arg Leu
1               5                   10                  15

Gln Gly Gln Lys Tyr Asn Ser Ala Pro Phe Ser
20 25

<210> SEQ ID NO 85
<211> LENGTH: 32
<212> TYPE: PRT
<213> ORGANISM: Artificial Sequence
<220> FEATURE:
<223> OTHER INFORMATION: synthetic

<400> SEQUENCE: 85

Ser Ser Ser Tyr Tyr Trp Gly Ser Ile Tyr Tyr Ser Gly Ser Thr Tyr
1 5 10 15

Tyr Asn Pro Ser Leu Lys Ser Gln Asp Gly Ile Thr Ala Phe Asp Ile
20 25 30

<210> SEQ ID NO 86
<211> LENGTH: 31
<212> TYPE: PRT
<213> ORGANISM: Artificial Sequence
<220> FEATURE:
<223> OTHER INFORMATION: synthetic

<400> SEQUENCE: 86

Thr Gly Asn Ser Asn Asn Val Gly Asn Gln Gly Ala Ala Arg Asn Asn
1 5 10 15

Asn Arg Pro Ser Ser Ala Trp Asp Ser Ser Leu Ser Ala Trp Val
20 25 30

<210> SEQ ID NO 87
<211> LENGTH: 39
<212> TYPE: PRT
<213> ORGANISM: Artificial Sequence
<220> FEATURE:
<223> OTHER INFORMATION: synthetic

<400> SEQUENCE: 87

Ser Tyr Ala Ile Ser Trp Ile Asn Pro Asn Ser Gly Gly Thr Asn Tyr
1 5 10 15

Ala Gln Lys Phe Gln Gly Asp Arg Ile Ala Ala Ala Gly Pro Tyr Tyr
20 25 30

Tyr Tyr Tyr Gly Met Asp Val
35

<210> SEQ ID NO 88
<211> LENGTH: 31
<212> TYPE: PRT
<213> ORGANISM: Artificial Sequence
<220> FEATURE:
<223> OTHER INFORMATION: synthetic

<400> SEQUENCE: 88

Ser Gly Ser Ser Ser Asn Ile Gly Ser Asn Ser Val His Arg Asn Asn
1 5 10 15

Gln Arg Pro Ser Ala Ala Trp Asp Asp Ser Leu Ser Gly Arg Leu
20 25 30

<210> SEQ ID NO 89
<211> LENGTH: 32
<212> TYPE: PRT
<213> ORGANISM: Artificial Sequence
<220> FEATURE:
<223> OTHER INFORMATION: synthetic

<400> SEQUENCE: 89

Ser Tyr Gly Met His Val Ile Ser Tyr Asp Gly Ser Asp Lys Tyr Tyr
1 5 10 15

Ala Asp Ser Val Lys Gly Asp Leu Ser Gly Leu Pro Ile Ile Asp Tyr
20 25 30

<210> SEQ ID NO 90
<211> LENGTH: 31
<212> TYPE: PRT
<213> ORGANISM: Artificial Sequence
<220> FEATURE:
<223> OTHER INFORMATION: synthetic

<400> SEQUENCE: 90

Thr Gly Thr Ser Ser Asp Val Gly Gly Tyr Asn Thr Val Ser Glu Val
1 5 10 15

Ser Asn Arg Pro Ser Ser Ser Tyr Thr Ser Ser Ser Thr Leu Val
20 25 30

<210> SEQ ID NO 91
<211> LENGTH: 38
<212> TYPE: PRT
<213> ORGANISM: Artificial Sequence
<220> FEATURE:
<223> OTHER INFORMATION: synthetic

<400> SEQUENCE: 91

Ser Tyr Gly Ile Ser Trp Ile Ser Ala Tyr Asn Gly Asn Thr Asn Tyr
1 5 10 15

Ala Gln Lys Leu Gln Gly Val Leu His Tyr Tyr Gly Ser Gly Ser Tyr
20 25 30

Gly Gly Trp Phe Asp Pro
35

<210> SEQ ID NO 92
<211> LENGTH: 31
<212> TYPE: PRT
<213> ORGANISM: Artificial Sequence
<220> FEATURE:
<223> OTHER INFORMATION: synthetic

<400> SEQUENCE: 92

Ala Ser Ser Thr Gly Ala Val Thr Ser Ala Tyr Tyr Pro Asn Asp Thr
1 5 10 15

Ser Asn Lys His Ser Leu Leu Tyr Ser Gly Gly Gly His Trp Val
20 25 30

<210> SEQ ID NO 93
<211> LENGTH: 41
<212> TYPE: PRT
<213> ORGANISM: Artificial Sequence
<220> FEATURE:
<223> OTHER INFORMATION: synthetic

<400> SEQUENCE: 93

Ser Tyr Ala Ile Ser Gly Ile Ile Pro Ile Phe Gly Thr Ala Asn Tyr
1 5 10 15

Ala Gln Lys Phe Gln Gly Lys Tyr Tyr Asp Phe Trp Ser Gly Tyr Phe
20 25 30

Pro Asn Tyr Tyr Tyr Gly Met Asp Val
35 40

<210> SEQ ID NO 94

<211> LENGTH: 27
<212> TYPE: PRT
<213> ORGANISM: Artificial Sequence
<220> FEATURE:
<223> OTHER INFORMATION: synthetic

<400> SEQUENCE: 94

```
Arg Ala Ser Gln Asp Ile Asp Asp Asp Met Asn Glu Gly Ser Asn Leu
1               5                   10                  15

Val Pro Leu Gln His Asp Ser Leu Pro His Thr
            20                  25
```

<210> SEQ ID NO 95
<211> LENGTH: 29
<212> TYPE: PRT
<213> ORGANISM: Artificial Sequence
<220> FEATURE:
<223> OTHER INFORMATION: synthetic

<400> SEQUENCE: 95

```
Asn Trp Trp Met Ser Asn Ile Asn Gln Asp Gly Ser Glu Arg Asn Tyr
1               5                   10                  15

Val Asp Ser Val Lys Gly Gly Pro Arg Ile Leu Asp Tyr
            20                  25
```

<210> SEQ ID NO 96
<211> LENGTH: 32
<212> TYPE: PRT
<213> ORGANISM: Artificial Sequence
<220> FEATURE:
<223> OTHER INFORMATION: synthetic

<400> SEQUENCE: 96

```
Thr Arg Ser Ser Ser Asp Ile Gly Ala Gly Tyr Asp Val His Gly Asn
1               5                   10                  15

Tyr His Arg Pro Ser Gln Ser Tyr Asp Pro Asn Leu Lys Gly Ser Ile
            20                  25                  30
```

<210> SEQ ID NO 97
<211> LENGTH: 40
<212> TYPE: PRT
<213> ORGANISM: Artificial Sequence
<220> FEATURE:
<223> OTHER INFORMATION: synthetic

<400> SEQUENCE: 97

```
Ser Tyr Gly Ile Ser Trp Ile Ser Ala Tyr Asn Gly Asn Thr Asn Tyr
1               5                   10                  15

Ala Gln Lys Leu Gln Gly Met Gly Asp Tyr Gly Asp Tyr Thr Thr Thr
            20                  25                  30

Tyr Tyr Tyr Tyr Gly Met Asp Val
        35                  40
```

<210> SEQ ID NO 98
<211> LENGTH: 31
<212> TYPE: PRT
<213> ORGANISM: Artificial Sequence
<220> FEATURE:
<223> OTHER INFORMATION: synthetic

<400> SEQUENCE: 98

```
Ser Gly Ser Ser Ser Asn Ile Gly Ser Asn Thr Val Ser Ile Asn Asn
1               5                   10                  15

Gln Arg Pro Ser Ala Ala Trp Asp Asp Ser Leu Asn Ala Tyr Val
            20                  25                  30
```

MESO-SCALE ENGINEERED PEPTIDES AND METHODS OF SELECTING

CROSS REFERENCE TO RELATED APPLICATION

This application claims priority to and the benefit of U.S. Patent Application No. 62/855,767, filed May 31, 2019 and titled "Meso-Scale Engineered Peptides and Methods of Selecting," which is incorporated herein by reference in its entirety.

REFERENCE TO SEQUENCE LISTING

This application includes an electronically submitted sequence listing in .txt format. The .txt file contains a sequence listing entitled "IBIO-1033US_ST25.txt" created on Jul. 31, 2026 and is 37,322 bytes in size. The sequence listing contained in this .txt file is part of the specification and is hereby incorporated by reference herein in its entirety.

BACKGROUND

Much of basic research in the therapeutic space is directed to identifying and developing novel molecules with desirable properties, such as new peptide therapeutics or new peptide immunogens from which to develop new therapeutic antibodies. However, the standard molecular discovery paradigm relies on random sampling using stochastic processes to identify promising functional molecules. These molecule candidates are then taken through multiple rounds of evaluation and testing with the hope that they will have the desired activity, function, pharmacokinetics, and/or other needed characteristics for a certain use. This system, beginning with screening of a random group, often results in failure, with one or more needed characteristics not being met. Thus, what is needed are methods of developing engineered peptides that incorporate elements of computational, chemical, and biological design.

BRIEF SUMMARY

In some aspects, provided herein is an engineered peptide, wherein the engineered peptide has a molecular mass of between 1 kDa and 10 kDa, comprises up to 50 amino acids, and comprises: a combination of spatially-associated topological constraints, wherein one or more of the constraints is a reference target-derived constraint; and wherein between 10% to 98% of the amino acids of the engineered peptide meet the one or more reference target-derived constraints, wherein the amino acids that meet the one or more reference target-derived constraints have less than 8.0 Å backbone root-mean-square deviation (RSMD) structural homology with the reference target.

In some embodiments, the amino acids that meet the one or more reference target-derived constraints have between 10% and 90% sequence homology with the reference target. In some embodiments, they have a van der Waals surface area overlap with the reference of between 30 $Å^2$ to 3000 $Å^2$. In certain embodiments, the combination comprises at least two, or at least five reference target-derived constraints. In some embodiments, the combination of constraints comprises one or more constraints not derived from a reference target. In some embodiments, the one or more non-reference target-derived constraints describes a desired structural, dynamical, chemical, or functional characteristic, or any combinations thereof. In still further embodiments, one or more constraints is independently associated with a biological response or biological function. In some embodiments, at least a portion of the atoms in the engineered peptide associated with a biological response or biological function are topologically constrained to a secondary structural element in the reference target, such as a beta-sheet, or an alpha helix.

In other aspects, provided herein is a method of selecting an engineered peptide, comprising:

- identifying one or more topological characteristics of a reference target;
- designing spatially-associated constraints for each topological characteristic to produce a combination of spatially-associated topological constraints derived from the reference target;
- comparing spatially-associated topological characteristics of candidate peptides with the combination of spatially-associated topological constraints derived from the reference target; and
- selecting a candidate peptide with spatially-associated topological characteristics that overlap with the combination of spatially-associated topological constraints derived from the reference target to produce the engineered peptide.

In some embodiments, the overlap between each characteristic is independently less than or equal to 75% Mean Percentage Error (MPE) as determined by one or more of Total Topological Constraint Distance (TCD), topological clustering coefficient (TCC), Euclidean distance, power distance, Soergel distance, Canberra distance, Sorensen distance, Jaccard distance, Mahalanobis distance, Hamming distance, Quantitative Estimate of Likeness (QEL), or Chain Topology Parameter (CTP). In certain embodiments, one or more constraints is derived from per-residue energy, per-residue interaction, per-residue fluctuation, per-residue atomic distance, per-residue chemical descriptor, per-residue solvent exposure, per-residue amino acid sequence similarity, per-residue bioinformatic descriptor, per-residue non-covalent bonding propensity, per-residue phi/psi angles, per-residue van der Waals radii, per-residue secondary structure propensity, per-residue amino acid adjacency, or per-residue amino acid contact. In some embodiments, the characteristics of one or more candidate peptides are determined by computer simulation. In still further embodiments, one or more constraints is independently associated with a biological response or biological function. In some embodiments, at least a portion of the atoms in the engineered peptide associated with a biological response or biological function are topologically constrained to a secondary structural element in the reference target, such as a beta-sheet, or an alpha helix.

In still further aspects, provided herein is a composition comprising two or more selection steering polypeptides, wherein each polypeptide is independently a positive selection molecule comprising one or more positive steering characteristics, or a negative selection molecule comprising one or more negative steering characteristics, wherein each characteristic type is independently selected from the group consisting of: amino acid sequence, polypeptide secondary structure, molecular dynamics, chemical features, biological function, immunogenicity, reference target(s) multi-specificity, cross-species reference target reactivity, selectivity of desired reference target(s) over undesired reference target (s), selectivity of reference target(s) within a sequence and/or structurally homologous family, selectivity of reference target(s) with similar protein function, selectivity of distinct desired reference target(s) from a larger family of undesired targets with high sequence and/or structurally homology, selectivity for distinct reference target alleles or mutations, selectivity for distinct reference target residue level chemical modifications, selectivity for cell type, selectivity for tissue type, selectivity for tissue environment, tolerance to reference target(s) structural diversity, tolerance to reference target(s) sequence diversity, and tolerance to reference target(s) dynamics diversity; and wherein at least one of the two or more polypeptides is an engineered peptide as described herein.

In some embodiments, at least one of the two or more polypeptides is a positive selection molecule, and at least one of the two or more polypeptides is a negative selection molecule. In some embodiments, at least one of the two or more polypeptides is a native protein.

In certain embodiments, at least one pair of counterpart positive and negative selection molecules comprising at least one shared characteristic type, wherein the positive selection molecule comprises the positive characteristic and the negative selection molecule comprises the negative characteristic.

In yet additional aspects, provided herein is a method of screening a library of binding molecules with a composition comprising two or more selection steering molecules as described herein, the method comprising subjecting a pool of candidate binding molecules to at least one round of selection, wherein each round of selection comprises:

a negative selection step of screening at least a portion of the pool against a negative selection molecule; and a positive selection step of screening at least a portion of the pool for a positive selection molecule;

wherein the order of selection steps within each round, and the order of rounds, result in the selection of a different subset of the pool than an alternative order.

In some embodiments, the library of binding molecules is a phage library, or a cell library, such as a B-cell library or a T-cell library. In some embodiments, the method comprises two or more rounds of selection, or three or more rounds of selection. In certain embodiments, each round comprises a different set of selection molecules. In some embodiments, at least two rounds comprise the same negative selection molecule, or the same positive selection molecule, or both. In some embodiments, the method comprises analyzing the subset of the pool obtained from a round of selection prior to proceeding to the next round of selection.

DESCRIPTION OF THE FIGURES

FIGS. 3A-3C provide schematics demonstrating the selection of a group of engineered peptides using the methods described herein. FIG. 3A shows the extraction of spatially-associated topological information about an interface of interest in a reference, and use thereof in defining a topological constraint for use in selecting an engineered peptide. FIG. 3B provides a schematic detailing the in silico screen step, demonstrating how mismatched candidates are discarded while candidates that match the topology are retained. FIG. 3C presents the top 12 selected engineered peptide candidates identified.

FIGS. 4A-4B provide a second set of schematics demonstrating the selection of a different group of engineered peptides based on a different set of reference parameters, using the methods described herein. FIG. 4A shows extraction of spatially-associated topological information and construction of a topology matrix. FIG. 4B provides a list of top 8 engineered peptide candidates selected by in silico comparing candidates to the topological constraints.

FIGS. 6A-6H provide an overview of the selection of five engineered peptides, and their use in a programmable in vitro selection protocol for phage panning. FIG. 6A demonstrates the selection of VEGF as the reference target, and identification of the portion of VEGF from which spatially-associated topological information was derived and used to construct a combination of spatially-associated topological constraints (Step 1). This combination was then used for in silico screening of candidate engineered peptides to identify positive selection molecules and negative selection molecules (Step 2). The selected candidates were further screened in silico for stabilizing cross-linking options. Once the identified, stabilized engineered peptides were obtained, they then were used to construct a programmable in vitro selection protocol for phage panning. FIG. 6B shows the analysis and identification of spatially-associated topological constraints based on the reference target (a portion of VEGF) to be used in selecting engineered peptides. FIG. 6C, FIG. 6D, FIG. 6E demonstrates the construction of a first, second, and third candidate engineered peptide, respectively, and derivation of the parameters to compare to the combination of constraints developed in FIG. 6B. FIG. 6F lists the mean percentage error (MPE) for each MEM compared to the reference target, and their rank based on the MPE. FIG. 6G shows how an additional set of constraints was added to the combination based on the reference target. In FIG. 611, this additional set of constraints is used to evaluate candidate MEM 1. The MPE of this comparison was 36.6%.

FIG. 7C shows the two eigenvectors that describe the two most dominant motions of the epitope in the reference target, with the x-, y-, and z-components of the ten Ca atoms in the epitope and the eigenvalues of the eigenvectors tabulated; structures show the projection of each Ca atom in the epitope along eigenvector 1 (arrows) and eigenvector 2 (arrows). Eigenvectors are orthonormal by definition. FIG. 7D is the eigenvectors describing the most dominant motion (mode) in the epitope of the reference target (left) and the MEM (right). Structure of the MEM superimposed on the epitope are shown along with the MEM variant ID and RMSIP.

FIG. 11 is a description of eight different panning programs, seven including engineered peptides as one or more selection molecules, and an eight program that uses conventional native proteins for selection. A naïve Hu scFV library was separately panned with each program.

As shown in FIG. 12A, MEM programmed in vitro selection does not significantly reduce full-length target binding propensity, with specific MEM program inputs, but not all inputs. Horizontal bars indicate mean; significant difference between P12 and P7: p-value<0.0001. As shown in FIG. 12B, MEM programmed in vitro selection directs towards putative-epitope selective clones in a statistically significant manner. Horizontal bars indicate mean, P12 vs. P6: p-value is 0.024; P12 vs. P9: p-value is 0.0004; P12 vs. P10: p-value is 0.049.

FIG. 16 (SEQ ID NOS: 8-45) is a summary of the binding, cross-blocking, CDR sequences and germline usage for all Fabs produced from the selection programs outlined in FIG. 11.

FIG. 20 summarizes the cross-blocking enrichment for a random-uniform selection of clones from across the panning programs described in FIG. 11.

FIG. 33 is a summary of the difference programmed in vitro selection panning programs using one or more of the engineered peptides described in FIG. 30, and a conventional panning method using native proteins (C1). The engineered peptides sMEM, nMEM, and iMEM in FIG. 30 are sMEM #1, sMEM #5, and iMEM in FIG. 33.

FIG. 35 is a graph and summary of ELISA binding response against the sMEM #1 for clones selected using each panning program described in FIG. 33.

FIG. 36 is a graph and summary of ELISA binding response against the nMEM #5 for clones selected using each panning program described in FIG. 33.

FIG. 40 is a table summarizing the anti-PD-L1 panning ELISA hit identification criteria used to analyze clones obtained from the selection programs described in FIG. 33.

FIG. 43 (SEQ ID NOS: 8, 54-98) summarized the 23 distinct clones from the programs described in FIG. 33, as identified from cross-blocking hits and their sequences.

FIGS. 45B and 45C summarize the blocking propensity of clones obtained from the different programs evaluated in FIG. 45A. The shaded entries in FIG. 45C were obtained using the conventional selection approach using native proteins.

FIG. 46 is a summary of the cross-blocking enrichment observed in pools of clones obtained using the programs described in FIG. 33, compared to the control (conventional approach).

FIG. 47 is an example of a topological matrix that can be used in the selection of an engineered peptide as described herein.

DETAILED DESCRIPTION

Figure 1:
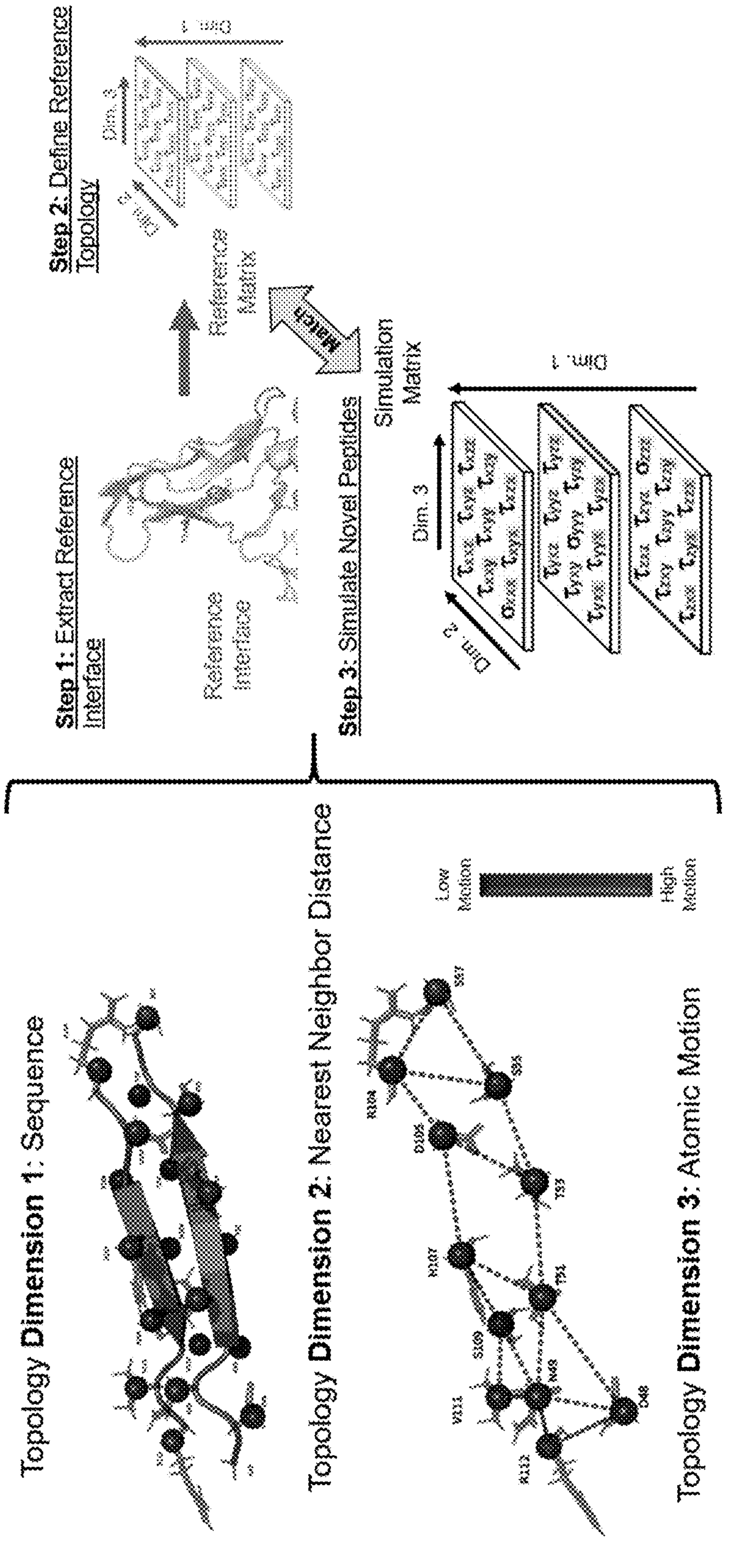
FIG. 1 provides a schematic demonstrating construction of an exemplary combination of three spatially-associated topological constraints, for use in selecting an engineered peptide as described herein.
Figure 2:
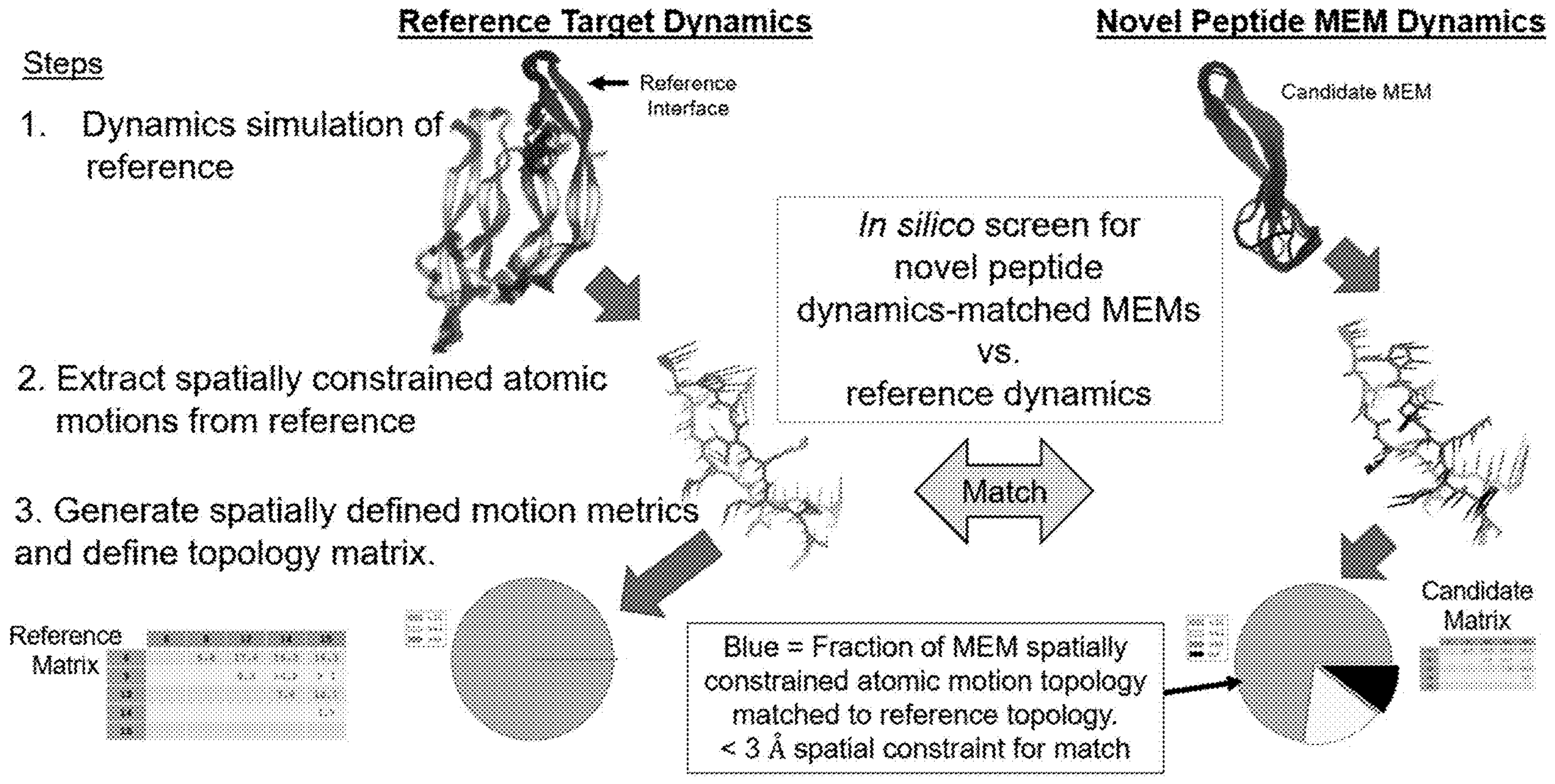
FIG. 2 provides a schematic of the steps involved in some exemplary methods of determining the reference-derived spatially-associated topological constraints and their use in selecting an engineered peptide (mesoscale molecule, MEM).
Figure 3B:
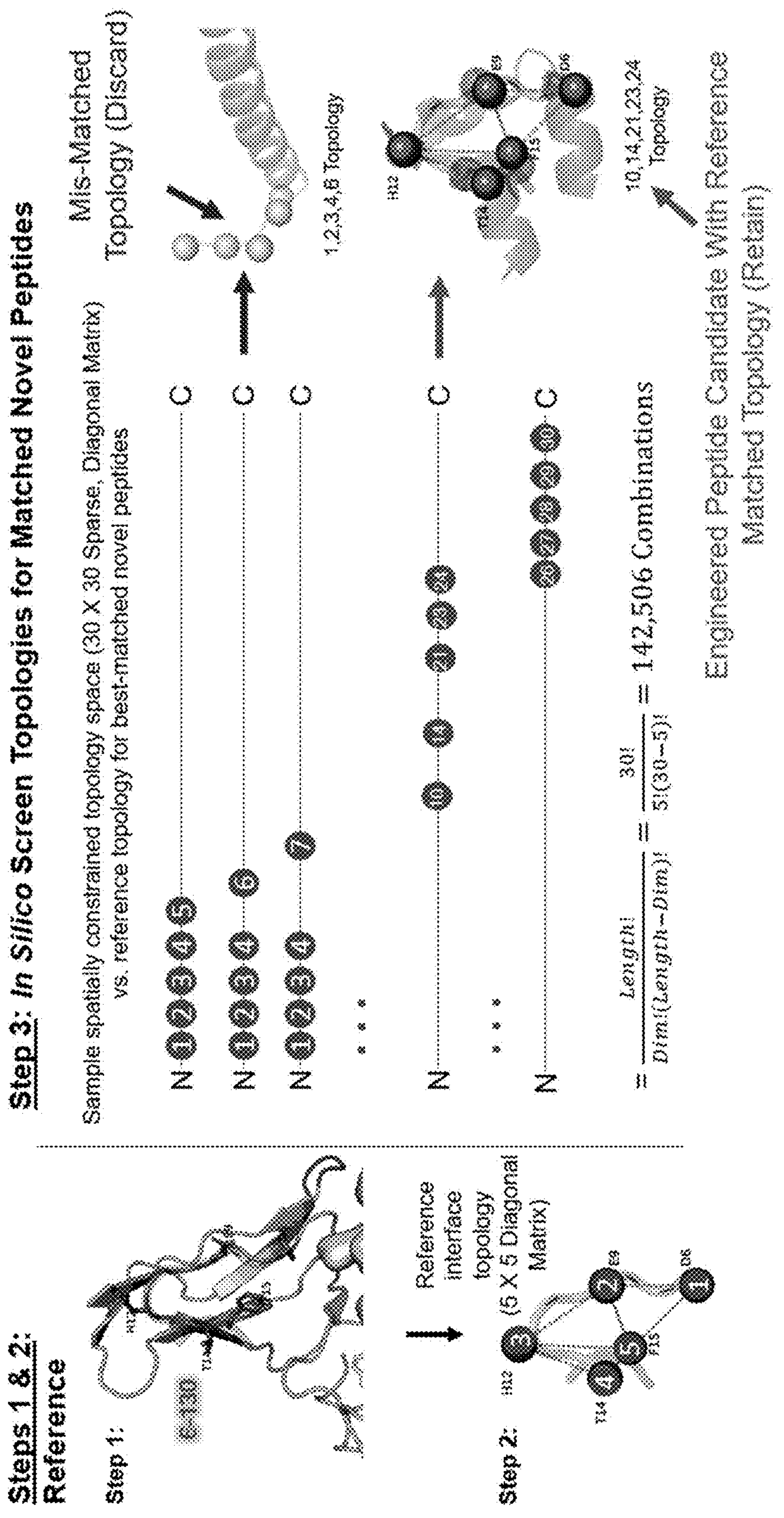
Figure 3C:
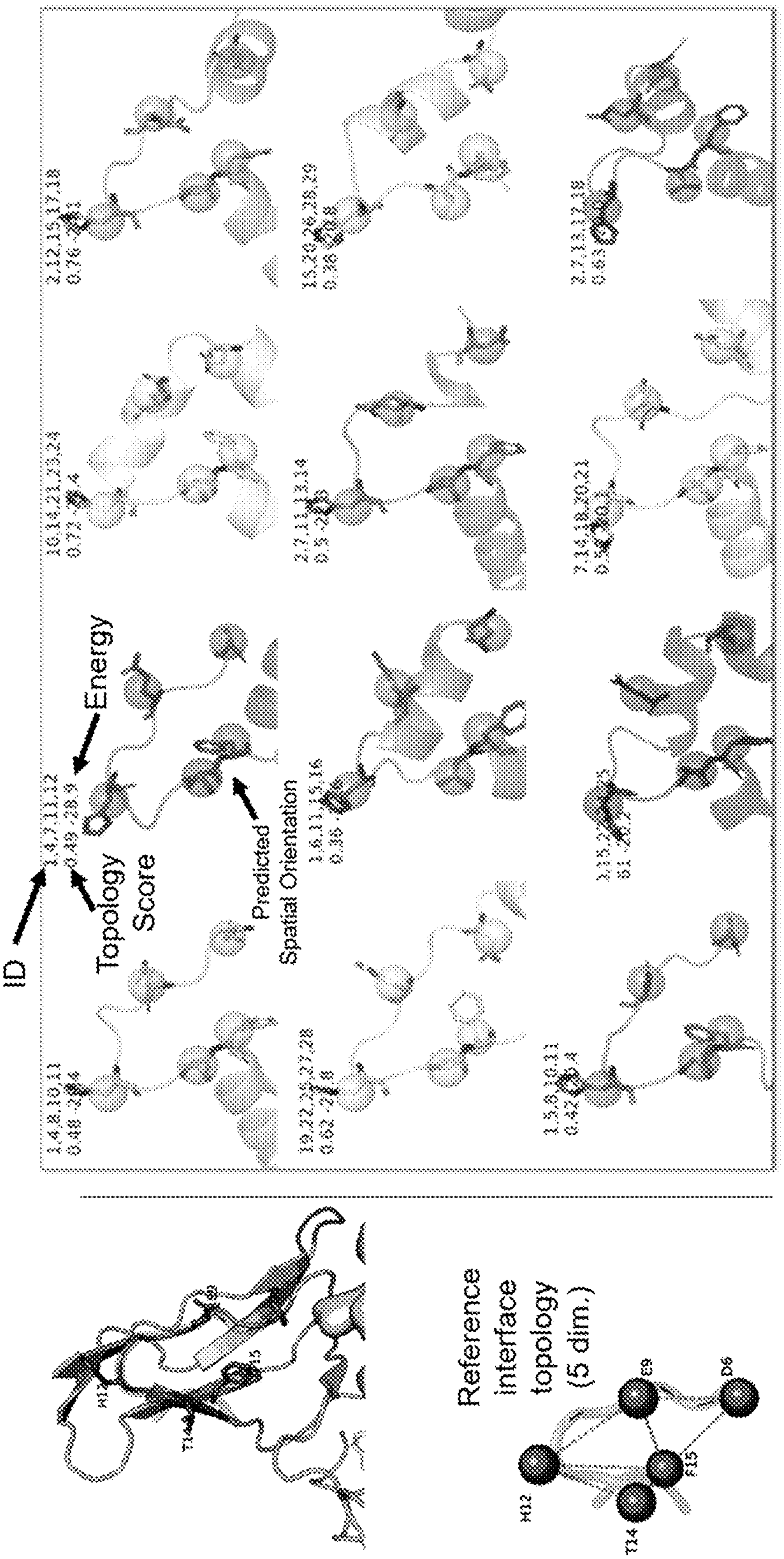
Figure 4B:
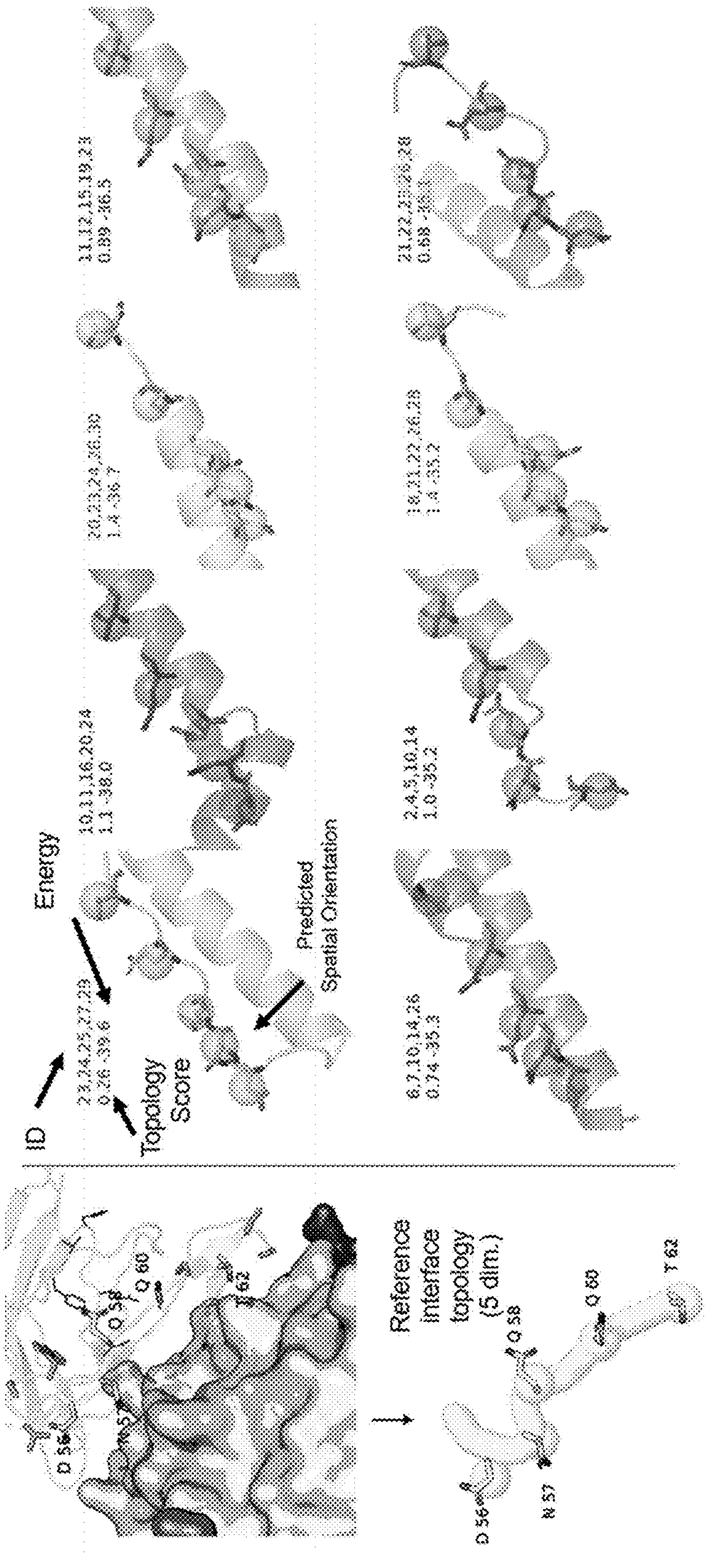

Provided herein are methods of selecting meso-scale engineered peptides, and compositions comprising and methods of using said engineered peptides. For example, provided herein are methods of using engineered peptides in in vitro selection of antibodies.

The engineered peptides of the present disclosure are between 1 kDa and 10 kDa, referred to herein as "meso-scale". Engineered peptides of this size may, in some embodiments, have certain advantages, such as protein-like functionality, a large theoretical space from which to select candidates, cell permeability, and/or structural and dynamical variability.

The methods provided herein comprise identifying a plurality of spatially-associated topological constraints, some of which may be derived from a reference target, constructing a combination of said constraints, comparing candidate peptides with said combination, and selecting a candidate that has constraints which overlap with the combination. By using spatially-associated topological constraints, different aspects of an engineered peptide can be included in the combination depending on the intended use, or desired function, or another desired characteristic. Further, not all constraints must, in some embodiments, be derived from a reference target. Through such methods, in some embodiments the selected engineered peptides are not simply variations of a reference target (such as might be obtained through peptide mutagenesis or progressive modification of a single reference), but rather may have a different overall structure than the reference peptide, while still retaining desired functional characteristics and/or key substructures.

Further provided herein are methods of using said engineered peptides, which include methods of programmable in vitro selection using one or more engineered peptides. Such selection may be used, for example, in the identification of antibodies.

These methods and engineered peptides are described in greater detail below.

I. Methods of Selecting Engineered Peptides

In some aspects, provided herein are methods of selecting an engineered peptide, comprising:

- identifying one or more topological characteristics of a reference target;
- designing spatially-associated constraints for each topological characteristic to produce a combination of reference target-derived constraints;
- comparing spatially-associated topological characteristics of candidate peptides with the combination derived from the reference target; and
- selecting a candidate peptide with spatially-associated topological characteristics that overlap with the combination of constraints derived from the reference target.

In some embodiments, one or more additional spatially-associated topological constraints that are not derived from the reference target are included in the combination.

a. Spatially-Associated Topological Constraints

The engineered peptides described herein are selected based on how closely they match a combination of spatially-associated topological constraints. This combination may also be described using the mathematical concept of a "tensor". In such a combination (or tensor), each constraint is independently described in three dimensional space (e.g., spatially-associated), and the combination of these constraints in three dimensional space provides, for example, a representational "map" of different desired characteristics and their desired level (if applicable) relative to location. This map is not, in some embodiments, based on a linear or otherwise pre-determined amino acid backbone, and therefore can allow for flexibility in the structures that could fulfill the desired combination, as described. For example, in some embodiments, the "map" includes a spatial area wherein the prescribed constraint limitations could be adequately met by two adjacent amino acids—in some embodiments, these amino acids could be directly bonded (e.g., two contiguous amino acids) while in other embodiments, the amino acids are not directly bonded to each other but could be brought together in space by the folding of the peptide (e.g., are not contiguous amino acids). The separate constraints themselves are also not necessarily based on structure, but could include, for example, chemical descriptors and/or functional descriptors. In some embodiments, constraints include structural descriptors, such as a desired secondary structure or amino acid residue. In certain embodiments, each constraint is independently selected.

For example, FIG. 1 is a schematic demonstrating the construction of a representative combination of spatially-associated topological constraints. The three constraints in FIG. 1 are sequence, nearest neighbor distance, and atomic motion, with nearest neighbor distance and atomic motion combined into one graphic. As shown, some constraints are mapped independent of the location of the backbone (e.g., atomic motion of certain side chains), therefore allowing for a much greater variety of structural configurations to be tried, compared to just varying one or more positions on a reference scaffold. The three different constraints and their spatial descriptions are combined into a matrix (e.g., tensor), and then a series of candidate peptides can be compared with this combination to identify new engineered peptides which meet the desired criteria. In some embodiments, one or more additional non-reference derived constraints is also included in the combination. Comparison of candidate peptides with a defined combination may be done, for example, using in silico methods to evaluate the constraints of each candidate peptide against the desired combination, and rate how well candidates match. Said candidates which have the desired level of overlap with the prescribed combination may then be synthesized using standard peptide synthetic methods known to one of skill in the art, and evaluated.

In some embodiments, the combination of constraints comprises at least 3, at least 4, at least 5, at least 6, at least 7, at least 8, at least 9, at least 10, at least 11, at least 12, between 3 to 12, between 3 to 10, between 3 to 8, between 3 to 6, or 3, or 4, or 5, or 6 independently selected spatially-associated topological constraints. One or more of the constraints is derived from a reference target. In some embodiments, each of the constraints is derived from a reference target. In other embodiments, at least one constraint is derived from a reference target, and the remaining constraints are not derived from the reference target. For example, in some embodiments, between 1 and 9 constraints, between 1 and 7 constraints, between 1 and 5 constraints, or between 1 and 3 constraints are derived from a reference target, and between 1 and 9 constraints, between 1 and 7 constraints, between 1 and 5 constraints, or between 1 and 3 constraints are not derived from the reference target.

Once the combination of constraints has been constructed, a series of candidate peptides is compared to said combination to identify one or more new engineered peptides which meet the desired criteria. In some embodiments, at least 5, at least 10, at least 15, at least 20, at least 25, at least 30, at least 40, at least 50, at least 60, at least 70, at least 80, at least 90, at least 100, at least 125, at least 150, at least 175, at least 200, or at least 250 or more candidate peptides are compared to the combination to identify one or more new engineered peptides which meet the desired criteria. In some embodiments, more than 250 candidate peptides, more than 300 candidate peptides, more than 400 candidate peptides, more than 500 candidate peptides, more than 600 candidate peptides, or more than 750 candidate peptides are compared, for example. In some embodiments, topological characteristic simulations are used to evaluate the topological characteristic overlap, if any, of a candidate peptide compared to the combination of constraints. In some embodiments, one or more candidate peptides are also compared to the reference target, and overlap, if any, of candidate peptide topological characteristics with reference target topological characteristics is evaluated. In some embodiments, the engineered peptide is identified from a computational sample of more than 5, more than 10, more than 20, more than 30, more than 40, more than 50, more than 60, more than 70, more than 80, more than 90, or more than 100 distinct peptide and topological characteristic simulations and an engineered peptide is selected, wherein the selected engineered peptide has the highest topological characteristic overlap compared the reference target, out of the total sampled population.

The spatially-associated topological constraints used to construct the desired combination (e.g., the desired tensor) may each be independently selected from a wide group of possible characteristics. These may include, for example, constraints describing structural, dynamical, chemical, or functional characteristics, or any combinations thereof.

Structural constraints may include, for example, atomic distance, amino acid sequence similarity, solvent exposure, phi angle, psi angle, secondary structure, or amino acid contact, or any combinations thereof.

Dynamical constraints may include, for example, atomic fluctuation, atomic energy, van der Waals radii, amino acid adjacency, or non-covalent bonding propensity. Atomic energy may include, for example, pairwise attractive energy between two atoms, pairwise repulsive energy between two atoms, atom-level solvation energy, pairwise charged attraction energy between two atoms, pairwise hydrogen bonding attraction energy between two atoms, or non-covalent bonding energy, or any combinations thereof.

Chemical characteristics may include, for example, chemical descriptors. Such chemical descriptors may include, for example, hydrophobicity, polarity, atomic volume, atomic radius, net charge, logP, HPLC retention, van der Waals radii, charge patterns, or H-bonding patterns, or any combinations thereof.

Functional characteristics may include, for example, bioinformatic descriptors, biological responses, or biological functions. Bioinformatic descriptors may include, for example, BLOSUM similarity, pKa, zScale, Cruciani Properties, Kidera Factors, VHSE-scale, ProtFP, MS-WHIM scores, T-scale, ST-scale, Transmembrane tendency, protein buried area, helix propensity, sheet propensity, coil propensity, turn propensity, immunogenic propensity, antibody epitope occurrence, and/or protein interface occurrence, or any combinations thereof.

In some embodiments, designing the constraints incorporates information about per-residue energy, per-residue interaction, per-residue fluctuation, per-residue atomic distance, per-residue chemical descriptor, per-residue solvent exposure, per-residue amino acid sequence similarity, per-residue bioinformatic descriptor, per-residue non-covalent bonding propensity, per-residue phi/psi angles, per-residue van der Waals radii, per-residue secondary structure propensity, per-residue amino acid adjacency, or per-residue amino acid contact. In some embodiments, these characteristics are used for a subset of the total residues in the reference target, or a subset of the total residues of the total combination of constraints, or a combination thereof. In some embodiments, one or more different characteristics are used for one or more different residues. That is, in some embodiments, one or more characteristics are used for a subset of residues, and at least one different characteristic is used for a different subset of residues. In some embodiments, one or more of said characteristics used to design one or more constraints is determined by computer simulation. Suitable computer simulation methods may include, for example, molecular dynamics simulations, Monte Carlo simulations, coarse-grained simulations, Gaussian network models, machine learning, or any combinations thereof.

In some embodiments multiple constraints are selected from one category. For example, in some embodiments, the combination comprises two or more constraints that are independently a type of biological response. In some embodiments, two or more constraints are independently a type of secondary structure. In certain embodiments, two or more constraints are independently a type of chemical descriptor. In other embodiments, the combination comprises no overlapping categories of constraints.

In some embodiments, one or more constraints is independently associated with a biological response or biological function. In some embodiments, said constraint is a spatially defined atom(s)-level constraint, or spatially defined shape/area/volume-level constraint (such as a characteristic shape/area/volume that can be satisfied by several different atomic compositions), or a spatially defined dynamic-level constraint (such as a characteristic dynamic or set of dynamics that can be satisfied by several different atomic compositions).

In some embodiments, one or more constraints is derived from a protein structure or peptide structure associated with a biological function or biological response. For example, in some embodiments, one or more constraints is derived from an extracellular domain, such as a G protein-coupled receptor (GPCR) extracellular domain, or an ion channel extracellular domain. In some embodiments, one or more constraints is derived from a protein-protein interface junction. In some embodiments, one or more constraints is derived from a protein-peptide interface junction, such as MHC-peptide or GPCR-peptide interfaces. In certain embodiments, the atoms or amino acids constrained to such a protein or peptide structure are atoms or amino acids associated with a biological function or biological response. In some embodiments, the atoms or amino acids in the engineered peptide constrained to such a protein or peptide structure are atoms or amino acids derived from a reference target. In some embodiments, one or more constraints is derived from a polymorphic region of a reference target (e.g., a region subject to allelic variation between individuals).

In some embodiments, the biological response or biological function is selected from the group consisting of gene expression, metabolic activity, protein expression, cell proliferation, cell death, cytokine secretion, kinase activity, epigenetic modification, cell killing activity, inflammatory signals, chemotaxis, tissue infiltration, immune cell lineage commitment, tissue microenvironment modification, immune synapse formation, IL-2 secretion, IL-10 secretion, growth factor secretion, interferon gamma secretion, transforming growth factor beta secretion, immunoreceptor tyrosine-based activation motif activity, immunoreceptor tyrosine-based inhibition motif activity, antibody directed cell cytotoxicity, complement directed cytotoxicity, biological pathway agonism, biological pathway antagonism, biological pathway redirection, kinase cascade modification, proteolytic pathway modification, proteostasis pathway modification, protein folding/pathways, post-translational modification pathways, metabolic pathways, gene transcription/translation, mRNA degradation pathways, gene methylation/acetylation pathways, histone modification pathways, epigenetic pathways, immune directed clearance, opsonization, hormone signaling, integrin pathways, membrane protein signal transduction, ion channel flux, and g-protein coupled receptor response.

In some embodiments, the one or more atoms associated with a biological function or biological response are selected from the group consisting of carbon, oxygen, nitrogen, hydrogen, sulfur, phosphorus, sodium, potassium, zinc, manganese, magnesium, copper, iron, molybdenum, and nickel. In certain embodiments, the atoms are selected from the group consisting of oxygen, nitrogen, sulfur, and hydrogen.

In some embodiments, wherein one of the constraints is one or more amino acids associated with a biological function or biological response, and/or the engineered peptide comprises one or more amino acids associated with a biological function or biological response, the one or more amino acids are independently selected from the group consisting of the 20 proteinogenic naturally occurring amino acids, non-proteinogenic naturally occurring amino acids, and non-natural amino acids. In some embodiments, the non-natural amino acids are chemically synthesized. In certain embodiments, the one or more amino acids are selected from the 20 proteinogenic naturally occurring amino acids. In other embodiments, the one or more amino acids are selected from the non-proteinogenic naturally occurring amino acids. In still further embodiments, the one or more amino acids are selected from non-natural amino acids. In still further embodiments, the one or more amino acids are selected from a combination of 20 proteinogenic naturally occurring amino acids, non-proteinogenic naturally occurring amino acids, and non-natural amino acids.

While the combination of constraints used to select an engineered peptide as described herein comprises at least one constraint derived from a reference target, in some embodiments one or more constraints of the combination are not derived from a reference target. Thus, in certain embodiments, the selected engineered peptide comprises one or more characteristics that are not shared with the reference target.

In some embodiments, one or more constraints derived from the reference target and used in the combination describes the inverse of the characteristic as observed in the reference target. Thus, for example, a reference target may have a certain pattern of positive charge, a constraint related to charge is derived from said reference target, and the derived constraint describes a similar pattern but of neutral charge, or of negative charge. Thus, in some embodiments one or more inverse constraints are derived from the reference target and included in the combination. Such inverse constraints may be useful, for example, in selecting engineered peptides as control molecules for certain assays or panning methods, or as negative selection molecules in the programmable in vitro selection methods described herein.

In some embodiments, the combination of spatially-defined topological constraints comprises one or more non-reference derived topological constraints. In some embodiments, the one or more non-reference derived topological constraints enforces or stabilizes one or more secondary structural elements, enforces atomic fluctuations, alters peptide total hydrophobicity, alters peptide solubility, alters peptide total charge, enables detection in a labeled or label-free assay, enables detection in an in vitro assay, enables detection in an in vivo assay, enables capture from a complex mixture, enables enzymatic processing, enables cell membrane permeability, enables binding to a secondary target, or alters immunogenicity. In certain embodiments, the one or more non-reference derived topological constraints constrains one or more atoms or amino acids in the combination of constraints (or subsequently selected peptide) that were derived from the reference target. For example, in some embodiments, the combination of constraints includes a secondary structure that was derived from the reference target, and the combination of constraints also comprises a constraint that stabilizes the secondary structural element (e.g., through additional hydrogen bonding, or hydrophobic interactions, or side chain stacking, or a salt bridge, or a disulfide bond), wherein the stabilizing constraint is not present in the reference target. In another example, in some embodiments the combination of constraints (or subsequently selected peptide) comprises one or more atoms or amino acids that was derived from the reference target, and the combination of constraints also includes a constraint that enforces atomic fluctuations in at least a portion of the atoms or amino acids derived from the target reference, wherein the constraint is not present in the target reference. In some embodiments, one or more non-reference derived constraints is an inverse constraint. For example, in some embodiments, two combinations of constraints are constructed to select engineered peptides with inverse characteristics. In some such embodiments, a first combination of constraints will comprise one or more constraints derived from the reference target, and one or more constraints not derived from the reference target; and a second combination of constraints will comprise the same one or more constraints derived from the reference target, and the inverse of one or more of non-reference target constraints of the first combination.

d. Reference Target

Any suitable reference target may be used to derive one or more spatially-associated topological constraints for use in the methods provided herein. In some embodiments, the reference target is a full-length native protein. In other embodiments, the reference target is a portion of a full-length native protein. In still further embodiments, the reference target is a non-native protein, or portion thereof.

For example, in some embodiments the reference target is a cell-surface receptor, or a transmembrane protein, or a signaling protein, or a multiprotein complex, or a protein-peptide complex, or a portion thereof. In some embodiments, the reference target is a portion of a protein of interest, wherein the protein of interest is involved in disease process in an organism, such as a human. In some embodiments, the protein of interest is involved in the growth or metastasis of cancer, or in an inflammatory disorder, and the reference target is a portion of said protein of interest that is a putative epitope. Thus, in some embodiments, the methods provided herein may be used to select one or more engineered peptides that may serve as an immunogen, and may be used to raise antibodies of a protein of interest. Examples of proteins that may be of interest include, for example, PD-1, PD-L1, CD25, IL2, MIF, CXCR4, or VEGF. Thus, in some embodiments, the reference target is PD-1, PD-L1, CD25, IL2, MIF, CXCR4, or VEGF, or a portion thereof, such as an epitope. In some embodiments, the methods provided herein may be used to select one or more engineered peptides that are immunogens, and which may be used to raise one or more antibodies that specifically bind to the protein from which the target reference is derived. In still further embodiments, the methods provided herein may be used to select one or more engineered peptides which in turn may be used to select one or more binding partners of a protein of interest, such as an antibody or a Fab-displaying phage.

c. Comparison of Constraints

In some embodiments, the one or more constraints (e.g., reference-derived or non-reference derived) are determined by molecular simulation (e.g. molecular dynamics), or laboratory measurement (e.g. NMR), or a combination thereof. Once the constraints have been derived and combined, engineered peptide candidates are, in some embodiments, generated using a computational protein design (e.g., Rosetta). In some embodiments, other methods of sampling peptide space are used. Dynamics simulations may then be carried out on the candidate engineered peptides to obtain the parameters of constraints that have been selected. A covariance matrix of atomic fluctuations is generated for the reference target, covariance matrices are generated for the residues in each of the candidate engineered peptides, and these covariance matrices are compared to determine overlap. Principal component analysis is performed to compute the eigenvectors and eigenvalues for each covariance matrix—one covariance matrix for the reference target and one covariance for each of the candidate engineered peptides—and those eigenvectors with the largest eigenvalues are retained.

The eigenvectors describe the most, second-most, third-most, N-most dominant motion observed in a set of simulated molecular structures. Without wishing to be bound by any theory, if a candidate engineered peptide moves like the reference target, its eigenvectors will be similar to the eigenvectors of the reference target. The similarity of eigenvectors corresponds to their components (a 3D vector centered on each CA atom) being aligned, pointing in the same direction. Exemplary eigenvector comparisons between a reference target and a candidate engineered peptide are shown in FIGS. 7C-7F.

Figure 7B:
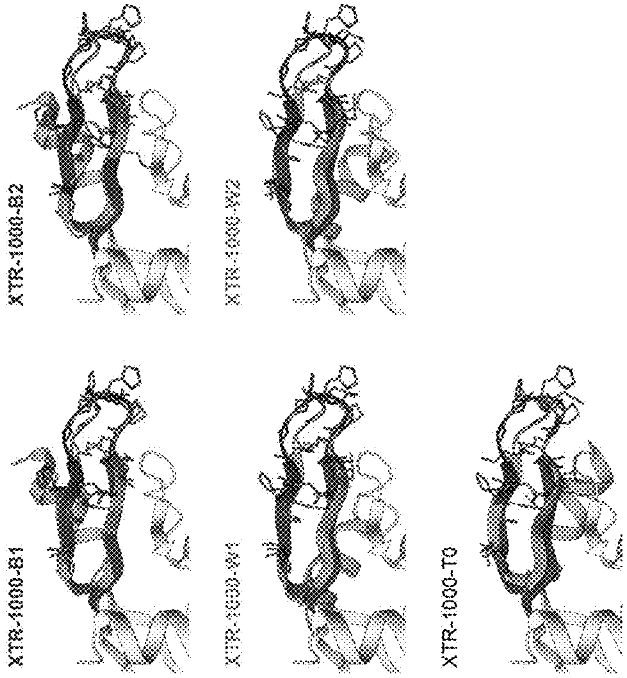
FIG. 7B are ribbon diagrams of 5 candidate engineered peptides selected based on the constraints developed from the target reference in FIG. 7A. The sequences and root-mean square RMSIP are listed in Table 1.
Figure 7A:
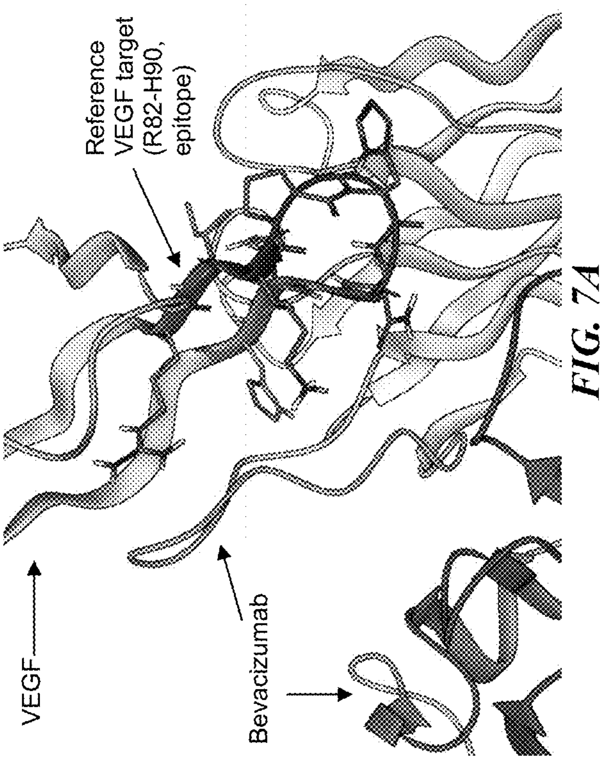
FIG. 7A is ribbon diagram of VEGF, with the reference section used to select engineered peptides indicated (R82-H90).
Figure 7E:
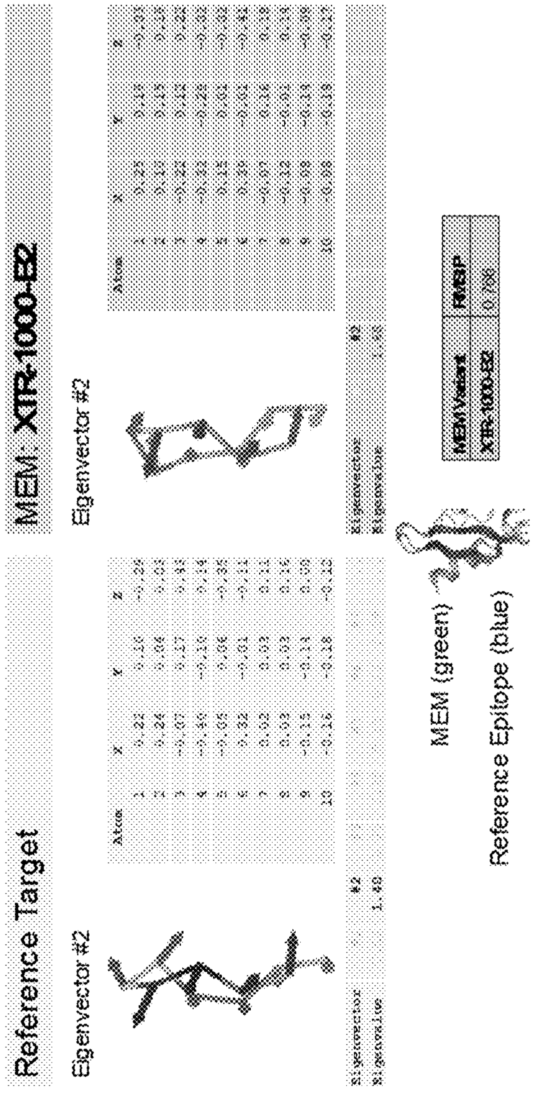
FIG. 7E provide the eigenvectors describing the second most dominant motion (mode) in the epitope of the reference target (left) and the MEM (right). Structure of the MEM superimposed on the epitope are shown along with the MEM variant ID and RMSIP.
Figure 7F:
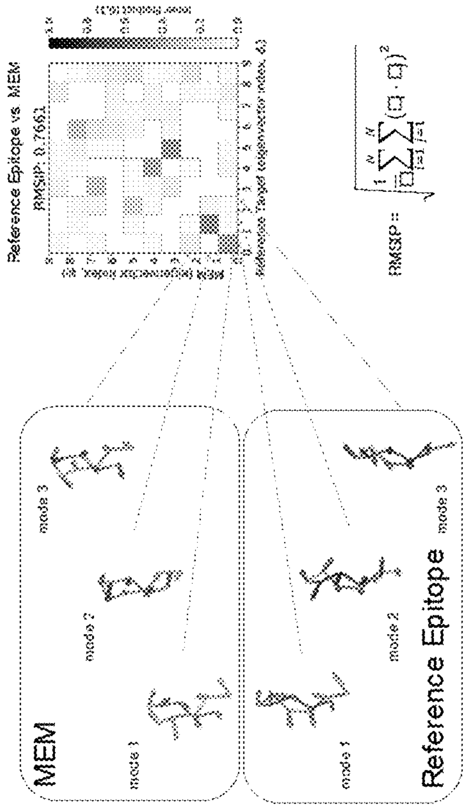
FIG. 7F provide the structures of the reference target and the MEM with associated projections along the three most dominant motions (modes, eigenvectors 1-3) in relation to their location in the inner product matrix used to compute RMSIP. The RMSIP equation used is shown for reference.

In some embodiments, this similarity between candidate engineered peptide and reference target eigenvectors is computed using the inner product of two eigenvectors. The inner product value is 0 if two eigenvectors are 90 degrees to each other or 1 if the two eigenvectors point precisely in the same direction. Without wishing to be bound by theory, since the ordering of eigenvectors is based on their eigenvalues, and eigenvalues may not necessarily be the same between two different molecules due to the stochastic nature by which molecular dynamics (MD) simulations sample the underlying energy landscape of those different molecules, the inner product between multiple, differentially ranked eigenvectors is, in some embodiments, needed (e.g. eigenvector 1 of the engineered peptide by eigenvector 2, 3, 4, etc. of the reference target). In addition, molecular motions are complex and may involve more than one (or more than a few) dominant/principal modes of motion. Thus, in some embodiments, the inner product between all pairs of eigenvectors in a candidate engineered peptide and the reference target are computed. This results in a matrix of inner products the dimensions of which are determined by the number of eigenvectors analyzed. For example, for 10 eigenvectors, the matrix of inner products is 10 by 10. This matrix of inner products can be distilled into a single value by computing the root mean-square value of the 100 (if 10 by 10) inner products. This is the root mean square inner product (RMSIP). The equation for RMSIP is shown in FIG. 7F. From this comparison, one or more candidate engineered peptides that have similarity with the defined combination of constraints are selected.

e. Additional Steps

In some embodiments, selection of one or more engineered peptides comprises one or more additional steps. For example, in some embodiments an engineered peptide candidate is selected based on similarity to the defined combination of spatially-associated topological constraints, as described herein, and then undergoes one or more analyses to determine one or more additional characteristics, and one or more structural adjustments to impart or enforce said desired characteristics. For example, in some embodiments, the selected candidate is analyzed, such as through molecule dynamics simulations, to determine overall stability of the molecule and/or propensity for a particular folded structure. In some embodiments, one or more modifications are made to the engineered peptide to impart or reinforce a desired level of stability, or a desired propensity for a desired folded structure. Such modifications may include, for example, the installation of one or more cross-links (such as a disulfide bond), salt bridges, hydrogen bonding interactions, or hydrophobic interactions, or any combinations thereof.

The methods provided herein may further comprise assaying one or more selected engineered peptides for one or more desired characteristics, such as desired binding interactions or activity. Any suitable assay may be used, as appropriate to measure the desired characteristic.

II. Selected Engineered Peptides

In other aspects, provided herein are engineered peptides, such as engineered peptides selected through the methods described herein. In some embodiments, the engineered peptide has a molecular mass between 1 kDa and 10 kDa, and comprises up to 50 amino acids. In certain embodiments, the engineered peptide has a molecular mass between 2 kDa and 10 kDa, between 2 kDa and 10 kDa, between 3 kDa and 10 kDa, between 4 kDa and 10 kDa, between 5 kDa and 10 kDa, between 6 kDa and 10 kDa, between 7 kDa and 10 kDa, between 8 kDa and 10 kDa, between 9 kDa and 10 kDa, between 1 kDa and 9 kDa, between 1 kDa and 8 kDa, between 1 kDa and 7 kDa, between 1 kDa and 6 kDa, between 1 kDa and 5 kDa, between 1 kDa and 4 kDa, between 1 kDa and 3 kDa, or between 1 kDa and 2 kDa. In certain embodiments, the engineered peptide comprises up to 45 amino acids, up to 40 amino acids, up to 35 amino acids, up to 30 amino acids, up to 25 amino acids, up to 20 amino acids, at least 5 amino acids, at least 10 amino acids, at least 15 amino acids, at least 20 amino acids, at least 25 amino acids, at least 30 amino acids, at least 35 amino acids, or at least 40 amino acids.

In certain embodiments, the engineered peptide comprises a combination of spatially-associated topological constraints, wherein one or more of the constraints is a reference target-derived constraint. Any constraints described herein may be used in the combination, in some embodiments. In still further embodiments, between 10% to 98% of the amino acids of the engineered peptide meet the one or more reference target-derived constraints (e.g., if the engineered peptide comprises 50 amino acids, between 5 to 49 amino acids meet the one or more reference target-derived constraints). In some embodiments, between 20% to 98%, between 30% to 98%, between 40% to 98%, between 50% to 98%, between 60% to 98%, between 70% to 98%, between 80% to 98%, between 90% to 98%, between 10% to 90%, between 10% to 80%, between 10% to 70%, between 10% to 60%, between 10% to 50%, between 10% to 40%, between 10% to 30%, or between 10% to 20% of the amino acids of the engineered peptide meet the one or more reference target-derived constraints. In still further embodiments, the one or more amino acids that meet the one or more reference target-derived constraints have less than 8.0 Å, less than 7.5 Å, less than 7.0 Å, less than 6.5 Å, less than 6.0 Å, less than 5.5 Å, or less than 5.0 Å backbone root-mean-square deviation (RSMD) structural homology with the reference target. In some embodiments, the engineered peptide has a molecular mass of between 1 kDa and 10 kDa; comprises up to 50 amino acids; a combination of spatially-associated topological constraints, wherein one or more of the constraints is a reference target-derived constraint; between 10% to 98% of the amino acids of the engineered peptide meet the one or more reference target-derived constraints; and the amino acids that meet the one or more reference target-derived constraints have less than 8.0 Abackbone root-mean-square deviation (RSMD) structural homology with the reference target.

In some embodiments, the amino acids of the engineered peptide that meet the one or more reference target-derived constraints have between 10% and 90% sequence homology, between 20% and 90% sequence homology, between 30% and 90% sequence homology, between 40% and 90% sequence homology, between 50% and 90% sequence homology, between 60% and 90% sequence homology, between 70% and 90% sequence homology, or between 80% and 90% sequence homology with the reference target. In some embodiments, the amino acids that meet the one or more reference target-derived constraints have a van der Waals surface area overlap with the reference of between 30 $Å^2$ to 3000 $Å^2$, or between 100 $Å^2$ to 3000 $Å^2$, or between 250 $Å^2$ to 3000 $Å^2$, or between 500 $Å^2$ to 3000 $Å^2$, or between 750 $Å^2$ to 3000 $Å^2$, or between 1000 $Å^2$ to 3000 $Å^2$, or between 1250 $Å^2$ to 3000 $Å^2$, or between 1500 $Å^2$ to 3000 $Å^2$, or between 1750 $Å^2$ to 3000 $Å^2$, or between 2000 $Å^2$ to 3000 $Å^2$, or between 2250 $Å^2$ to 3000 $Å^2$, or between 2500 $Å^2$ to 3000 $Å^2$, or between 2750 $Å^2$ to 3000 $Å^2$.

The combination of constraints that the engineered peptide meets may comprise two or more, three or more, four or more, five or more, six or more, or seven or more reference target-derived constraints. The combination may comprise one or more constraints not derived from the reference target, as described elsewhere in the present disclosure. These reference-derived constraints, and non-reference derived constraints if present, may independently be any of the constraints described herein, such as any of the structural, dynamical, chemical, or functional characteristics described herein, or any combinations thereof.

In some embodiments, the engineered peptide comprises at least one structural difference when compared to the reference target. Such structural differences may include, for example, a difference in the sequence, number of amino acid residues, total number of atoms, total hydrophilicity, total hydrophobicity, total positive charge, total negative charge, one or more secondary structures, shape factor, Zernike descriptors, van der Waals surface, structure graph nodes and edges, volumetric surface, electrostatic potential surface, hydrophobic potential surface, local diameter, local surface features, skeleton model, charge density, hydrophilic density, surface to volume ratio, amphiphilicity density, or surface roughness, or any combinations thereof. In some embodiments, the difference in one or more characteristics (such as one or more characteristics described herein) is at least 10%, at least 20%, at least 30%, at least 40%, at least 50%, at least 60%, at least 70%, at least 80%, at least 90%, at least 100%, or greater than 100% when compared to the characteristic in the reference target, as applicable to the type of characteristic. For example, in some embodiments the difference is the total number of atoms, and the engineered peptide has at least 10%, at least 20%, or at least 30% more atoms than the reference target, or at least 10%, at least 20%, or at least 30% fewer atoms than the reference target. In some embodiments, the difference is in total positive charge, and the total positive charge of the engineered peptide is at least 10%, at least 20%, at least 30%, at least 40%, or at least 50% larger (e.g., more positive) than the reference target, while in other embodiments the total positive charge of the engineered peptide is at least 10%, at least 20%, at least 30%, at least 40%, or at least 50% smaller (e.g., less positive) than the reference target.

In some embodiments, the combination of spatially-defined topological constraints includes one or more secondary structural elements not present in the reference target. Thus, in some embodiments, the engineered peptide comprises one or more secondary structural elements that are not present in the reference target. In some embodiments, the combination and/or engineered peptide comprises one secondary structural element, two secondary structural elements, three secondary structural elements, four secondary structural elements, or more than four secondary structural elements not found in the reference target. In some embodiments, each secondary structural element is independently selected form the group consisting of helices, sheets, loops, turns, and coils. In some embodiments, each secondary structural element not present in the reference target is independently an α-helix, β-bridge, β-strand, $3_{10}$ helix, π-helix, turn, loop, or coil.

In some embodiments, the engineered peptide comprises one or more atoms, or one or more amino acids, or a combination thereof, that is associated with a biological response or a biological function. In some embodiments, the biological response or biological function is selected from the group consisting of gene expression, metabolic activity, protein expression, cell proliferation, cell death, cytokine secretion, kinase activity, epigenetic modification, cell killing activity, inflammatory signals, chemotaxis, tissue infiltration, immune cell lineage commitment, tissue microenvironment modification, immune synapse formation, IL-2 secretion, IL-10 secretion, growth factor secretion, interferon gamma secretion, transforming growth factor beta secretion, immunoreceptor tyrosine-based activation motif activity, immunoreceptor tyrosine-based inhibition motif activity, antibody directed cell cytotoxicity, complement directed cytotoxicity, biological pathway agonism, biological pathway antagonism, biological pathway redirection, kinase cascade modification, proteolytic pathway modification, proteostasis pathway modification, protein folding/pathways, post-translational modification pathways, metabolic pathways, gene transcription/translation, mRNA degradation pathways, gene methylation/acetylation pathways, histone modification pathways, epigenetic pathways, immune directed clearance, opsonization, hormone signaling, integrin pathways, membrane protein signal transduction, ion channel flux, and g-protein coupled receptor response.

In certain embodiments, the reference target comprises one or more atoms associated with a biological response or a biological function (such as one described herein); the engineered peptide comprises one or more atoms associated with a biological response or a biological function (such as one described herein); and the atomic fluctuations of said atoms in the engineered peptide overlap with the atomic fluctuations of said atoms in the reference target. Thus, for example, in some embodiments the atoms themselves are different atoms, but their atomic fluctuations overlap. In other embodiments, the atoms are the same atoms, and their atomic fluctuations overlap. In still further embodiments, the atoms are independently the same or different. In some embodiments, the overlap is a root mean square inner product (RMSIP) greater than 0.25. In some embodiments, the overlap is a RMSIP greater than 0.3, greater than 0.35, greater than 0.4, greater than 0.45, greater than 0.5, greater than 0.55, greater than 0.6, greater than 0.65, greater than 0.7, greater than 0.75, greater than 0.8, greater than 0.85, greater than 0.9, or greater than 0.95. In certain embodiments, the RMSIP is calculated by:

$$RMSIP = \left( \frac{1}{10} \sum_{i=1}^{10} \sum_{j=1}^{10} (\eta_i \cdot v_j)^2 \right)^{1/2},$$

where n is the eigenvector of the engineered peptide topological constraints, and v is the eigenvector of the reference target topological constraints.

In some embodiments, the engineered peptide comprises atoms or amino acids (or combination thereof) associated with a biological response or biological function, and at least a portion of said atoms or amino acids or combination is derived from a reference target, and certain constraints of the set of atoms or amino acids in the engineered peptide and the set in the reference target can be described by a matrix. In some embodiments, the matrix is an L×L matrix. In other embodiments, the matrix is an S×S×M matrix. In still further embodiments, the matrix is an L×2 phi/psi angle matrix For example in some embodiments, the atomic fluctuations of the atoms or amino acids in the engineered peptide that are associated with a biological response or biological function are described by an L×L matrix; a portion of said atoms or amino acids are derived from the reference target; and the atomic fluctuations in the reference target of said portion are described by an L×L matrix. In some embodiments, the adjacency of each set (related to amino acid location) is described by corresponding L×L matrices. In certain embodiments, the mean percentage error (MPE) across all matrix elements (i, j) of the engineered peptide L×L atomic fluctuation or adjacency matrix is less than or equal to 75% relative to the corresponding (i, j) elements in the reference target atomic fluctuation or adjacency matrix, for the fraction of the engineered peptide derived from the reference target. In some embodiments, the MPE is less than 70%, less than 65%, less than 60%, less than 55%, less than 50%, less than 45%, or less than 40% relative to the corresponding elements in the reference target matrix, for the fraction of the engineered peptide derived from the reference target. In some embodiments, wherein the matrices represent atomic fluctuations, L is the number of amino acid positions and the (i, j) value in the atomic fluctuation matrix element is the sum of intra-molecular atomic fluctuations for the $i^{th}$ and $j^{th}$ amino acid respectively if the (i, j) atomic distance is less than or equal to 7 Å, or zero if the (i, j) atomic distance is greater than 7 Å or if (i, j) is on the diagonal. Alternatively, in some embodiments the atomic distance can serve as a weighting factor for the atomic fluctuation matrix element (i, j) instead of a 0 or 1 multiplier. In certain embodiments, the $i^{th}$ and $j^{th}$ atomic fluctuations and distances can be determined by molecular simulation (e.g. molecular dynamics) and/or laboratory measurement (e.g. NMR). In other embodiments, wherein the matrices represent adjacency, L is the number of amino acid positions and the value in adjacency matrix element (i, j) is the intra-molecular atomic distance between the $i^{th}$ and $j^{th}$ amino acid respectively if the atomic distance is less than or equal to 7 Å, or zero if the atomic distance is greater than 7 Å or if (i, j) is on the diagonal. Alternatively, in some embodiments the atomic distance can serve as a weighting factor for the adjacency matrix element (i, j) instead of a 0 or 1 multiplier. In certain embodiments, the $i^{th}$ and $j^{th}$ atomic distances could be determined by molecular simulation (e.g. molecular dynamics) and/or laboratory measurement (e.g. NMR).

Figure 48:
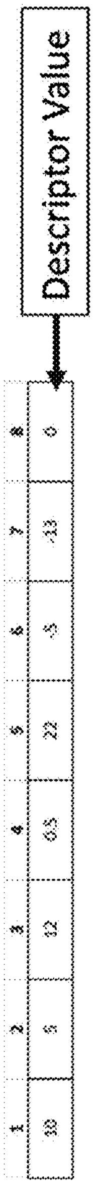
FIG. 48 is an example of a topological constraint chemical descriptor vector that can be used in the selection of an engineered peptide as described herein.

In certain embodiments, the atoms or amino acids associated with a response or function in the engineered peptide have a topological constraint chemical descriptor vector and a mean percentage error (MPE) less than 75% relative to the reference described by the same chemical descriptor, for the fraction of the engineered peptide derived from the reference target, wherein each $i^{th}$ element in the chemical descriptor vector corresponds to an amino acid position index. In some embodiments, the MPE is less than 70%, less than 65%, less than 60%, less than 55%, less than 50%, less than 45%, or less than 40% relative to the reference described by the same chemical descriptor, for the fraction of the engineered peptide derived from the reference target. An exemplary vector is presented in FIG. 48.

Figure 49:
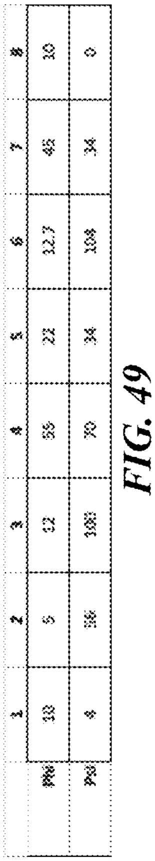
FIG. 49 is an exemplary L×2 phi/psi matrix that can be used in the selection of an engineered peptide as described herein.

In still further embodiments, the matrix is an L×2 phi/psi angel matrix, and the atoms or amino acids associated with a response or function in the engineered peptide have an MPE less than 75% with respect to the reference phi/psi angles matrix in the fraction of the engineered peptide derived from the reference target, wherein L is the number of amino acid positions and phi, psi values are in dimensions (L,1) and (L,2) respectively. In some embodiments, the MPE is less than 70%, less than 65%, less than 60%, less than 55%, less than 50%, less than 45%, or less than 40% with respect to the reference phi/psi angles matrix in the fraction of the engineered peptide derived from the reference target. In some embodiments, the phi/psi values are determined by molecular simulation (e.g. molecular dynamics), knowledge-based structure prediction, or laboratory measurement (e.g. NMR). An exemplary L×2 phi/psi matrix is shown in FIG. 49.

Figure 50:
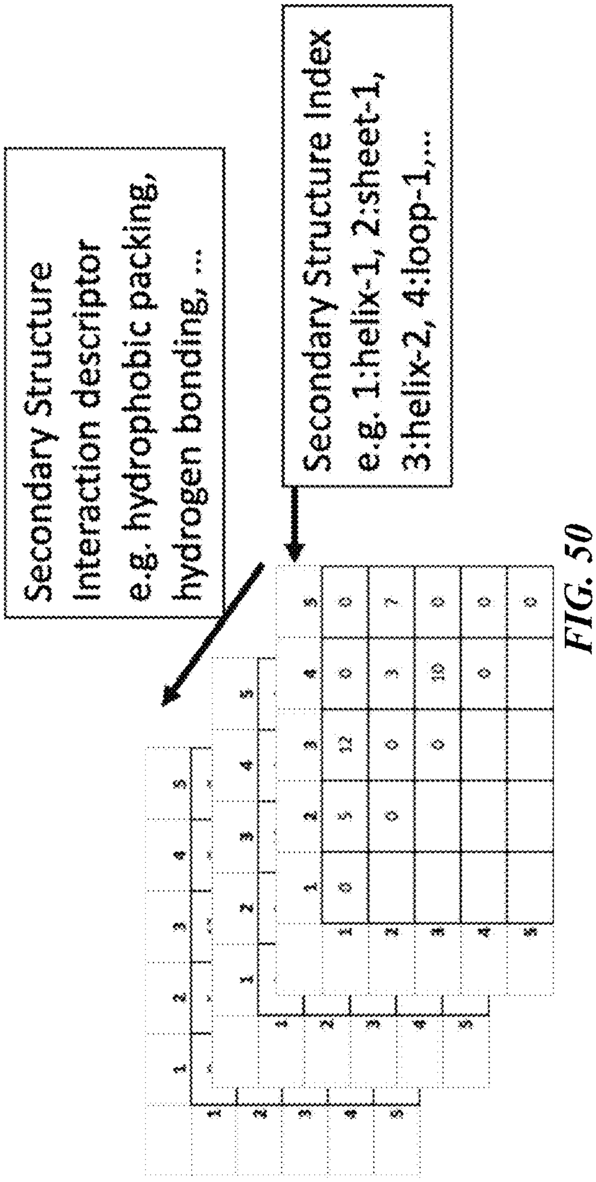
FIG. 50 is an exemplary S×S×M matrix for secondary structure interaction descriptors that can be used in the selection of an engineered peptide as described herein.

In some embodiments, the matrix is an S×S×M secondary structural element interaction matrix, and the atoms or amino acids associated with a response or function in the engineered peptide have less than 75% mean percentage error (MPE) relative to the reference secondary structural element relationship matrix, in the fraction of the engineered peptide derived from the reference target, where S is the number of secondary structural elements and M is the number of interaction descriptors. In some embodiments, the MPE is less than 70%, less than 65%, less than 60%, less than 55%, less than 50%, less than 45%, or less than 40% relative to the reference secondary structural element relationship matrix, in the fraction of the engineered peptide derived from the reference target. Interaction descriptors may include, for example, hydrogen bonding, hydrophobic packing, van der Waals interaction, ionic interaction, covalent bridge, chirality, orientation, or distance, or any combinations thereof. In the secondary structural element interaction matrix index, (i, j, m)=$m^{th}$ interaction descriptor value between the $i^{th}$ and $j^{th}$ secondary structural elements. An exemplary S×S×M matrix is presented in FIG. 50.

Mean Percentage Error (MPE) for different matrices as described herein may be calculated by:

$$\text{Mean Percentage Error } (MPE) = \frac{100\%}{n}\sum_{n}^{1}\frac{|ref_n - eng_n|}{ref_n},$$

where n is the topological constraint vector or matrix position index for the engineered peptide ($eng_n$) and the corresponding reference ($ref_n$), summed up to vector or matrix position n. An exemplary example of a topological matrix is provided in FIG. 47.

In some embodiments, the engineered peptide has an MPE of less than 75% compared to the reference target. In certain embodiments, the engineered peptide has an MPE of less than 70%, less than 65%, less than 60%, less than 55%, less than 50%, less than 45%, or less than 40% compared to the reference target. In some embodiments, the MPE is determined by Total Topological Constraint Distance (TCD), topological clustering coefficient (TCC), Euclidean distance, power distance, Soergel distance, Canberra distance, Sorensen distance, Jaccard distance, Mahalanobis distance, Hamming distance, Quantitative Estimate of Likeness (QEL), or Chain Topology Parameter (CTP).

a. Secondary Structural Element

In some embodiments, at least a portion of the engineered peptide is topologically constrained to one or more secondary structural elements. In some embodiments, the atoms or amino acids associated with a biological response or biological function in the engineered peptide are topologically constrained to one or more secondary structural elements. In some embodiments, the secondary structural element is independently a sheet, helix, turn, loop, or coil.

In some embodiments, the secondary structural element is independently an α-helix, β-bridge, β-strand, $3_{10}$ helix, π-helix, turn, loop, or coil. In certain embodiments, one or more of the secondary structural elements to which at least a portion of the engineered peptide is topologically constrained is present in the reference target. In some embodiments, at least a portion of the engineered peptide is topologically constrained to a combination of secondary structural elements, wherein each element is independently selected from the group consisting of sheet, helix, turn, loop, and coil. In still further embodiments, each element is independently selected from the group consisting of an α-helix, β-bridge, β-strand, $3_{10}$ helix, π-helix, turn, loop, and coil.

In some embodiments, the secondary structural element is a parallel or anti-parallel sheet. In some embodiments, a sheet secondary structure comprises greater than or equal to 2 residues. In some embodiments, a sheet secondary structure comprises less than or equal to 50 residues. In still further embodiments, a sheet secondary structure comprises between 2 and 50 residues. Sheets can be parallel or anti-parallel. In some embodiments, a parallel sheet secondary structure may be described as having two strands i, j in a parallel (N-termini of i and j strands opposing orientation), and a pattern of hydrogen bonding of residues i:j. In some embodiments, an anti-parallel sheet secondary structure may also be described as having two strands i, j in an anti-parallel (N-termini of i and j strands same orientation), and a pattern of hydrogen bonding of residues i:j−1, i:j+l. In certain embodiments, the orientation and hydrogen bonding of strands can be determined by knowledge-based or molecular dynamics simulation and/or laboratory measurement.

In some embodiments, the secondary structural element is a helix. Helices may be right or left handed. In some embodiments, the helix has a residue per turn (residues/turn) value of between 2.5 and 6.0, and a pitch between 3.0 Å and 9.0 Å. In some embodiments, the residues/turn and pitch are determined by knowledge-based or molecular dynamics simulation and/or laboratory measurement.

In some embodiments, the secondary structural element is a turn. In some embodiments, a turn comprises between 2 to 7 residues, and 1 or more inter-residue hydrogen bonds. In some embodiments, the turn comprises 2, 3, or 4 inter-residue hydrogen bonds. In certain embodiments, the turn is determined by knowledge-based or molecular dynamics simulation and/or laboratory measurement.

In still further embodiments, the secondary structural element is a coil. In certain embodiments, the coil comprises between 2 to 20 residues and zero predicted inter-residue hydrogen bonds. In some embodiments, these coil parameters are determined by knowledge-based or molecular dynamics simulation and/or laboratory measurement.

Figure 53:
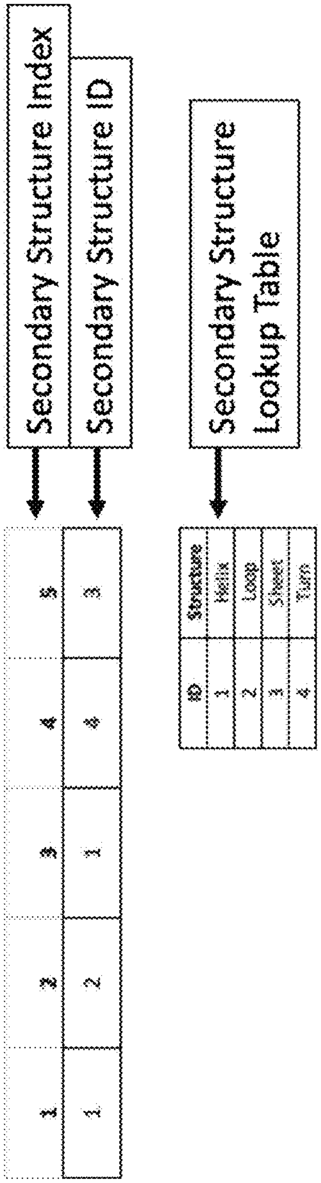
FIG. 53 is an exemplary secondary structure index and lookup table that can be used in the selection of an engineered peptide as described herein.
Figure 54:
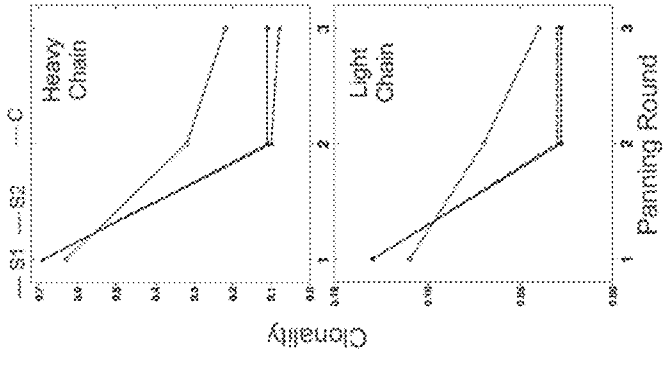
FIG. 54 is another representation of the data obtained from the VEGF panning programs. S1 refers to anti-VEGF Panning Program 6, S2 refers to anti-VEGF Panning Program 13, and C is the conventional full length VEGF program.
Figure 55:
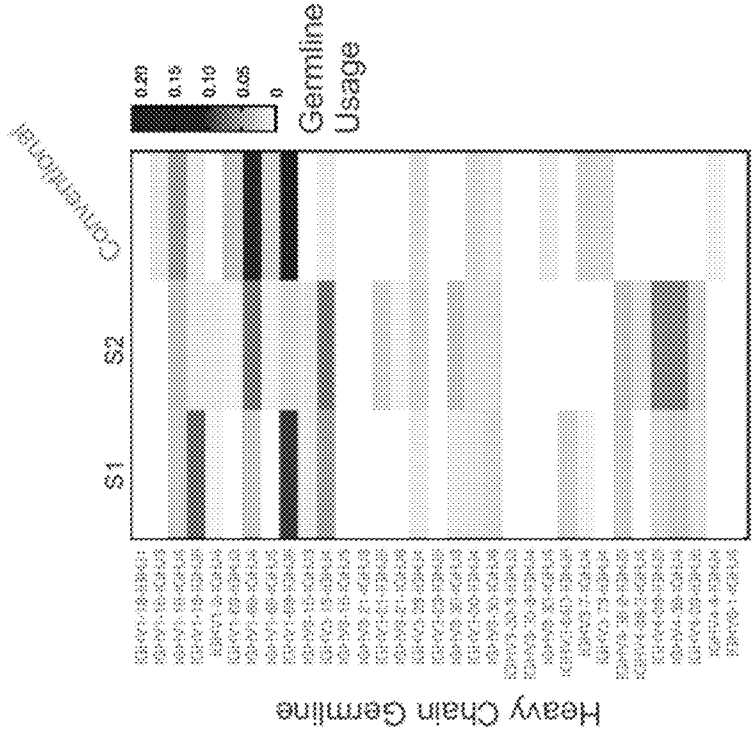
FIG. 55 is another representation of the data provided in FIG. 24I. S1 refers to anti-VEGF Panning Program 6, S2 refers to anti-VEGF Panning Program 13, and C is the conventional full length VEGF program.
Figure 56:
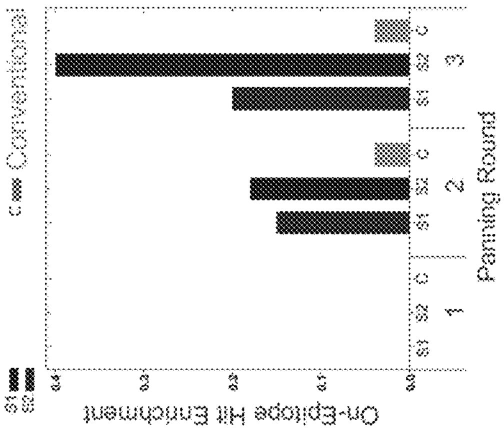
FIG. 56 is another representation of the data provided in FIG. 26. S1 refers to anti-VEGF Panning Program 6, S2 refers to anti-VEGF Panning Program 13, and C is the conventional full-length VEGF program.
Figure 57A:
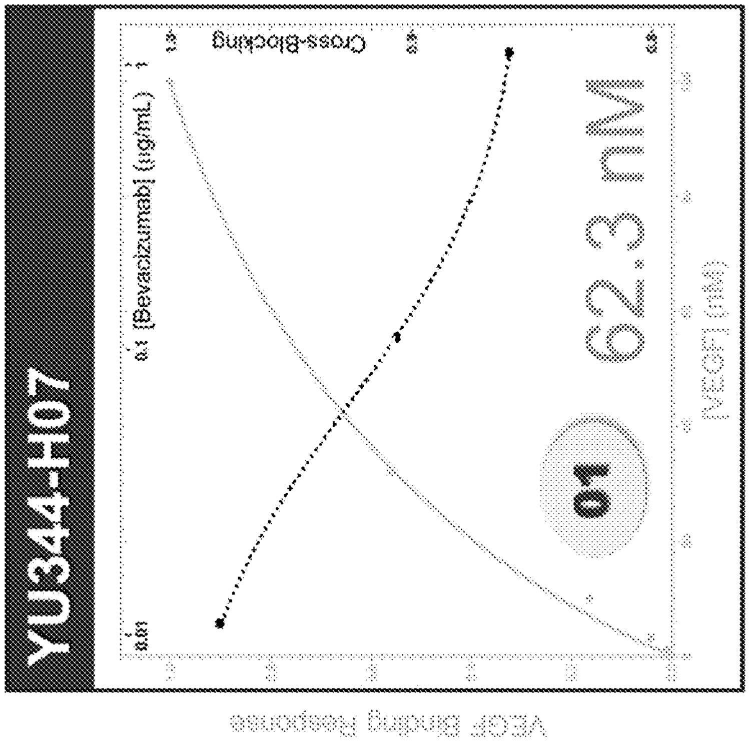
FIGS. 57A-57E are graphs of the VEGF (gray solid line) and cross-blocking (dotted line) binding data for selected on-epitope clones from programmed in vitro selection.
Figure 57B:
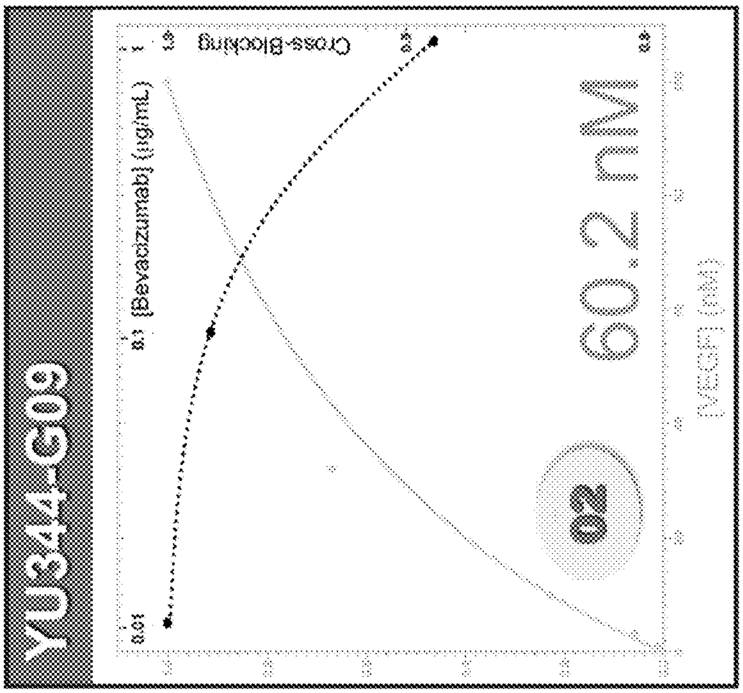
Figure 57C:
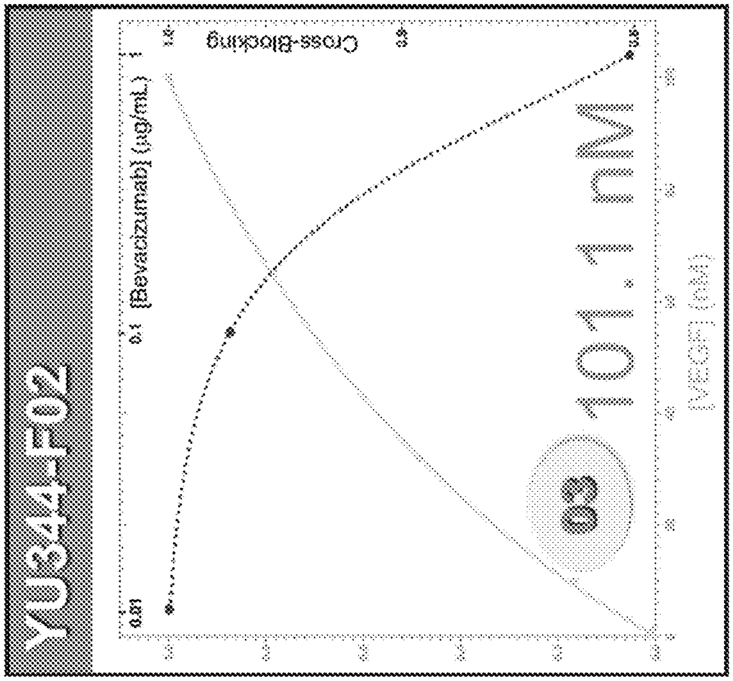
Figure 57D:
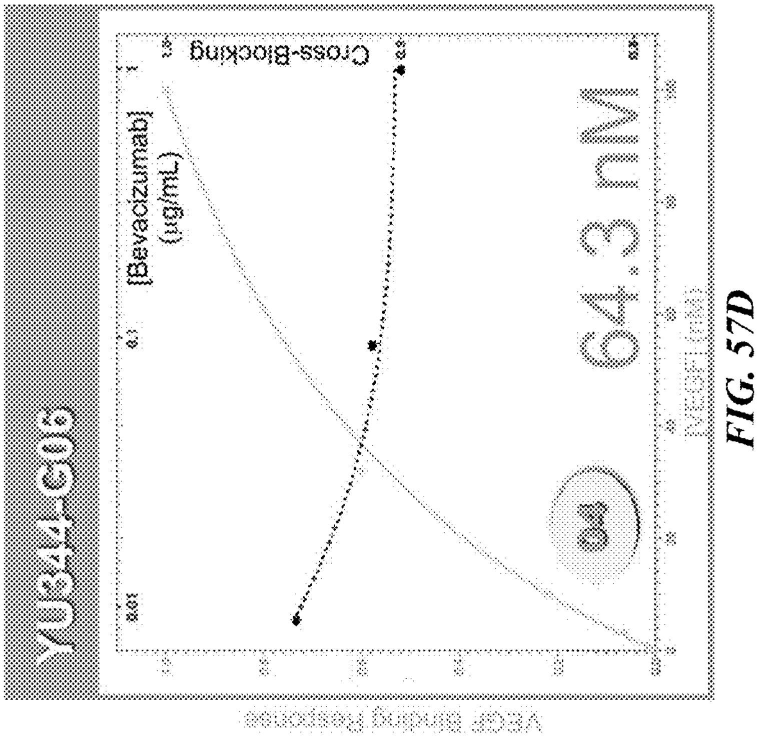
Figure 57E:
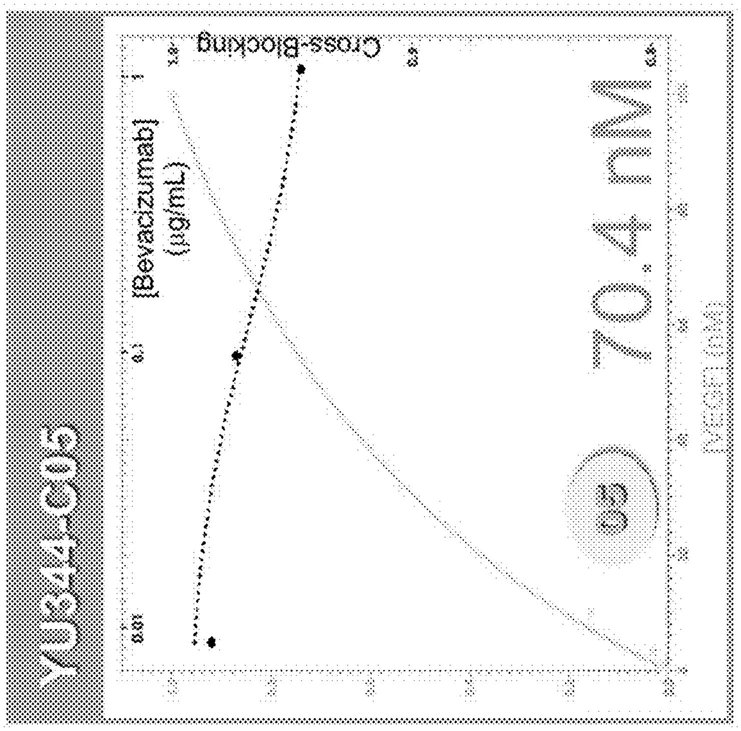
Figure 58A:
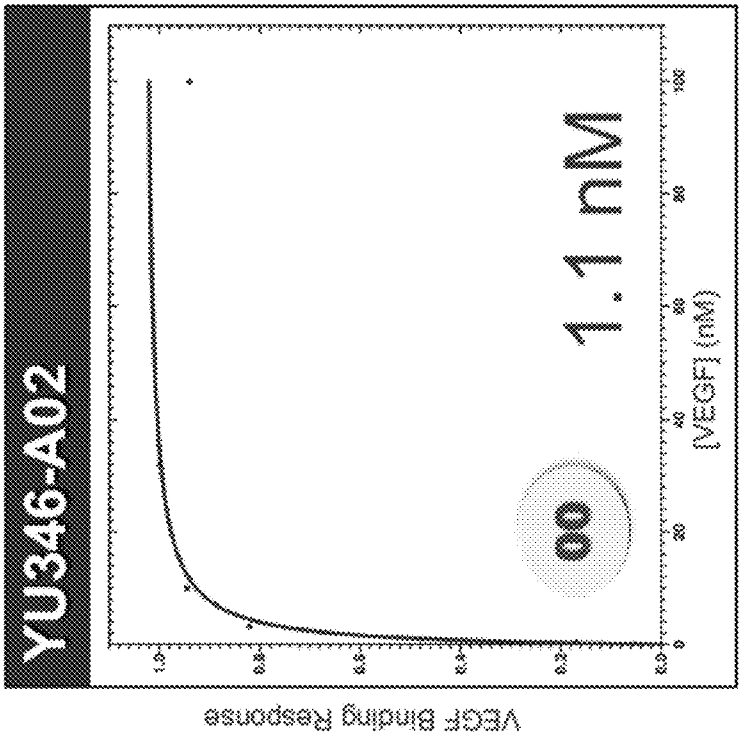
FIGS. 58A-58C are graphs of VEGF binding data for off-epitope selected clones from full length in vitro selection.
Figure 58C:
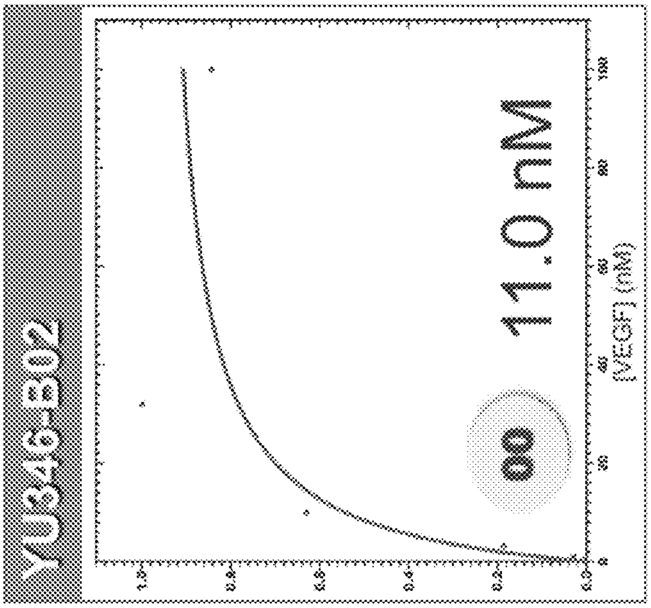
Figure 58B:
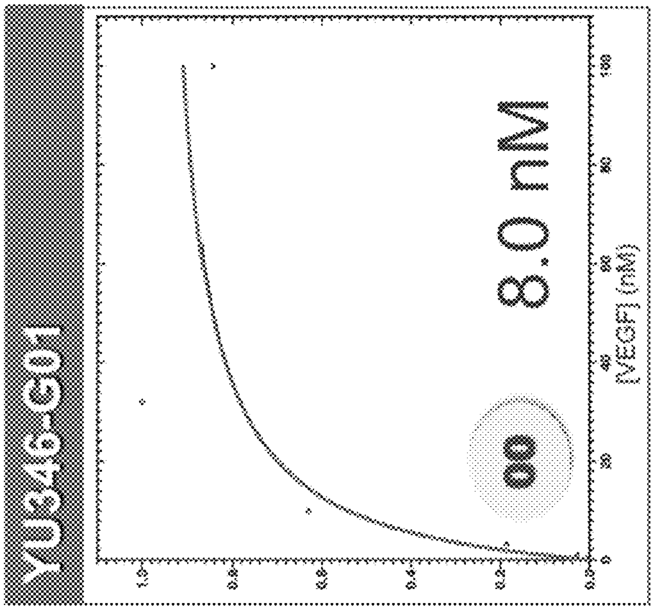
Figure 59B:
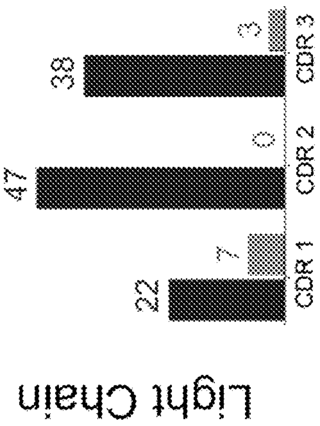
FIG. 59A-59B summarize the antibody clone hits CDR loop sequence diversity for anti-VEGF programmed in vitro selection (red) and conventional in vitro selection (gray).
Figure 59A:
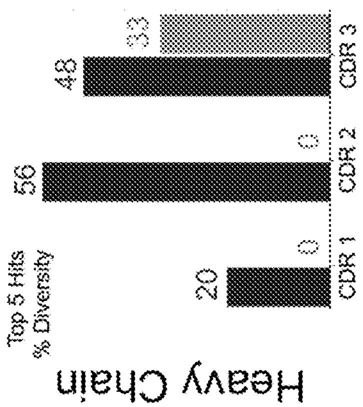
Figure 60:
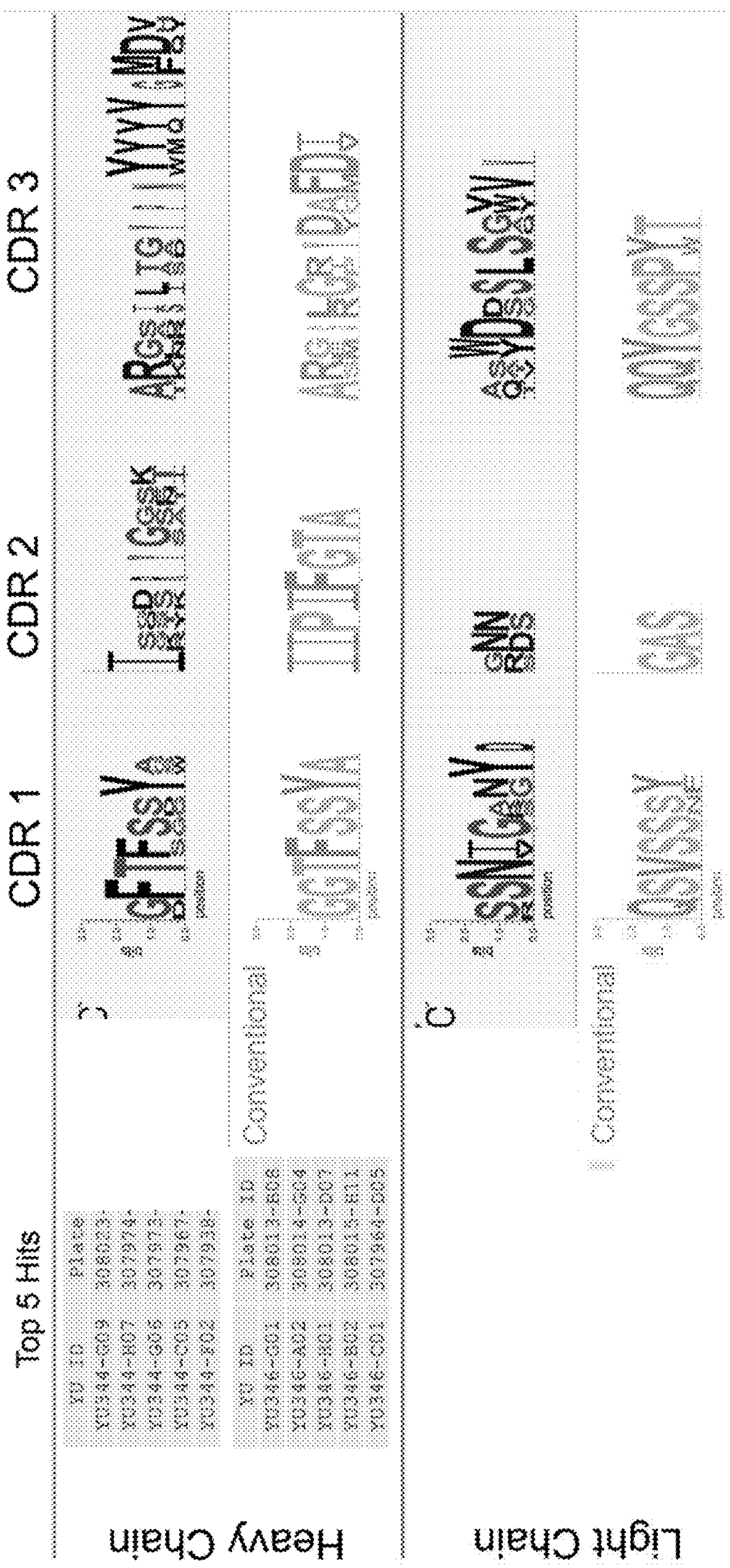
FIG. 60 is a sequence alignment of clones selected using the programmable in vitro selection methods described herein, using exemplary engineered peptides as described herein. The top row is an alignment of heavy chain sequences of the top five on-epitope clones selected across all programmed in vitro selection programs; the second row is an alignment of heavy chain sequences of the top five off-epitope clones selected using a conventional approach, using VEGF and BSA as selection molecules; the third row is an alignment of light chain sequences of the top five on-epitope clones selected across all programmed in vitro selection programs; and the bottom row is an alignment of light chain sequences of clones selected using the conventional approach with VEGF and BSA.

In still further embodiments, the engineered peptide comprises one or more atoms or amino acids derived from the reference target, wherein said atoms or amino acids have a secondary structure. In some embodiments, these atoms or amino acids are associated with a biological response or biological function. In some embodiments, the secondary structure motif vector of the atoms or amino acids in the engineered peptide has a cosine similarity greater than 0.25 relative to the reference target secondary structure motif vector for the fraction of the engineered peptide derived from the reference target, wherein the length of the vector is the number of secondary structure motifs and the value at the $i^{th}$ vector position defines the identity of the secondary structure motif (e.g. helix, sheet) derived from a lookup table. In some embodiments, each motif comprises two or more amino acids. In certain embodiments, motifs include, for example, α-helix, β-bridge, β-strand, $3_{10}$ helix, π-helix, turn, and loop. In some embodiments, the cosine similarity is greater than 0.3, greater than 0.35, greater than 0.4, greater than 0.45, or greater than 0.5 relative to the reference target secondary structure motif vector for the fraction of the engineered peptide derived from the reference target. An exemplary secondary structure index and lookup table is provided in FIG. 53. Cosine similarity may be calculated by:

$$\text{Cosine Similarity} = \frac{\sum_{i=1}^{n} A_i B_i}{\sqrt{\sum_{i=1}^{n} A_i^2}\sqrt{\sum_{i=1}^{n} B_i^2}}$$

wherein A is the peptide vector of secondary structure motif identifiers, B is the reference vector of secondary structure motif identifiers, n is the length of the secondary structure motif vector, and i is the $i^{th}$ secondary structure motif.

In some embodiments, one or more atoms or amino acids of the engineered peptide which are derived from the reference target can be compared to the corresponding reference target atoms or amino acids using a total topological constraint distance (TCD). In some embodiments, the total TCD of said engineered peptide atoms or amino acids derived from the reference target is +/−75% relative to the TCD distance of the corresponding atoms in the reference target, wherein two intra-molecule topological constraints are interacting if their pairwise distance is less than or equal to 7 Å. In some embodiments, the atoms or amino acids in the engineered peptide being compared are associated with a biological function or biological response. The $i^{th}$, $j^{th}$ pairwise distance of two atoms or amino acids can, in some embodiments, be determined by molecular simulation (e.g. molecular dynamics) and/or laboratory measurement (e.g. NMR). An exemplary equation for calculating total topological constraint distance (TCD) is:

$$\frac{1}{L^2}\sum_{i<j}^{i=1:L} |S_{ij}|\Delta_{ij},$$

where i, j are the intra-molecular position indices for amino acids (i, j), $S_{ij}$ is the difference between constraints S(i) and S(j), Δ(i,j)=1 if amino acids (i, j) are within the 7 Å interaction threshold, and L is the number of amino acid positions in the peptide or the corresponding reference target. Alternatively, in some embodiments, Δ(i,j) can serve as a weighting factor for the $S_{ij}$ difference instead of a 0 or 1 multiplier.

In some embodiments, one or more atoms or amino acids of the engineered peptide which are derived from the reference target can be compared to the corresponding reference target atoms or amino acids using a chain topology parameter (CTP). In some embodiments, the CTP of said engineered peptide atoms or amino acids is +/−50% relative to the CTP of the corresponding atoms or amino acids in the reference target, wherein intra-chain topological interaction is a pairwise distance less than or equal to 7 Å. In some embodiments, the atoms or amino acids in the engineered peptide being compared are associated with a biological function or biological response. In some embodiments, $i^{th}$, $l^{th}$ pairwise distance can be determined by molecular simulation (e.g. molecular dynamics) and/or laboratory measurement (e.g. NMR): An exemplary equation for evaluating CTP is:

$$\text{Chain Topology Parameter}\,(CTP) = \frac{1}{L \cdot N} \sum_{i<j}^{i=1:L} S_{ij}^2 \Delta_{ij},$$

where i, j are the position indices for amino acids (i, j), $S_{ij}$ is the difference between topological constraints S(i) and S(j), Δ(i,j)=1 if amino acids (i, j) are within the 7 Å chain topological interaction threshold, L is the number of amino acid positions in the peptide or the corresponding reference target, and N is the total number of intra-chain contacts that meet the 7 Å topological interaction threshold in the engineered peptide or reference target. Alternatively, in some embodiments Δ(i,j) can serve as a weighting factor for the $S_{ij}$ difference instead of a 0 or 1 multiplier.

In some embodiments, one or more atoms or amino acids of the engineered peptide which are derived from the reference target can be compared to the corresponding reference target atoms or amino acids using a quantitative estimate of likeness (QEL). In some embodiments, the QEL of said engineered peptide atoms or amino acids is +/−50% relative to the QEL of the corresponding atoms or amino acids in the reference target. In some, embodiments, the atoms or amino acids in the engineered peptide being compared are associated with a biological function or biological response. An exemplary equation for determining QEL is:

$$\text{Quantitative Estimate of Likeness}\,(QEL) = \exp\left(\frac{1}{n}\sum_{i=1}^{n} \ln di\right),$$

wherein di is a topological constraint for the $i^{th}$ amino acid or atom position, or a composition function (e.g. linear regression function) that combines multiple topological constraints for the $i^{th}$ amino acid or atom position, and n is the number of amino acid or atom positions in the peptide or the reference target.

Figure 51:
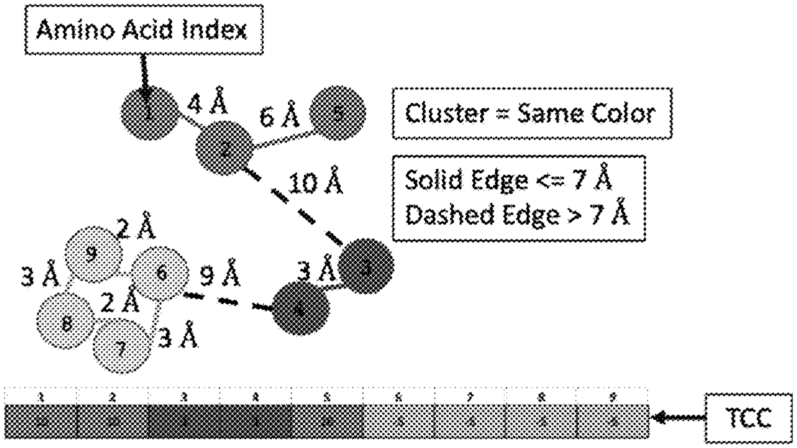
FIG. 51 is an exemplary diagram showing clusters and TCC vector for an exemplary engineered peptide that can be used in the selection of an engineered peptide as described herein.

In some embodiments, one or more atoms or amino acids of the engineered peptide which are derived from the reference target can be compared to the corresponding reference target atoms or amino acids using a topological clustering coefficient (TCC) vector and a mean percentage error (MPE). In some embodiments, the TCC vector and MPE is less than 75% relative to the TCC of the corresponding atoms or amino acids in the reference target, wherein each element (i) of the vector is a topological clustering coefficient for the $i^{th}$ amino acid position, intra-molecule clusters are defined by an interacting edge distance less than or equal to 7 Å, and two edges: i-j, j−1 from the $i^{th}$ amino acid position. In some embodiments, the atoms or amino acids in the engineered peptide being compared are associated with a biological function or biological response. In some embodiments, the $i^{th}$, j and $l^{th}$ edge distance can be determined by molecular simulation (e.g. molecular dynamics) and/or laboratory measurement (e.g. NMR). An exemplary equation for evaluating the topological clustering coefficient for the $i^{th}$ position is:

$$\text{Topological Clustering Coefficient for the } i^{th} \text{ position } (TCC_i) = \frac{{}^{i=1:L} S_{ijl}\Delta_{ij}\Delta_{il}\Delta_{jl}}{N_c(N_c-1)/2},$$

wherein Δ(i,j)=1, Δ(i,l)=1, Δ(j,l)=1 if intra-molecular amino acid positions: (i, j), (i, l), (j, l) are within the 7 Å interacting edge threshold respectively, $S_{iji}$ is the combination (e.g. sum) of topological constraints for the $i^{th}$, $j^{th}$ and $l^{th}$ amino acid, L is the number of amino acid positions in the peptide vector or corresponding reference target vector, Nc is the number of intra-molecular interacting amino acid positions for the $i^{th}$ amino acid, meeting the 7 Å edge threshold and two edges: i-j, j−1 from the $i^{th}$ amino acid. Alternatively, in some embodiments, Δ(i,j), Δ(i,l) and Δ(j,l) can serve as weighting factors for the clustering coefficient vector element (i) instead of a 0 or 1 multiplier. An exemplary diagram showing clusters and TCC vector for an exemplary engineered peptide is provided in FIG. 51.

Figure 52:
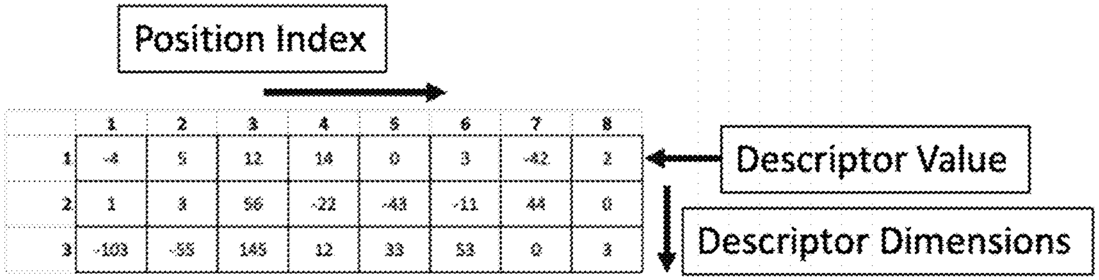
FIG. 52 is an exemplary LxM topological constraint matrix that can be used in the selection of an engineered peptide as described herein.

In still further embodiments, one or more atoms or amino acids of the engineered peptide which are derived from the reference target can be compared to the corresponding reference target atoms or amino acids using an L×M topological constraint matrix and mean percentage error (MPE) of: Euclidean distance, power distance, Soergel distance, Canberra distance, Sorensen distance, Jaccard distance, Mahalanobis distance, or Hamming distance across all M-dimensions. The L×M matrix element (l, m) contains the $m^{th}$ constraint value for the $l^{th}$ amino acid position, wherein L is the number of amino acid positions and M is the number of distinct topological constraints. In some embodiments, the MPE of the engineered peptide L×M matrix is less than 75% relative to the matrix of the corresponding reference target atoms or amino acids. In some embodiments, the MPE is less than 70%, less than 65%, less than 60%, less than 55%, less than 50%, or less than 45%. In some embodiments, the atoms or amino acids in the engineered peptide being compared are associated with a biological function or biological response. An exemplary L×M matrix is provided in FIG. 52.

III. Programmable In Vitro Selection

In other aspects, further provided herein are methods of using the engineered peptides described herein in selecting binding partners using a series of programmed selection steps, wherein at least one selection step includes evaluating the interactions of a pool of potential binding partners with an engineered peptide.

Figure 5:
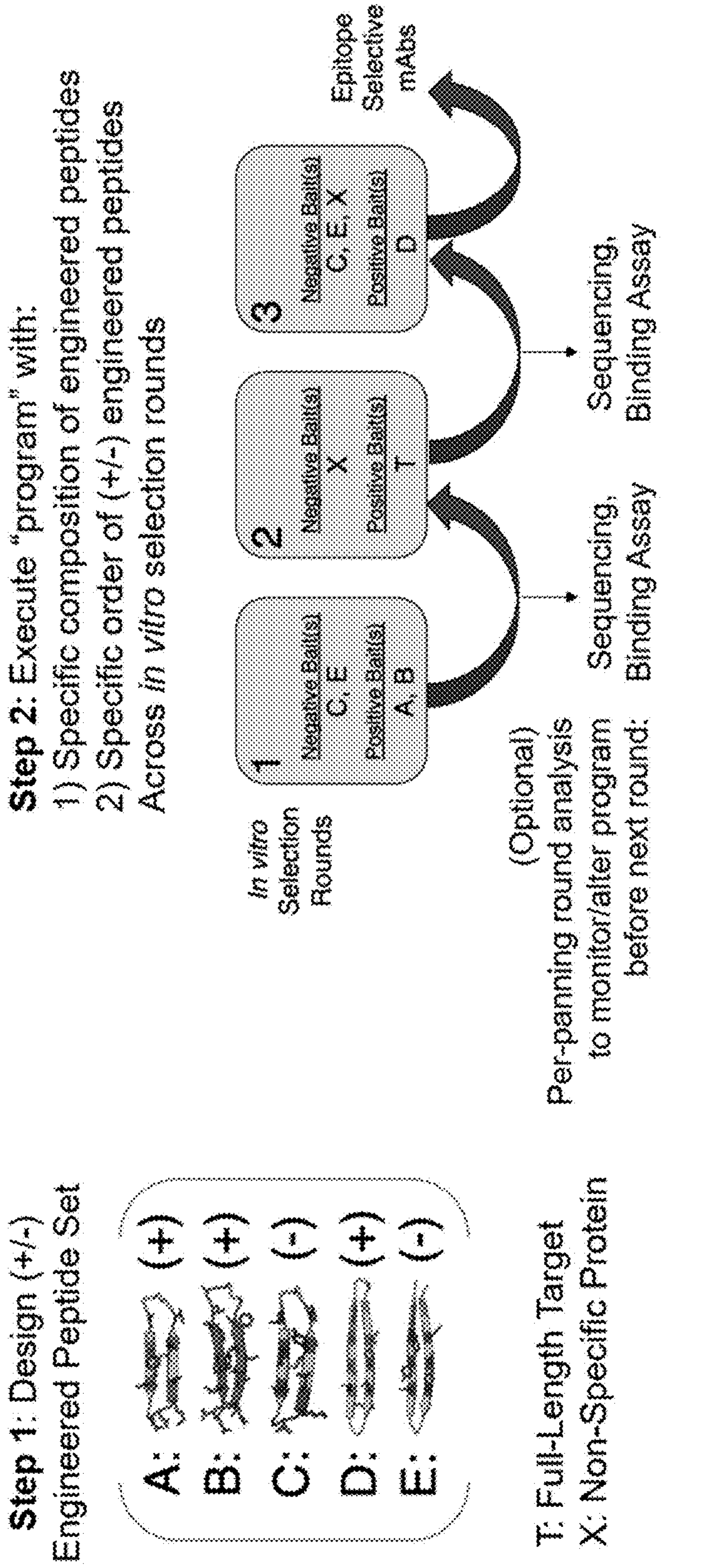
FIG. 5 is a schematic providing an overview of the design of an exemplary programmable in vitro selection using engineered peptides as described herein, and also using native proteins as positive (T) or negative (X) selection molecules.

In some embodiments, provided herein are methods of steering the selection of a binding molecule using two or more selection molecules. In some embodiments, the methods include subjecting a pool of candidate binding molecules to at least one round of selection, wherein each round comprises at least one negative selection step wherein at least a portion of the pool is screened against a negative selection molecule, and at least one positive selection step wherein at least a portion of the pool is screened against a positive selection molecule. In some embodiments the method comprises at least two rounds, at least three rounds, at least four rounds, at least five rounds, at least six rounds, at least seven rounds, at least eight rounds, at least nine rounds, at least ten rounds, or more, wherein each round independently comprises at least one negative selection step and at least one positive selection step. In some embodiments, each round independently comprises more than one negative selection step, or more than one positive selection step, or a combination thereof. FIG. 5 provides an exemplary schematic detailing three rounds of selection, wherein the first and third round comprise more than one negative selection step, and the first round further comprises more than one positive selection round. As shown in the scheme, two negative selection molecules ("baits") are used in the first round, and three negative selection molecules are used in the third round. In addition, two positive selection molecules are used in the first round.

In some embodiments wherein the method comprises more than one round, each negative and positive selection molecule is independently chosen. In other embodiments, the same negative selection molecule, or the same positive selection molecule, or a combination thereof, may be used in more than one round. For example, in FIG. 5, the same negative selection molecules used in round 1 are used again in round 3, with an additional third negative selection molecule also included in round 3. The order of negative and positive selection steps may be, in certain embodiments, independently chosen within each round of selection. Thus, for example, in some embodiments, the method comprises one or more rounds of selection, wherein each round comprises first a negative selection step, and then a positive selection step. In other embodiments, the method comprises one or more rounds of selection, wherein each round comprises first a positive selection step, and then a negative selection step. In still further embodiments, the method comprises one or more rounds of selection, wherein each round independently comprise a negative selection step and a positive selection step, wherein in each round the negative selection step is independently before the positive selection step or after the positive selection step.

Such methods of selection use positive (+) and negative (−) steps to steer the library of candidate binding molecules towards and away from certain desired characteristics, such as binding specificity or binding affinity. By using multiple steps with both positive and negative selection molecules, the pool of candidates can be directed in a stepwise manner to select for characteristics that are desirable and against characteristics that are undesirable. Further, in some embodiments the order of each step within each round, and the order of the rounds relative to each other can direct the selection in different directions. Thus, for example, in some embodiments a method comprising one round with (+) selection followed by (−) selection will result in a different final pool of candidates than if (−) selection is first, followed by (+) selection. Extrapolating this out to methods comprising multiple rounds, the order of selection steps may result in a different final pool of selected candidates even if the same positive and negative selection molecules are used overall.

In some embodiments a selection molecule is used that has in inverse characteristic of another selection molecule. This may be useful, for example, to ensure that the candidate binding partners identified using the positive selection molecule (or excluded because of a negative selection molecule) were identified (or excluded) because of a desired trait (or undesired trait), not because of a separate, unrelated binding interaction. To remove binding partners that are binding through unrelated interactions, an inverse selection molecule can be used that has similar or the same structure and characteristics as the selection molecule, except for the residues/structures conveying the desired trait (or undesired trait). For example, if interaction with a particular charge pattern in a positive selection molecule is desired, an inverse negative selection molecule may be used that has replaced the residues providing that charge pattern with uncharged residues, and/or residues of the opposite charge. Thus, for certain selection molecules, multiple different corresponding inverse selection molecules may be possible.

In the selection methods provided herein, at least one of the selection molecules is an engineered peptide as described herein. In some embodiments, more than one engineered peptide is used. In some embodiments, each engineered peptide is independently a positive or negative selection molecule. In certain embodiments, each selection molecule used in the one or more rounds of selection is independently an engineered peptide. In other embodiments, at least one molecule that is not an engineered peptide is used as a selection molecule. Such selection molecules that are not engineered peptides may comprise, for example, a naturally-occurring polypeptide, or a portion thereof. In other embodiments, one or more selection molecules that are not engineered peptides may comprise, for example, a non-naturally occurring polypeptide or portion thereof. For example, in some embodiments one or more selection molecules (e.g., positive selection molecule or negative selection molecule) is an immunogen, an antibody, cell-surface receptor, or a transmembrane protein, or a signaling protein, or a multiprotein complex, or a peptide-protein complex, or any portions thereof, or any combinations thereof. In some embodiments, one or more selection molecules is PD-1, PD-L1, CD25, IL2, MIF, CXCR4, or VEGF, or a portion of any of these, or an antibody to any of these (such as Bevacizumab, Avelumab, or Durvalumab).

The positive and negative characteristics being selected for or against in each step may be selected from a variety of traits, and may be tailored depending on the desired features of the final one or more binding molecules obtained. Such desired features may depend, for example, on the intended use of the one or more binding molecules. For example, in some embodiments the methods provided herein are used to screen antibody candidates for one or more positive characteristics such as high specificity, and against one or more negative characteristics such as cross-reactivity. It should be understood that what is considered a positive characteristic in one context might be a negative characteristic in another context, and vice versa. Thus, a positive selection molecule in one series of selection rounds may, in some embodiments, be a negative selection molecule in a different series of selection rounds, or in selecting a different type of binding molecule, or in selecting the same type of binding molecule but for a different purpose.

In some embodiments, each selection characteristic is independently selected from the group consisting of amino acid sequence, polypeptide secondary structure, molecular dynamics, chemical features, biological function, immunogenicity, reference target(s) multi-specificity, cross-species reference target reactivity, selectivity of desired reference target(s) over undesired reference target(s), selectivity of reference target(s) within a sequence and/or structurally homologous family, selectivity of reference target(s) with similar protein function, selectivity of distinct desired reference target(s) from a larger family of undesired targets with high sequence and/or structurally homology, selectivity for distinct reference target alleles or mutations, selectivity for distinct reference target residue level chemical modifications, selectivity for cell type, selectivity for tissue type, selectivity for tissue environment, tolerance to reference target(s) structural diversity, tolerance to reference target(s) sequence diversity, and tolerance to reference target(s) dynamics diversity. In some embodiments, each selection characteristic is a different type of selection characteristic. In other embodiments, two or more selection characteristics are different characteristics but of the same type. For example, in some embodiments, two or more selection characteristics are polypeptide secondary structure, wherein one is a positive selection for a desired polypeptide secondary structure and one is a negative selection for an undesired polypeptide secondary structure. In some embodiments, two or more selection characteristics are selectivity for cell type, wherein a positive selection characteristic is selectivity for a specific desired cell type, and a negative selection characteristic is selectivity for a specific undesired cell type. In some embodiments, two or more, three or more, four or more, five or more, or six or more selection characteristics are of the same type.

In yet another aspect, provided herein is a composition comprising two or more selection steering polypeptides, wherein each polypeptide is independently a positive selection molecule comprising one or more positive steering characteristics, or a negative selection molecule comprising one or more negative steering characteristics. Such characteristics may, in some embodiments, be selected from the group consisting of amino acid sequence, polypeptide secondary structure, molecular dynamics, chemical features, biological function, immunogenicity, reference target(s) multi-specificity, cross-species reference target reactivity, selectivity of desired reference target(s) over undesired reference target(s), selectivity of reference target(s) within a sequence and/or structurally homologous family, selectivity of reference target(s) with similar protein function, selectivity of distinct desired reference target(s) from a larger family of undesired targets with high sequence and/or structurally homology, selectivity for distinct reference target alleles or mutations, selectivity for distinct reference target residue level chemical modifications, selectivity for cell type, selectivity for tissue type, selectivity for tissue environment, tolerance to reference target(s) structural diversity, tolerance to reference target(s) sequence diversity, and tolerance to reference target(s) dynamics diversity.

Thus, in further aspects, provided herein is a method of screening a library of binding molecules with a selection steering composition as described herein, wherein each round of selection comprises: a negative selection step of screening at least a portion of the pool against a negative selection molecule; and a positive selection step of screening at least a portion of the pool for a positive selection molecule; wherein the order of selection steps within each round, and the order of rounds, result in the selection of a different subset of the pool than an alternative order.

In some embodiments, the binding partners being evaluated using the composition of selection steering polypeptides as described herein, or the methods of screening as described herein, are a phage library, for example a Fab-containing phage library; or a cell library, for example a B-cell library or a T-cell library.

In some embodiments of the methods of screening provided herein, the methods comprise two or more, three or more, four or more, five or more, six or more, or seven or more rounds of selection. In some embodiments, wherein there is more than one round, each round comprises a different set of selection molecules. In other embodiments, wherein there is more than one round, at least two rounds comprise the same negative selection molecule, the same positive selection molecule, or both.

In some embodiments of the screening methods, the method comprises analyzing the subset of the pool prior to proceeding to the next round of selection. In certain embodiments, each subset pool analysis is independently selected from the group consisting of peptide/protein biosensor binding, peptide/protein ELISA, peptide library binding, cell extract binding, cell surface binding, cell activity assay, cell proliferation assay, cell death assay, enzyme activity assay, gene expression profile, protein modification assay, Western blot, and immunohistochemistry. In some embodiments, gene expression profile comprises full sequence repertoire analysis of the subset pool, such as next-generation sequencing. In some embodiments, statistical and/or informatic scoring, or machine learning training is used to evaluate one or more subsets of the pool in one or more selection rounds.

In some embodiments, the identity and/or order of positive and/or negative selection molecules for a subsequent round is determined by analyzing a subset pool from one selection round. In some embodiments, statistical and/or informatic scoring, or machine learning training, is used to evaluate one or more subsets of the pool in one or more selection rounds to determine the identity and/or order of the positive and/or negative selection molecules for a subsequent round (such as the next round, or a round further along in the program).

In still further embodiments, the methods of selection include modifying a subset pool obtained from a selection round before proceeding to the next selection round. Such modifications may include, for example, genetic mutation of the subset pool, genetic depletion of the subset pool (e.g., selecting a subset of the subset pool to move forward in selection), genetic enrichment of the subset pool (e.g., increasing the size of the pool), chemical modification of at least a portion of the subset pool, or enzymatic modification of at least a portion of the subset pool, or any combinations thereof. In some embodiments, statistical and/or informatic scoring, or machine learning training is used to evaluate a subset pool and determine the one or more modifications to make prior to moving the modified subset pool forward in selection. In certain embodiments, such statistical and/or informatic scoring, or machine learning training, is also used to determine the identity and/or order of positive and/or negative selection molecules for a subsequent round of selection.

Any suitable assay may be used to evaluate the binding of a pool of binding partners with the selection molecules in each step. In some embodiments, binding is directly evaluated, for example by directly detecting a label on the binding partner. Such labels may include, for example, fluorescent labels, such as a fluorophore or a fluorescent protein. In other embodiments, binding is indirectly evaluated, for example using a sandwich assay. In a sandwich assay, a binding partner binds to the selection molecule, and then a secondary labeled reagent is added to label the bound binding partner. This secondary labeled reagent is then detected. Examples of sandwich assay components include His-tagged-binding partner detected with an anti-His-tag antibody or His-tag-specific fluorescent probe; a biotin-labeled binding partner detected with labeled streptavidin or labeled avidin; or an unlabeled binding partner detected with an anti-binding-partner antibody.

In some embodiments, the binding partners being selected in each step are identified based on the binding signal, or dose-response, using any number of available detection methods. These detection methods may include, for example, imaging, fluorescence-activated cell sorting (FACS), mass spectrometry, or biosensors. In some embodiments, a hit threshold is defined (for example the median signal), and any with signal above that signal is flagged as a putative hit motif.

IV. Use of Engineered Peptides to Produce Antibodies

The engineered peptides provided herein, and identified by the methods provided herein, may be used, for example, to produce one or more antibodies. In some embodiments, the antibody is a monoclonal or polyclonal antibody. Thus, in some embodiments, provided herein is an antibody produced by immunizing an animal with an immunogen, wherein the immunogen is an engineered peptide as provided herein. In some embodiments, the animal is a human, a rabbit, a mouse, a hamster, a monkey, etc. In certain embodiments, the monkey is a cynomolgus monkey, a macaque monkey, or a rhesus macaque monkey. Immunizing the animal with an engineered peptide can comprise, for example, administering at least one dose of a composition comprising the peptide and optionally an adjuvant to the animal. In some embodiments, generating the antibody from an animal comprises isolating a B cell which expresses the antibody. Some embodiments further comprise fusing the B cell with a myeloma cell to create a hybridoma which expresses the antibody. In some embodiments, the antibody generated using the engineered peptide can cross react with a human and a monkey, for example a cynomolgus monkey.

The description provided herein sets forth numerous exemplary configurations, methods, parameters, and the like. It should be recognized, however, that such description is not intended as a limitation on the scope of the present disclosure, but is instead provided as a description of exemplary embodiments.

Exemplary Embodiments

Embodiment I-1. An engineered peptide, wherein the engineered peptide has a molecular mass of between 1 kDa and 10 kDa and comprises up to 50 amino acids, and wherein the engineered peptide comprises:

- a combination of spatially-associated topological constraints, wherein one or more of the constraints is a reference target-derived constraint; and
- wherein between 10% to 98% of the amino acids of the engineered peptide meet the one or more reference target-derived constraints,
- wherein the amino acids that meet the one or more reference target-derived constraints have less than 8.0 Å backbone root-mean-square deviation (RSMD) structural homology with the reference target.

Embodiment I-2. The engineered peptide of embodiment I-1, wherein the amino acids that meet the one or more reference target-derived constraints have between 10% and 90% sequence homology with the reference target.

Embodiment I-3. The engineered peptide of embodiment I-1 or 1-2, wherein the amino acids that meet the one or more reference target-derived constraints have a van der Waals surface area overlap with the reference of between 30 $Å^2$ to 3000 $Å^2$.

Embodiment I-4. The engineered peptide of any one of embodiments I-1 to I-3, wherein the combination comprises at least two reference target-derived constraints.

Embodiment I-5. The engineered peptide of any one of embodiments I-1 to I-4, wherein the combination comprises at least five reference target-derived constraints.

Embodiment I-6. The engineered peptide of any one of embodiments I-1 to I-5, wherein the combination of constraints comprises one or more constraints not derived from a reference target.

Embodiment I-7. The engineered peptide of embodiment I-6, wherein the one or more non-reference target-derived constraints describes a desired structural, dynamical, chemical, or functional characteristic, or any combinations thereof.

Embodiment I-8. The engineered peptide of any one of embodiments I-1 to I-7, wherein the constraints are independently selected from the group consisting of:

- atomic distances;
- atomic fluctuations;
- atomic energies;
- chemical descriptors;
- solvent exposures;
- amino acid sequence similarity;
- bioinformatic descriptors;
- non-covalent bonding propensity;
- phi angles;
- psi angles;
- van der Waals radii;
- secondary structure propensity;
- amino acid adjacency; and
- amino acid contact.

Embodiment I-9. The engineered peptide of any one of embodiments I-1 to I-8, wherein one or more constraints is independently an atomic fluctuation.

Embodiment I-10. The engineered peptide of any one of embodiments I-1 to I-9, wherein one or more constraints is independently a chemical descriptor.

Embodiment I-11. The engineered peptide of any one of embodiments I-1 to I-10, wherein one or more constraints is independently atomic distance.

Embodiment I-12. The engineered peptide of any one of embodiments I-1 to I-11, wherein one or more constraints is independently secondary structure.

Embodiment I-13. The engineered peptide of any one of embodiments I-1 to I-12, wherein one or more constraints is independently van der Waals surface.

Embodiment I-14. The engineered peptide of any one of embodiments I-1 to I-13, wherein one or more constraints is independently associated with a biological response or biological function.

Embodiment I-15. The engineered peptide of any one of embodiments I-1 to I-14, comprising one or more atoms associated with a biological response or biological function.

Embodiment I-16. The engineered peptide of any one of embodiments I-1 to I-15, comprising one or more amino acids associated with a biological response or biological function.

Embodiment I-17. The engineered peptide of any one of embodiments I-14 to I-16, wherein the biological response or biological function is selected from the group consisting of gene expression, metabolic activity, protein expression, cell proliferation, cell death, cytokine secretion, kinase activity, epigenetic modification, cell killing activity, inflammatory signals, chemotaxis, tissue infiltration, immune cell lineage commitment, tissue microenvironment modification, immune synapse formation, IL-2 secretion, IL-10 secretion, growth factor secretion, interferon gamma secretion, transforming growth factor beta secretion, immunoreceptor tyrosine-based activation motif activity, immunoreceptor tyrosine-based inhibition motif activity, antibody directed cell cytotoxicity, complement directed cytotoxicity, biological pathway agonism, biological pathway antagonism, biological pathway redirection, kinase cascade modification, proteolytic pathway modification, proteostasis pathway modification, protein folding/pathways, post-translational modification pathways, metabolic pathways, gene transcription/translation, mRNA degradation pathways, gene methylation/acetylation pathways, histone modification pathways, epigenetic pathways, immune directed clearance, opsonization, hormone signaling, integrin pathways, membrane protein signal transduction, ion channel flux, and g-protein coupled receptor response.

Embodiment I-18. The engineered peptide of embodiment I-15, wherein the reference target comprises one or more atoms associated with a biological response or biological function, and wherein the atomic fluctuations of the one or more atoms in the engineered peptide associated with a biological response or biological function overlap with the atomic fluctuations of the one or more atoms in the reference target associated with a biological response or biological function.

Embodiment I-19. The engineered peptide of embodiment I-18, wherein the overlap is a root mean square inner product (RMSIP) greater than 0.25.

Embodiment I-20. The engineered peptide of embodiment I-19, wherein the overlap has a root mean square inner product (RMSIP) greater than 0.75.

Embodiment I-21. The engineered peptide of any one of embodiments I-18 to I-20, wherein at least a portion of the atoms in the engineered peptide associated with a biological response or biological function are topologically constrained to a secondary structural element in the reference target.

Embodiment I-22. The engineered peptide of embodiment I-21, wherein the secondary structural element is a beta-sheet.

Embodiment I-23. The engineered peptide of embodiment I-21, wherein the secondary structural element is an alpha helix.

Embodiment I-24. The engineered peptide of embodiment I-21, wherein the secondary structural element is a turn, wherein the turn comprises between 2 to 7 residues, and comprises at least one inter-residue hydrogen bond.

Embodiment I-25. The engineered peptide of embodiment I-21, wherein the secondary structural element is a coil, wherein the coil comprises between 2 to 20 residues.

Embodiment I-26. The engineered peptide of embodiment I-25, wherein the coil comprises no inter-residue hydrogen bonds.

Embodiment I-27. The engineered peptide of any one of embodiments I-21 to I-26, wherein at least a portion of the atoms in the engineered peptide associated with a biological response or biological function are topologically constrained to a combination of two or more secondary structural elements independently selected from the group consisting of a beta-sheet, an alpha helix, a turn, and a coil.

Embodiment I-28. The engineered peptide of any one of embodiments I-1 to I-27, wherein one or more spatially-associated topological constraints is atomic distance.

Embodiment I-29. The engineered peptide of any one of embodiments I-1 to I-28, wherein one or more spatially-associated topological constraints is an atomic energy.

Embodiment I-30. The engineered peptide of embodiment I-29, wherein each atomic energy is independently pairwise attractive energy between two atoms, pairwise repulsive energy between two atoms, atom-level solvation energy, pairwise charged attraction energy between two atoms, pairwise hydrogen bonding attraction energy between two atoms, or non-covalent bonding energy.

Embodiment I-31. The engineered peptide of any one of embodiments I-1 to I-30, wherein one or more spatially-associated topological constraints is a chemical descriptor.

Embodiment I-32. The engineered peptide of embodiment I-31, wherein each chemical descriptor is independently hydrophobicity, polarity, volume, net charge, logP, high performance liquid chromatography retention, or van der Waals radii.

Embodiment I-33. The engineered peptide of any one of embodiments I-1 to I-32, wherein one or more spatially-associated topological constraints is a bioinformatic descriptor.

Embodiment I-34. The engineered peptide of embodiment I-33, wherein each bioinformatics descriptor is independently BLOSUM similarity, pKa, zScale, Cruciani Properties, Kidera Factors, VHSE-scale, ProtFP, MS-WHIM scores, T-scale, ST-scale, Transmembrane tendency, protein buried area, helix propensity, sheet propensity, coil propensity, turn propensity, immunogenic propensity, antibody epitope occurrence, or protein interface occurrence.

Embodiment I-35. The engineered peptide of any one of embodiments I-1 to I-34, wherein one or more spatially-associated topological constraints is solvent exposure.

Embodiment I-36. The engineered peptide of any one of embodiments I-1 to I-35, wherein at least one of the one or more reference target-derived constraints is a GPCR extracellular domain.

Embodiment I-37. The engineered peptide of any one of embodiments I-1 to I-36, wherein at least one of the one or more reference target-derived constraints is an ion channel extracellular domain.

Embodiment I-38. The engineered peptide of any one of embodiments I-1 to I-37, wherein at least one of the one or more reference target-derived constraints is a protein-protein or peptide-protein interface junction.

Embodiment I-39. The engineered peptide of any one of embodiments I-1 to I-38, wherein at least one of the one or more reference target-derived constraints is derived from a polymorphic region of the target.

Embodiment I-40. The engineered peptide of any one of embodiments I-1 to I-39, comprising one or more atoms associated with a biological response or biological function, wherein each of the one or more atoms is independently selected from the group consisting of carbon, oxygen, nitrogen, hydrogen, sulfur, phosphorus, sodium, potassium, zinc, manganese, magnesium, copper, iron, molybdenum, and nickel.

Embodiment I-41. The engineered peptide of any one of embodiments I-1 to I-40, comprising one or more amino acids associated with a biological function or biological response, wherein each of the one or more amino acids is independently a proteinogenic naturally occurring amino acid, a non-proteinogenic naturally occurring amino acid, or a chemically synthesized non-natural amino acid.

Embodiment I-42. The engineered peptide of any one of embodiments I-1 to I-41, wherein the engineered peptide has at least one structural difference when compared to the reference target.

Embodiment I-43. The engineered peptide of embodiment I-42, wherein the at least one structural difference is independently selected from the group consisting of sequence, number of amino acid residues, total number of atoms, total hydrophilicity, total hydrophobicity total positive charge, total negative charge, one or more secondary structures, shape factor, Zernike descriptors, van der Waals surface, structure graph nodes and edges, volumetric surface, electrostatic potential surface, hydrophobic potential surface, local diameter, local surface features, skeleton model, charge density, hydrophilic density, surface to volume ratio, amphiphilicity density, and surface roughness Embodiment I-44. The engineered peptide of embodiment I-16, wherein the difference in one or more secondary structures is the presence of one or more additional secondary structural elements in the engineered peptide compared to the reference target, wherein each additional secondary structural element is independently selected from the group consisting of alpha helices, beta-sheets, loops, turns, and coils.

Embodiment I-45. The engineered peptide of any one of embodiments I-1 to I-44, wherein between 10% to 90% of the amino acids meet one or more non-reference target-derived topological constraints.

Embodiment I-46. The engineered peptide of embodiment I-45, wherein the one or more non-reference target-derived topological constraints enforce a pre-specified function.

Embodiment I-47. The engineered peptide of embodiment I-46, wherein the non-reference derived topological constraints enforce or stabilize secondary structural elements in the reference derived fraction of the peptide;

non-reference derived topological constraints enforce atomic fluctuations in the reference derived fraction of the peptide;

non-reference derived topological constraints alter peptide total hydrophobicity;

non-reference derived topological constraints alter peptide solubility;

non-reference derived topological constraints alter peptide total charge;

non-reference derived topological constraints enable detection in a labeled or label-free assay;

non-reference derived topological constraints enable detection in an in vitro assay;

non-reference derived topological constraints enable detection in an in vivo assay;

non-reference derived topological constraints enable capture from a complex mixture;

non-reference derived topological constraints enable enzymatic processing;

non-reference derived topological constraints enable cell membrane permeability;

non-reference derived topological constraints enable binding to a secondary target, and non-reference derived topological constraints alter immunogenicity.

Embodiment I-48. A method of selecting an engineered peptide, comprising:

identifying one or more topological characteristics of a reference target;

designing spatially-associated constraints for each topological characteristic to produce a combination of spatially-associated topological constraints derived from the reference target;

comparing spatially-associated topological characteristics of candidate peptides with the combination of spatially-associated topological constraints derived from the reference target; and selecting a candidate peptide with spatially-associated topological characteristics that overlap with the combination of spatially-associated topological constraints derived from the reference target to produce the engineered peptide.

Embodiment I-49. The method of embodiment I-48, wherein the overlap between each characteristic is independently less than or equal to 75% Mean Percentage Error (MPE) as determined by one or more of Total Topological Constraint Distance (TCD), topological clustering coefficient (TCC), Euclidean distance, power distance, Soergel distance, Canberra distance, Sorensen distance, Jaccard distance, Mahalanobis distance, Hamming distance, Quantitative Estimate of Likeness (QEL), or Chain Topology Parameter (CTP).

Embodiment I-50. The method of embodiment I-48 or I-49, wherein one or more constraints is derived from per-residue energy, per-residue interaction, per-residue fluctuation, per-residue atomic distance, per-residue chemical descriptor, per-residue solvent exposure, per-residue amino acid sequence similarity, per-residue bioinformatic descriptor, per-residue non-covalent bonding propensity, per-residue phi/psi angles, per-residue van der Waals radii, per-residue secondary structure propensity, per-residue amino acid adjacency, per-residue amino acid contact.

Embodiment I-51. The method of any one of embodiments I-48 to I-50, wherein the characteristics of one or more candidate peptides are determined by computer simulation.

Embodiment I-52. The method of embodiment I-51, wherein the computer simulation comprises molecular dynamics simulations, Monte Carlo simulations, coarse-grained simulations, Gaussian network models, machine learning, or any combinations thereof.

Embodiment I-53. The method of any one of embodiments I-48 to I-52, wherein the characteristics of one or more candidate peptides are determined by experimental characterization.

Embodiment I-54. The method of any one of embodiments I-48 to I-53, wherein the amino acids meeting the one or more reference target-derived constraints have between 10% and 90% sequence homology with the reference target.

Embodiment I-55. The method of any one of embodiments I-48 to I-54, wherein the amino acids meeting the one or more reference target-derived constraints have a van der Waals surface area overlap with the reference of between 30 $Å^2$ to 3000 $Å^2$.

Embodiment I-56. The method of any one of embodiments I-48 to I-55, wherein the combination comprises at least two reference target-derived constraints.

Embodiment I-57. The method of any one of embodiments I-48 to I-56, wherein the combination comprises at least five reference target-derived constraints.

Embodiment I-58. The method of any one of embodiments I-48 to I-57, wherein the combination of constraints comprises one or more constraints not derived from a reference target.

Embodiment I-59. The method of embodiment I-58, wherein the one or more non-reference target-derived constraints describes a desired structural, dynamical, chemical, or functional characteristic, or any combinations thereof.

Embodiment I-60. The method of any one of embodiments I-48 to I-59, wherein the constraints are independently selected from the group consisting of:

atomic distances;

atomic fluctuations;

atomic energies;

chemical descriptors;

solvent exposures;

amino acid sequence similarity;

bioinformatic descriptors;

non-covalent bonding propensity;

phi angles;

psi angles;

van der Waals radii;

secondary structure propensity;

amino acid adjacency; and amino acid contact.

Embodiment I-61. The method of any one of embodiments I-48 to I-60, wherein one or more constraints is independently an atomic fluctuation.

Embodiment I-62. The method of any one of embodiments I-48 to I-61, wherein one or more constraints is independently a chemical descriptor.

Embodiment I-63. The method of any one of embodiments I-48 to I-62, wherein one or more constraints is independently atomic distance.

Embodiment I-64. The method of any one of embodiments I-48 to I-63, wherein one or more constraints is independently secondary structure.

Embodiment I-65. The method of any one of embodiments I-48 to I-64, wherein one or more constraints is independently van der Waals surface.

Embodiment I-66. The method of any one of embodiments I-48 to I-65, wherein one or more constraints is independently associated with a biological response or biological function.

Embodiment I-67. The method of any one of embodiments I-48 to I-66, wherein the engineered peptide comprises one or more atoms associated with a biological response or biological function.

Embodiment I-68. The method of any one of embodiments I-48 to I-66, wherein the engineered peptide comprises one or more amino acids associated with a biological response or biological function Embodiment I-69. The method of any one of embodiments I-66 to I-68, wherein the biological response or biological function is selected from the group consisting of gene expression, metabolic activity, protein expression, cell proliferation, cell death, cytokine secretion, kinase activity, epigenetic modification, cell killing activity, inflammatory signals, chemotaxis, tissue infiltration, immune cell lineage commitment, tissue microenvironment modification, immune synapse formation, IL-2 secretion, IL-10 secretion, growth factor secretion, interferon gamma secretion, transforming growth factor beta secretion, immunoreceptor tyrosine-based activation motif activity, immunoreceptor tyrosine-based inhibition motif activity, antibody directed cell cytotoxicity, complement directed cytotoxicity, biological pathway agonism, biological pathway antagonism, biological pathway redirection, kinase cascade modification, proteolytic pathway modification, proteostasis pathway modification, protein folding/pathways, post-translational modification pathways, metabolic pathways, gene transcription/translation, mRNA degradation pathways, gene methylation/acetylation pathways, histone modification pathways, epigenetic pathways, immune directed clearance, opsonization, hormone signaling, integrin pathways, membrane protein signal transduction, ion channel flux, and g-protein coupled receptor response.

Embodiment I-70. The method of embodiment I-66, wherein the reference target comprises one or more atoms associated with a biological response or biological function, and wherein the atomic fluctuations of the one or more atoms in the engineered peptide associated with a biological response or biological function overlap with the atomic fluctuations of the one or more atoms in the reference target associated with a biological response or biological function.

Embodiment I-71. The method of embodiment I-70, wherein the overlap is a root mean square inner product (RMSIP) greater than 0.25.

Embodiment I-72. The method of embodiment I-71, wherein the overlap has a root mean square inner product (RMSIP) greater than 0.75.

Embodiment I-73. The method of any one of embodiments I-67 to I-69, wherein at least a portion of the atoms in the engineered peptide associated with a biological response or biological function are topologically constrained to a secondary structural element in the reference target.

Embodiment I-74. The method of embodiment I-73, wherein the secondary structural element is a beta-sheet.

Embodiment I-75. The method of embodiment I-73, wherein the secondary structural element is an alpha helix.

Embodiment I-76. The method of embodiment I-73, wherein the secondary structural element is a turn, wherein the turn comprises between 2 to 7 residues, and comprises at least one inter-residue hydrogen bond.

Embodiment I-77. The method of embodiment I-73, wherein the secondary structural element is a coil, wherein the coil comprises between 2 to 20 residues.

Embodiment I-78. The method of embodiment I-73, wherein the coil comprises no inter-residue hydrogen bonds.

Embodiment I-79. The method of any one of embodiments I-67 to I-69, wherein at least a portion of the atoms in the engineered peptide associated with a biological response or biological function are topologically constrained to a combination of two or more secondary structural elements independently selected from the group consisting of a beta-sheet, an alpha helix, a turn, and a coil.

Embodiment I-80. The method of any one of embodiments I-48 to I-79, wherein one or more spatially-associated topological constraints is atomic distance.

Embodiment I-81. The method of any one of embodiments I-48 to I-80, wherein one or more spatially-associated topological constraints is an atomic energy.

Embodiment I-82. The method of embodiment I-81, wherein each atomic energy is independently pairwise attractive energy between two atoms, pairwise repulsive energy between two atoms, atom-level solvation energy, pairwise charged attraction energy between two atoms, pairwise hydrogen bonding attraction energy between two atoms, or non-covalent bonding energy.

Embodiment I-83. The method of any one of embodiments I-48 to I-82, wherein one or more spatially-associated topological constraints is a chemical descriptor.

Embodiment I-84. The method of embodiment I-83, wherein each chemical descriptor is independently hydrophobicity, polarity, volume, net charge, logP, high performance liquid chromatography retention, or van der Waals radii.

Embodiment I-85. The method of any one of embodiments I-48 to I-84, wherein one or more spatially-associated topological constraints is a bioinformatic descriptor.

Embodiment I-86. The method of embodiment I-85, wherein each bioinformatics descriptor is independently BLOSUM similarity, pKa, zScale, Cruciani Properties, Kidera Factors, VHSE-scale, ProtFP, MS-WHIM scores, T-scale, ST-scale, Transmembrane tendency, protein buried area, helix propensity, sheet propensity, coil propensity, turn propensity, immunogenic propensity, antibody epitope occurrence, or protein interface occurrence.

Embodiment I-87. The method of any one of embodiments I-48 to I-86, wherein one or more spatially-associated topological constraints is solvent exposure.

Embodiment I-88. The method of any one of embodiments I-48 to I-87, wherein at least one of the one or more reference target-derived constraints is a GPCR extracellular domain.

Embodiment I-89. The method of any one of embodiments I-48 to I-88, wherein at least one of the one or more reference target-derived constraints is an ion channel extracellular domain.

Embodiment I-90. The method of any one of embodiments I-48 to I-89, wherein at least one of the one or more reference target-derived constraints is a protein-protein or protein-peptide interface junction.

Embodiment I-91. The method of any one of embodiments I-48 to I-90, wherein at least one of the one or more reference target-derived constraints is derived from a polymorphic region of the target.

Embodiment I-92. The method of any one of embodiments I-48 to I-91, wherein the engineered peptide comprises one or more atoms associated with a biological response or biological function, wherein each of the one or more atoms is independently selected from the group consisting of carbon, oxygen, nitrogen, hydrogen, sulfur, phosphorus, sodium, potassium, zinc, manganese, magnesium, copper, iron, molybdenum, and nickel.

Embodiment I-93. The method of any one of embodiments I-48 to I-92, wherein the engineered peptide comprises one or more amino acids associated with a biological function or biological response, wherein each of the one or more amino acids is independently a proteinogenic naturally occurring amino acid, a non-proteinogenic naturally occurring amino acid, or a chemically synthesized non-natural amino acid.

Embodiment I-94. The method of any one of embodiments I-48 to I-93, wherein the engineered peptide has at least one structural difference when compared to the reference target.

Embodiment I-95. The method of embodiment I-94, wherein the at least one structural difference is independently selected from the group consisting of sequence, number of amino acid residues, total number of atoms, total hydrophilicity, total hydrophobicity total positive charge, total negative charge, one or more secondary structures, shape factor, Zernike descriptors, van der Waals surface, structure graph nodes and edges, volumetric surface, electrostatic potential surface, hydrophobic potential surface, local diameter, local surface features, skeleton model, charge density, hydrophilic density, surface to volume ratio, amphiphilicity density, and surface roughness Embodiment I-96. The method of embodiment I-95, wherein the difference in one or more secondary structures is the presence of one or more additional secondary structural elements in the engineered peptide compared to the reference target, wherein each additional secondary structural element is independently selected from the group consisting of alpha helices, beta-sheets, loops, turns, and coils.

Embodiment I-97. The method of any one of embodiments I-48 to I-96, wherein between 10% to 90% of the amino acids of the engineered peptide meet one or more non-reference target-derived topological constraints.

Embodiment I-98. The method of embodiment I-97, wherein the one or more non-reference target-derived topological constraints enforce a pre-specified function.

Embodiment I-99. The method of embodiment I-98, wherein:

- non-reference derived topological constraints enforce or stabilize secondary structural elements in the reference derived fraction of the peptide;
- non-reference derived topological constraints enforce atomic fluctuations in the reference derived fraction of the peptide;
- non-reference derived topological constraints alter peptide total hydrophobicity;
- non-reference derived topological constraints alter peptide solubility;
- non-reference derived topological constraints alter peptide total charge;
- non-reference derived topological constraints enable detection in a labeled or label-free assay;
- non-reference derived topological constraints enable detection in an in vitro assay;
- non-reference derived topological constraints enable detection in an in vivo assay;
- non-reference derived topological constraints enable capture from a complex mixture;
- non-reference derived topological constraints enable enzymatic processing;
- non-reference derived topological constraints enable cell membrane permeability;
- non-reference derived topological constraints enable binding to a secondary target, or
- non-reference derived topological constraints alter immunogenicity, or any combinations thereof.

Embodiment I-100. A composition comprising two or more selection steering polypeptides, wherein each polypeptide is independently a positive selection molecule comprising one or more positive steering characteristics, or a negative selection molecule comprising one or more negative steering characteristics, wherein each characteristic type is independently selected from the group consisting of:

- amino acid sequence,
- polypeptide secondary structure,
- molecular dynamics,
- chemical features,
- biological function,
- immunogenicity,
- reference target(s) multi-specificity,
- cross-species reference target reactivity,
- selectivity of desired reference target(s) over undesired reference target(s),
- selectivity of reference target(s) within a sequence and/or structurally homologous family,
- selectivity of reference target(s) with similar protein function,
- selectivity of distinct desired reference target(s) from a larger family of undesired targets with high sequence and/or structurally homology,
    - selectivity for distinct reference target alleles or mutations,
    - selectivity for distinct reference target residue level chemical modifications,
    - selectivity for cell type,
    - selectivity for tissue type,
    - selectivity for tissue environment,
    - tolerance to reference target(s) structural diversity,
    - tolerance to reference target(s) sequence diversity, and
    - tolerance to reference target(s) dynamics diversity;
    - and wherein at least one of the two or more polypeptides is an engineered peptide according to embodiment I-1.

Embodiment I-101. The composition of embodiment I-100, wherein at least one of the two or more polypeptides is a positive selection molecule, and at least one of the two or more polypeptides is a negative selection molecule.

Embodiment I-102. The composition of embodiment I-100 or I-101, wherein at least one of the two or more polypeptides is a native protein.

Embodiment I-103. The composition of any one of embodiments I-100 to I-102, comprising at least one pair of counterpart positive and negative selection molecules comprising at least one shared characteristic type, wherein the positive selection molecule comprises the positive characteristic and the negative selection molecule comprises the negative characteristic.

Embodiment I-104. A method of screening a library of binding molecules with the composition of embodiment I-100, comprising subjecting a pool of candidate binding molecules to at least one round of selection, wherein each round of selection comprises:

a negative selection step of screening at least a portion of the pool against a negative selection molecule; and a positive selection step of screening at least a portion of the pool for a positive selection molecule;

wherein the order of selection steps within each round, and the order of rounds, result in the selection of a different subset of the pool than an alternative order.

Embodiment I-105. The method of embodiment I-104, wherein the library of binding molecules is a phage library.

Embodiment I-106. The method of embodiment I-105, wherein the library of binding molecules is a cell library.

Embodiment I-107. The method of embodiment I-106, wherein the library of binding molecules is a B-cell library.

Embodiment I-108. The method of embodiment I-106, wherein the library of binding molecules is a T-cell library.

Embodiment I-109. The method of any one of embodiments I-104 to I-108, comprising two or more rounds of selection.

Embodiment I-110. The method of any one of embodiments I-104 to I-109, comprising three or more rounds of selection.

Embodiment I-111. The method of embodiment I-109 or 1-110, wherein each round comprises a different set of selection molecules.

Embodiment I-112. The method of embodiment I-109 or I-110, wherein at least two rounds comprise the same negative selection molecule, or the same positive selection molecule, or both.

Embodiment I-113. The method of any one embodiments I-109 to I-112, comprising analyzing the subset of the pool obtained from a round of selection prior to proceeding to the next round of selection.

Embodiment I-114. The method of embodiment I-113, wherein the subset pool analysis determines the set of positive and/or negative selection molecules used in one or more subsequent rounds of selection.

Embodiment I-115. The method of embodiment I-113 or 1-114, wherein each subset pool analysis is independently selected from the group consisting of peptide/protein biosensor binding, peptide/protein ELISA, peptide library binding, cell extract binding, cell surface binding, cell activity assay, cell proliferation assay, cell death assay, enzyme activity assay, gene expression profile, protein modification assay, Western blot, and immunohistochemistry.

Embodiment I-116. The method of any one of embodiments I-113 to I-115, wherein the positive, negative, or both positive and negative selection molecules used in one or more subsequent rounds of selection are determined by statistical/informatic scoring, or machine learning training, of a subset pool analysis.

Embodiment I-117. The method of any one of embodiments I-109 to I-116, wherein the subset pool obtained from a round of selection is modified before moving to the next selection round.

Embodiment I-118. The method embodiment I-117, wherein the subset pool analysis determines the positive, negative, or both positive and negative selection molecules used in one or more subsequent rounds of selection; and modification of the subset pool before moving to the next selection round.

Embodiment I-119. The method of embodiment I-117 or I-118, wherein each modification is independently selected from the group selected from genetic mutation, genetic depletion, genetic enrichment, chemical modification, and enzymatic modification.

EXAMPLES

The following Examples are merely illustrative and are not meant to limit any aspects of the present disclosure in any way.

Figure 6A:
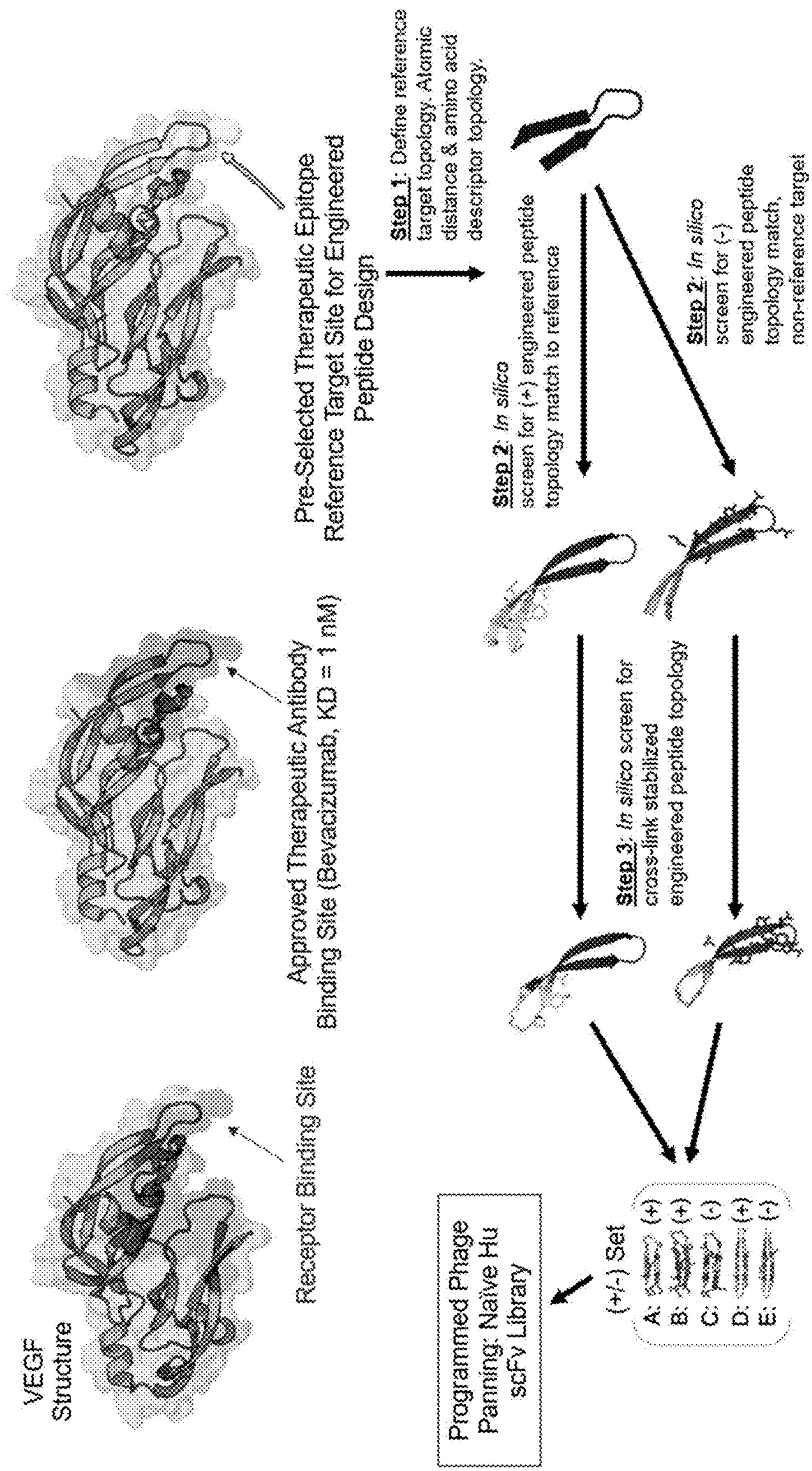
Figure 6B:
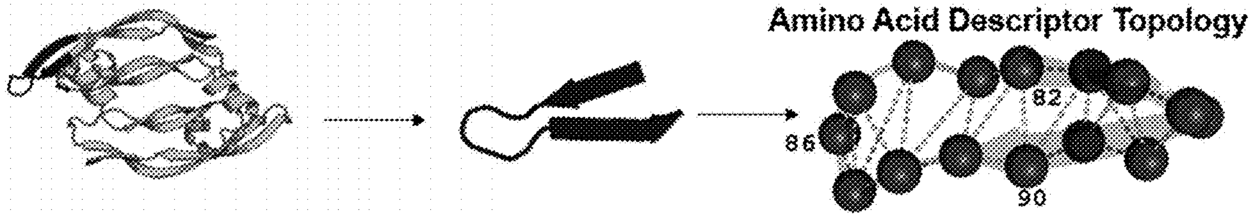
Figure 6D:
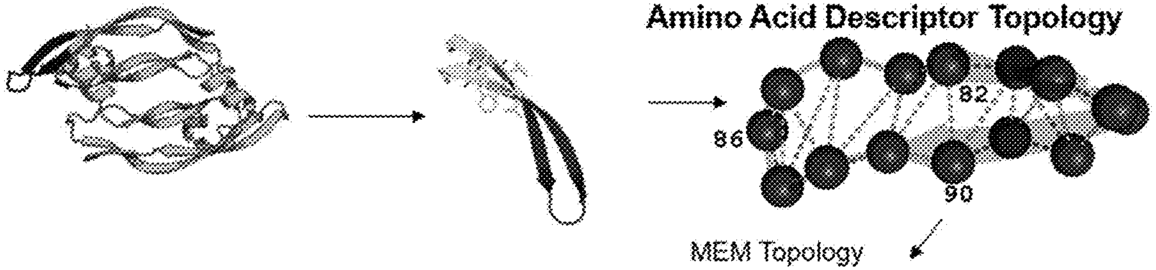
Figure 6E:
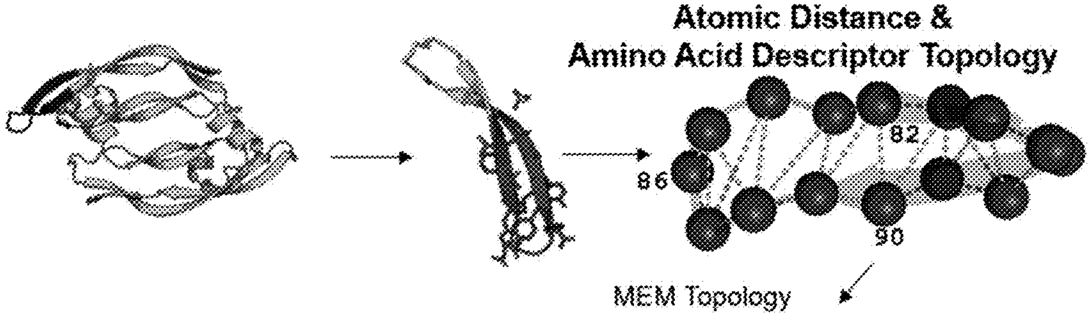
Figure 6H:
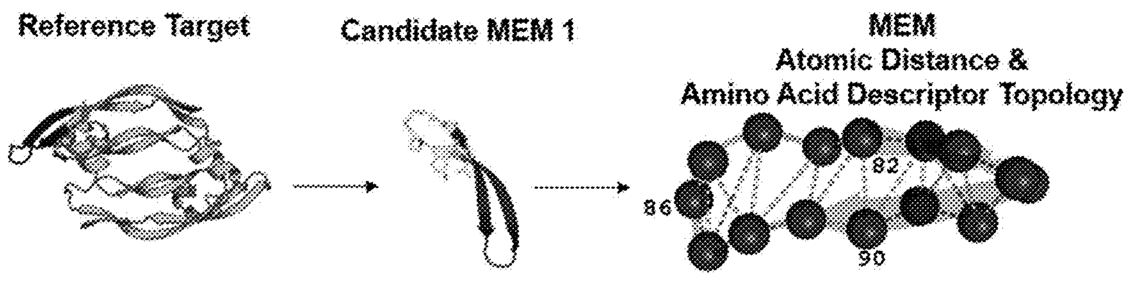

Example 1: Selection of Engineered Peptides Using a VEGF Epitope as the Reference Target As shown in FIGS. 6A and 7A, a putative therapeutic epitope of VEGF was identified as a reference target for engineered peptide selection, and atomic distance and amino acid descriptor topology were determined (FIG. 6B). The atomic distance and amino acid descriptor topology of the reference target were obtained using dynamic simulations, and a covariance matrix of atomic fluctuations was generated for the epitope in the reference target. Next, different engineered peptide candidates were generated using computational protein design (e.g. Rosetta), dynamics simulations performed on the candidates, and the atomic distance and amino acid descriptor topologies determined (FIGS. 6C-6E). These mean percentage error (MPE) of these topologies were compared (FIGS. 6G-6H). The MPE values were: reference topology vs. candidate 1 topology: 6.03%; reference topology vs. candidate 2 topology: 6.00%; and reference topology vs. candidate 3 topology: 22.8%.

An additional constraint was added to the combination for evaluation of one candidate engineered peptide—atomic fluctuation (FIGS. 6G-6H). Comparing the higher dimension topological similarity between this candidate and the VEGF-derived reference target, the MPE was 36.6%.

Example 2: Selection of Engineered Peptides Using a VEGF Epitope as the Reference Target Using the same reference target identified in Example 1 above, a second set of engineered peptides were developed. Engineered peptide candidates were generated using computational protein design (e.g. Rosetta) or other methods of sampling peptide space, and dynamics simulations were performed on the candidates. A covariance matrix of atomic fluctuations was generated for the reference target epitope, and for the residues in the candidates corresponding to the residues in the epitope of the reference target.

Figure 8:
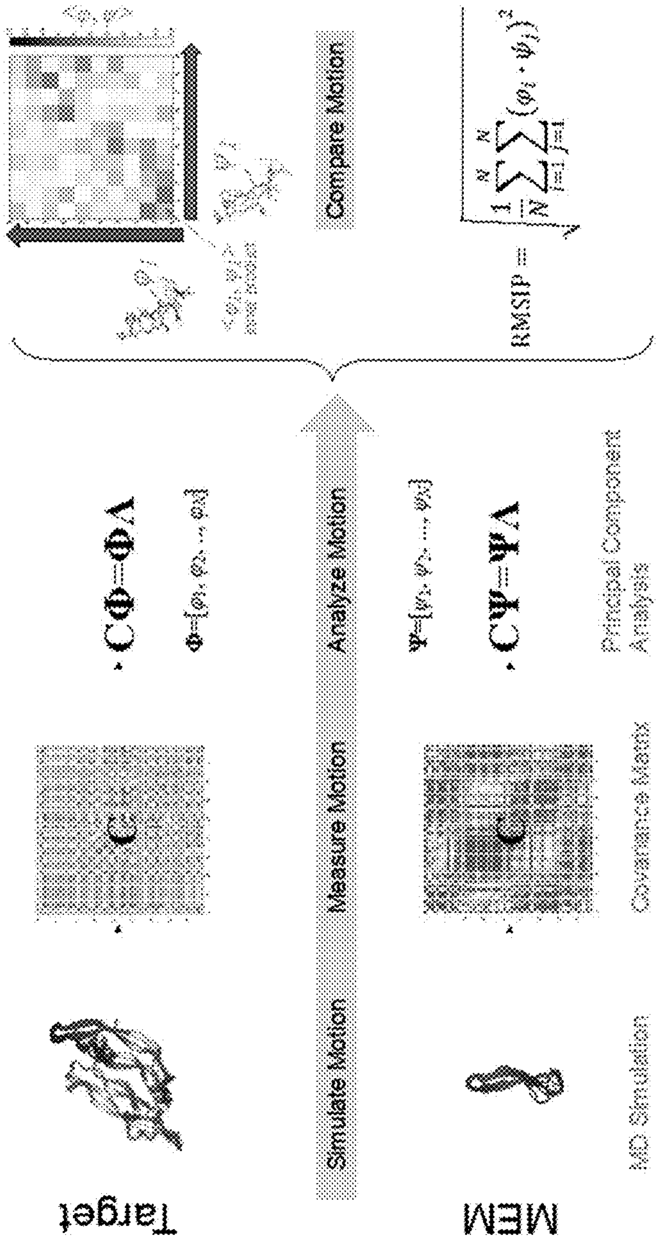
FIG. 8 shows the structure ensembles and coordinate covariance matrices of the reference target (TOP) and the MEM (BOTTOM) generated from experimental data or computer simulation. The epitope is the darker section on the upper right of the reference target.

Principal component analysis was performed to compute the eigenvectors and eigenvalues for each covariance matrix—one covariance matrix for the reference target and one covariance for each of the candidates—and only those eigenvectors with the largest eigenvalues are retained (FIG. 8). Eigenvectors describe the most, second-most, third-most, N-most dominant motion observed in a set of simulated molecular structures. If a candidate moves like the reference epitope, its eigenvectors will be similar to the eigenvectors of the reference target (epitope). The similarity of eigenvectors corresponds to their components (a 3D vector centered on each CA atom) being aligned—pointing in the same direction (FIGS. 7D-7G). This similarity between candidates and reference target eigenvectors was computed using the inner product of two eigenvectors. The inner product value was 0 if two eigenvectors are 90 degrees to each other or 1 if the two eigenvectors point precisely in the same direction.

motions most closely matched the motions of the reference target, computed by RMSIP). Candidates XTR-1000-W1 and W2 had the lowest dynamics-matching score, shown to demonstrate the RMSIP dynamic range in this 1000 candidate data set, RMSIP range 0.772-0.545. Structures of the candidates aligned to the VEGF reference epitope are shown in FIG. 7B.

TABLE 1

| Reference Epitope<br>MEM Variant ID | QIMRIKPHQGQHIGE<br>MEM Sequence | RMSIP |
|---|---|---|
| XTR-1000-T0 | QQIMCIKPHQGQCIGEAEEALKITAKA (SEQ ID NO: 46) | 0.673 |
| XTR-1000-B1 | SQIMCIKPHQGQHIGETSEDCDKAAKS (SEQ ID NO: 47) | 0.772 |
| XTR-1000-B2 | SQICRIKPHQGQHCGETSEDADKAAKS (SEQ ID NO: 48) | 0.766 |
| XTR-1000-W1 | QQIMCIKPHQGQCIGEAEEVYKKRKKS (SEQ ID NO:49) | 0.545 |
| XTR-1000-W2 | QQIMCIKPHOGOCIGEAEEYYTKAKRS (SEQ ID NO: 50) | 0.550 |

Since the ordering of eigenvectors is based on their eigenvalues, and eigenvalues may not necessarily be the same between two different molecules due to the stochastic nature by which molecular dynamics simulations sample the underlying energy landscape of those different molecules, the inner product between multiple, differentially ranked eigenvectors was needed (e.g. eigenvector 1 of the candidate by eigenvector 2, 3, 4, etc. of the reference target). In addition, without wishing to be bound by any theory, molecular motions are complex and may involve more than one (or more than a few) dominant/principal modes of motion.

To solve these two challenges, the inner product between all pairs of eigenvectors in the candidates and the reference target were computed. This resulted in a matrix of inner products the dimensions of which were determined by the number of eigenvectors analyzed—for 10 eigenvectors, the matrix of inner products is 10 by 10. This matrix of inner products was distilled into a single value by computing the root mean-square value of the inner products. This is the root mean square inner product (RMSIP).

Principal component analysis (PCA) reduces the 3L×3L dimensional coordinate covariance matrices (L being number of atoms) into sets of eigenvectors, Φ (reference target) and Ψ (MEM), and eigenvalues, A. The set Φ contains N eigenvectors $\varphi_i$ for the reference target and the set Ψ contains N eigenvectors $\psi_j$ for the MEM, where eigenvectors are ordered in their respective sets by their associated eigenvalues. The eigenvector with the largest eigenvalue accounts for the largest fraction of total coordinate covariation. The inner product of each $\varphi_i$ and $\psi_j$ eigenvector is computed to compare the similarity of motion between the reference target and the MEM. The root mean square of all inner product combinations of $\varphi_i$ and $\psi_j$ eigenvectors renders the total similarity of motion of the engineered peptide candidate (MEM) to the reference target (RMSIP) (FIG. 8).

Figure 9:
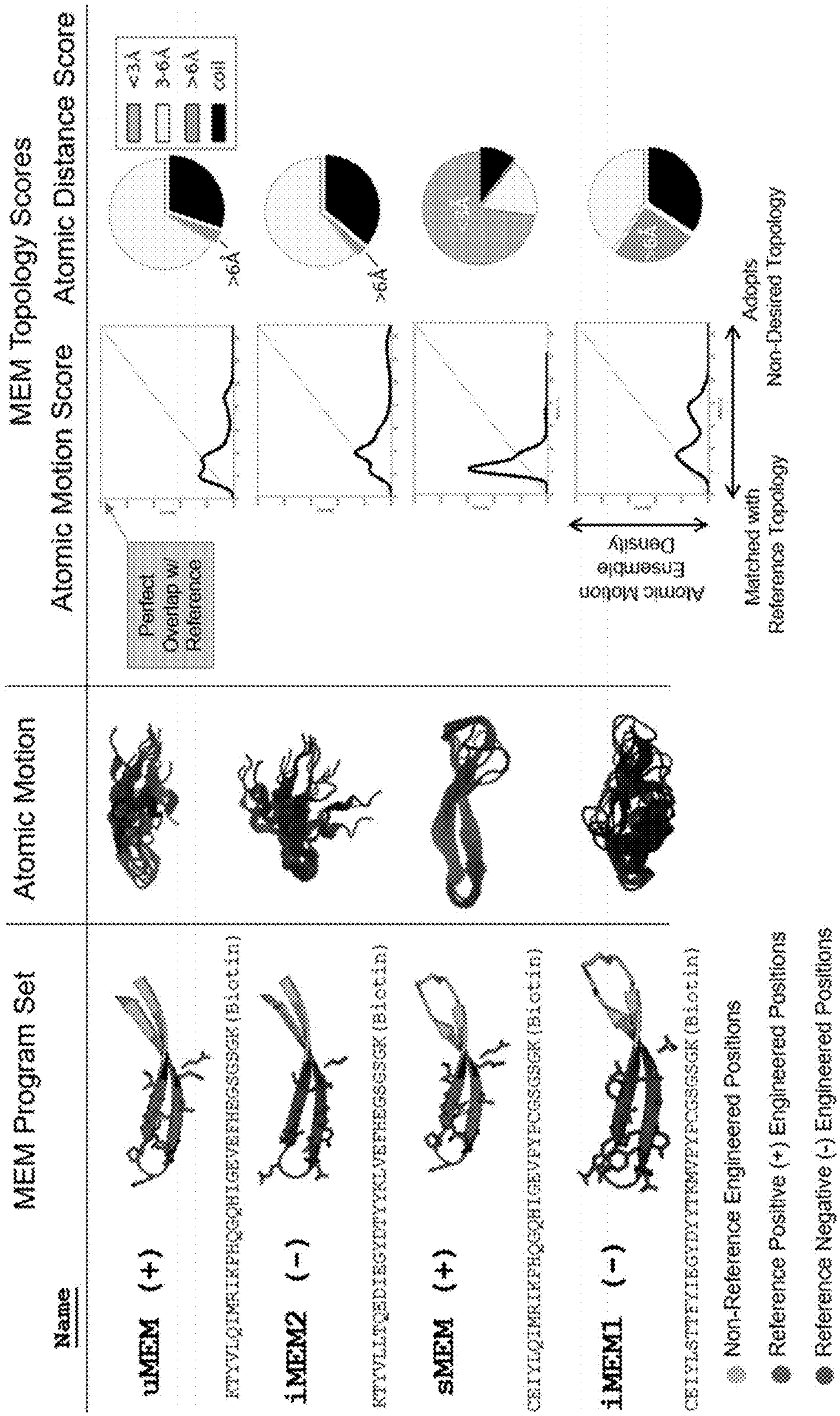
FIG. 9 is an overview of an in vitro programmable selection design, using four engineered peptides (also called meso-scale engineered molecules, or MEMs) for positive or negative selection. The atomic motion and topology scores of the MEMs are included for reference. The sequences are provided as SEQ ID NOS: 1-4.
Figures 10A, 10B:
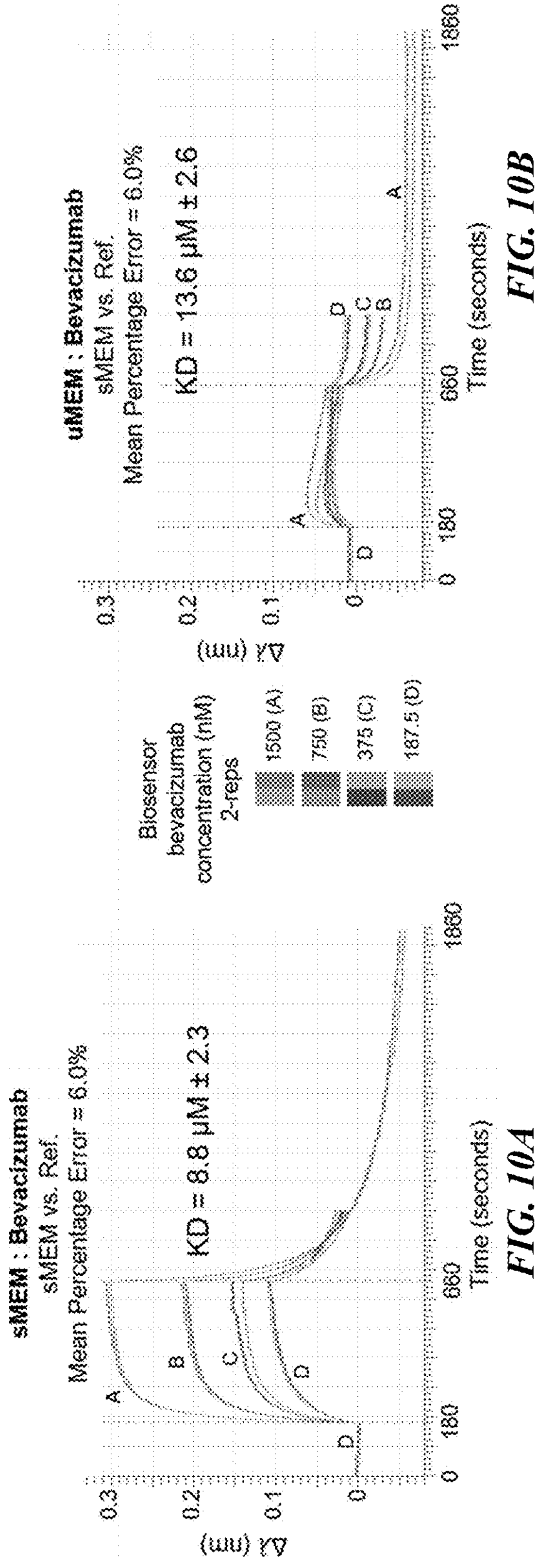
FIGS. 10A-10D are graphs of a binding biosensor assay using the different engineered peptides from FIG. 9 against Bevacizumab.
Figures 10C, 10D:
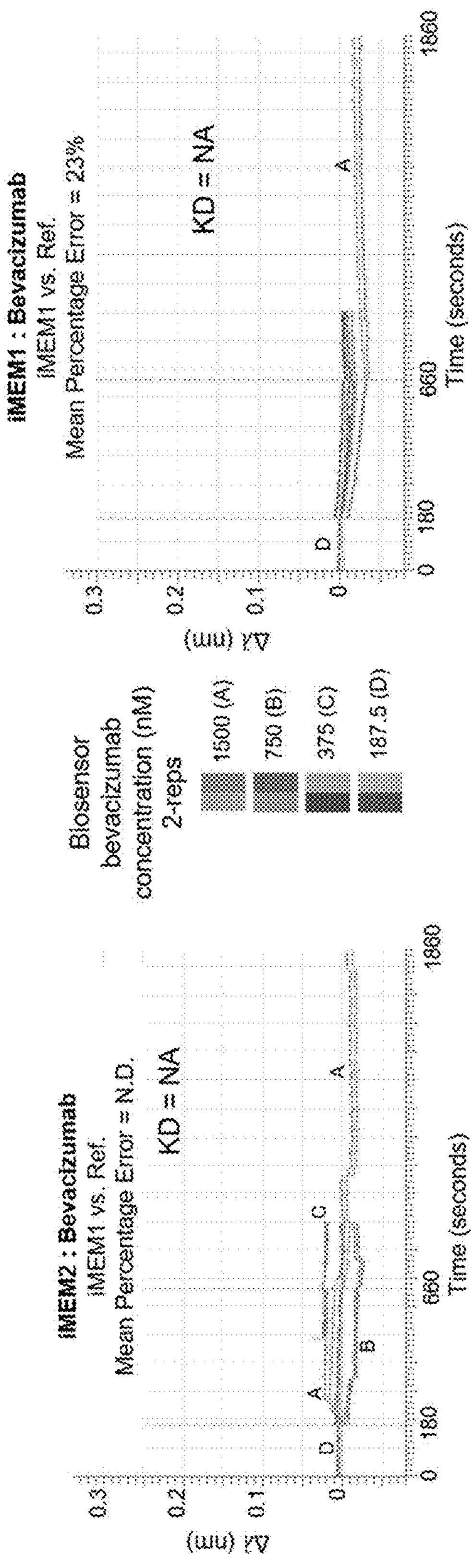
Figure 12A:
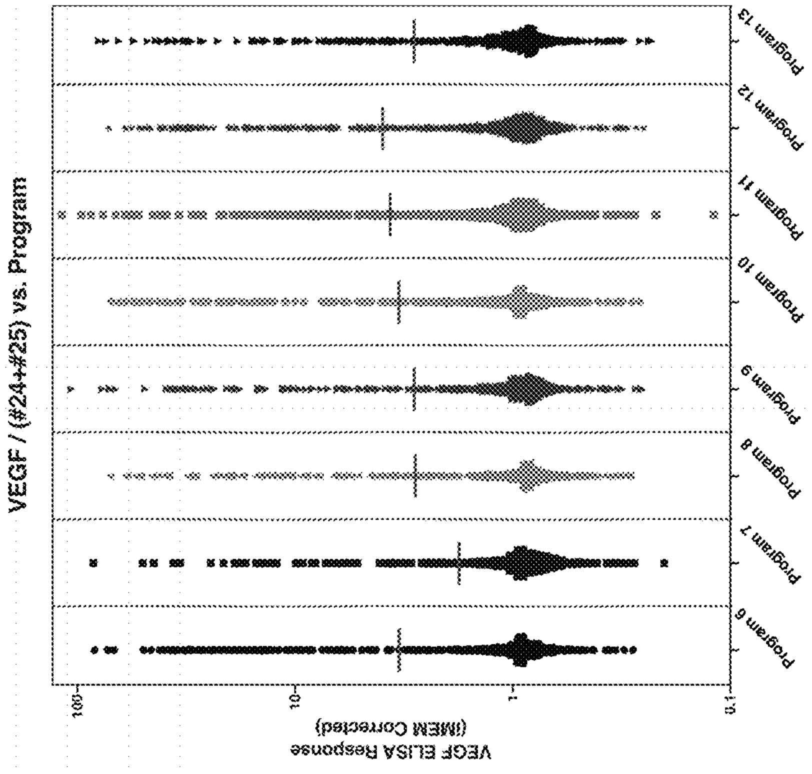
FIGS. 12A and 12B are VEGF ELISA response graphs comparing the VEGF binding response against binding partners selected using the different panning programs described in FIG. 11.
Figure 12B:
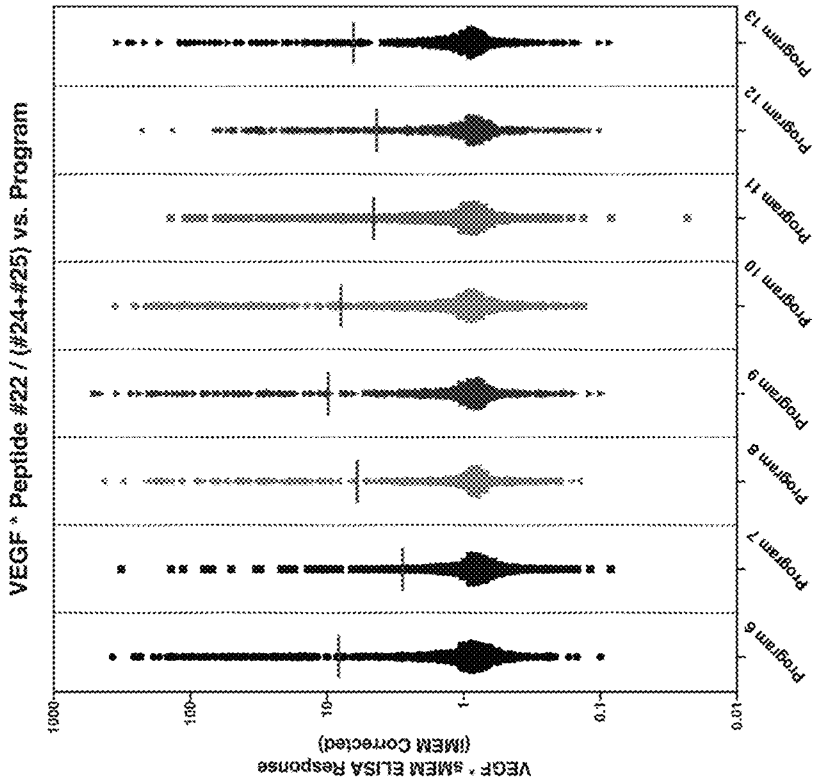
Figure 13B:
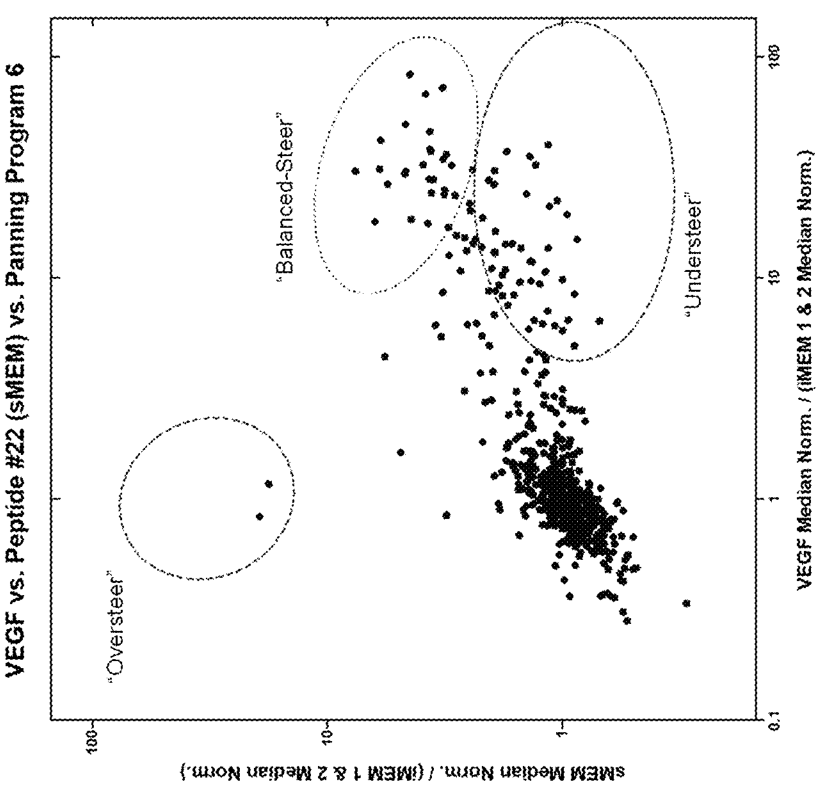
FIGS. 13A-13H are graphs demonstrating the binding of binding partners selected using the different panning programs described in FIG. 11 with the sMEM engineered peptide vs. VEGF (reference).
Figure 13A:
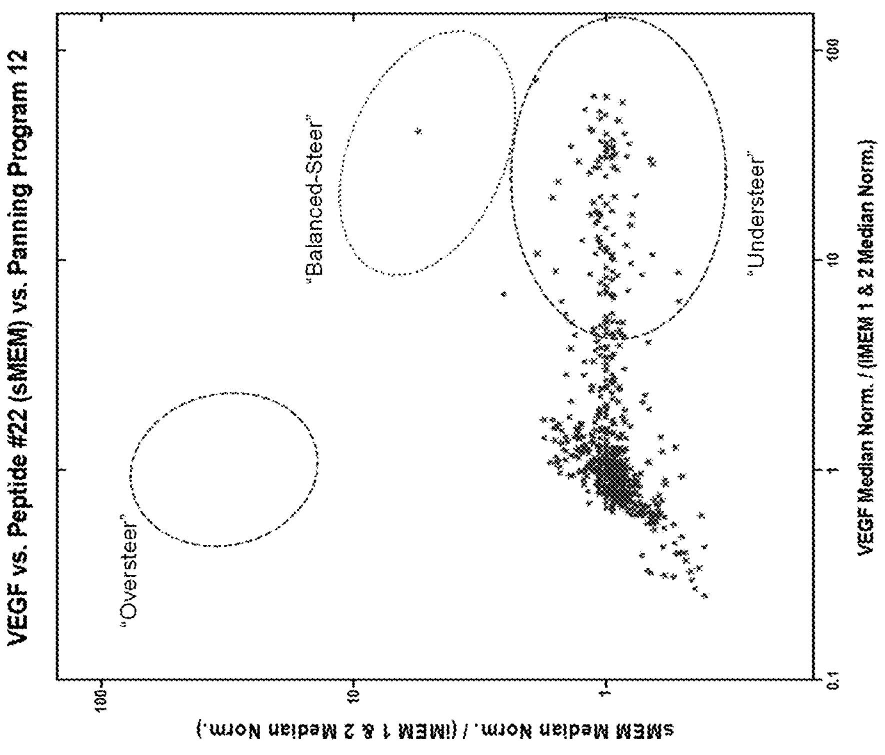
Figure 13D:
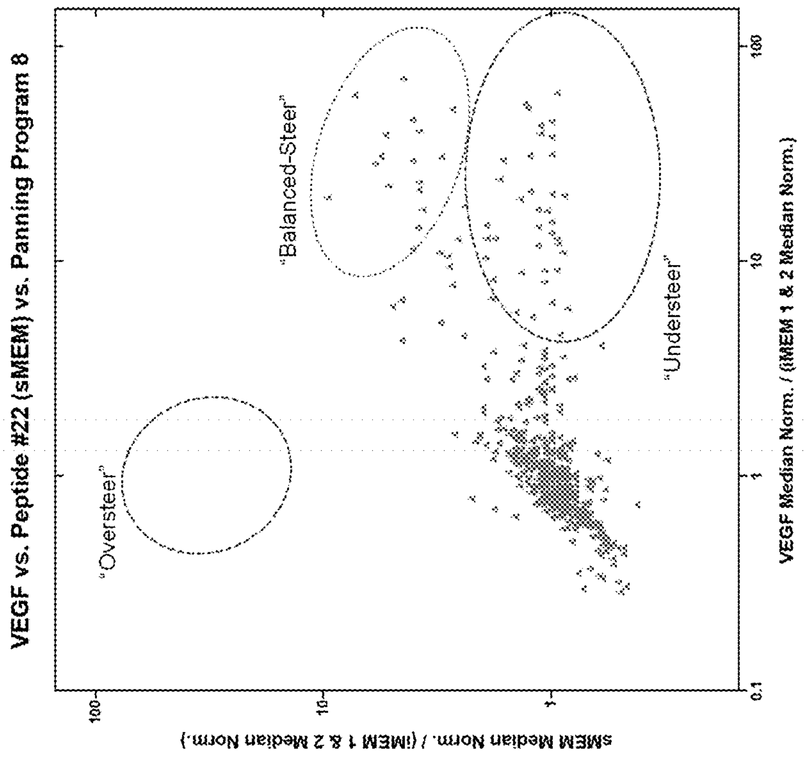
Figure 13C:
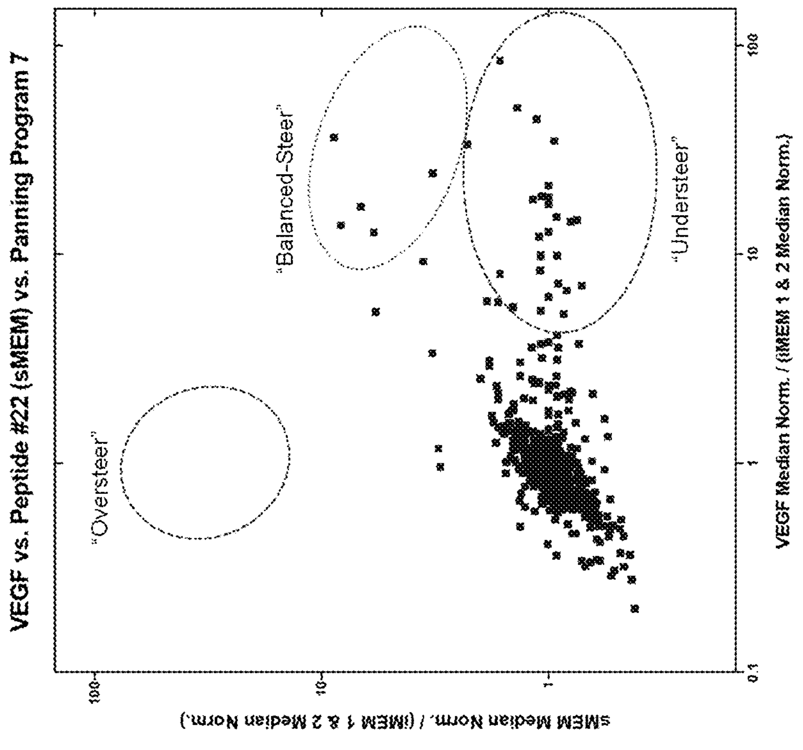
Figure 13F:
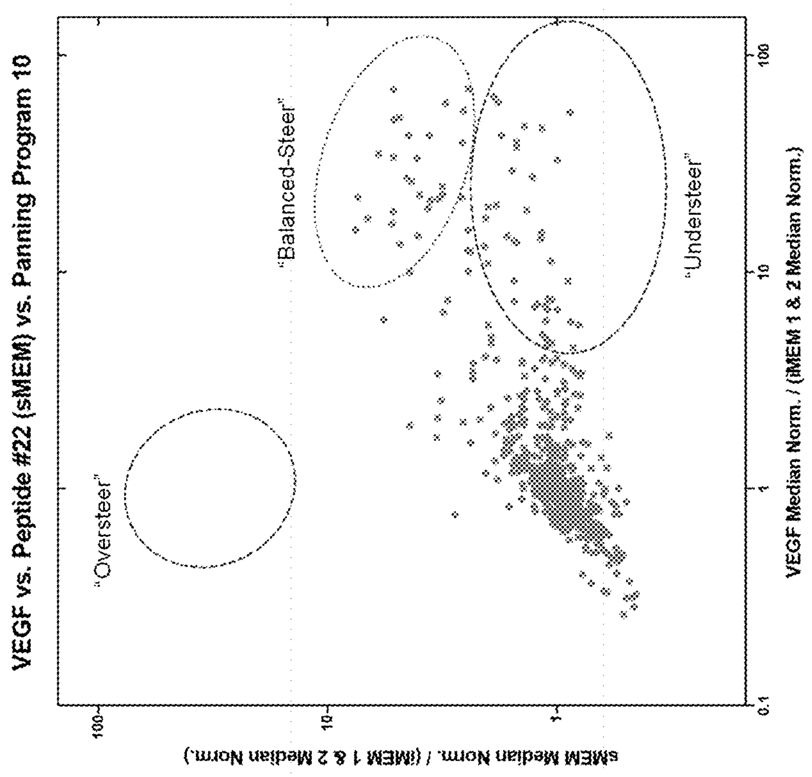
Figure 13E:
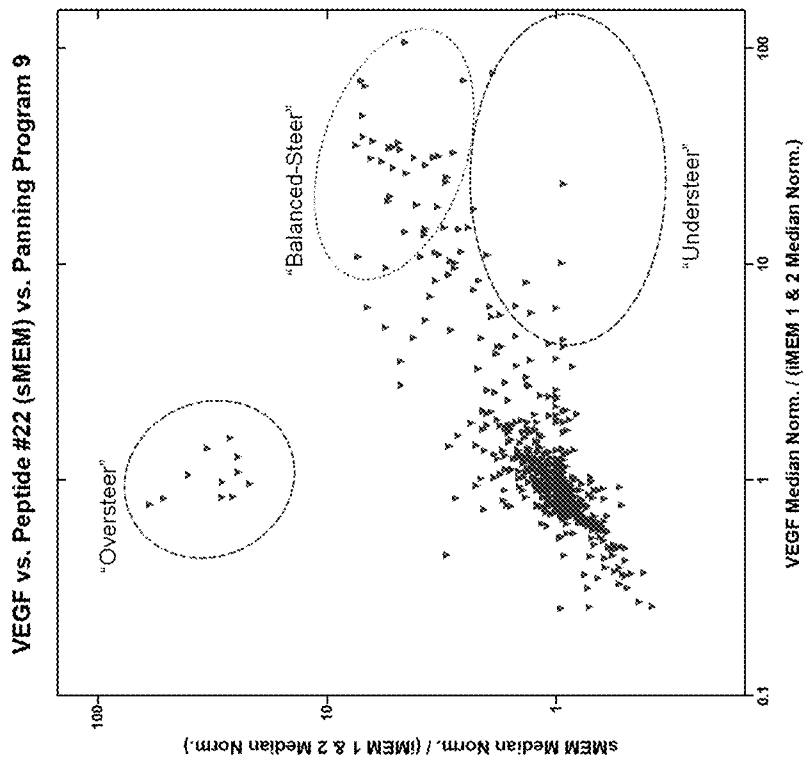
Figure 13G:
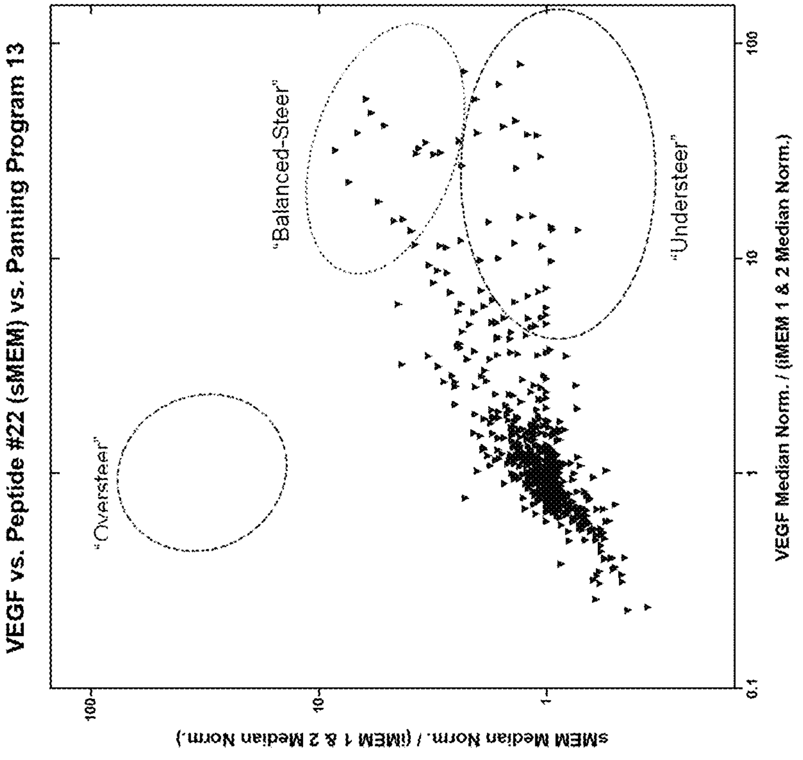
Figure 13H:
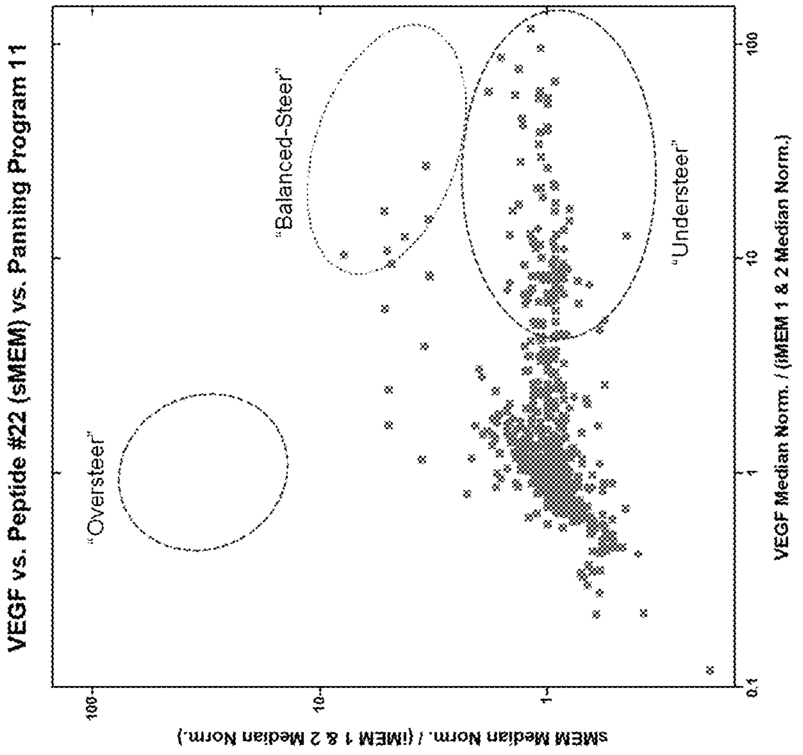
Figure 14A:
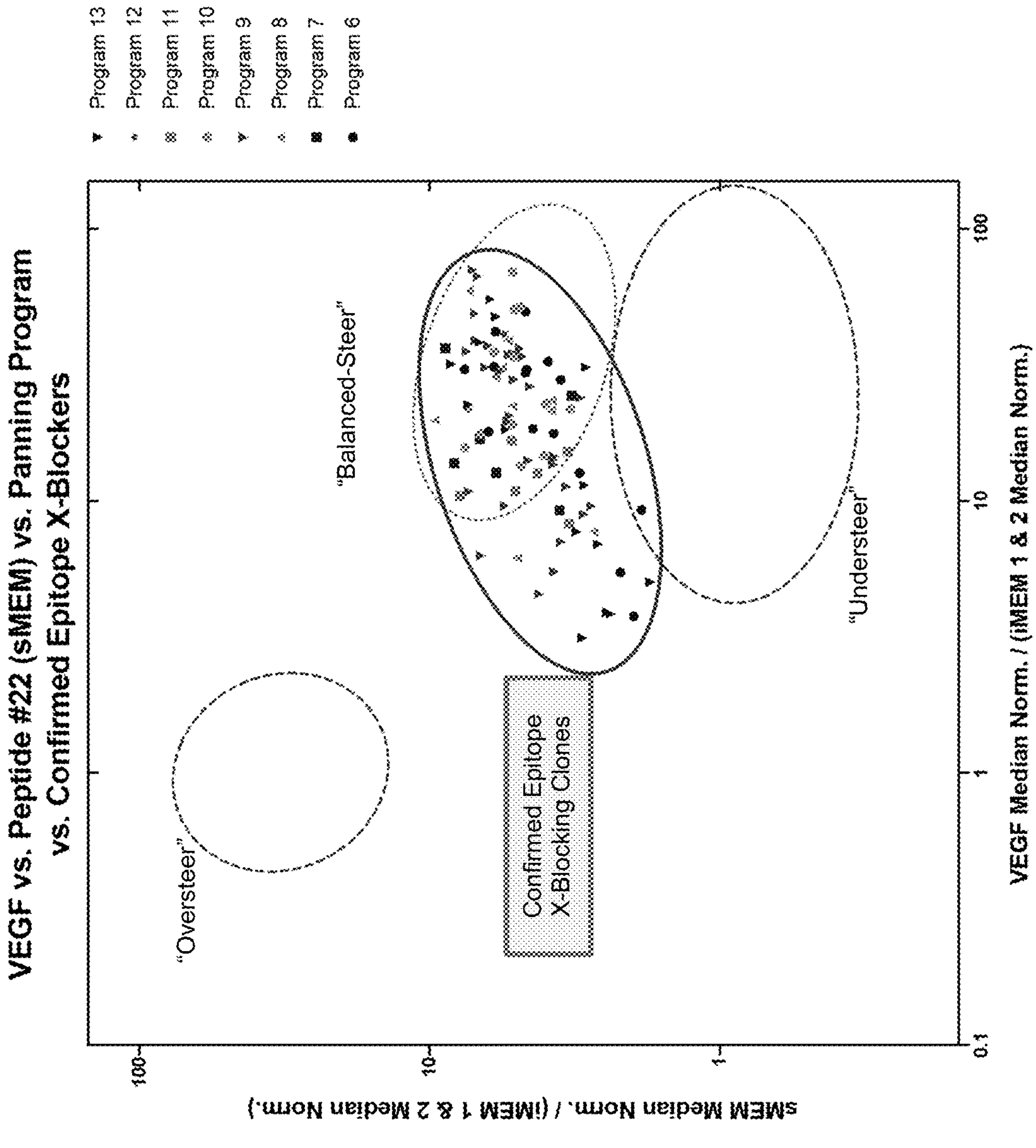
FIGS. 14A-14I are graphs demonstrating the binding of binding partners selected using the different panning programs described in FIG. 11 in a cross blocking assay of VEGF with dose-responsive competition with Bevacizumab (0 nM, 67 pM, 670 pM, 6.7 nM).
Figure 14B:
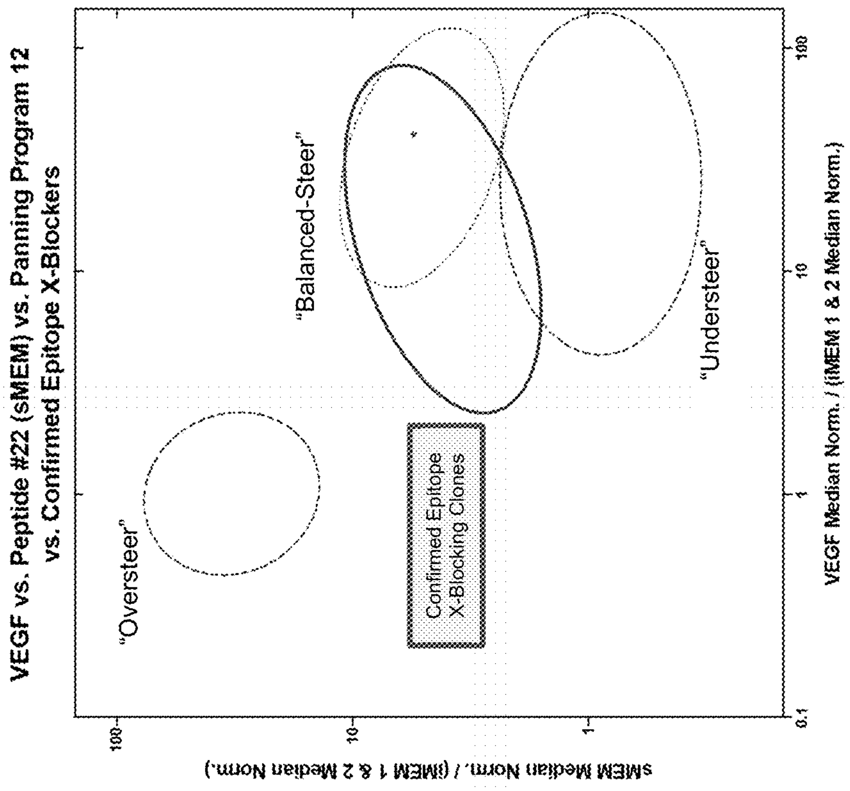
Figure 14C:
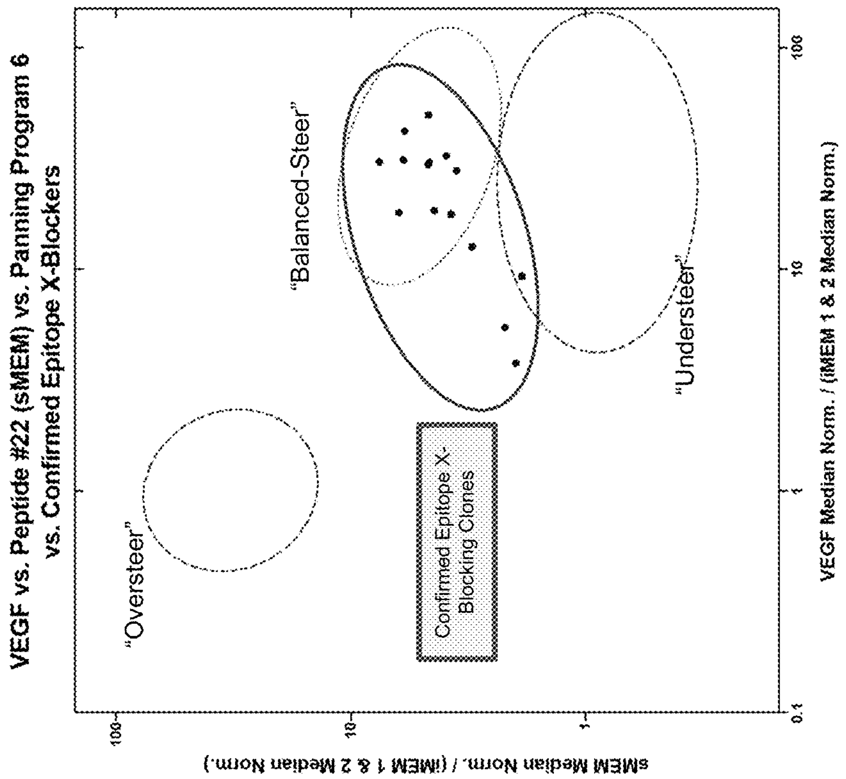
Figure 14D:
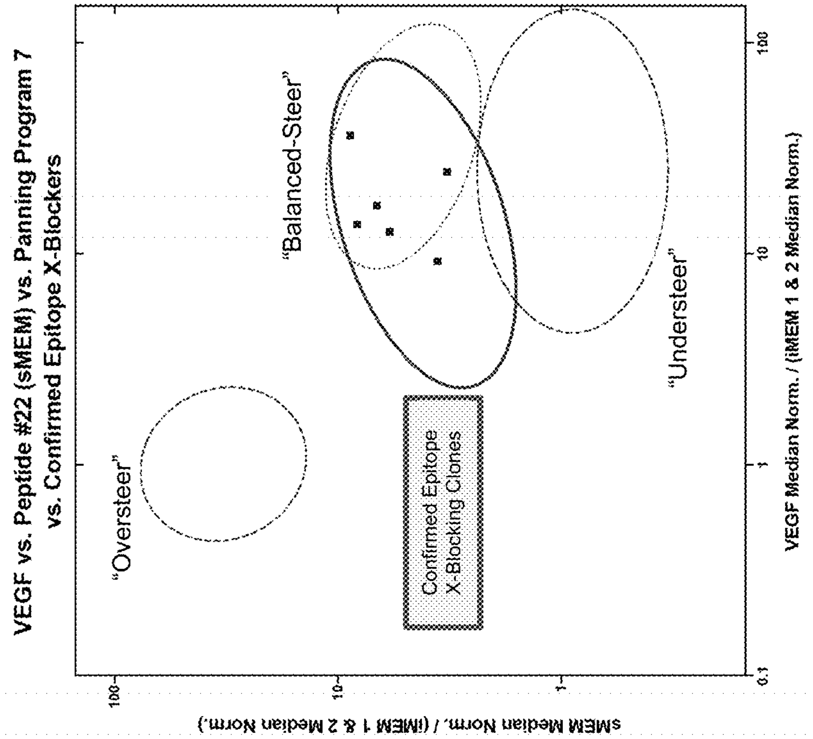
Figure 14E:
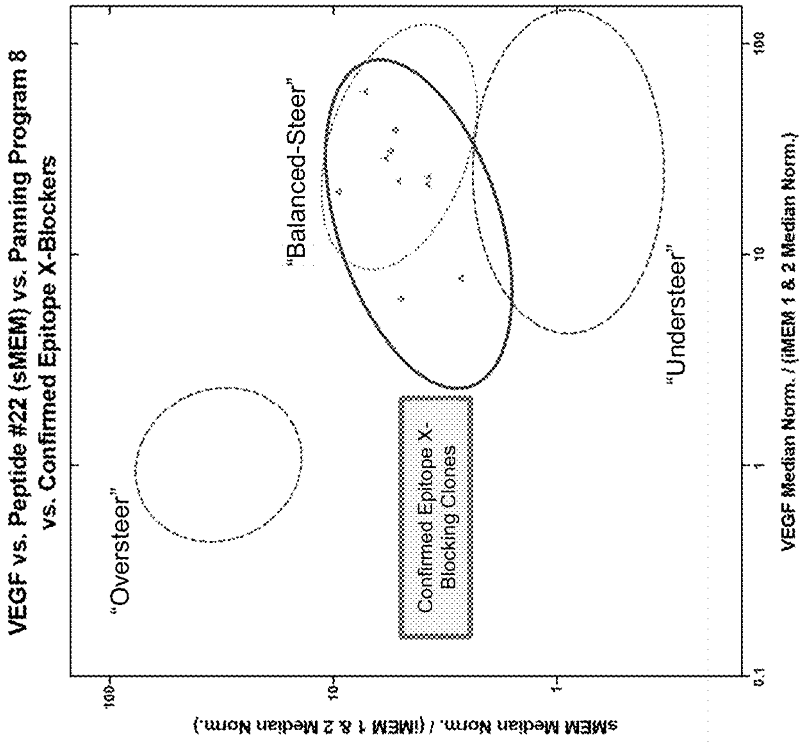
Figure 14G:
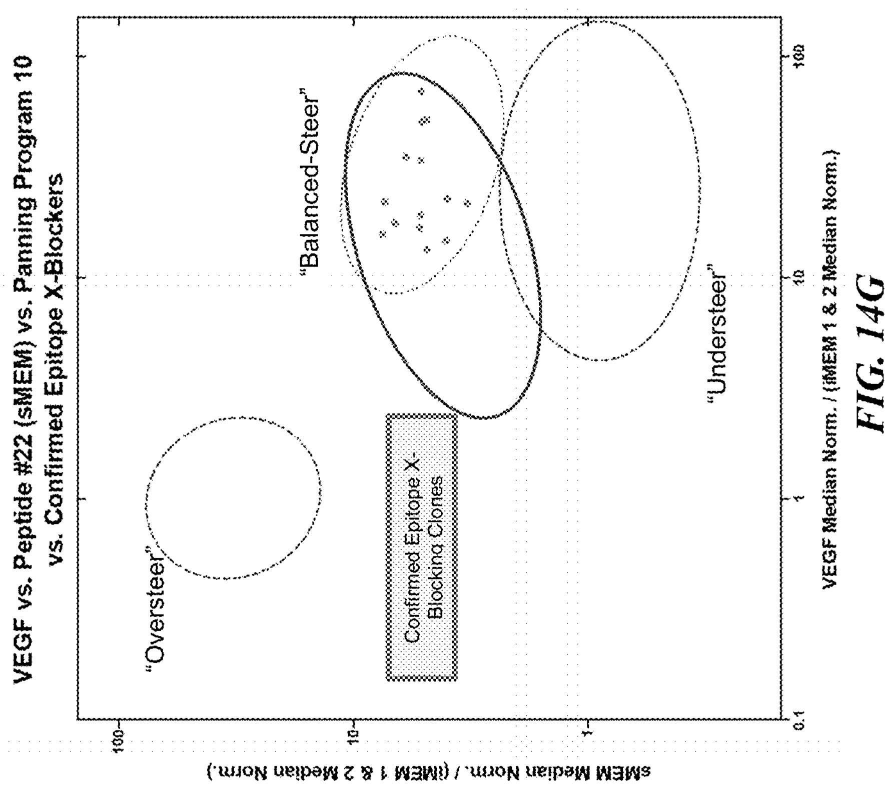
Figure 14F:
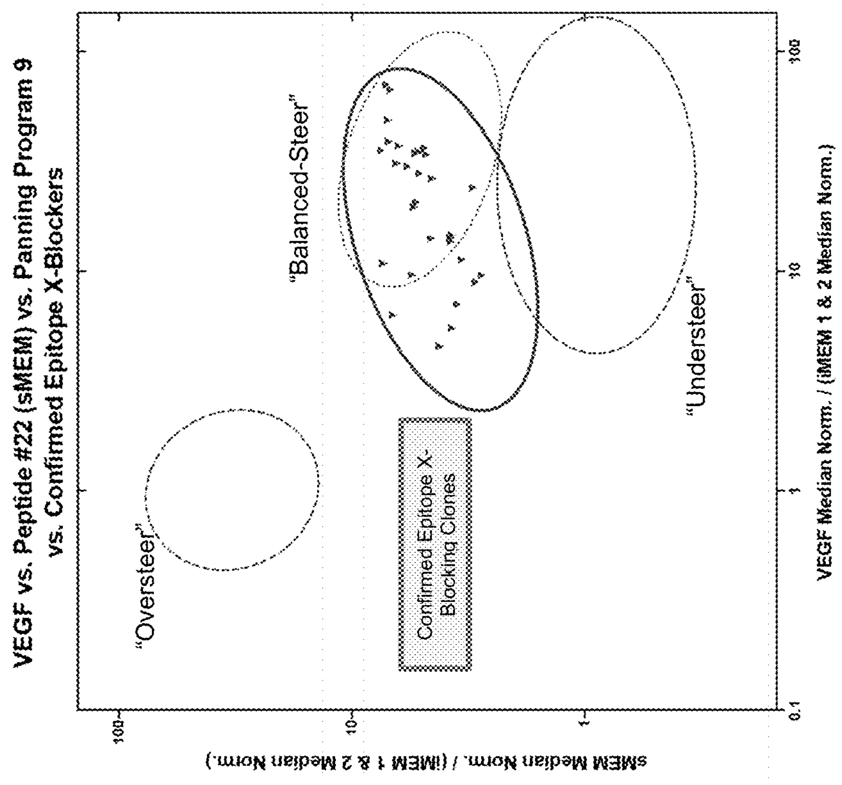
Figure 14I:
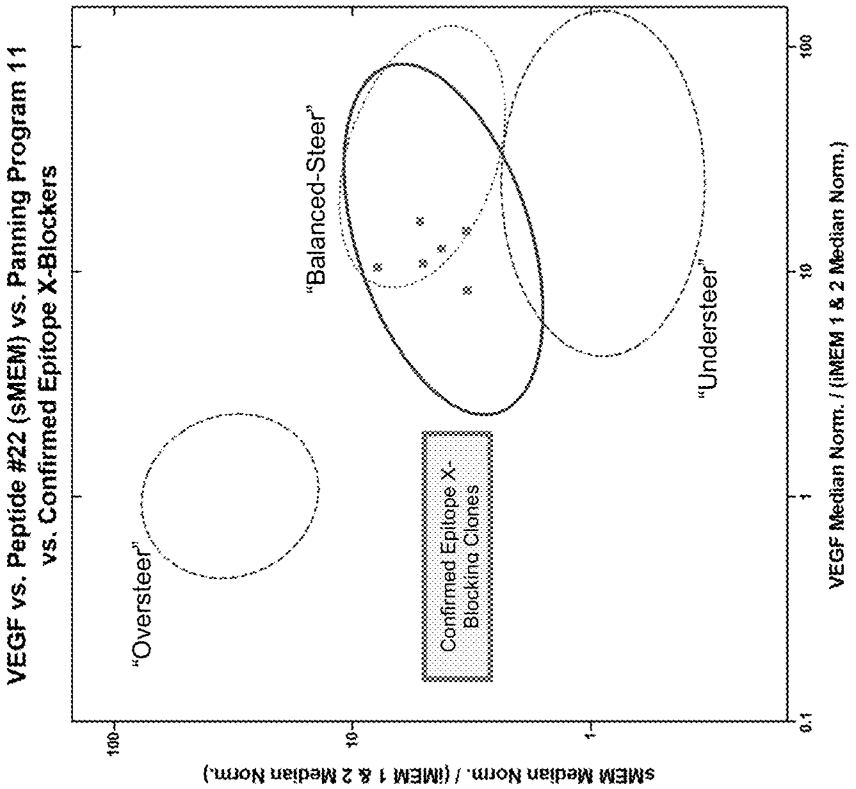
Figure 14H:
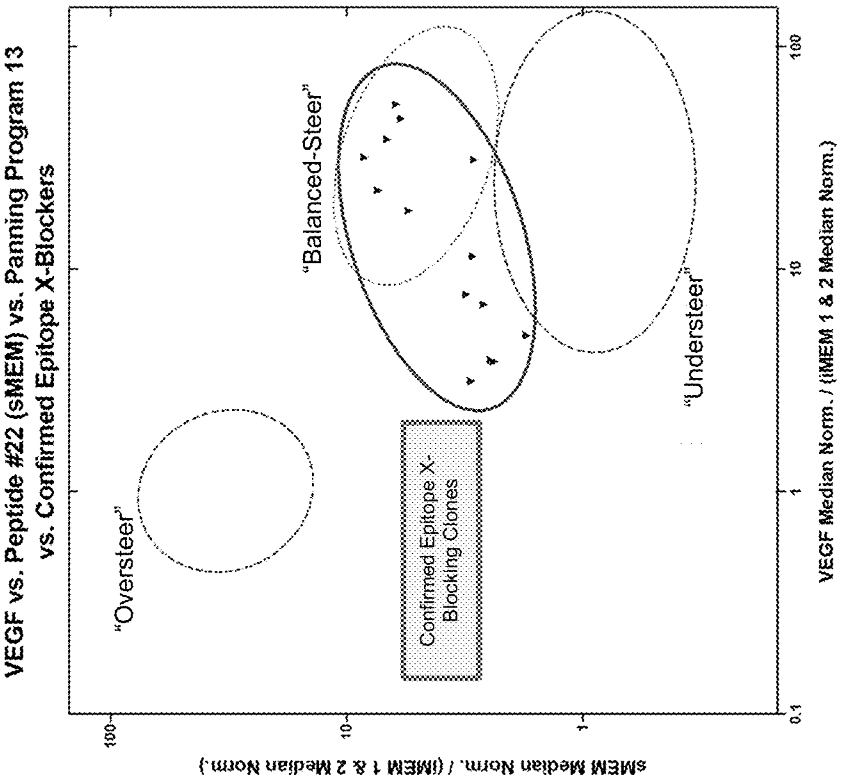

The RMSIP results from 5 candidate engineered peptides vs. the VEGF reference epitope are shown in Table 1. These data were sampled from a total simulation of 1000 candidates generated using Rosetta design with a candidate vs. reference static structure RMSD cutoff. Of the 1000 candidates, XTR-1000-TO had the lowest Rosetta (static structure) Energy (lower is more favorable), but intermediate RMSIP dynamics matching. Candidates XTR-1000-B1 and B2 had the highest dynamics-matching score (e.g., their Example 3: Programmed In Vitro Selection of Phage Using Engineered Peptides for VEGF Putative Epitope The three engineered peptides described in Example 1, and an additional fourth engineered peptide developed following a similar procedure were used in series of phage panning procedures. These peptides are shown in FIG. 9. Two of the peptides were positive selection molecules (uMEM and sMEM) and two were negative selection molecules (iMEM2 and iMEM1). The sMEM peptide was a high topology reference match, and the uMEM was a lower topology reference match. The two iMEM peptides were zero topology reference matches, and were included as inverse versions of the sMEM and uMEM to select against binding partners that would bind to sMEM or uMEM for reasons other than the desired binding interactions. Analysis of the biotin-bound peptides using biosensor assays confirmed binding to Bevacizumab, which was predicted by similarity of the candidate topology to the reference target.

Octet/Biosensor Screening: The affinity of the different engineered peptides were evaluated on an Octet Red 384 instrument, using a single-cycle kinetics assay design. The peptides were evaluated separately, and immobilized via a biotin linker to the streptavidin-coated tip of the biosensor. The remaining open streptavidin sites were blocked with biocytin. An analyte was washed over the sensor tip and the binding of the molecules in the analyte to the peptides recorded. For this assay, the analyte was a serial dilution of Bevacizumab, from 0.19 uM to 1.5 uM. Each assay was run in duplicate. Controls were also run, using just a buffer (to control for sensor drift) and a separate control of purified IgG from human ND serum (to control for non-specific IgG binding).

Seven different panning programs were devised, each comprising three rounds, with each round comprising a positive selection step and a negative selection step (FIG. 11). Each program used at least one engineered peptide as a selection molecule. A conventional selection was also included using conventional methods (VEGF as the positive target and BSA as a negative target selecting against non-specific binding). 738 clones were selected for ELISA response analysis after three rounds of panning.

The panning protocol began with a human naïve scFv library, and panning was performed in solution, with the selection molecules bound to biotin (but still in solution). For each round, the starting pool was combined with the negative selection molecule first in solution, and then a streptavidin-coated substrate (e.g., magnetic beads) was applied to the mixture to bind the negative selection molecules. Thus, any phage in the pool that was bound to the negative selection molecule was also bound to the streptavidin-coated support. The remaining solution was removed, and this flow through was then taken on to the positive selection step. The flow through was combined with positive selection molecule, allowed to bind, and then a streptavidin-coated solid substrate applied to the mixture. In this step, the bound phage were retained while the remaining unbound phage were removed. Then the bound phage were then eluted. *E. coli* were transfected with the eluted phage using a 30 minute cultivation, the transfected cells were split for next-generation sequencing and DNA isolation for analysis, and then the phage amplified for use in the subsequent panning round. For each panning program, in each round negative selection was performed first, and positive selection second.

Figure 15:
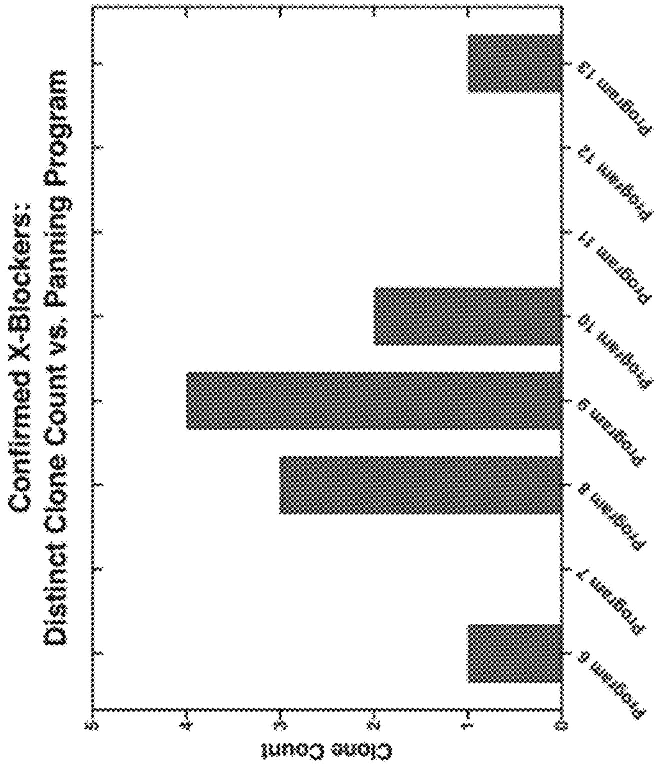
FIG. 15 is a graph of the distinct clones with confirmed cross-blocking characteristics obtained from each of the different selection programs outlined in FIG. 11.

The candidate pools obtained from each of the seven panning programs plus the conventional panning method were then analyzed using ELISA for response to VEGF and sMEM positive selection molecule (iMEM corrected), to evaluate binding to full-length VEGF and to the putative epitope sMEM. The analyses of these ELISA tests are shown in FIGS. 12A-12B and 13A-13H. These results demonstrate that the in vitro selection programs using the engineered peptides did not reduce full-length VEGF binding propensity, and they produced a putative epitope-selective binding bias in the panned clones. The candidate pools were also tested in a cross-blocking ELISA assay for blocking of bevacizumab:VEGF binding (dose-responseive competition with bevacizumab at 0 nM, 67 pM, 670 pM, and 6.7 nM). These results are shown in FIGS. 14A-14I and Table 2, and the total count of confirmed cross-blocking clones obtained from each program is summarized in FIG. 15. These demonstrate that the programmable in vitro selection programs using the engineered peptides were able to isolate clones from the full clone library that cross-block bevacizumab, which shares the reference target epitope used to derive the engineered peptides.

TABLE 2

| Clone ID | Program | X-blocking response slope: Rubust Z-score | sMEM − IMEM | VEGF − IMEM | (sMEM + VEGF) − IMEM | Blocking propensity |
|---|---|---|---|---|---|---|
| Putative ELISA Cross-Blockers, Corroborated with Cross-Blocking Assay | | | | | | |
| YU344-H07 | S9 | 2159.1 | 43.2 | 229.5 | 276.0 | 2435.1 |
| YU344-G05 | S13 | 2055.0 | 17.1 | 44.4 | 61.5 | 2116.5 |
| YU344-G02 | S8 | 1742.9 | 21.6 | 125.1 | 147.9 | 1890.7 |
| YU344-G09 | S10 | 1430.7 | 15.7 | 126.8 | 142.5 | 1573.2 |
| YU344-C11 | S6 | 1326.7 | 29.9 | 165.8 | 198.0 | 1524.6 |
| YU344-A11 | S10 | 1378.7 | 19.8 | 57.1 | 77.8 | 1456.5 |
| YU344-B02 | S8 | 1326.7 | 19.8 | 67.2 | 87.9 | 1414.6 |
| YU344-H03 | S9 | 650.3 | 21.4 | 92.8 | 115.5 | 765.8 |
| YU344-G06 | S9 | 650.3 | 31.3 | 32.2 | 64.6 | 714.9 |
| YU344-B06 | S13 | 650.3 | 12.8 | 29.9 | 46.8 | 697.1 |
| YU344-C04 | S9 | 442.2 | 15.7 | 96.0 | 111.9 | 554.1 |
| YU344-F02 | S8 | 338.2 | 20.0 | 122.9 | 142.2 | 480.4 |
| YU344-G10 | S10 | 286.1 | 58.9 | 113.0 | 178.4 | 464.6 |
| YU344-H01 | S8 | 338.2 | 19.8 | 85.5 | 105.7 | 443.9 |
| YU344-C05 | S13 | 78.0 | 30.4 | 211.4 | 243.8 | 321.8 |
| YU344-H02 | S8 | 78.0 | 18.2 | 45.3 | 70.3 | 148.3 |
| YU344-D05 | S13 | −26.0 | 12.8 | 134.7 | 150.4 | 124.4 |
| YU344-F04 | S9 | 26.0 | 16.9 | 47.5 | 64.3 | 90.4 |
| Putative ELISA Cross-Blockers, Not Corroborated with Cross-Blocking Assay | | | | | | |
| YU344-C02 | S8 | −78.0 | 16.6 | 62.4 | 78.6 | 0.5 |
| YU344-B07 | S9 | −390.2 | 44.1 | 187.6 | 235.2 | −155.0 |
| YU344-G04 | S9 | −962.5 | 49.2 | 198.5 | 254.3 | −708.2 |
| YU344-A03 | S9 | −1742.9 | 24.1 | 181.2 | 213.3 | −1529.5 |
| YU344-G03 | S9 | −1846.9 | 40.0 | 204.8 | 250.2 | −1596.7 |

Figure 17:
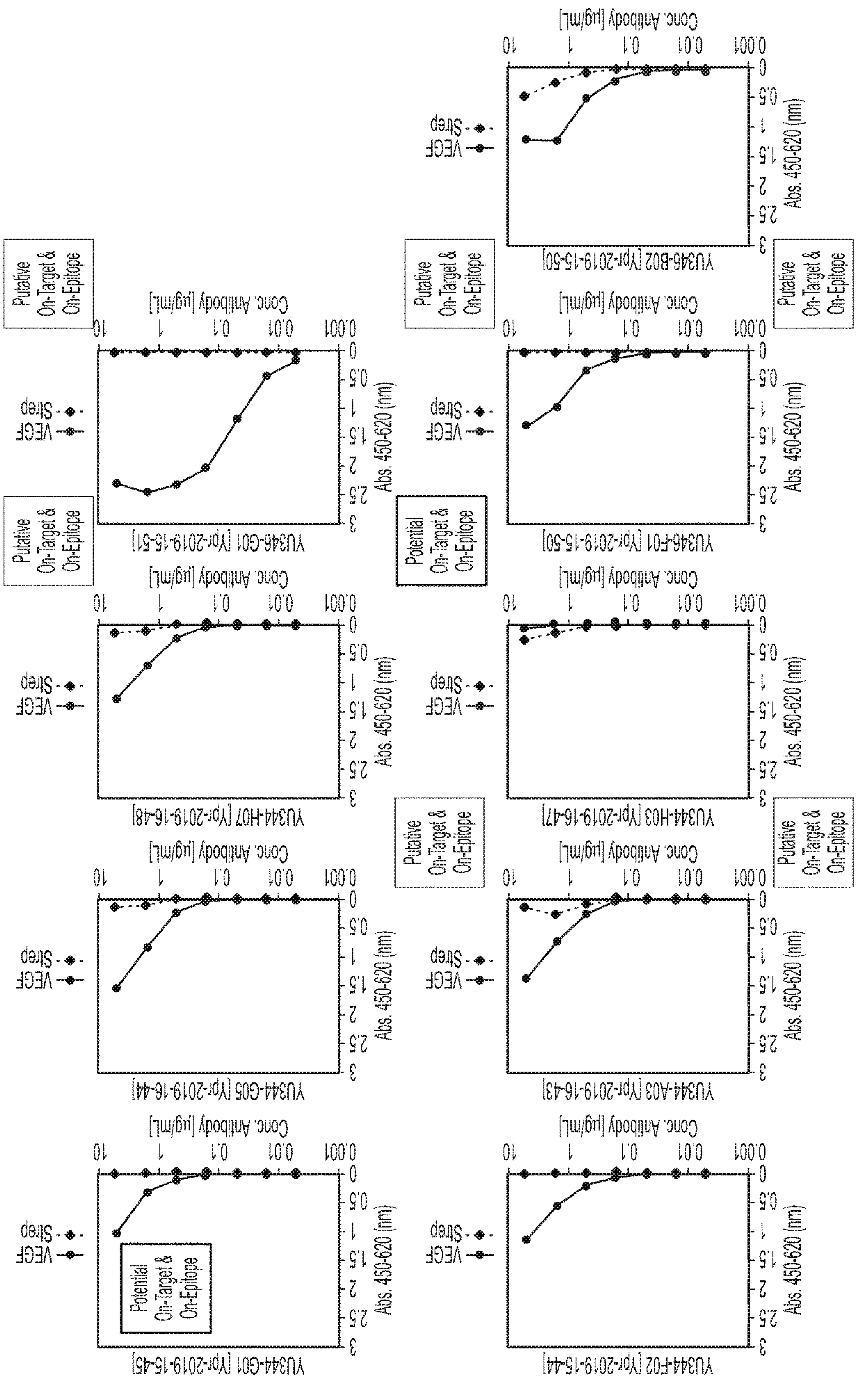
FIG. 17 and FIG. 18 are ELISA binding results for all of the Fabs listed in FIG. 17.
Figure 18:
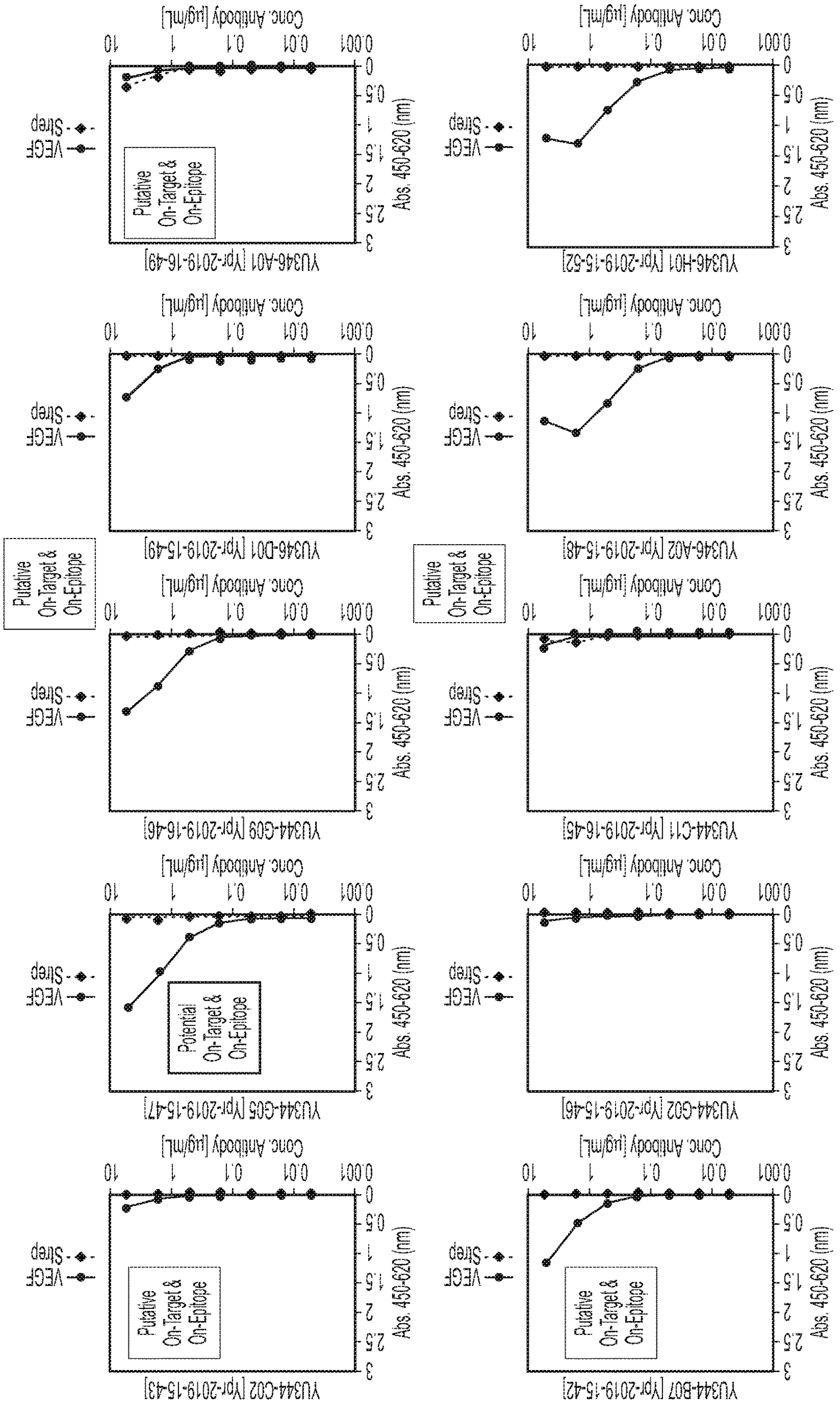

The clones that exhibited cross-blocking behavior were sequenced via Sanger sequencing, and it was found that 11 distinct clones were confirmed. Those obtained from the programmed in vitro selection using engineered peptides are shown in Table 3 Å. Those obtained via the conventional selection with VEGF and BSA are listed in Table 3B. FIG. 17 summarizes the binding, cross-blocking, CDR sequences, and germline usage for all Fabs produced for further testing. FIG. 17 and FIG. 18 show ELISA binding results for the Fabs listed in Tables 3A and 3B. These demonstrate that the programmable in vitro selection steered antibody CDR loop diversity and Ig germline usage in a manner different than conventional panning.

TABLE 3A

| ID | Prog | SEQ ID NO | VH CDR | SEQ ID NO | VL CDR | VH Germline | VL Germline |
|---|---|---|---|---|---|---|---|
| YU344-H07 | S9 | 8 | SYAMS_AISGSGGSTYYADSVKG_GSSGWYQYFQH | 9 | TGSSSNIGAGYDVH_GNSNRPS_QSYDSSLSGYVV | IGHV3-23*04 | IGLV1-40*01 |
| YU344-F02 | S8 | 22 | SYWMS_NIKQDGSEKYYVDSVKG_NRAYYYYGMDV | 23 | SGSRSNVGKNYVY_SDNQRPS_AVWDDSQWV | IGHV3-7*02 | IGLV1-47*02 |
| YU344-B07 | S9 | 28 | NYGMT_FIRSKRYGGTTEYAASVKG_LALADYMYYFDY | 29 | TGRTSNIGTYDVH_GNNNRPP_QSYDNSLRAWL | IGHV3-49*04 | IGLV1-40*01 |
| YU344-C11 | S6 | 14 | DYGMS_FIRSKRYGGTTEYAASVKD_LALAGYMYYFDY | 15 | TGSSSNIGAGYHVH_GNNNRPS_QSYDRSLSGWV | IGHV3-49*04 | IGLV1-40*01 |
| YU344-C05 | S13 | 24 | DYGMT_FIRSKRYGATTEYAASVKG_LALADYMYYFDY | 25 | TGSSSNIGAGYDVH_GNSNRPS_QSYDSSLSAWV | IGHV3-49*04 | IGLV1-40*01 |
| YU344-G06 | S9 | 20 | GYSMN_YIGTSSGSIYYADSVKG_GSSITGYMD | 21 | SGSSSNIGSNYVS_RNNQRPS_ATWDGSLSGVV | IGHV3-48*01 | IGLV1-47*01 |

TABLE 3A-continued

| ID | Prog | SEQ ID NO | VH CDR | SEQ ID NO | VL CDR | VH Germline | VL Germline |
|---|---|---|---|---|---|---|---|
| YU344-G02 | S8 | 10 | SNSVAWN_RTYYRSKWYDDYAVSVKS_YNYAYDAFDI | 11 | TGTSSDVGGYNLVS_DVTKRPS_YSYVGSYTWV | IGHV6-1* 01 | IGLVv11*01 |
| YU344-G09 | S10 | 12 | SYAMH_VISYDGSNKYYADSVKG_GDILTGYPNYYYYGMDV | 13 | SGSSSNIGRNYVY_RDNQRPS_TAWDDSLSGV | IGHV3-30*11 | IGLV1-47*01 |
| YU344-H03 | S9 | 18 | SYGIS_WISAYNGNTNYAQKLQG_ADAFSSGWYFDY | 19 | SGSSSNIGSNSIN_STTQRPS_AAWDDRLNAYV | IGHV1-18*04 | IGLV1-44*01 |
| YU344-C02 | S8 | 26 | SYGMH_AISYDGSNKYYADSVKG_DFNYGDYMGGGMDV | 27 | TGGSSNIGAGYAVR_TNSNRPS_SAWDSSLSGWV | IGHV3-30*18 | IGLV1-40*01 |
| YU344-A03 | S9 | 30 | SSNWWS_EIYHSGSTNYNPSLKS_VLGYSGYGVGAFDI | 31 | ASSTGAVTSGYYPN_STSNKHS_LLSYSGARKI | IGHV4-4*02 | IGLV7-43*01 |

TABLE 3B

| Clone ID | Prog | SEQ ID NO | VH CDR | SEQ ID NO | VL CDR | VH Germline | VL Germline |
|---|---|---|---|---|---|---|---|
| YU346-B02 | S12 | 32 | SYAIS_GIIPIFGTANYAQKFQG_ERGIDAFDI | 33 | GASQSVSSSYLA_GASSRAT_QQYGSSPYT | IGHV1-69D*01 | IGKV3-20*01 |
| YU346-A02 | S12 | 34 | SYAIS_GIIPIFGTANYAQKFQG_GSLGPYYGMDV | 35 | RASQSVSSNFLA_GASSRAT_QQYGSSPWT | IGHV1-69D*01 | IGKV3-20*01 |
| YU346-G01 | S12 | 36 | SYAIS_GIIPIFGTANYAQKFQG_MRGRDAFDI | 37 | RASQSVSSSYLA_GASSRAT_QQYGSSPYT | IGHV1-69D*01 | IGKV3-20*01 |
| YU346-H01 | S12 | 38 | SYAIS_GIIPIFGTANYAQKFQG_GLGRDAFDI | 39 | RASQSVSSSYLA_GASSRAT_QQYGSSPYT | IGHV1-69D*01 | IGKV3-20*01 |

TABLE 4

| Approved Tx mAbs | | | | |
|---|---|---|---|---|
| bevacizumab | SEQ ID NO | GYTFTNYG_INTYTGEP_AKYPHYYGSSHWYFDV | SEQ ID NO | QDISNY_FTS_QQYSTVPWT |
| ranibizumab | 51<br>52 | GYDFTHYG_INTYTGEP_AKYPYYYGTSHWYFDV | 53<br>53 | QDISNY_FTS_QQYSTVPWT |

The selection pools were scored using the following equation:

Blocking Propensity=SUM(*X*-blocking Slope, (sMEM+VEGF)−iMEM), where *X*-blocking Slope, sMEM and VEGF are Robust *Z*-Scores.

Figure 19:
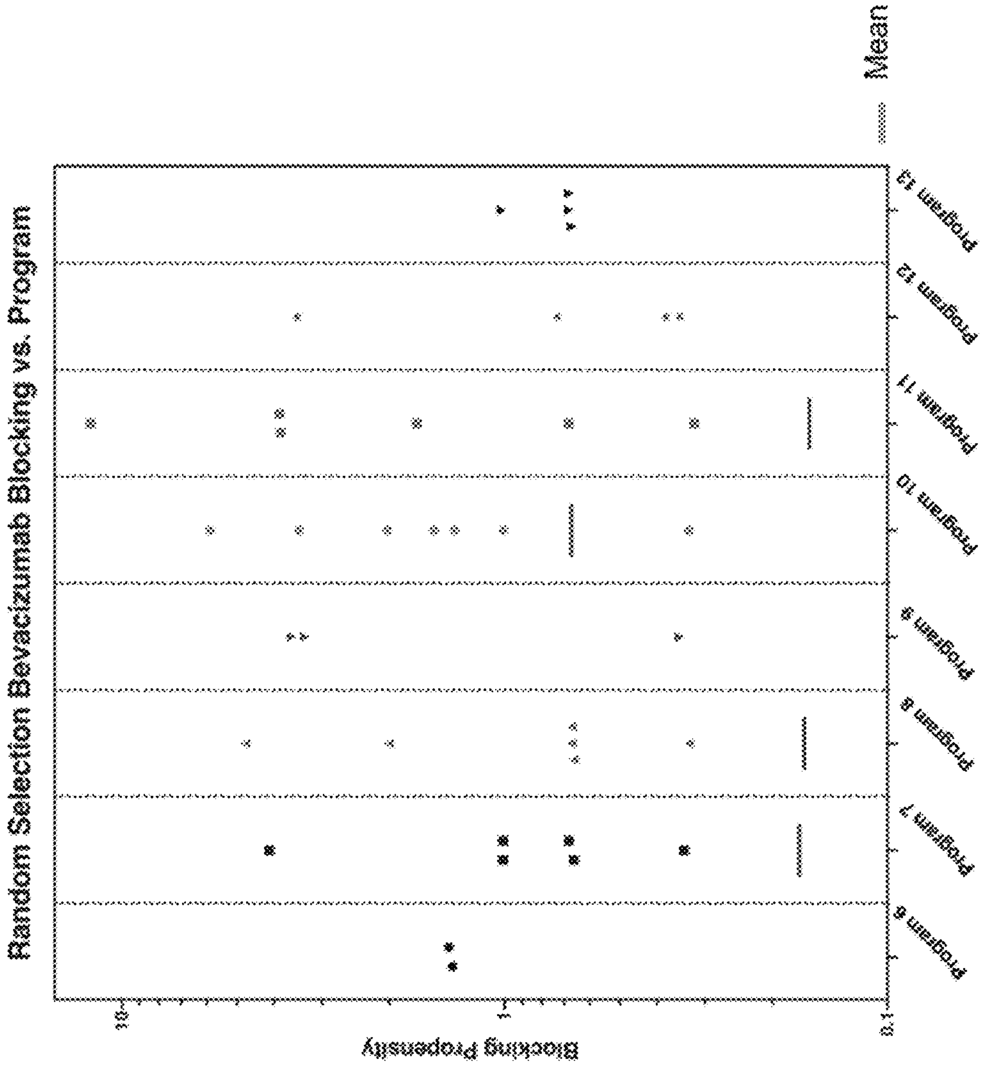
FIG. 19 shows the Bevacizumab blocking propensity score for random clones vs. those selected from the selection programs outlined in FIG. 11 (0 nM, 67 pM, 670 pM, 6.7 nM). The ELISA Z-Score(sMEM+VEGF−iMEM)+Bevacizumab Blocking Z-Score.

Scoring rationale: If a blocking response is observed, through a significant (by robust z-score) negative slope, then blocking propensity is a combination of z-scores for VEGF binding and X-blocking slope. The blocking propensity is summarized in FIG. 19, and in the below table.

TABLE 6

| Summary of clones obtained from different programmed selection protocols (S#) and blocking propensity. | | |
|---|---|---|
| Clone ID | Strategy | Blocking Propensity |
| YU348-A12 | S6 | 1.40 |
| YU348-C12 | S6 | 1.37 |
| YU348-B12 | S6 | 0.00 |
| YU348-H11 | S6 | 0.00 |
| YU348-E12 | S6 | 0.00 |
| YU348-G04 | S6 | 0.00 |
| YU348-F04 | S6 | 0.00 |
| YU348-F12 | S6 | 0.00 |

TABLE 6-continued

Summary of clones obtained from different programmed selection protocols (S#) and blocking propensity.

| Clone ID | Strategy | Blocking Propensity |
|---|---|---|
| YU348-E04 | S6 | 0.00 |
| YU348-D12 | S6 | 0.00 |
| YU348-G11 | S6 | 0.00 |
| YU348-F11 | S6 | 0.00 |
| YU348-D01 | S7 | 4.12 |
| YU348-E01 | S7 | 1.01 |
| YU348-C01 | S7 | 1.01 |
| YU348-A01 | S7 | 0.68 |
| YU348-A11 | S7 | 0.66 |
| YU348-H10 | S7 | 0.34 |
| YU348-E10 | S7 | 0.00 |
| YU348-F10 | S7 | 0.00 |
| YU348-G10 | S7 | 0.00 |
| YU348-C10 | S7 | 0.00 |
| YU348-D10 | S7 | 0.00 |
| YU348-B01 | S7 | 0.00 |
| YU348-A04 | S8 | 4.76 |
| YU348-B09 | S8 | 2.01 |
| YU348-H01 | S8 | 0.67 |
| YU348-C09 | S8 | 0.67 |
| YU348-D11 | S8 | 0.66 |
| YU348-F01 | S8 | 0.33 |
| YU348-H08 | S8 | 0.00 |
| YU348-A02 | S8 | 0.00 |
| YU348-E11 | S8 | 0.00 |
| YU348-G01 | S8 | 0.00 |
| YU348-A09 | S8 | 0.00 |
| YU348-D09 | S8 | 0.00 |
| YU348-D04 | S9 | 3.61 |
| YU348-B04 | S9 | 3.33 |
| YU348-A06 | S9 | 0.35 |
| YU348-C04 | S9 | 0.00 |
| YU348-D02 | S9 | 0.00 |
| YU348-B02 | S9 | 0.00 |
| YU348-C11 | S9 | 0.00 |
| YU348-H05 | S9 | 0.00 |
| YU348-E02 | S9 | 0.00 |
| YU348-G05 | S9 | 0.00 |
| YU348-B11 | S9 | 0.00 |
| YU348-C02 | S9 | 0.00 |
| YU348-F09 | S10 | 5.88 |
| YU348-G09 | S10 | 3.45 |
| YU348-E09 | S10 | 2.03 |
| YU348-G06 | S10 | 1.53 |
| YU348-D07 | S10 | 1.35 |
| YU348-A10 | S10 | 1.01 |
| YU348-B10 | S10 | 0.33 |
| YU348-B07 | S10 | 0.00 |
| YU348-H09 | S10 | 0.00 |
| YU348-C07 | S10 | 0.00 |
| YU348-A07 | S10 | 0.00 |
| YU348-H06 | S10 | 0.00 |
| YU348-A05 | S11 | 12.06 |
| YU348-D05 | S11 | 3.87 |
| YU348-D06 | S11 | 3.85 |
| YU348-E05 | S11 | 1.70 |
| YU348-B06 | S11 | 0.68 |
| YU348-C05 | S11 | 0.32 |
| YU348-E06 | S11 | 0.00 |
| YU348-F05 | S11 | 0.00 |
| YU348-F06 | S11 | 0.00 |
| YU348-C06 | S11 | 0.00 |
| YU348-B05 | S11 | 0.00 |
| YU348-H04 | S11 | 0.00 |
| YU348-B03 | S12 | 3.49 |
| YU348-B08 | S12 | 0.73 |
| YU348-F07 | S12 | 0.38 |
| YU348-C08 | S12 | 0.35 |
| YU348-E07 | S12 | 0.00 |
| YU348-H07 | S12 | 0.00 |
| YU348-A08 | S12 | 0.00 |
| YU348-H02 | S12 | 0.00 |
| YU348-G02 | S12 | 0.00 |
| YU348-A03 | S12 | 0.00 |
| YU348-F02 | S12 | 0.00 |
| YU348-G07 | S12 | 0.00 |
| YU348-D08 | S13 | 1.02 |
| YU348-G03 | S13 | 0.68 |
| YU348-C03 | S13 | 0.68 |
| YU348-H03 | S13 | 0.67 |
| YU348-F03 | S13 | 0.00 |
| YU348-F08 | S13 | 0.00 |
| YU348-H12 | S13 | 0.00 |
| YU348-G08 | S13 | 0.00 |
| YU348-D03 | S13 | 0.00 |
| YU348-G12 | S13 | 0.00 |
| YU348-E08 | S13 | 0.00 |
| YU348-E03 | S13 | 0.00 |

The different selection programs were also evaluated for cross-blocking enrichment compared with the control (conventional) program, using a uniform, random sampling of all in vitro selection programs as compared to the conventional program (using just VEGF and BSA as selection molecules), at least four of the programs using engineered peptides showed enrichment, summarized in FIG. 20. The statistical test for cross-blocking enrichment was the Kruskal-Wallis Test, as follows:

1. Random-uniform sample of 96-clones from all panning programs, measure cross-blocking activity
2. Rank cross-blocking across all 96-clones
3. Perform Kruskal-Wallis test to calculate per-program mean cross-blocking rank vs. control
4. X-blocking enrichment=100%*(program cross-blocking mean rank−control mean rank)/(control mean rank)

Figure 21:
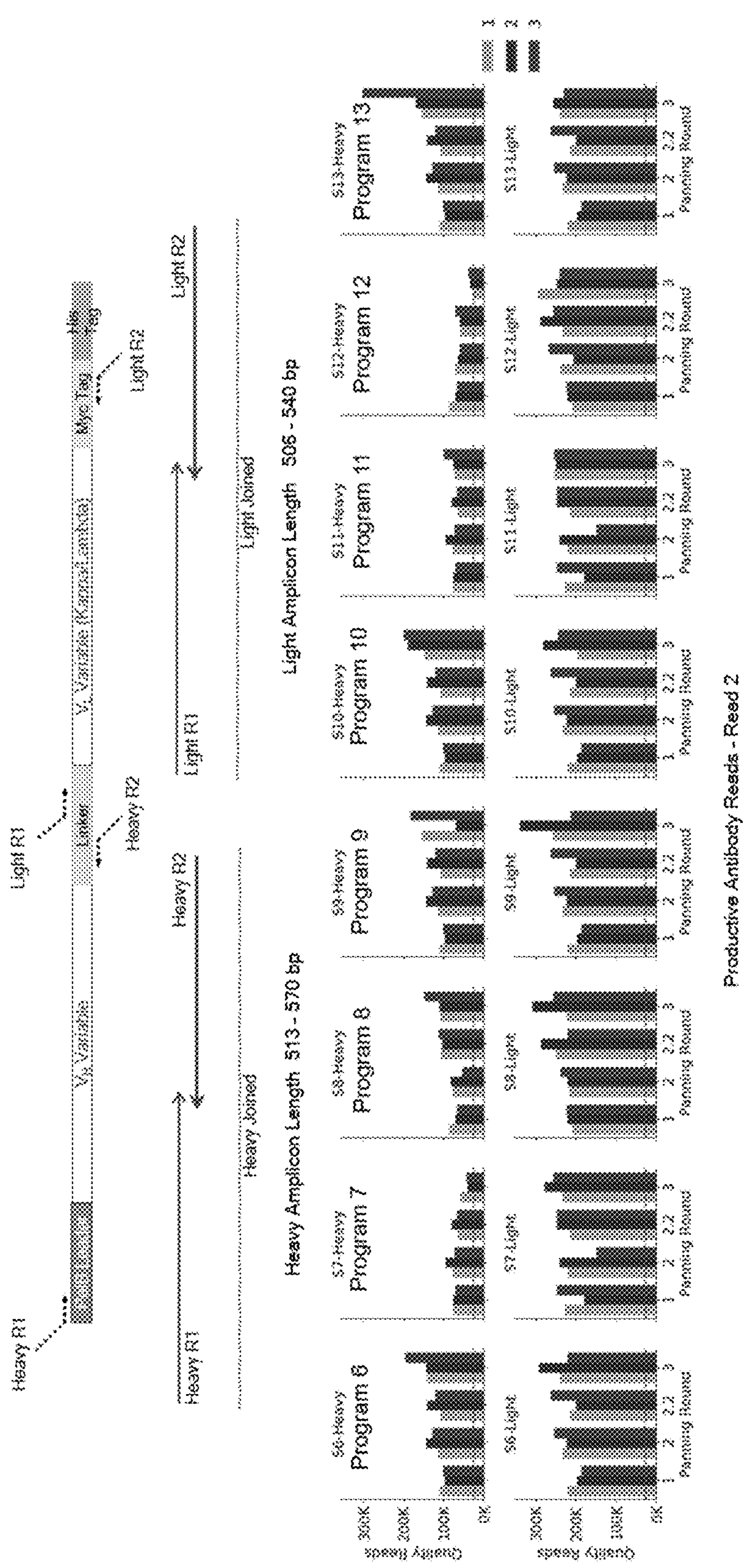
FIG. 21 is a schematic showing how next-generation sequencing samples of the selected clones were prepared. Individual heavy and light chain sequence at constant portions of the expression vector were cloned out, using a 2×250 paired end sequencing run. The ends were then joined and the reads annotated (e.g., using PyIg). The reads obtained from clones selected using each selection program are shown in the bar graphs.

The clones were also subjected to next-generation sequencing (NGS) to obtain information about the CDR loops on a genomic level. FIG. 21 provides schematic overview of the preparation of NGS samples. Briefly, samples were prepared by cloning out individual heavy and light chain sequences at constant portions of the expression vector. A 2×250 paired end sequencing run was used, and the reads were joined and annotated with a tool such as PyIg.

Figure 22:
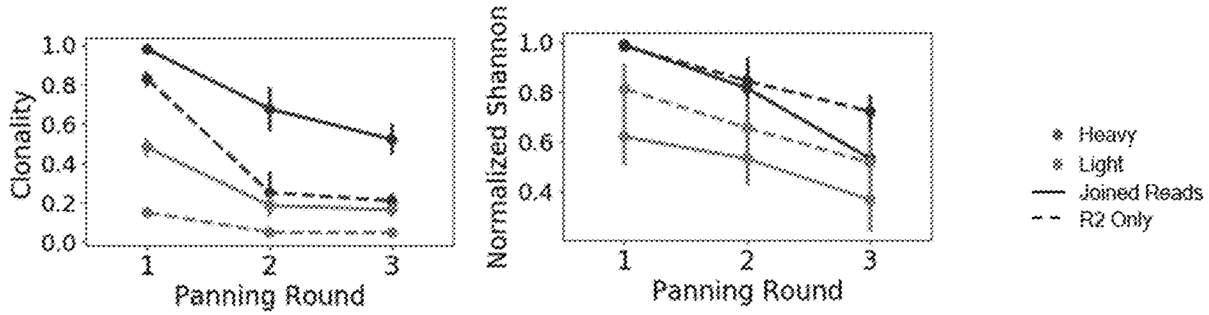
FIG. 22 demonstrates a clonality analysis (number of distinct antibodies) of the different panning rounds, and normalized Shannon analysis.
Figure 23:
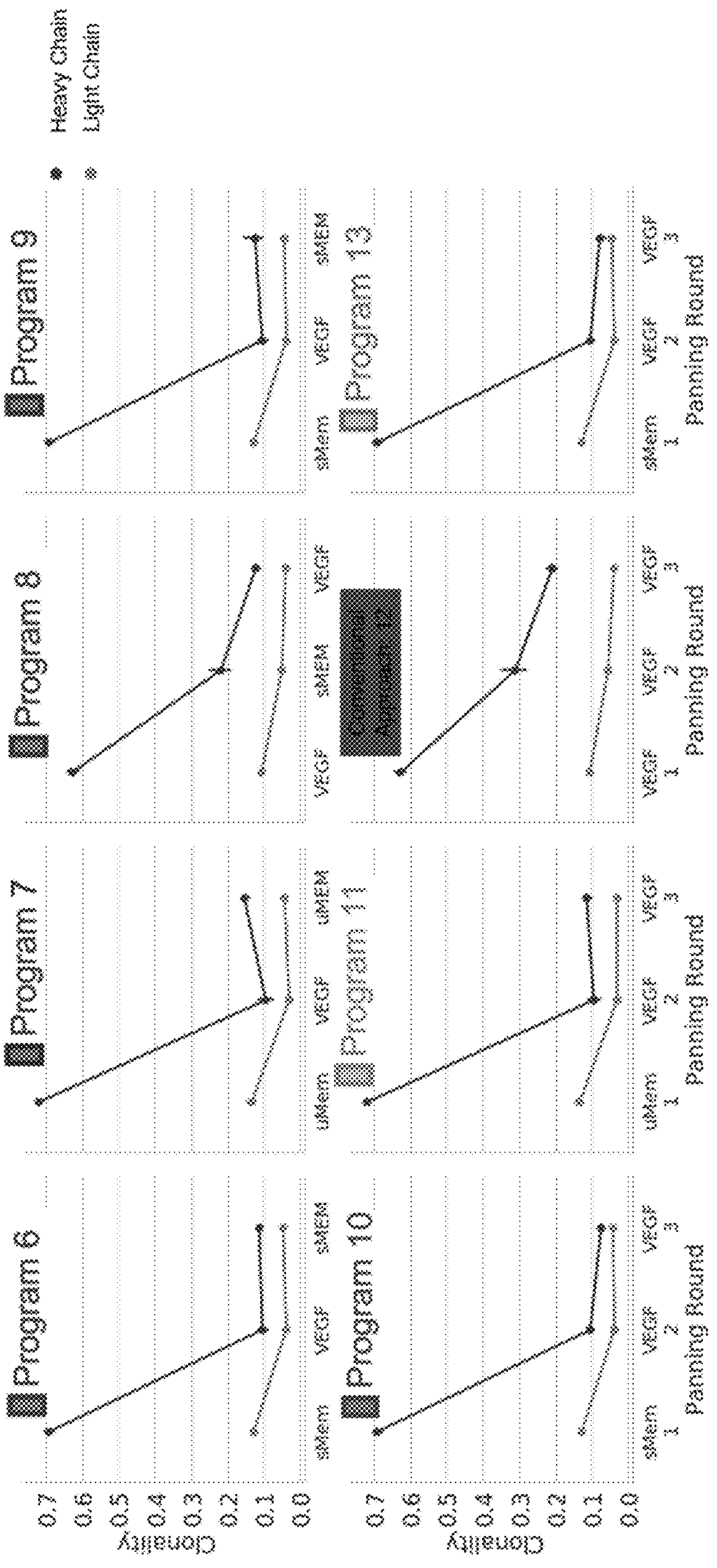
FIG. 23 shows the clonality of the different screening programs described in FIG. 11.
Figure 24A:
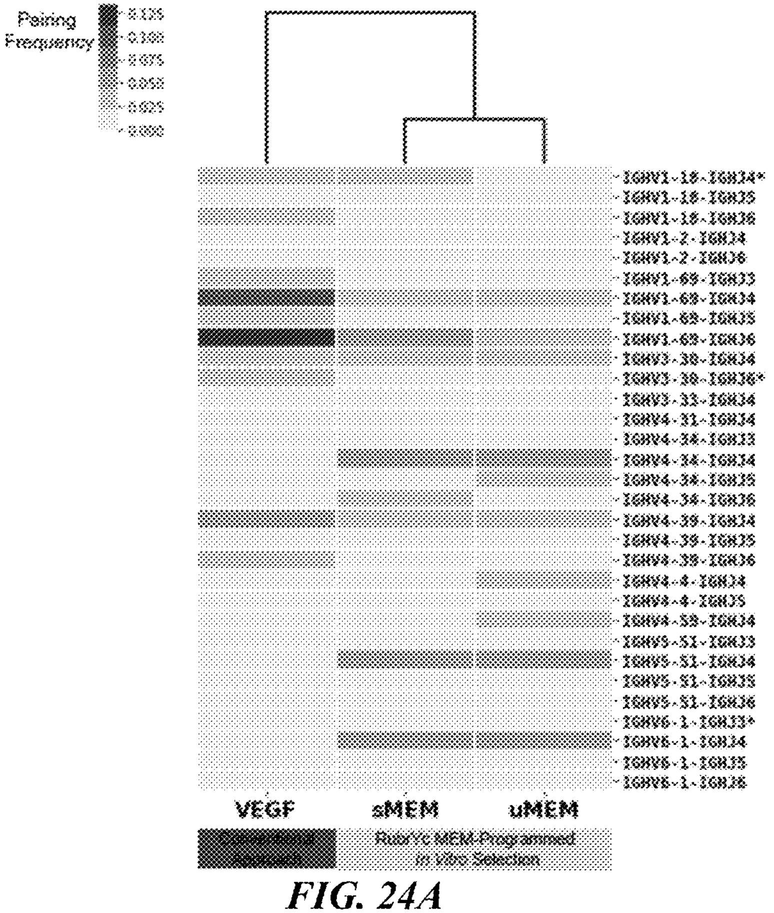
FIGS. 24A-24L are germline usage heatmaps and dimension reduction plots analyzing how the different screening rounds and programs, for round 1 (FIGS. 24A-24D), round 2 (FIGS. 24E-24H), and round 3 (FIGS. 24I-24L), shape diversity of the resulting selected pools.
Figure 24B:
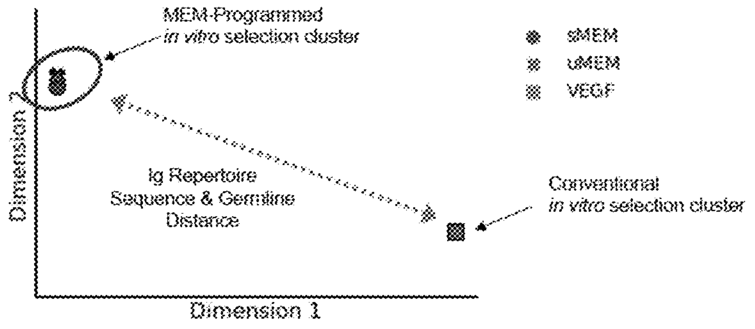
Figure 24C:
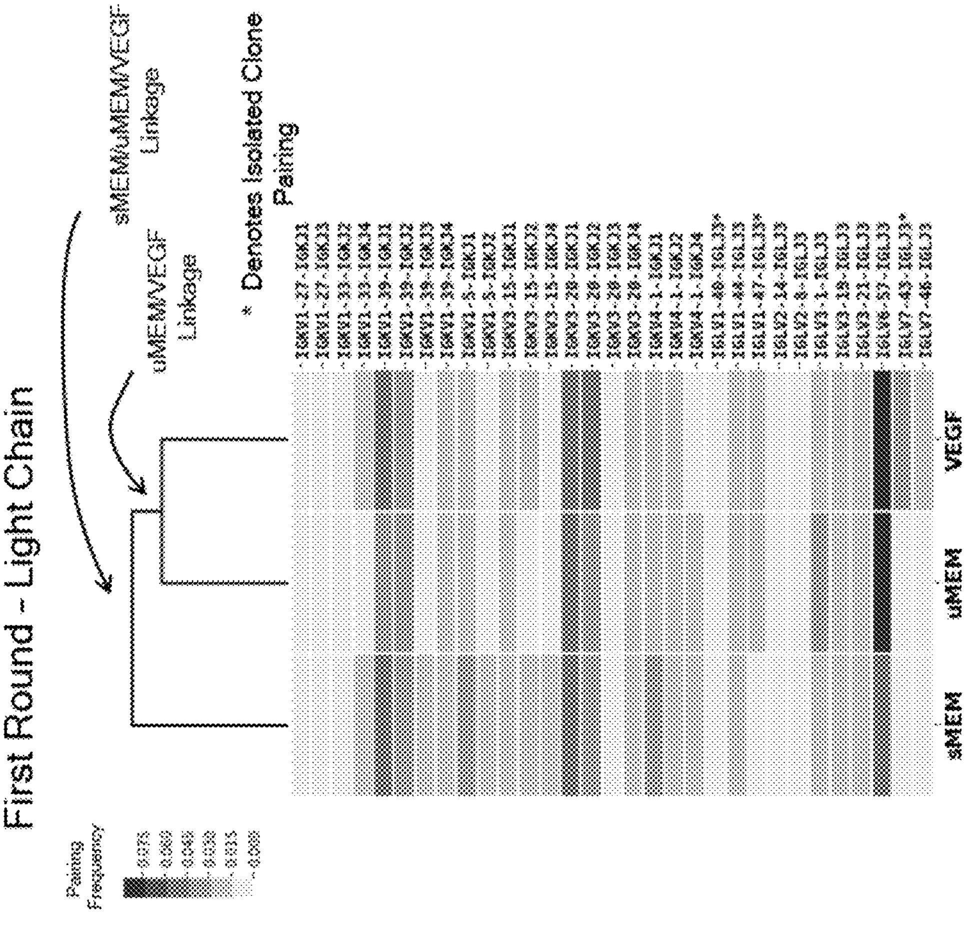
Figure 24D:
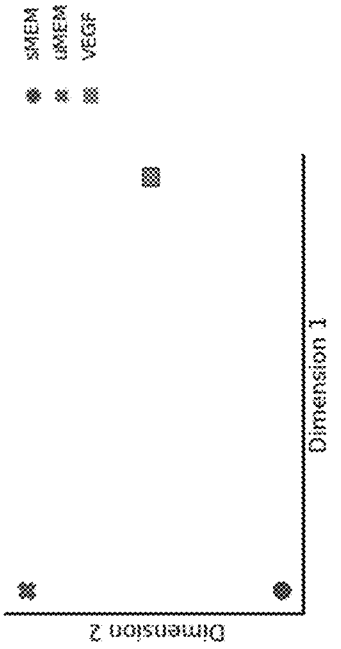
Figure 24F:
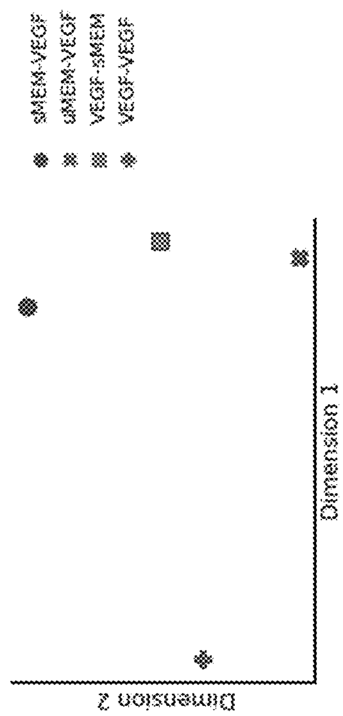
Figure 24E:
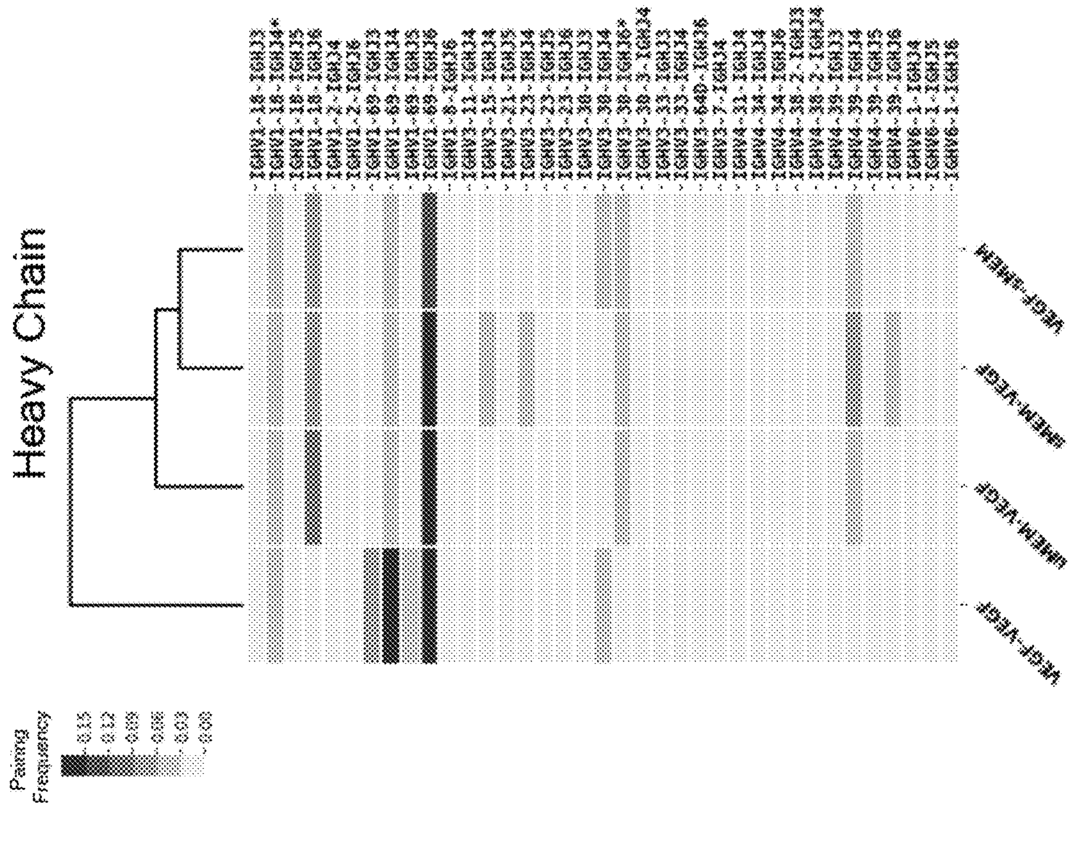
Figure 24G:
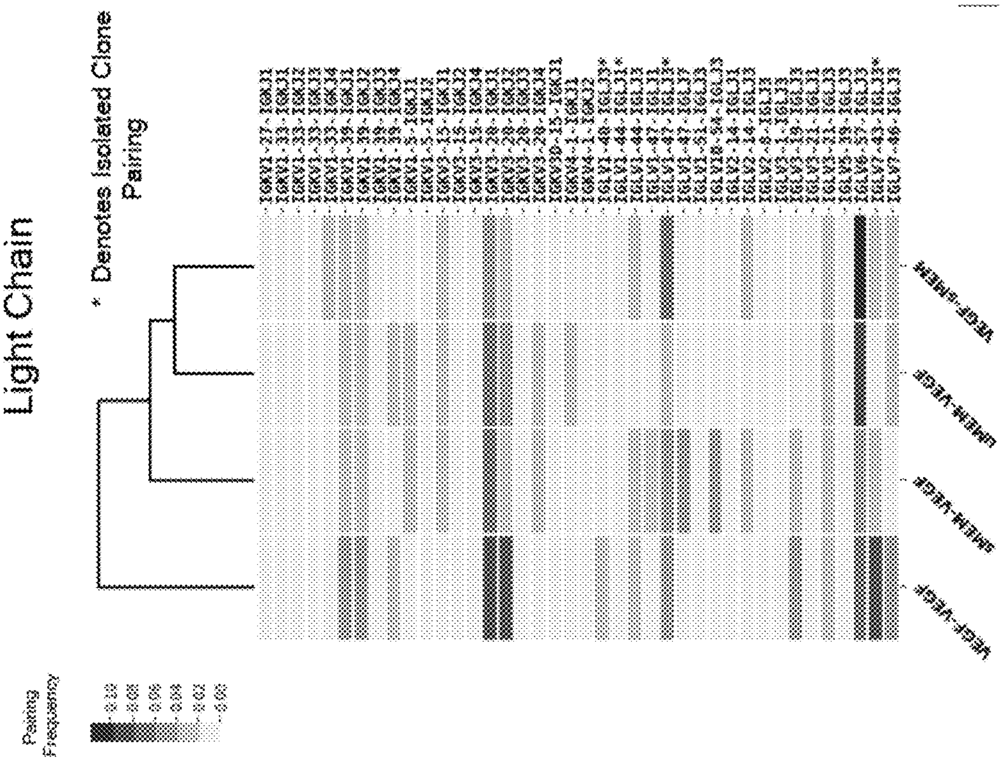
Figure 24H:
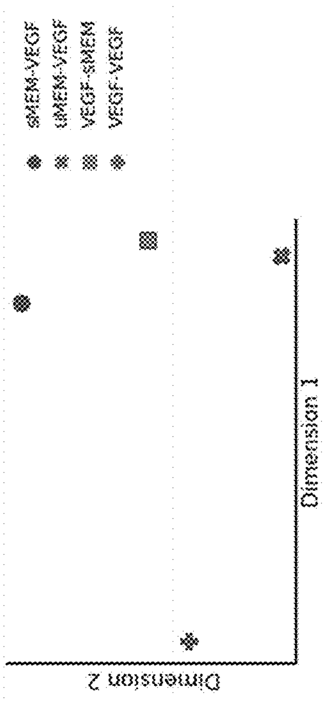
Figure 24J:
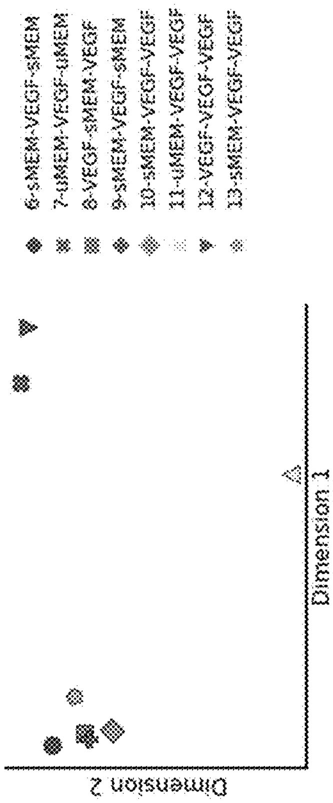
Figure 24I:
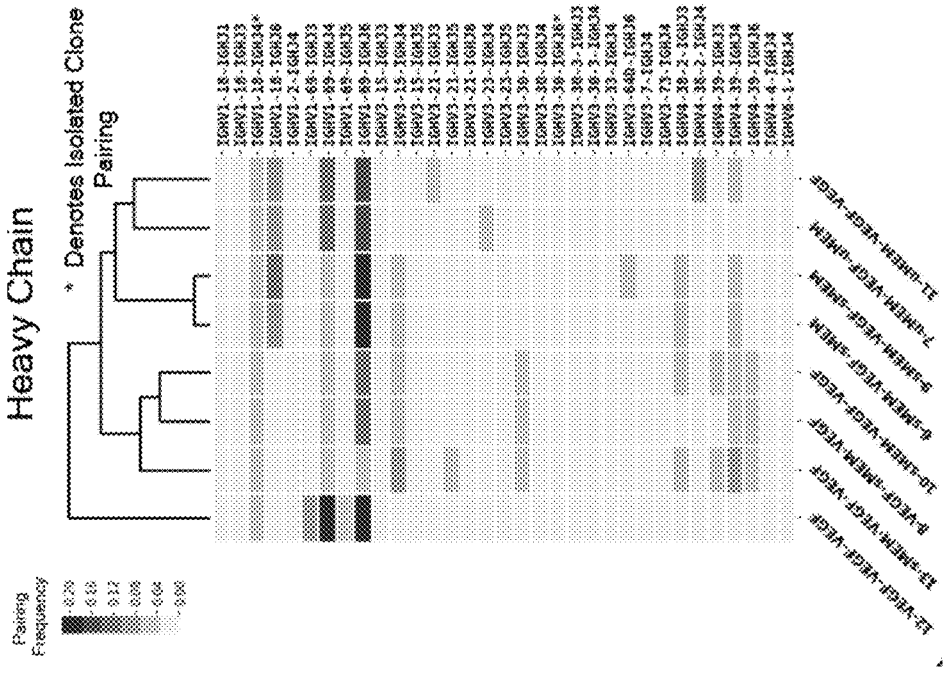
Figure 24K:
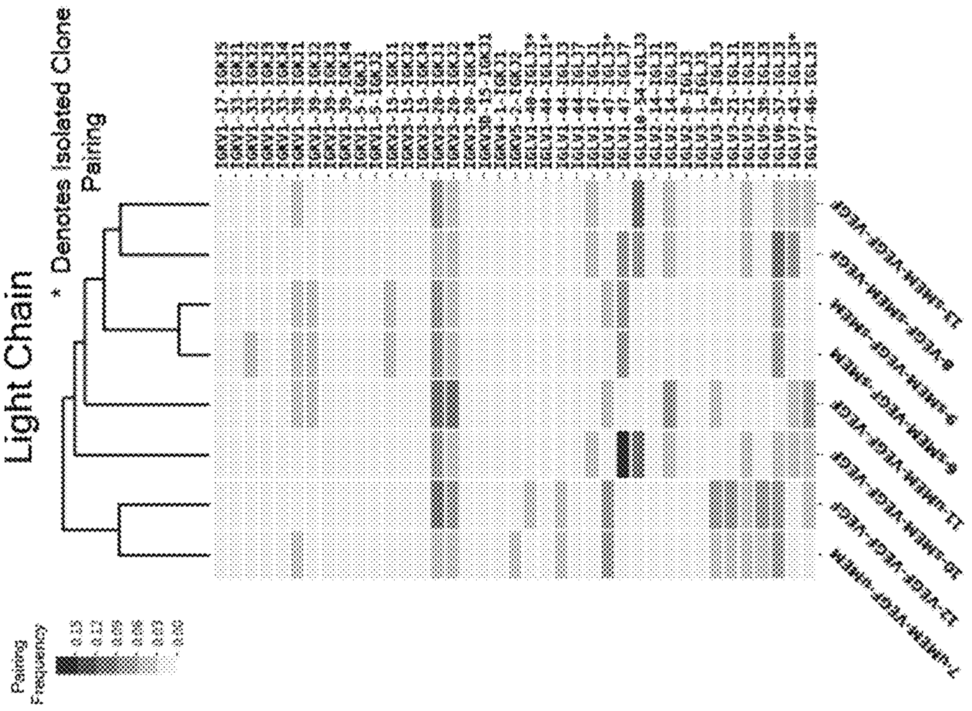
Figure 24L:
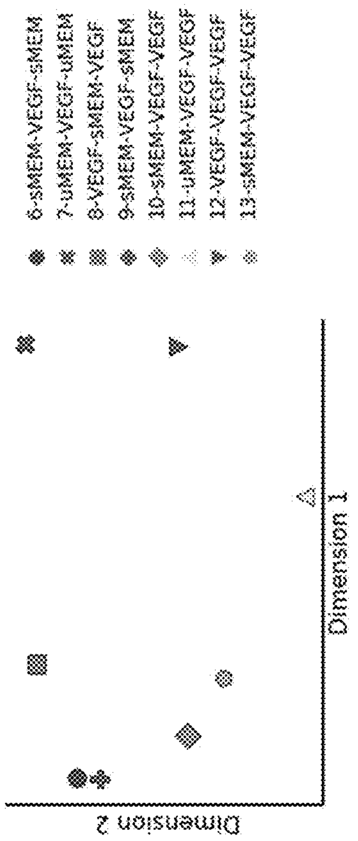

The sequences were analyzed to determine if two unique sequences were actually different antibodies, versus sequencing errors, referred to as "clonality". Normalized Shannon evaluation was also used, as shown in FIG. 22. A summary of the clonality for each round of each program is shown in FIG. 23.

While a classical panning approach using only a full length protein (VEGF) does focus diversity (Program 12), an engineered-peptide-programmed panning approach focuses repertoire diversity at least 2× more efficiently. FIGS. 24A-24L are pairing frequency comparisons and dimensional charts analyzing how the different screening rounds, for round 1 (FIGS. 24A-24D), round 2 (FIGS. 24E-24H), and round 3 (FIGS. 24I-24L), shape diversity of the resulting selected pools.

The engineered peptide (MEM)-programmed in vitro selection isolates distinct antibody clonotypes with higher diversity germline usage vs. conventional approach at the first round of selection. Using the sMEM-based in vitro selection produces more diverse light chain germline usage at round 1 vs. full length antigen and uMEM. MEM-based in vitro selection programs produce distinct heavy chain germline usage at round 2 vs. full length antigen. The order and identity of the MEM used in the in vitro selection program affect heavy chain germline usage. MEM-based in vitro selection programs produce distinct light chain germline usage at round 2 vs. full length antigen. The order and identity of the MEM used in the in vitro selection program affect light chain germline usage. MEM-based in vitro selection programs produce distinct, AND more diverse heavy chain germline usage at round 3 vs. full length antigen. The order and identity of the MEM used in the in vitro selection program affect heavy chain germline usage and diversity. MEM-based in vitro selection programs produce distinct, AND more diverse light chain germline usage at round 3 vs. full length antigen. The order and identity of the MEM used in the in vitro selection program affect light chain germline usage and diversity.

Figure 25A:
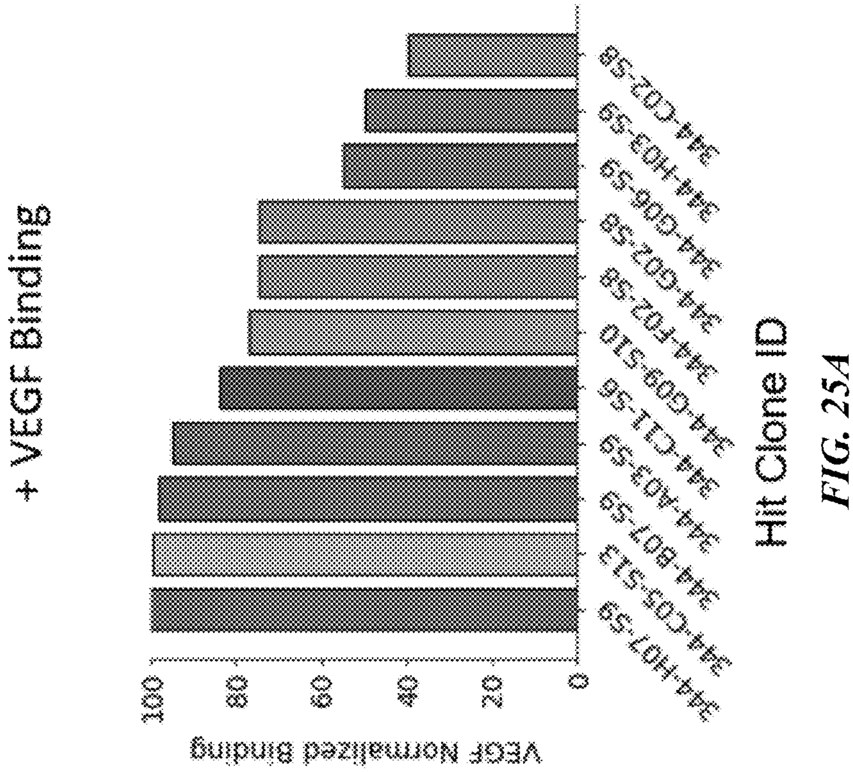
FIGS. 25A-25B summarize the clones isolated from each selection program (S # in x-axis) and their binding to VEGF and the engineered peptide sMEM.
Figure 25B:
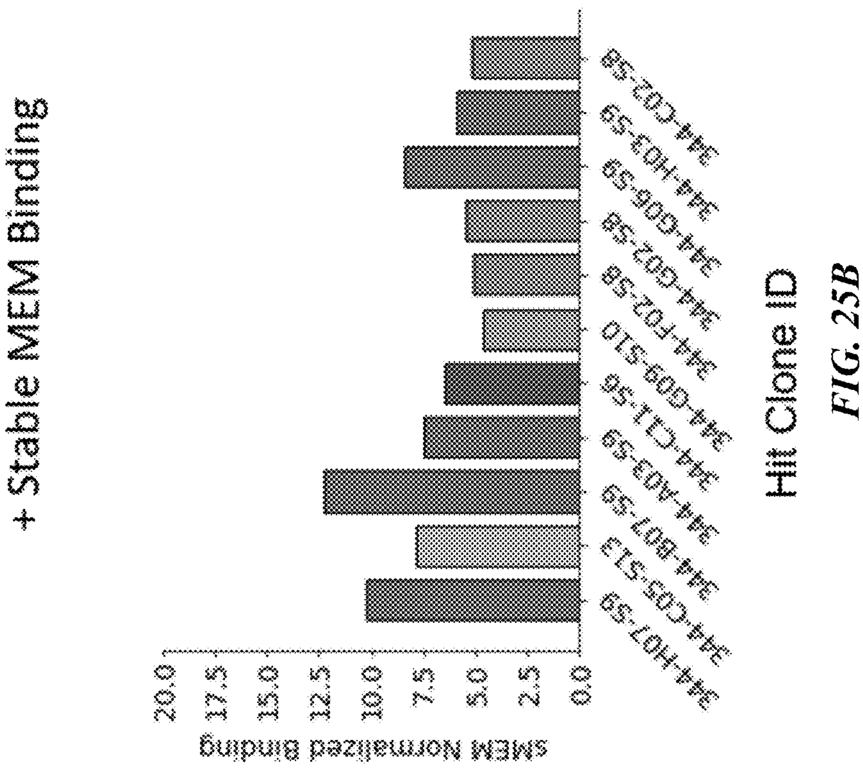

A summary of how the different phage panning programs focused Fab hits is provided in FIGS. 25A and 25B.

Figure 26:
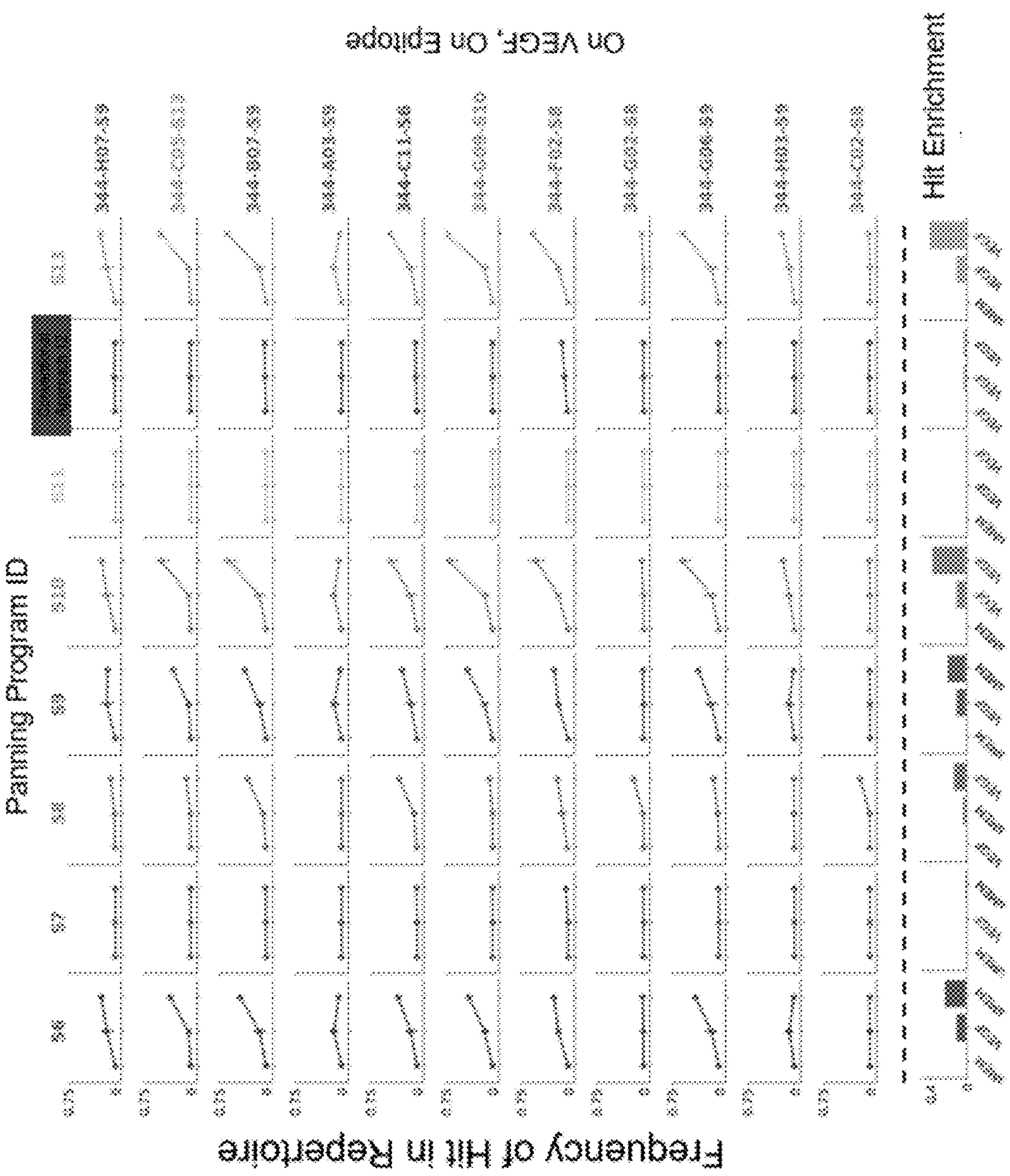
FIG. 26 is a summary of the rate of enrichment of unique mAb hits obtained from each round of each program that were confirmed to bind VEGF and cross-block Bevacizumab, and which were not identified in the conventional panning not using engineered peptides (program 12).
Figure 27:
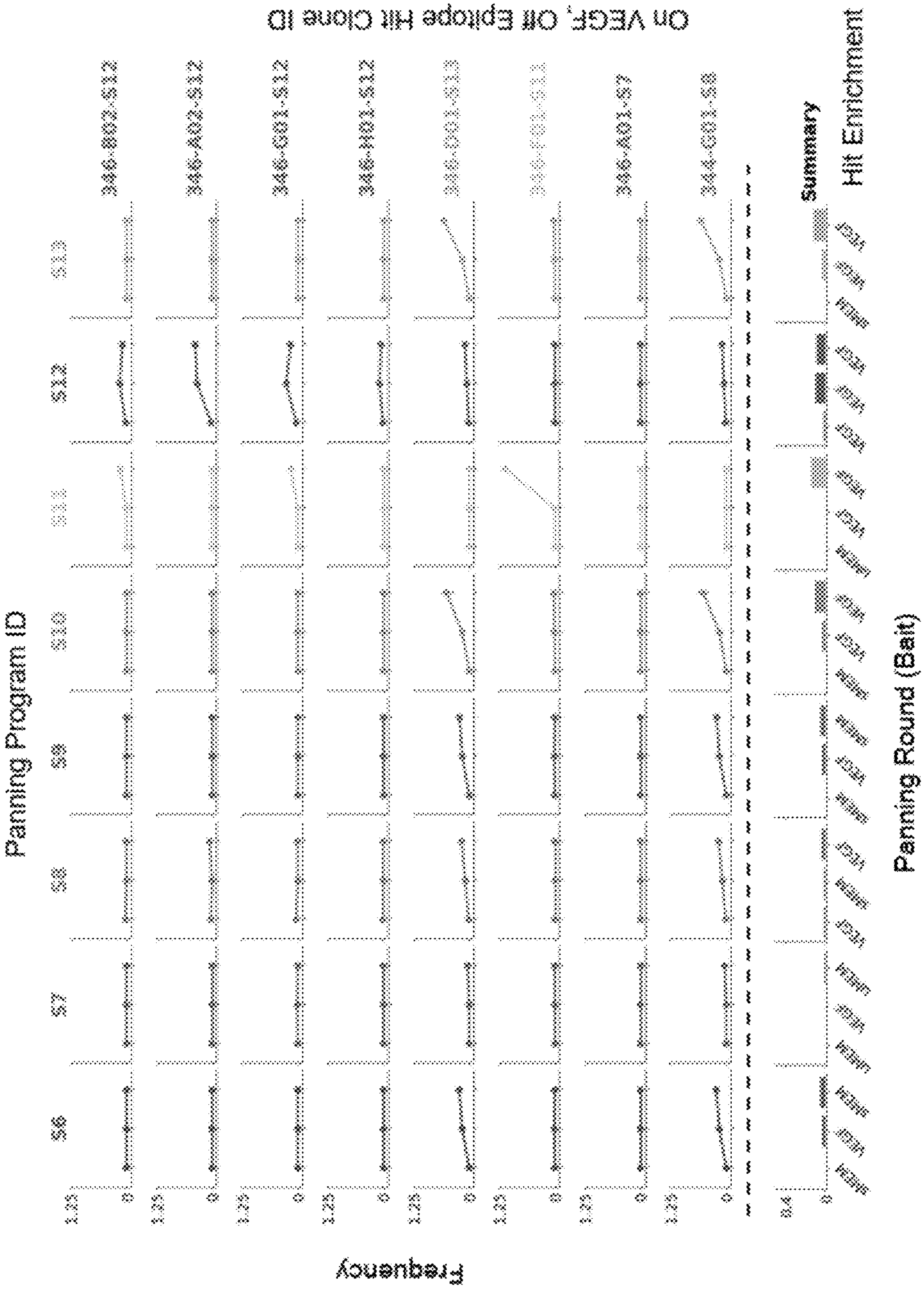
FIG. 27 is a summary of the rate of enrichment of mAb hits obtained the convention panning program (12) which were confirmed to bind VEGF but which were not putative epitope-selective mAb hits.
Figure 28:
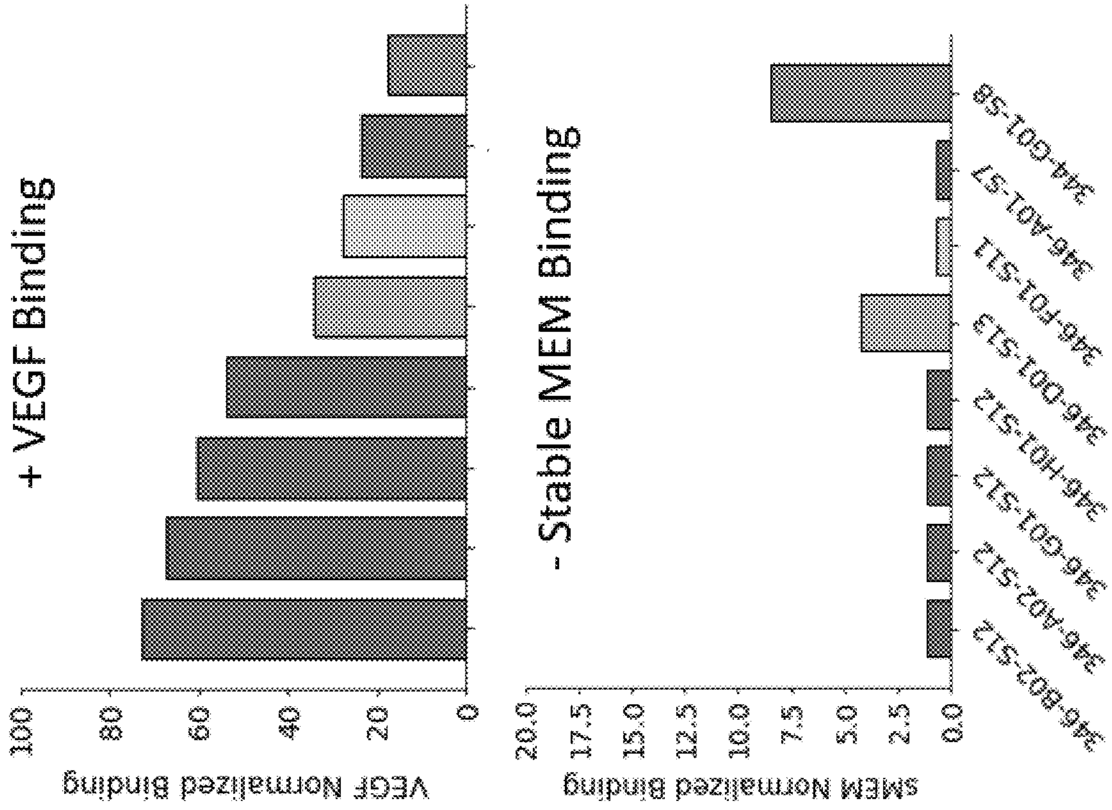
FIG. 28 summarizes binding to sMEM or VEGF of different clones obtained from different panning programs.
Figure 29:
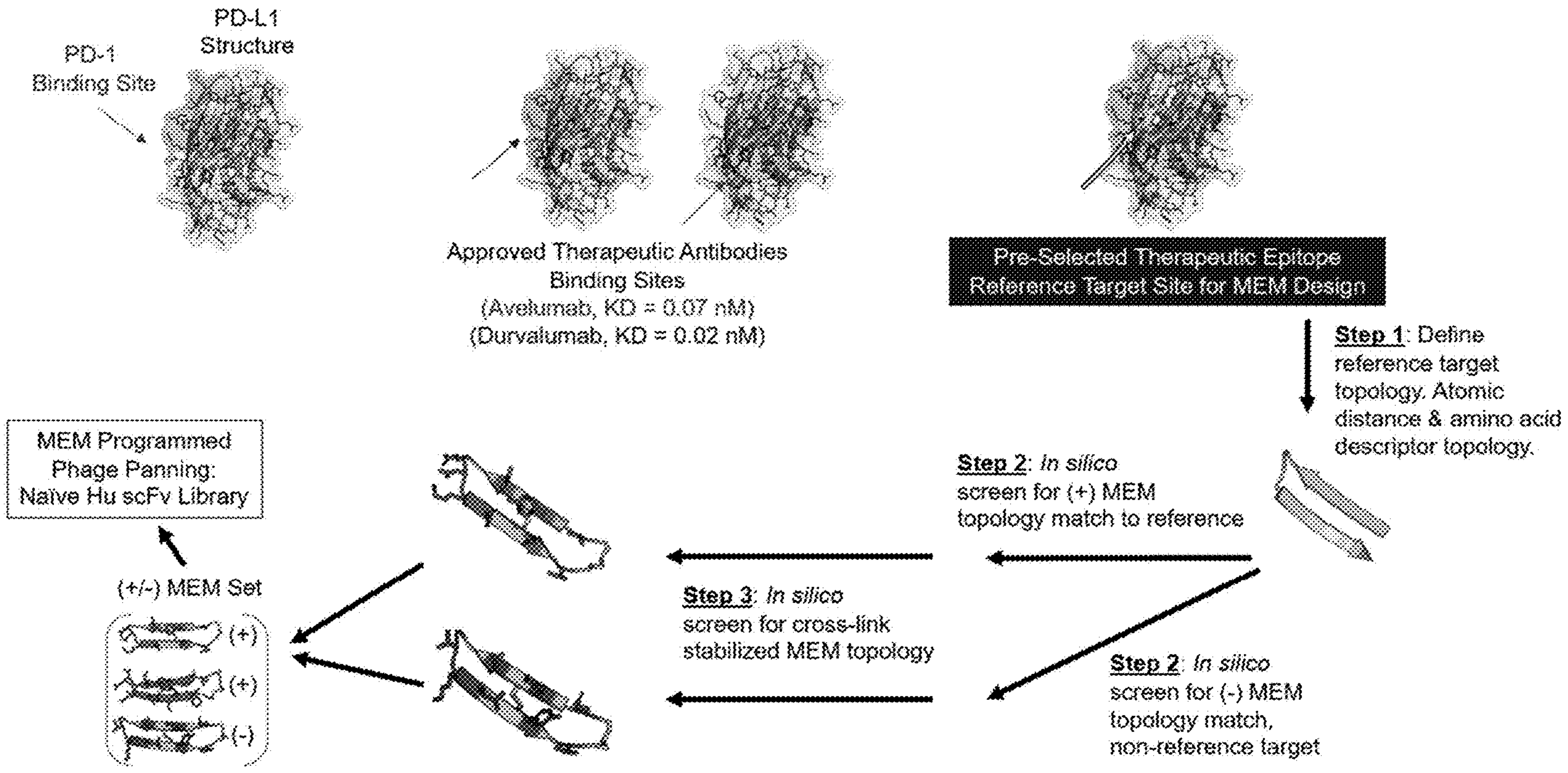
FIG. 29 is a schematic overview of a second exemplary set of programmed in vitro selection protocols, targeting a proposed therapeutic epitope reference site on PD-L1. Spatially-associated topological constraints were derived from this putative site, combined, and used to screen in silico for engineered peptides that had overlapping characteristics with the combination of constraints. These were then used in rounds of selection in phage panning of a naïve Hu scFv library.
Figure 30:
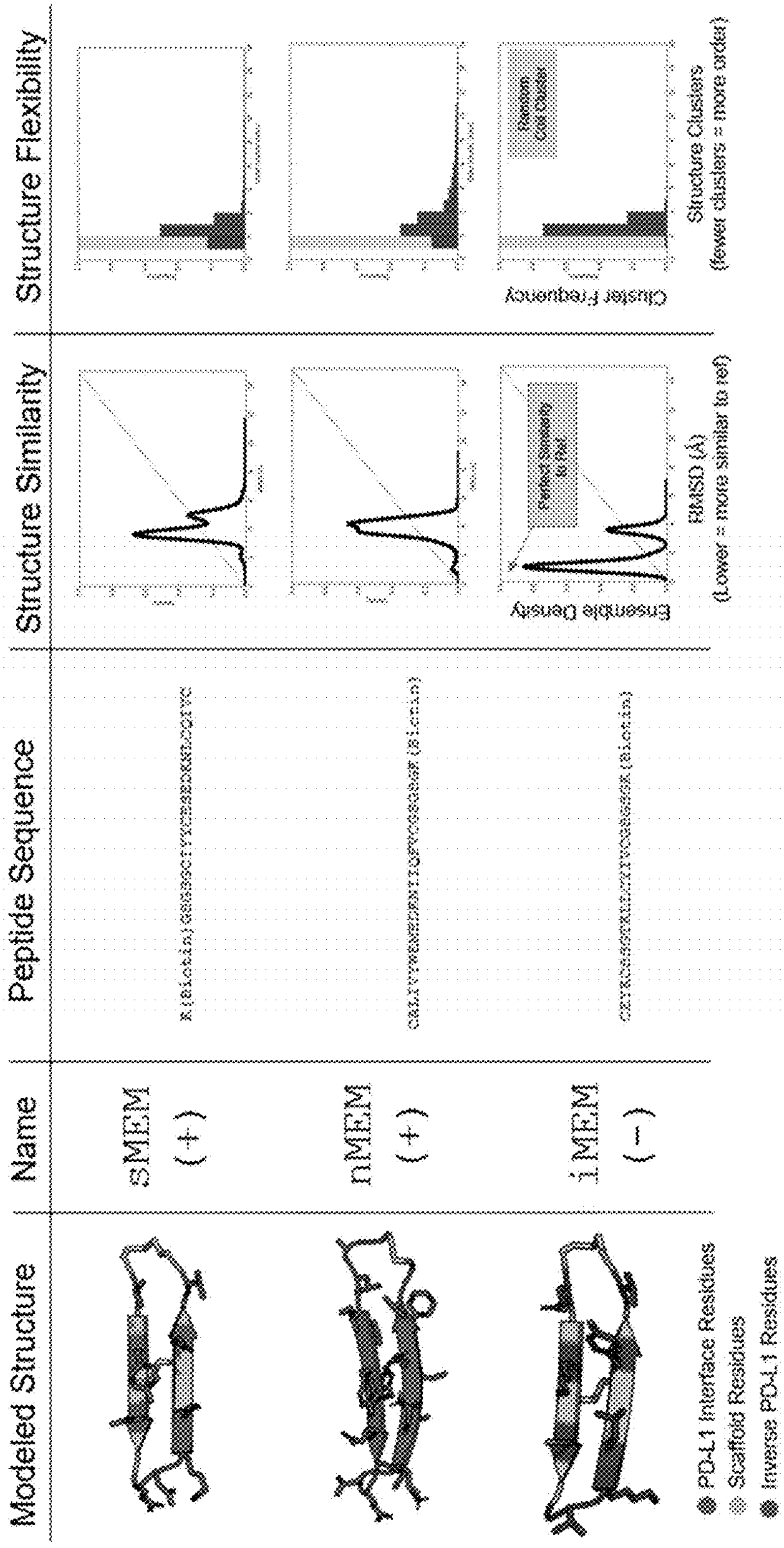
FIG. 30 provides the modeled structure and peptide sequences of the three engineered peptides selected according to the schematic in FIG. 29. Sequences are provided as SEQ ID NOS: 5-7.
Figure 31A:
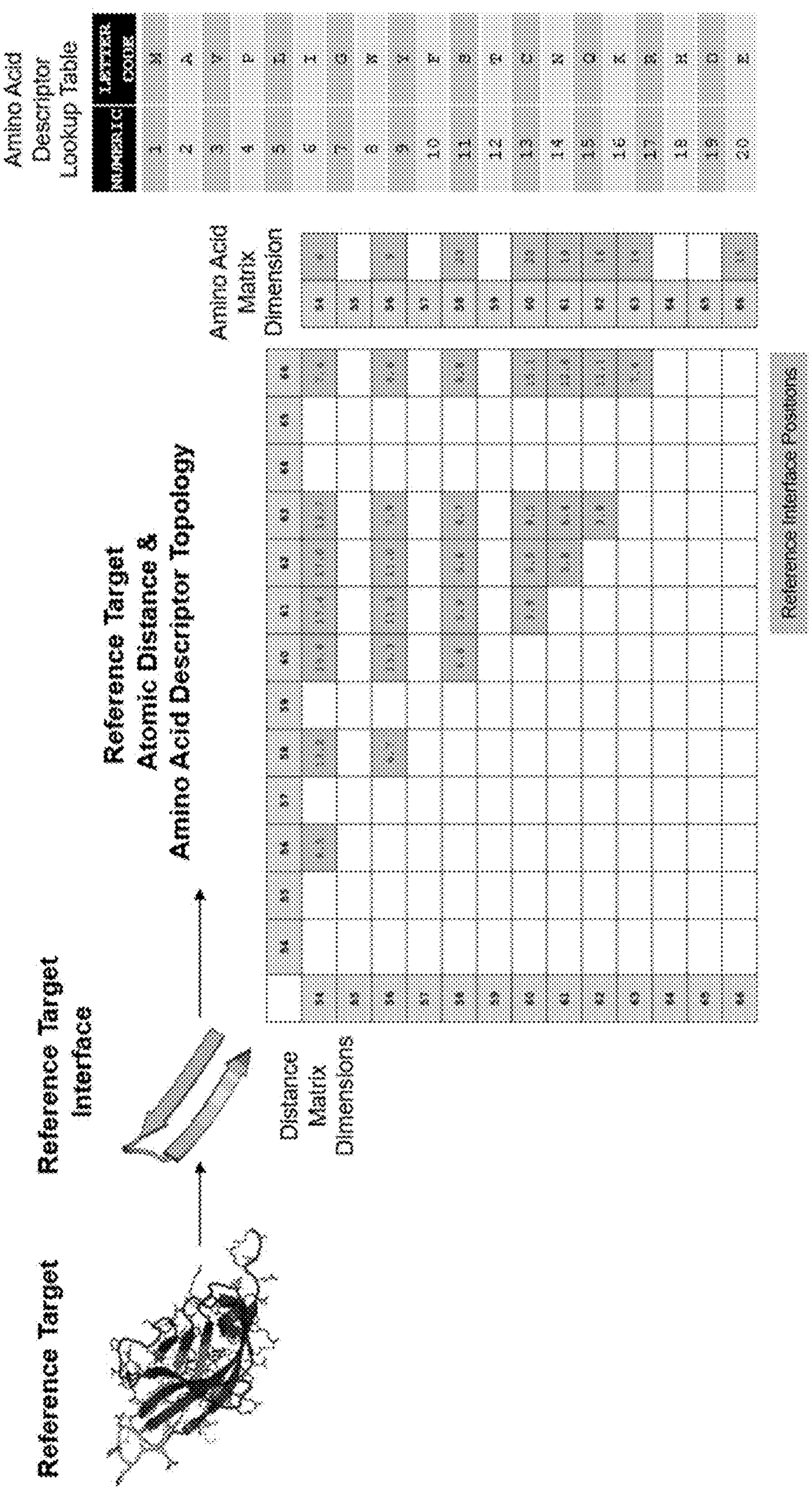
FIGS. 31A-31D are the atomic distance and amino acid descriptor matrices derived from the reference (FIG. 31A), and the engineered peptides sMEM (FIG. 31B), nMEM (FIG. 31C), and iMEM (FIB. 31D). When compared to the reference topology, the mean percentage error of the sMEM, nMEM, and iMEM topologies were 3.58%, 0.84%, and 19.3%, respectively.
Figure 31B:
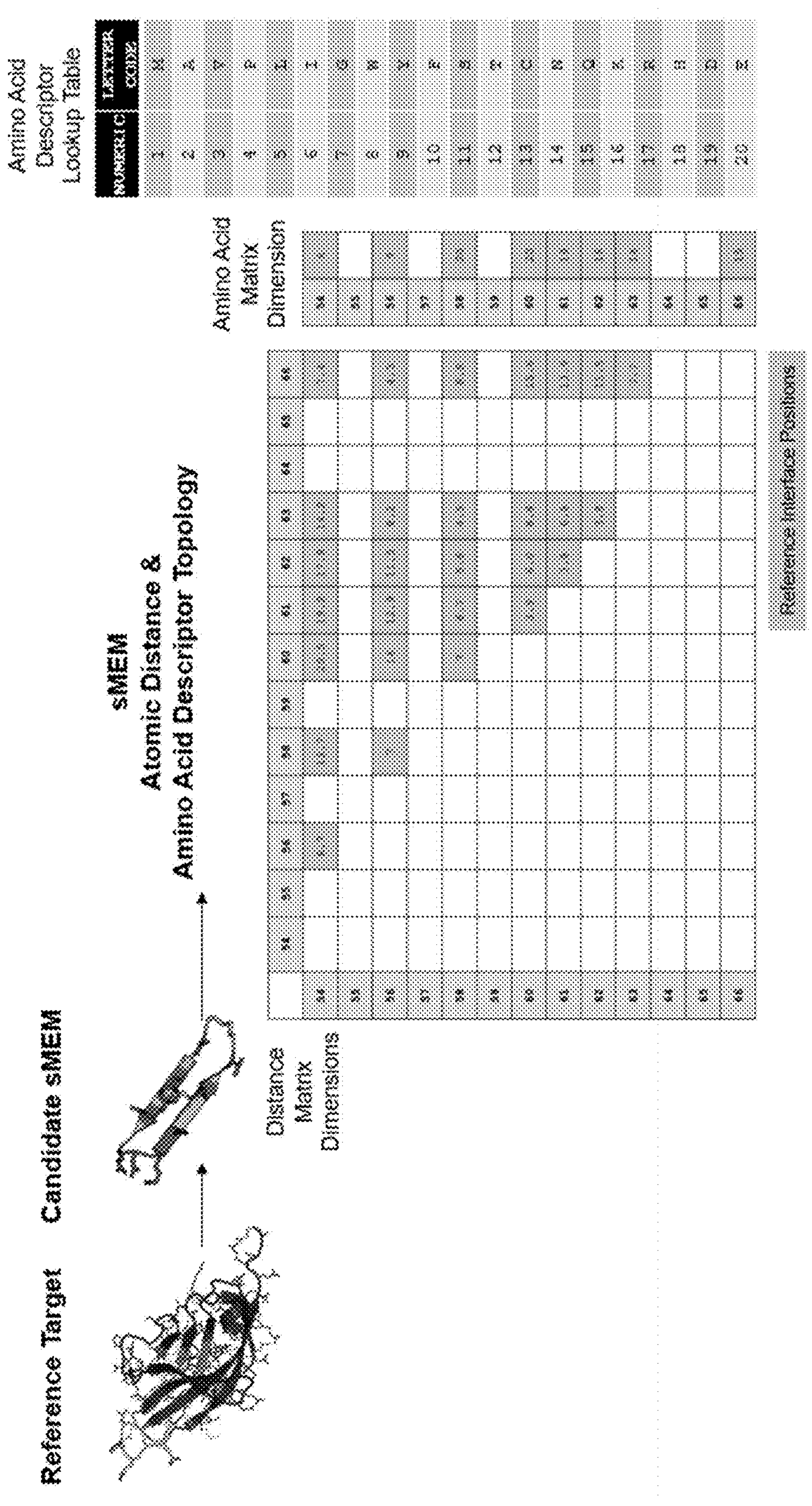
Figure 31C:
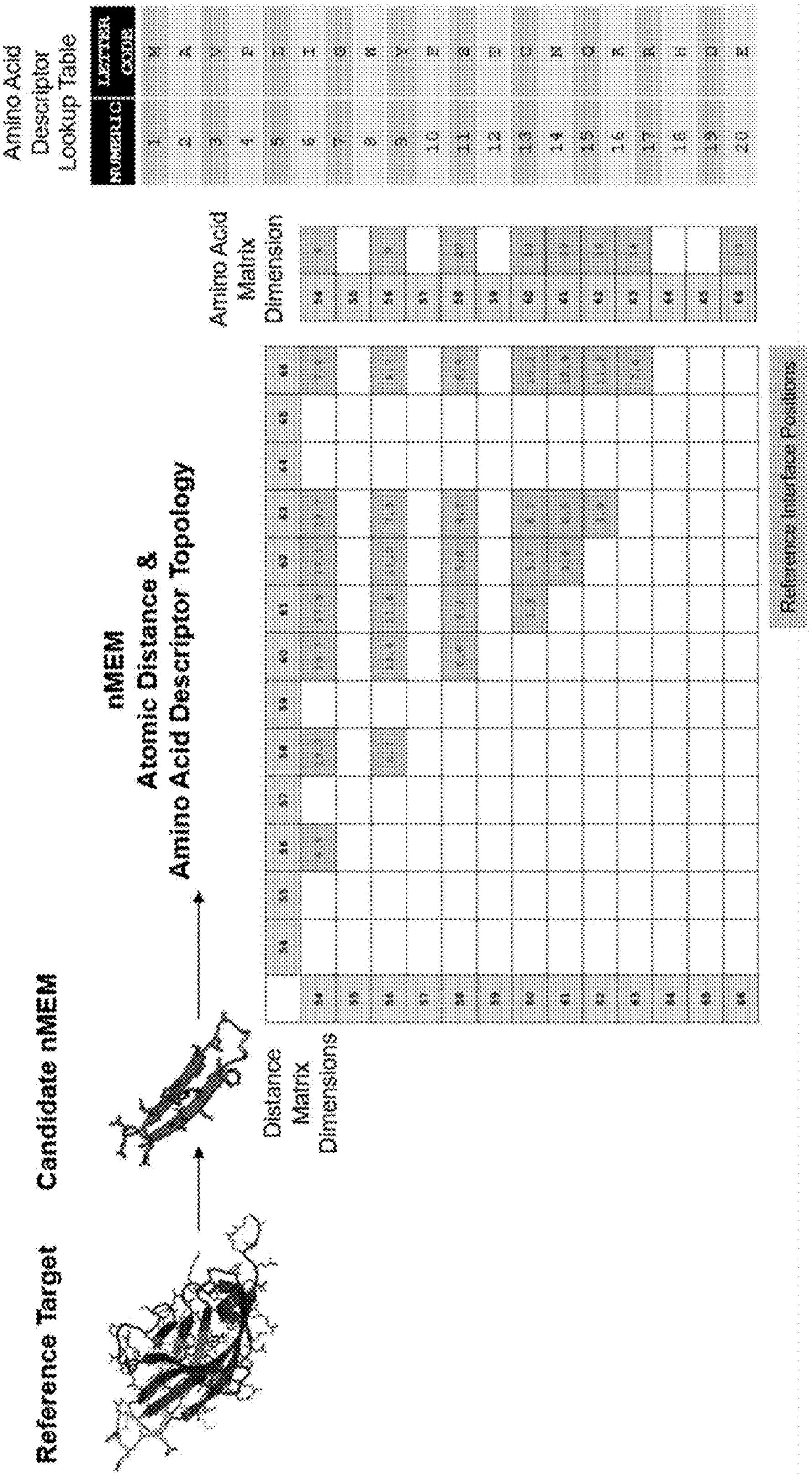
Figure 31D:
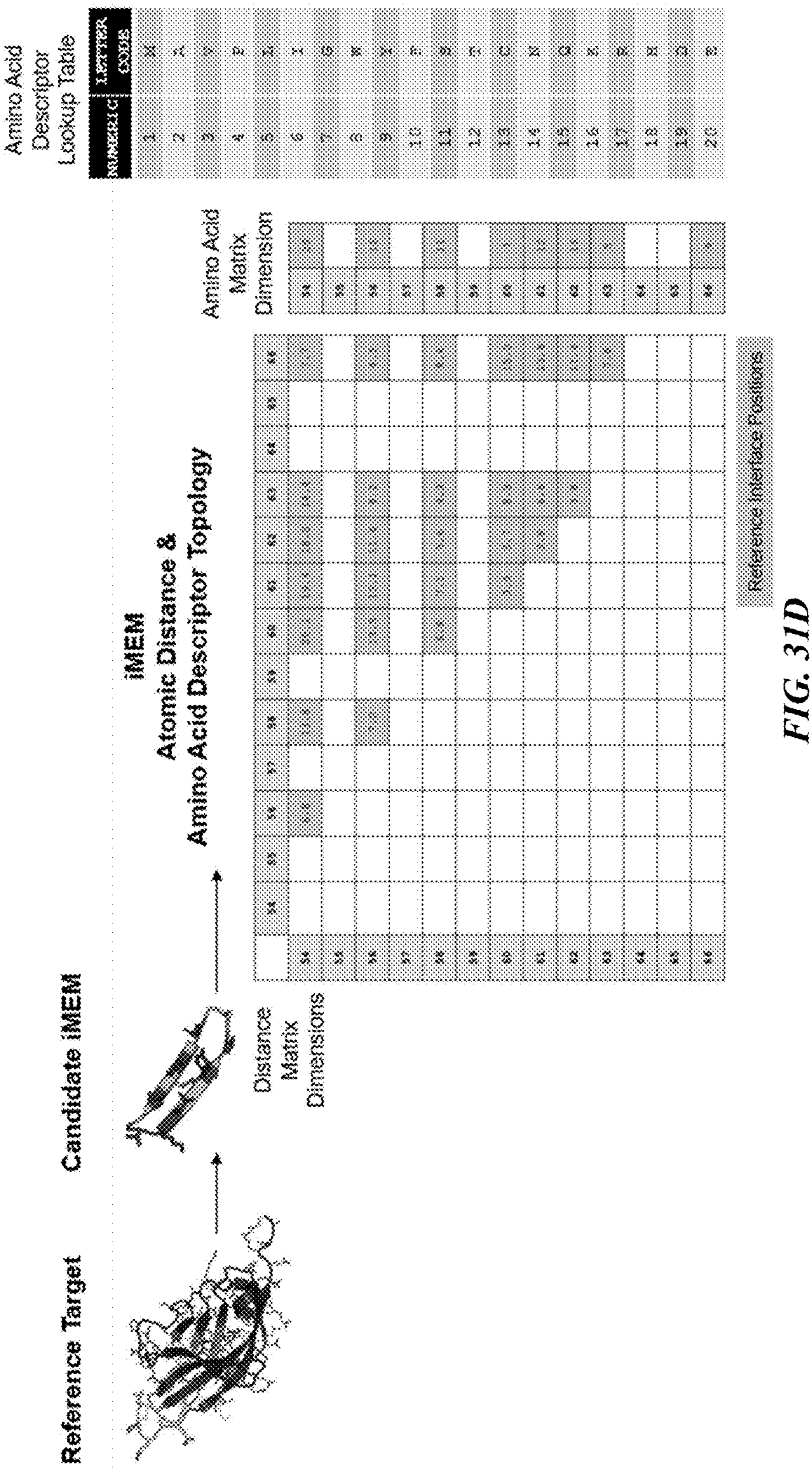
Figure 31F:
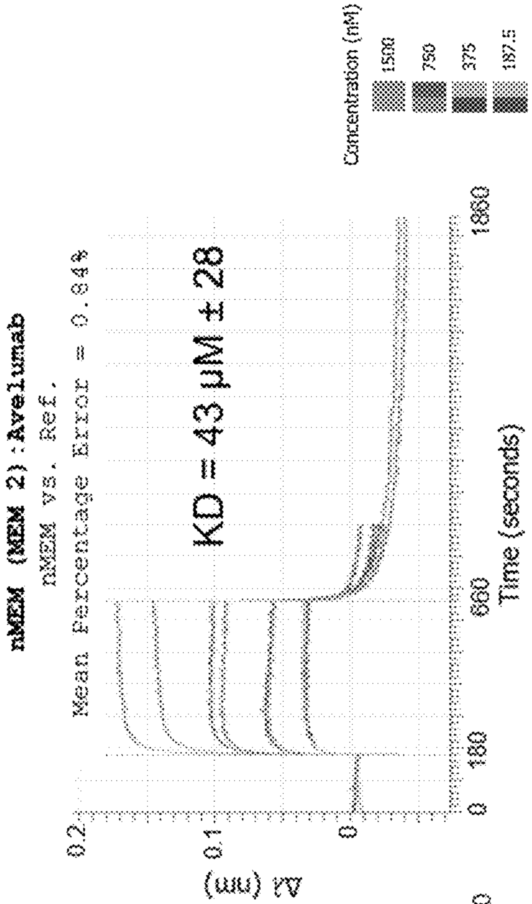
FIG. 31E-31G are biosensor binding graphs demonstrating the binding between the engineered peptides described in FIG. 30 with Avelumab. The KD of nMEM binding with Avelumab was 43.4 uM.
Figure 31E:
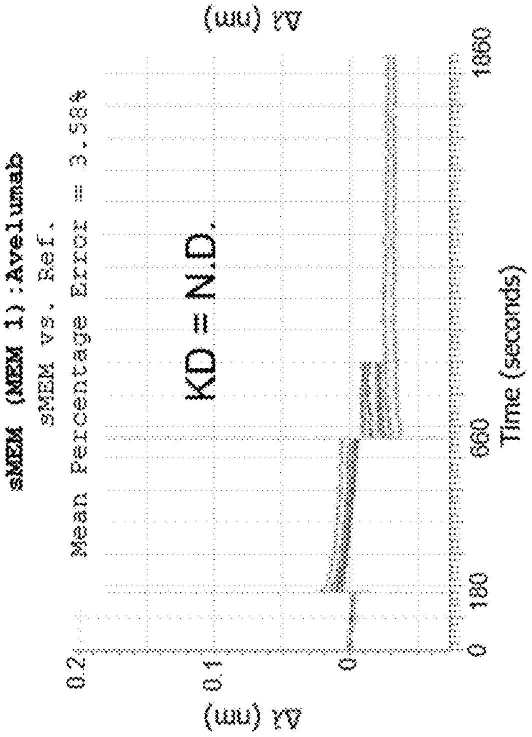
Figure 31G:
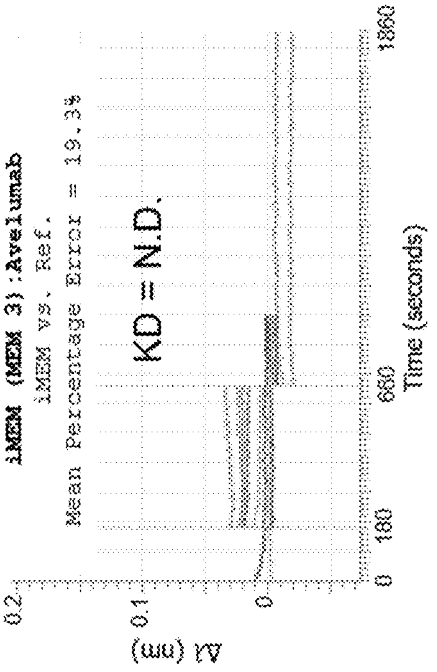
Figure 32A:
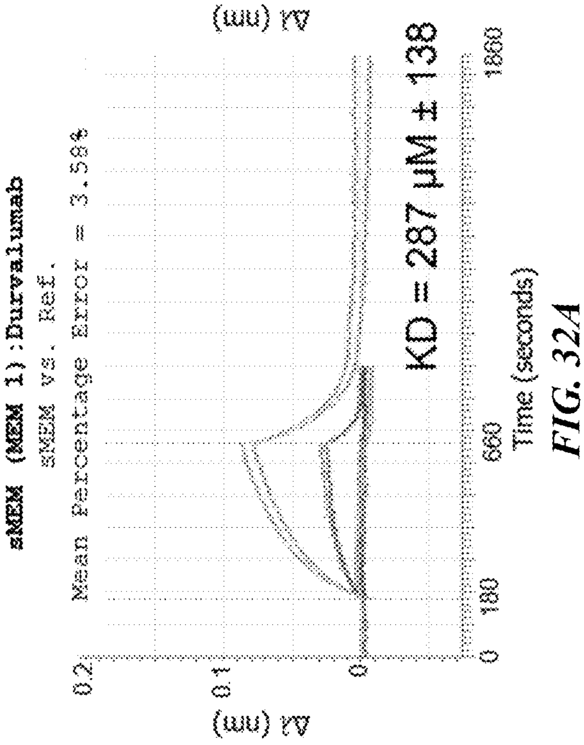
FIGS. 32A-32C are biosensor binding graphs demonstrating the binding between the engineered peptides described in FIG. 30 with Durvalumab.
Figure 32B:
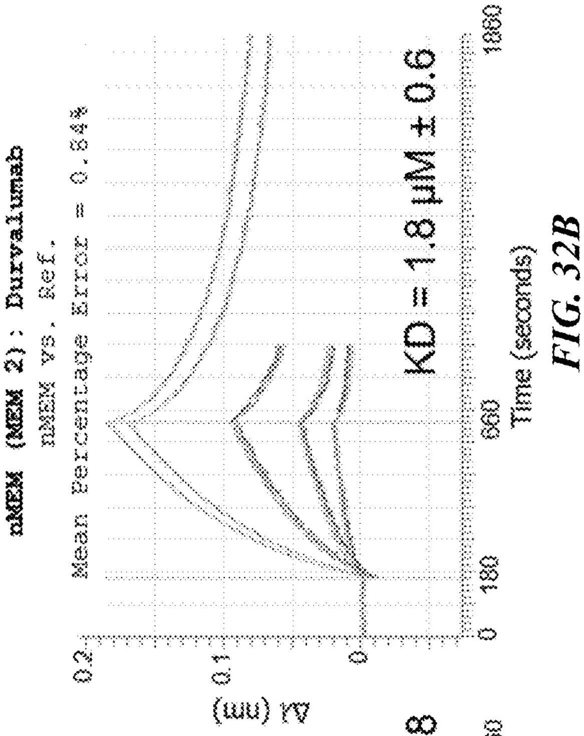
Figure 32C:
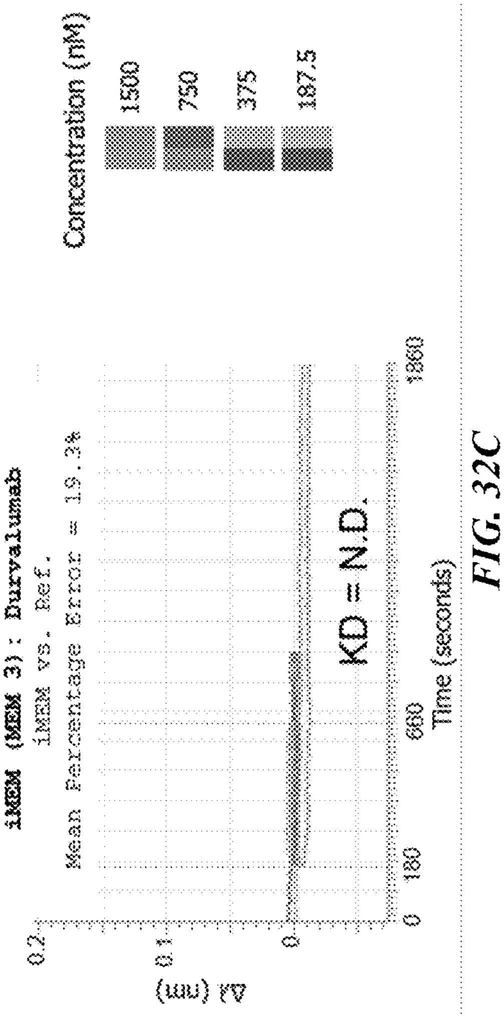
Figure 34:
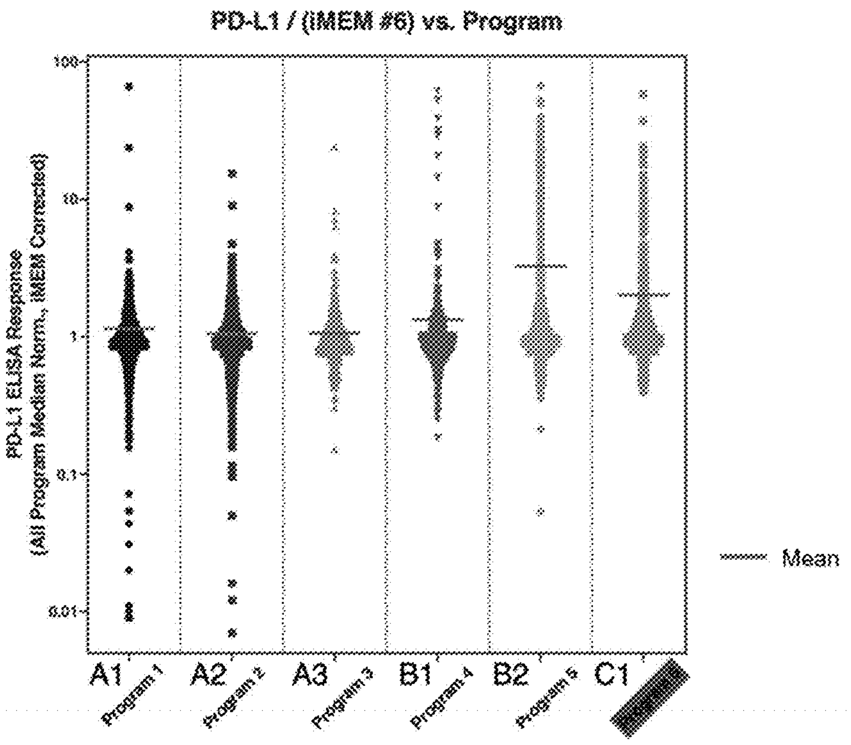
FIG. 34 is a graph and summary of PD-L1 ELISA binding response for clones selected using each panning program described in FIG. 33.
Figure 37:
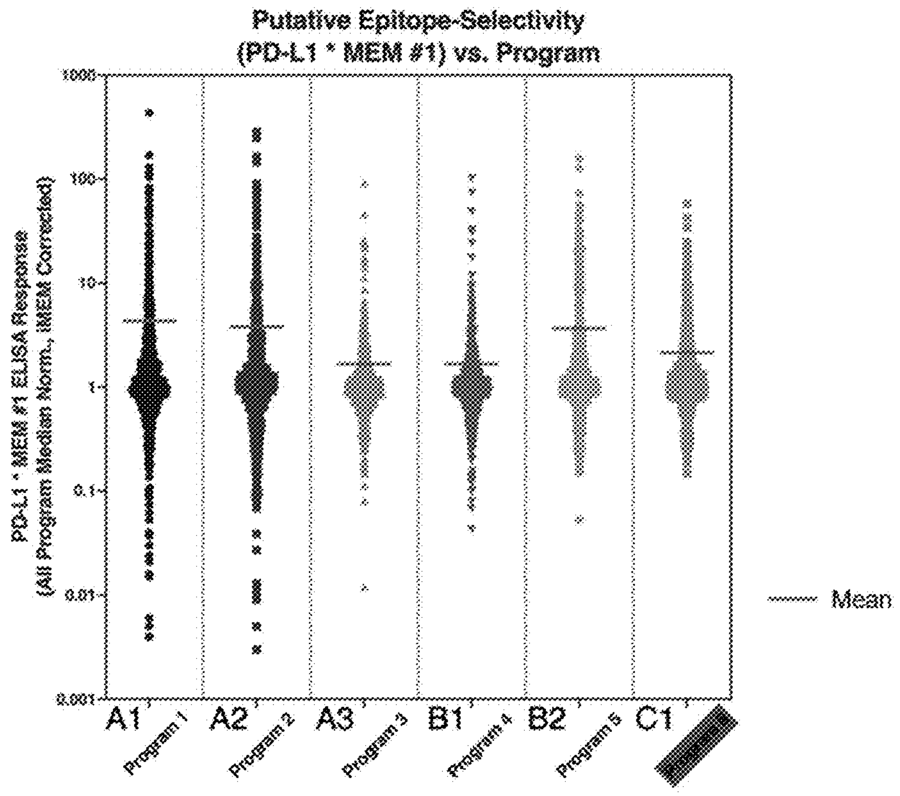
FIG. 37 is a graph and summary of ELISA epitope selectivity response against PD-L1 and sMEM #1 for clones selected using each panning program described in FIG. 33.
Figure 38:
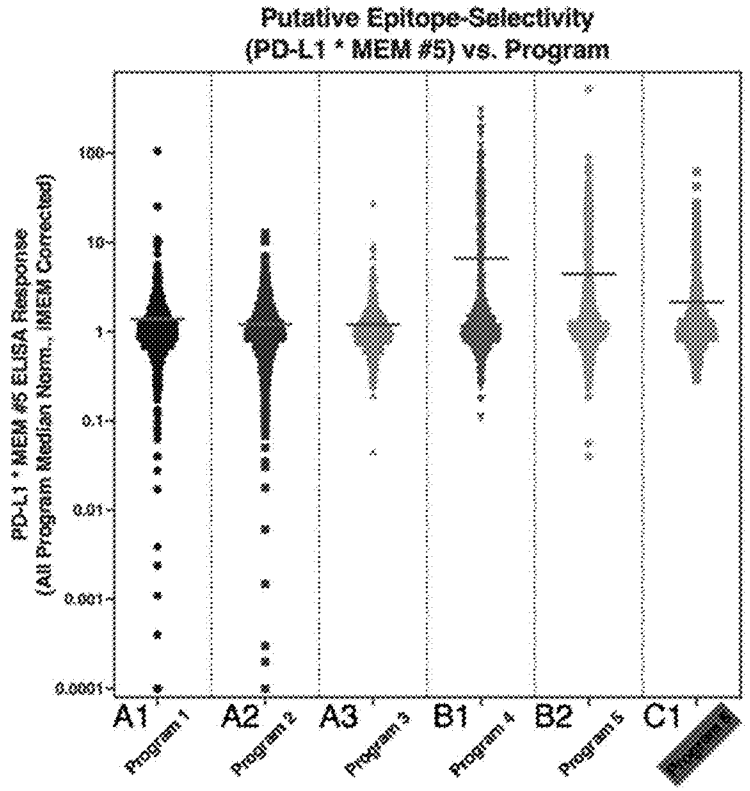
FIG. 38 is a graph and summary of ELISA epitope selectivity response against PD-L1 and nMEM #5 for clones selected using each panning program described in FIG. 33.

The graphs summarizing on-epitope (sMEM) VEGF hit frequency per panning round for each program shown in FIG. 26 indicate the engineered-peptide in vitro selection protocols identified unique mAb hits confirmed to bind to VEGF and cross-block Bevacizumab, where many of these hits were not identified in the conventional approach. FIG. 27 summarizes off-epitope VEGF hit frequency per panning round for each program, demonstrating the conventional program identified mAb hits confirmed to bind VEGF but not putative epitope-selective mAb hits. FIG. 28 summarizes the binding.

Example 4: Programmed In Vitro Selection of Phage Using Engineered Peptides for PD-L1 Therapeutic Epitope Using an identified therapeutic epitope reference target site on PD-L1, a series of engineered peptides (MEMs) were designed generally following a similar protocol as described in Example 2, as summarized in FIGS. 29-31D. The ability of these three engineered peptides, sMEM, nMEM (both positive selection molecules), and iMEM (negative selection molecule with inverse characteristics) were evaluated for binding to the two anti-PD-L1 avelumab and durvalumab using a biosensor (both antibodies known to bind to the reference target epitope), with data shown in FIGS. 31A-32C. A series of five different panning programs using the engineered peptides were designed, as was a control program using conventional selection molecules PD-L1 and BSA, as shown in FIG. 33, and used to screen a naïve human Ig scFv format library displayed on phage. A similar panning protocol as described above in Example 3 was used. For each panning program, in each round negative selection was performed first, and positive selection second.

Figure 39B:
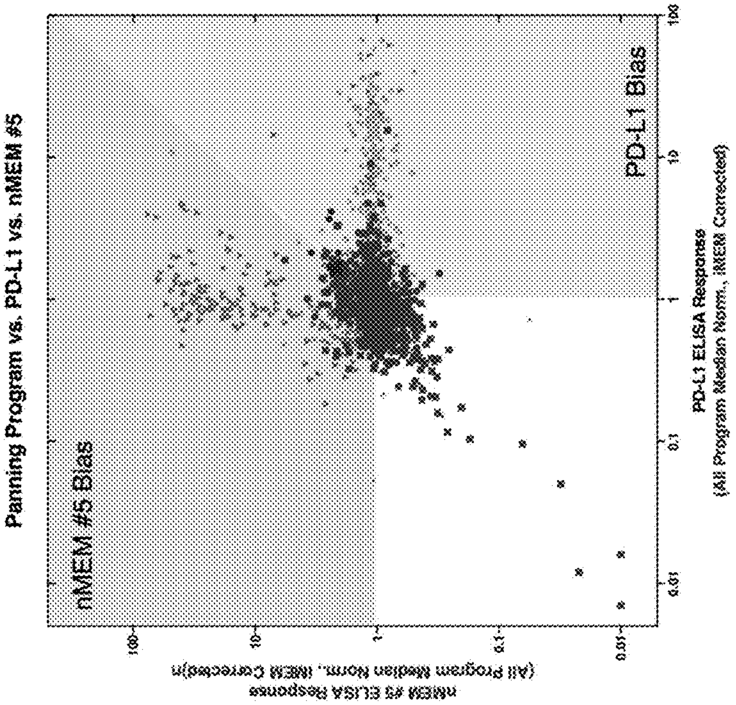
FIGS. 39A-39U are diagrams comparing the different ELISA binding responses of FIGS. 34-38, demonstrating the selectivity of binding partners selected using the different programs.
Figure 39A:
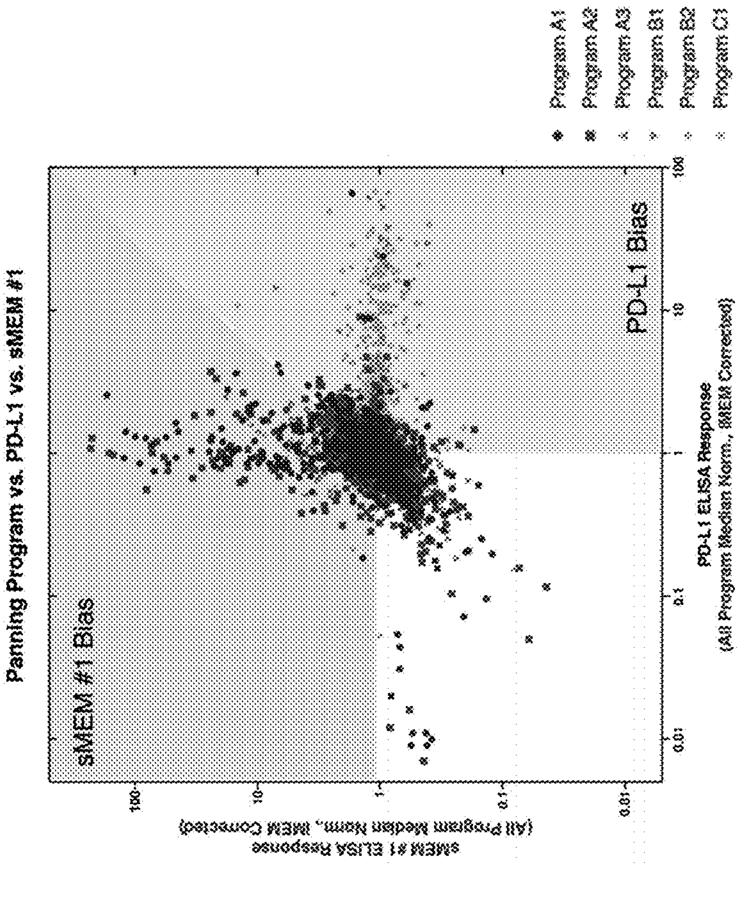
Figure 39D:
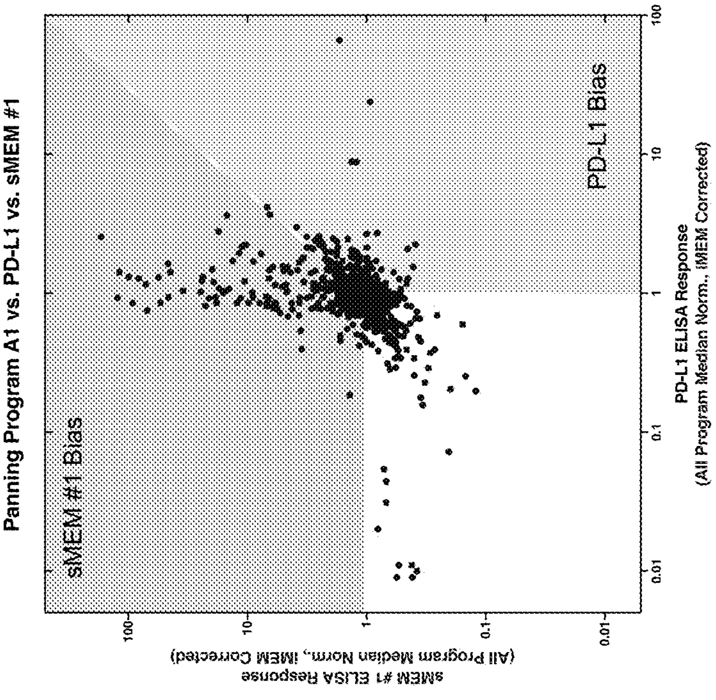
Figure 39C:
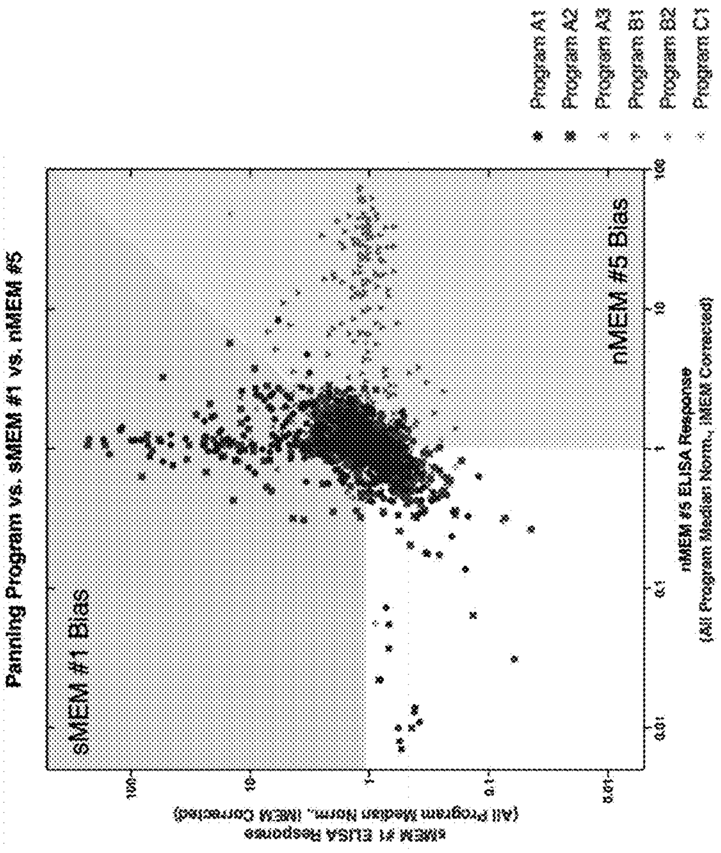
Figure 39E:
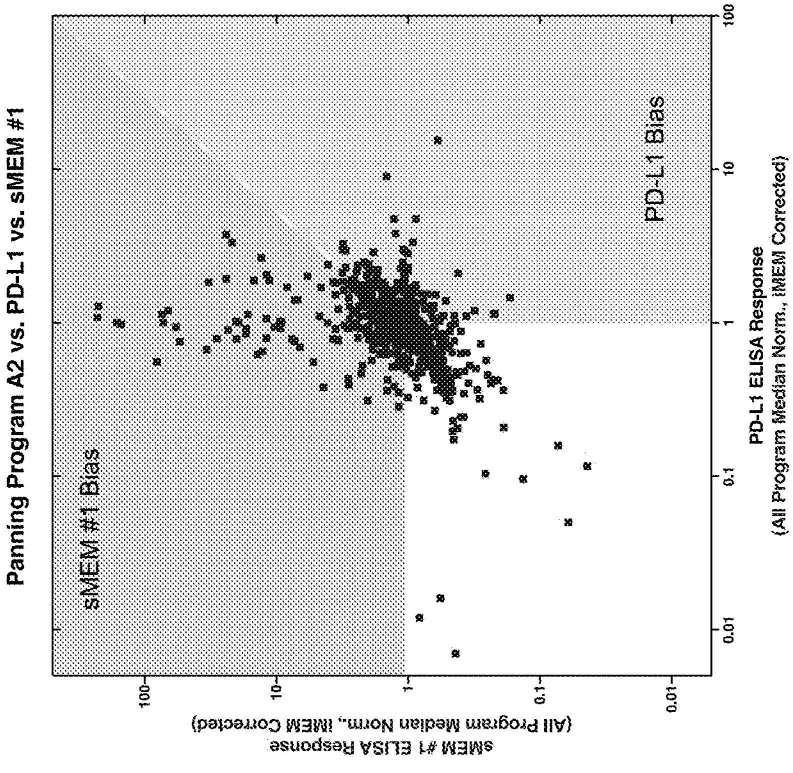
Figure 39F:
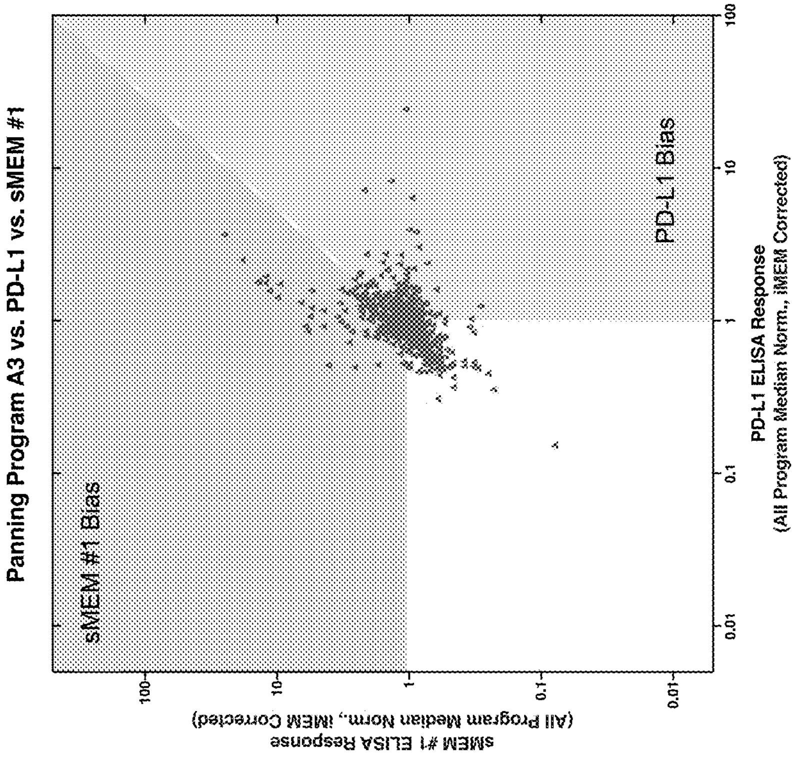
Figure 39G:
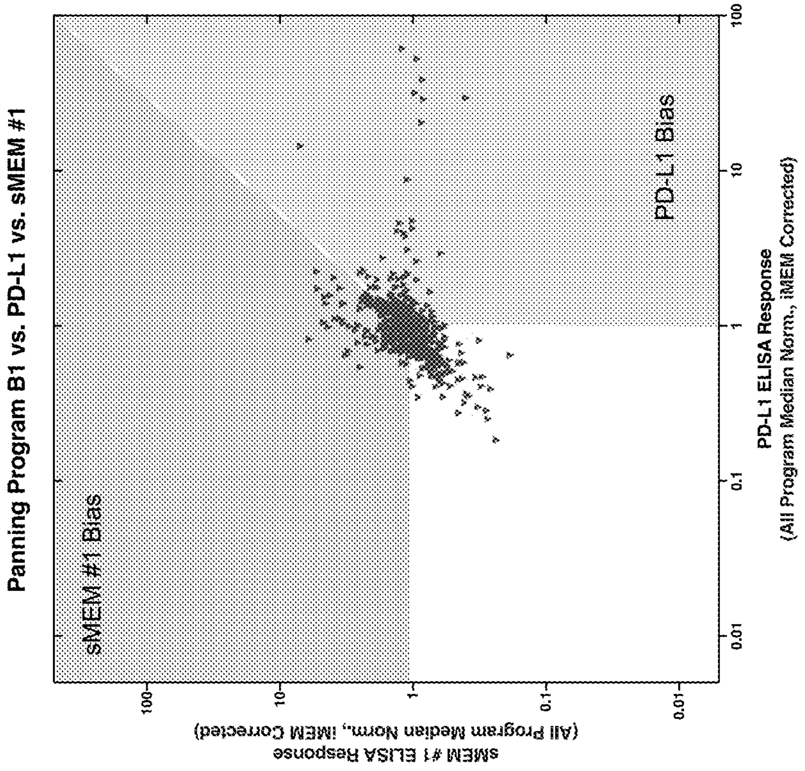
Figure 39H:
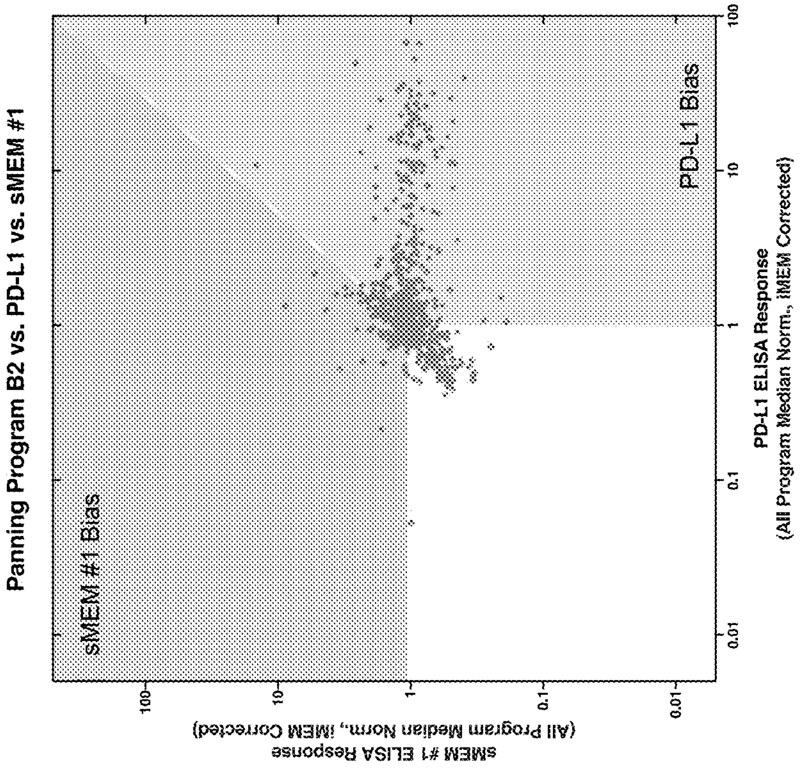
Figure 39I:
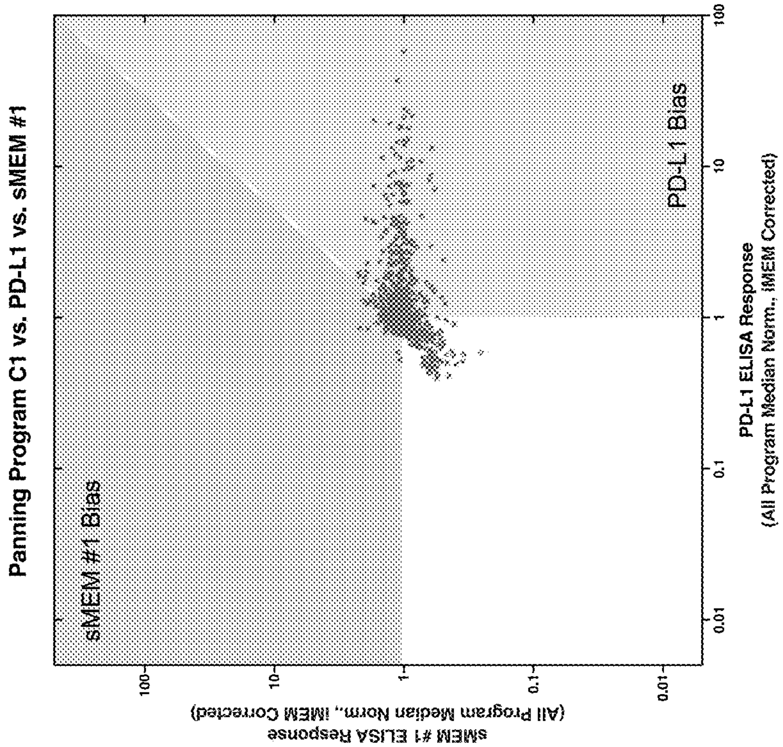
Figure 39J:
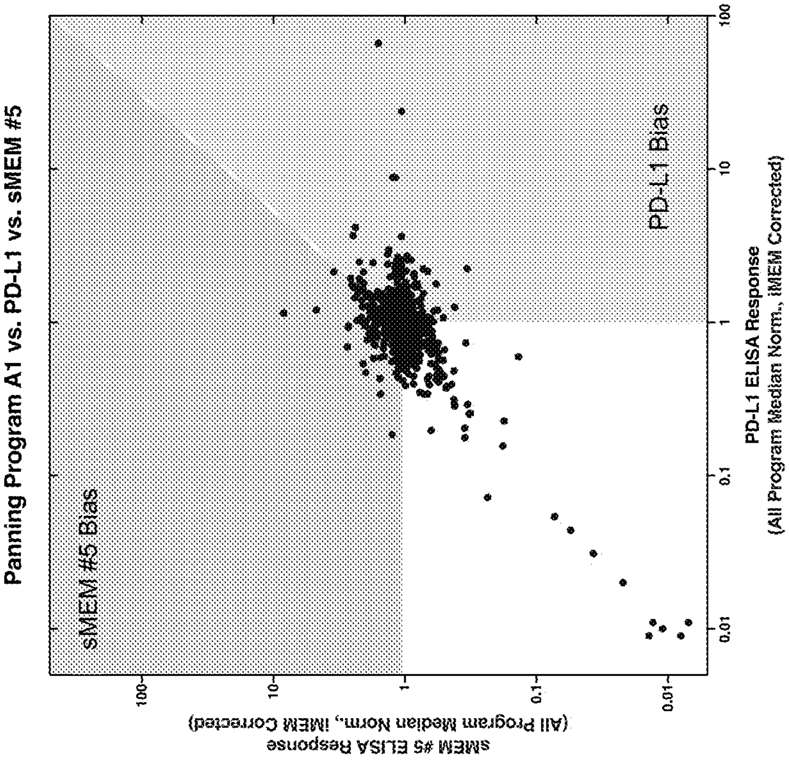
Figure 39K:
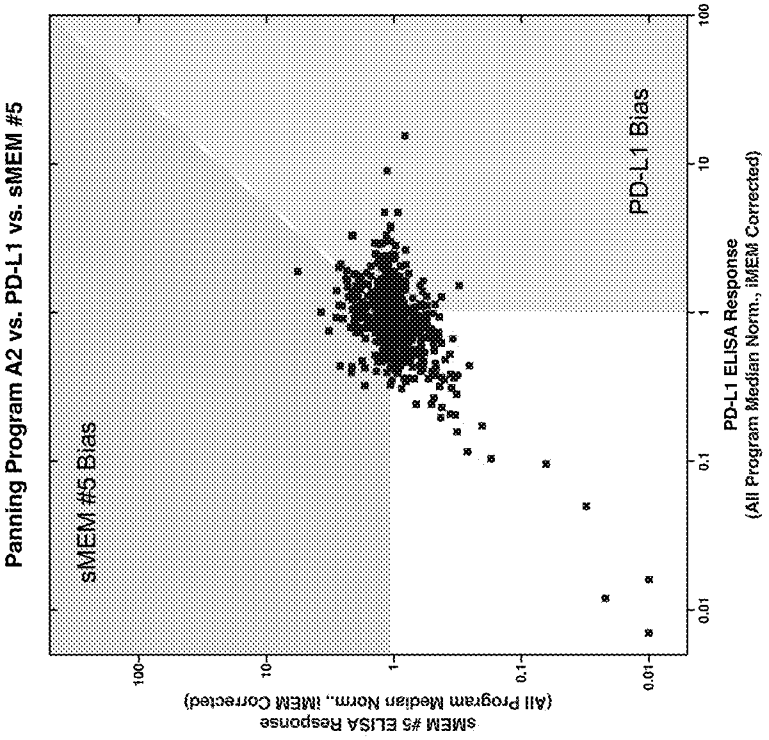
Figure 39L:
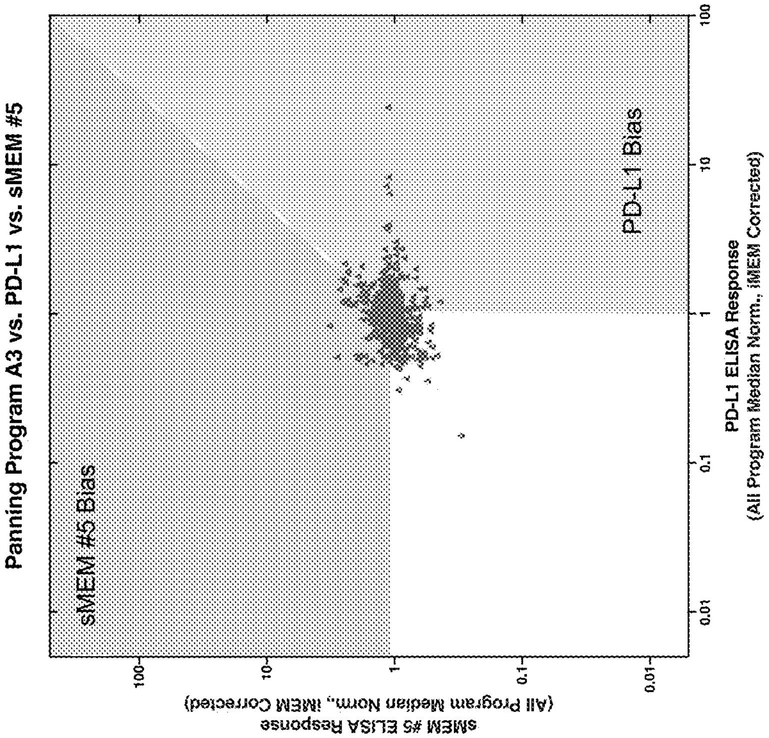
Figure 39N:
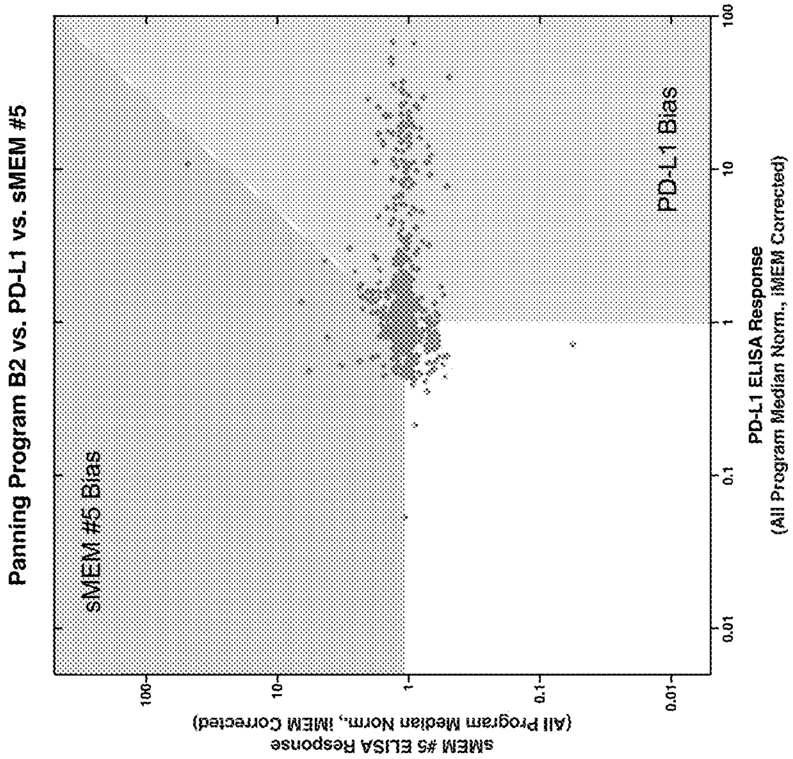
Figure 39M:
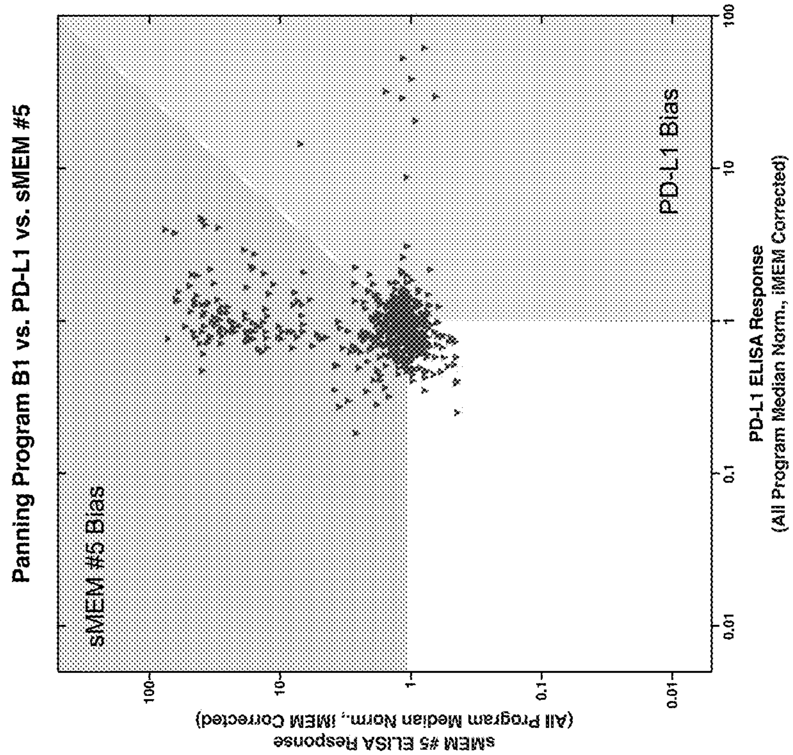
Figure 39O:
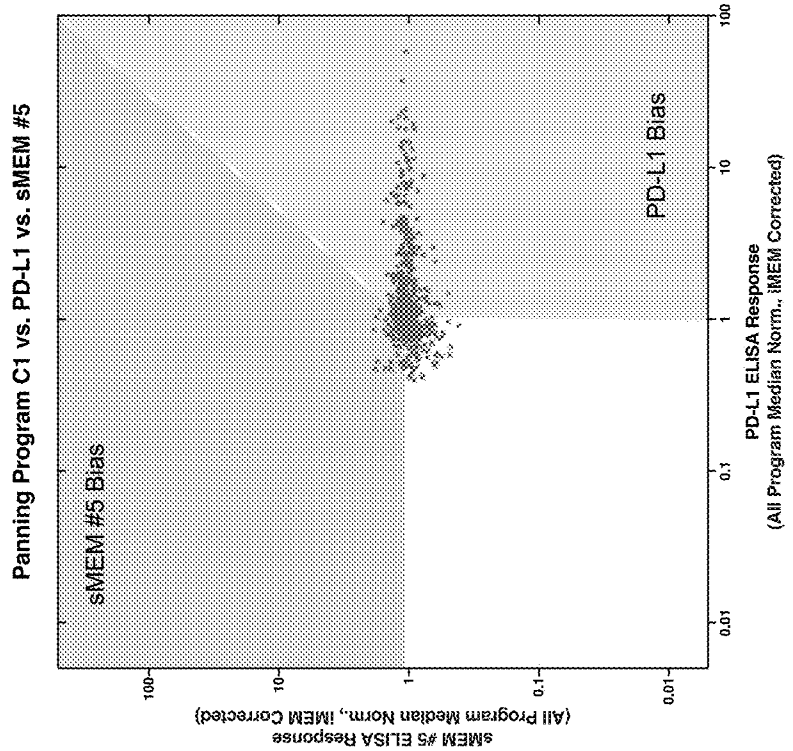
Figure 39P:
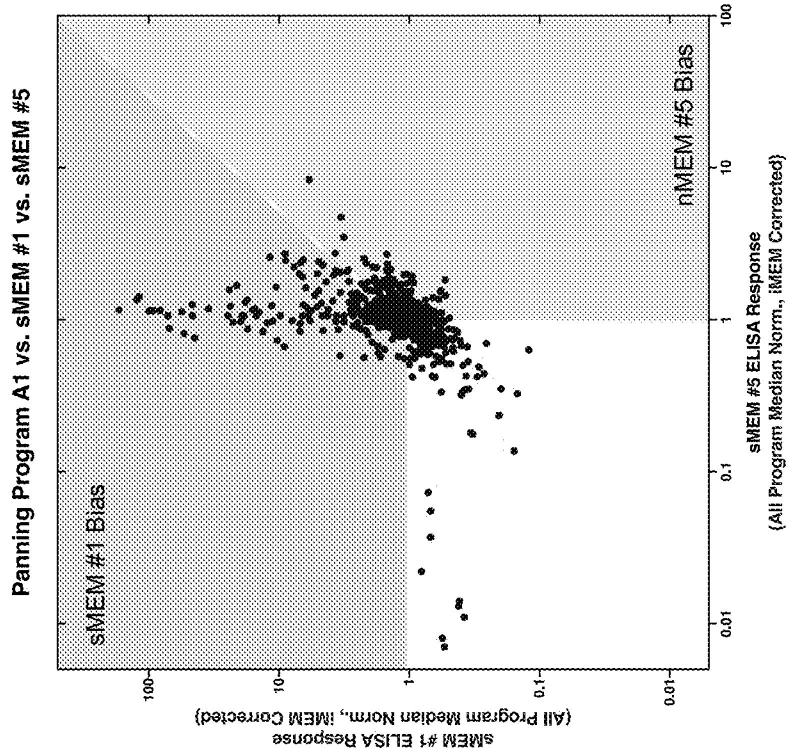
Figure 39R:
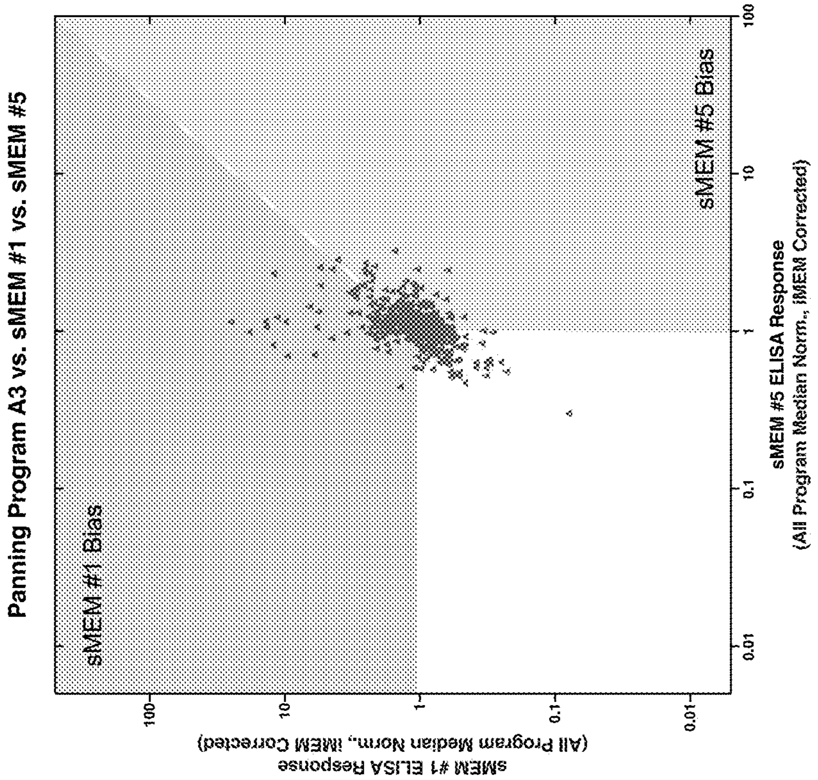
Figure 39Q:
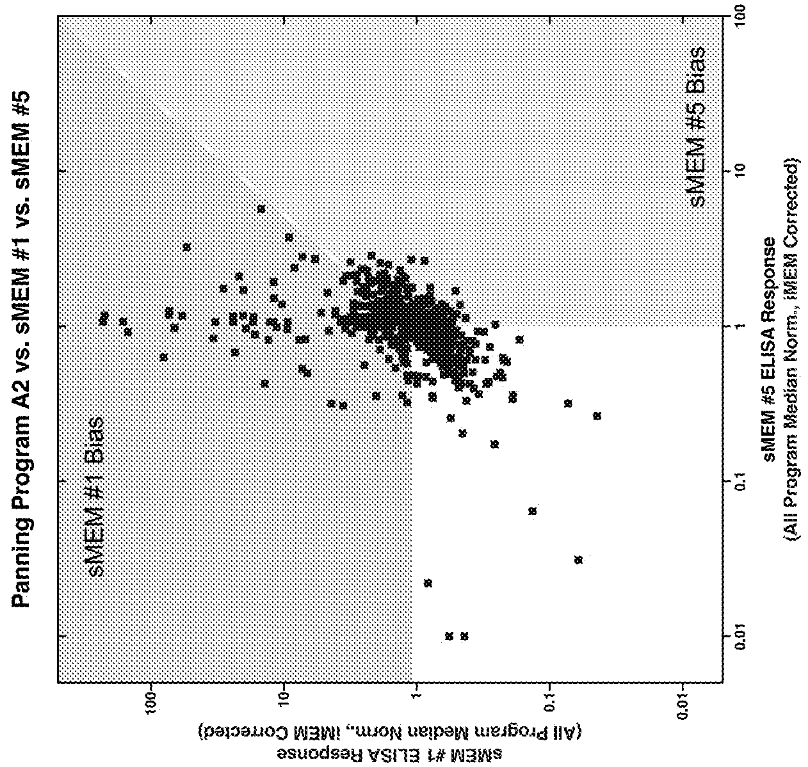
Figure 39T:
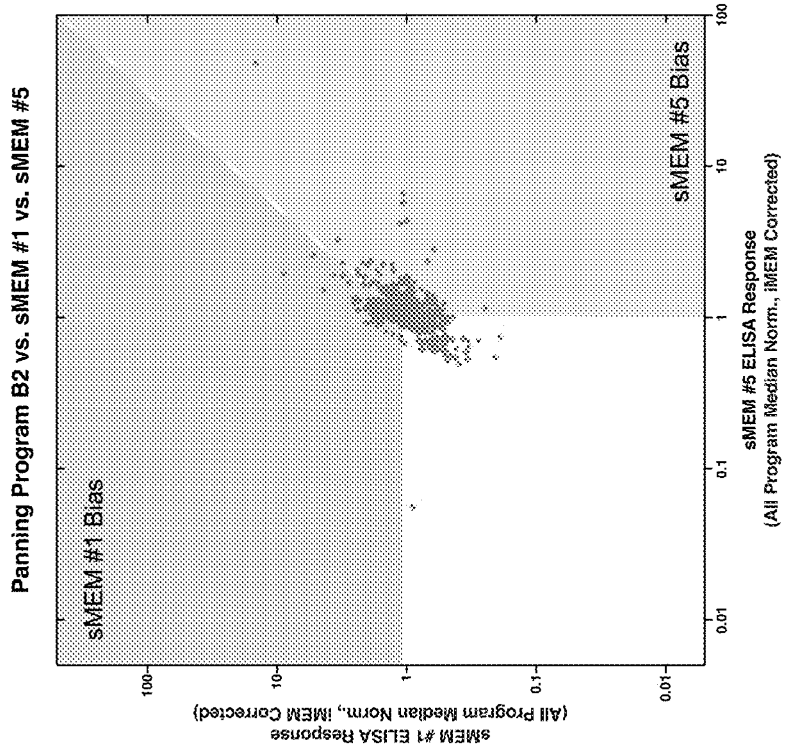
Figure 39S:
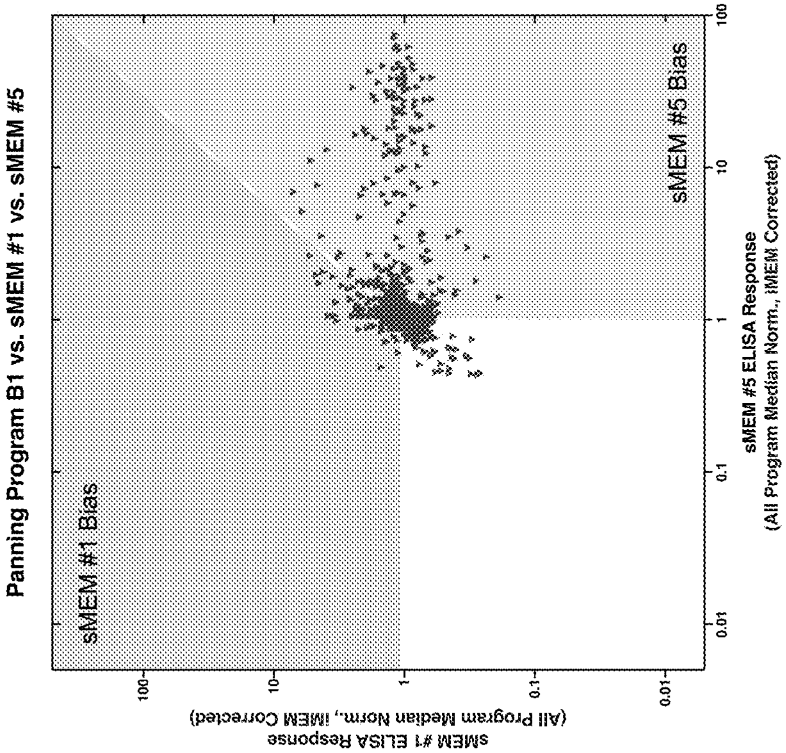
Figure 39U:
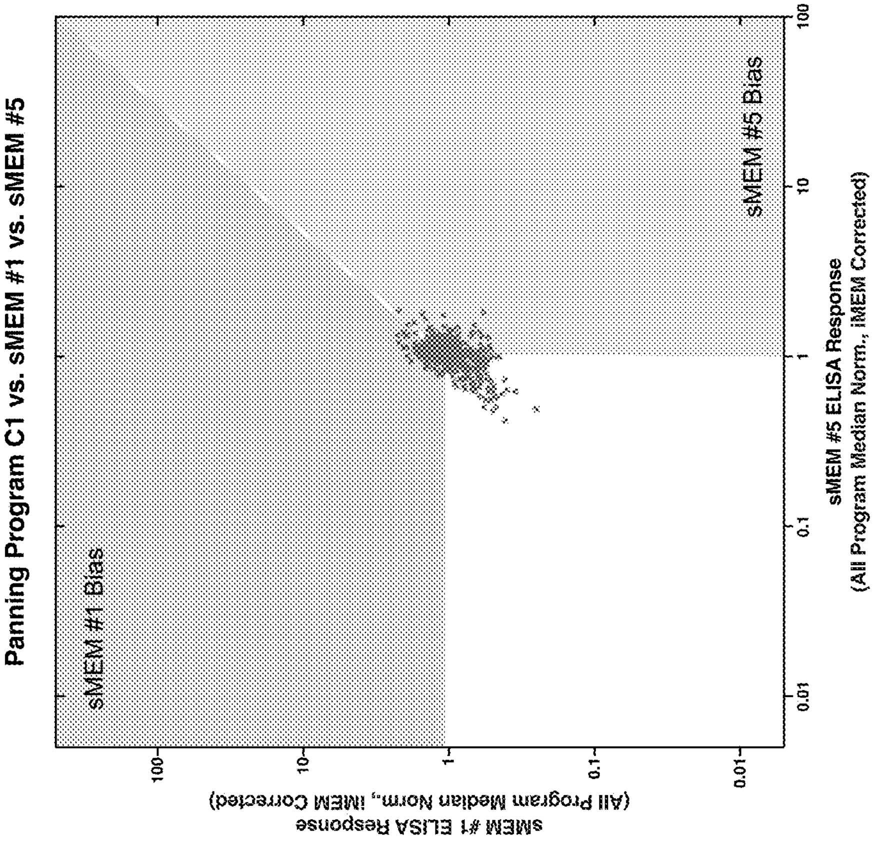
Figure 41B:
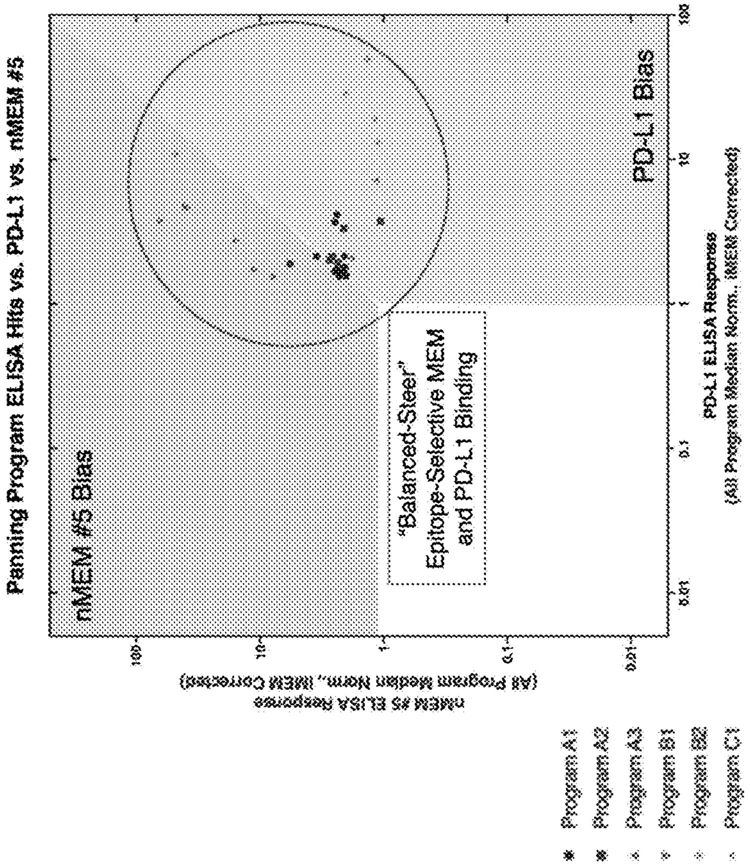
FIGS. 41A-41C are diagrams comparing the different ELISA binding responses to sMEM #1 and nMEM #5 compared to PD-L1 (FIGS. 41A and 42B respectively), and sMEM #1 compared to nMEM #5 (FIG. 41C) for binding partners selected using the different panning programs described in FIG. 33.
Figure 41A:
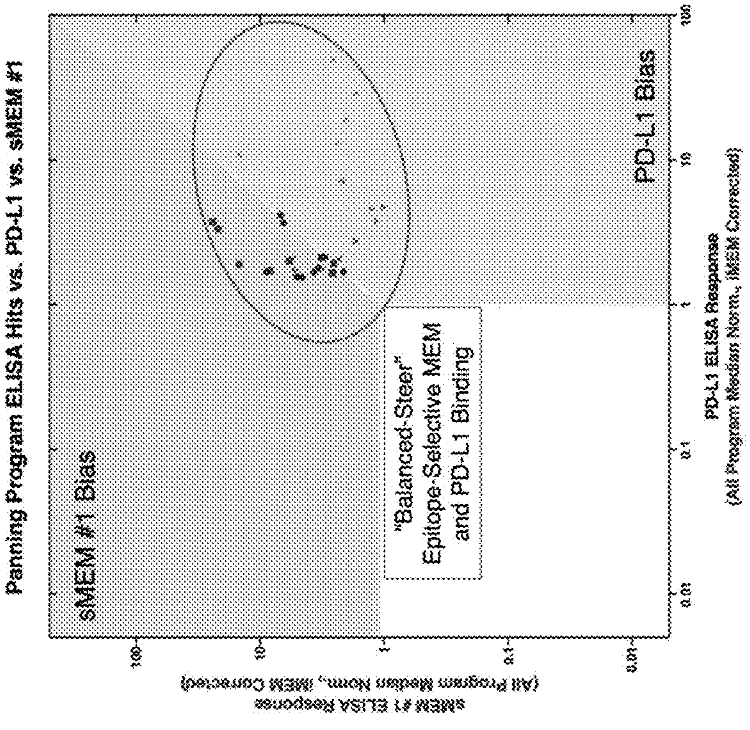
Figure 41C:
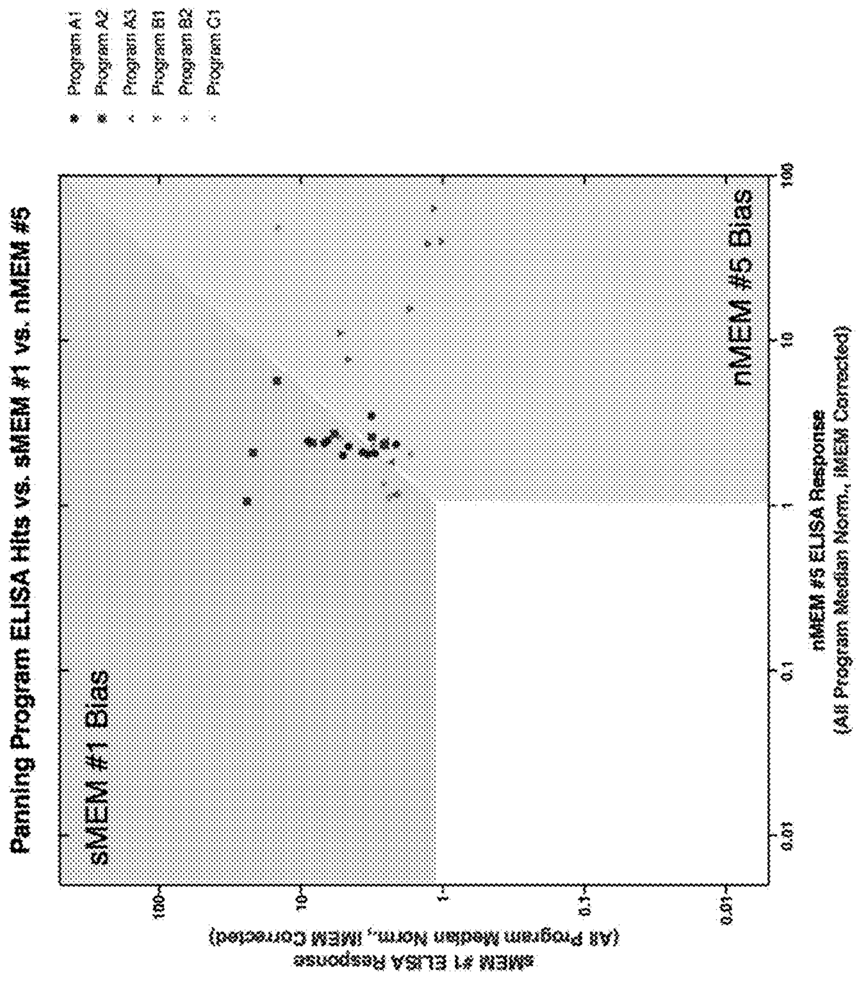
Figure 42A:
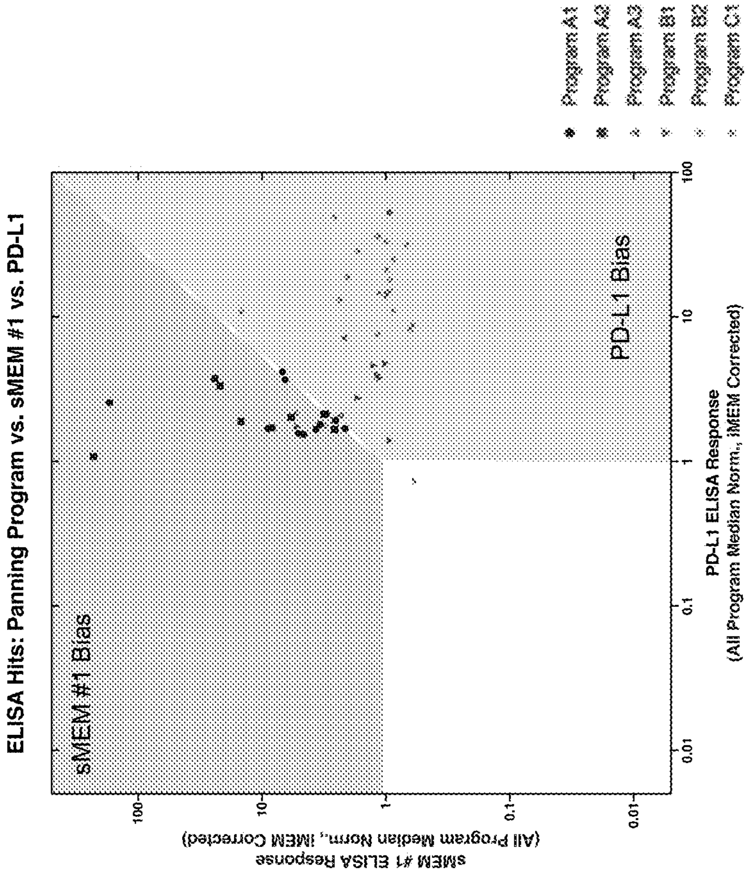
FIGS. 42A-42F are diagrams comparing the different ELISA responses and confirmed Tx mAb X-blockers for all of the programs described in FIG. 33.
Figure 42B:
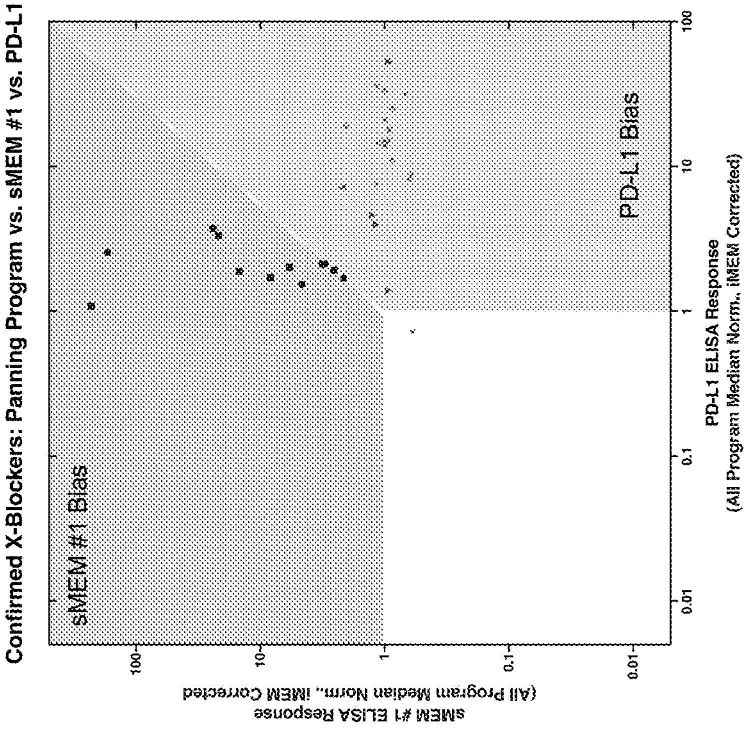
Figure 42C:
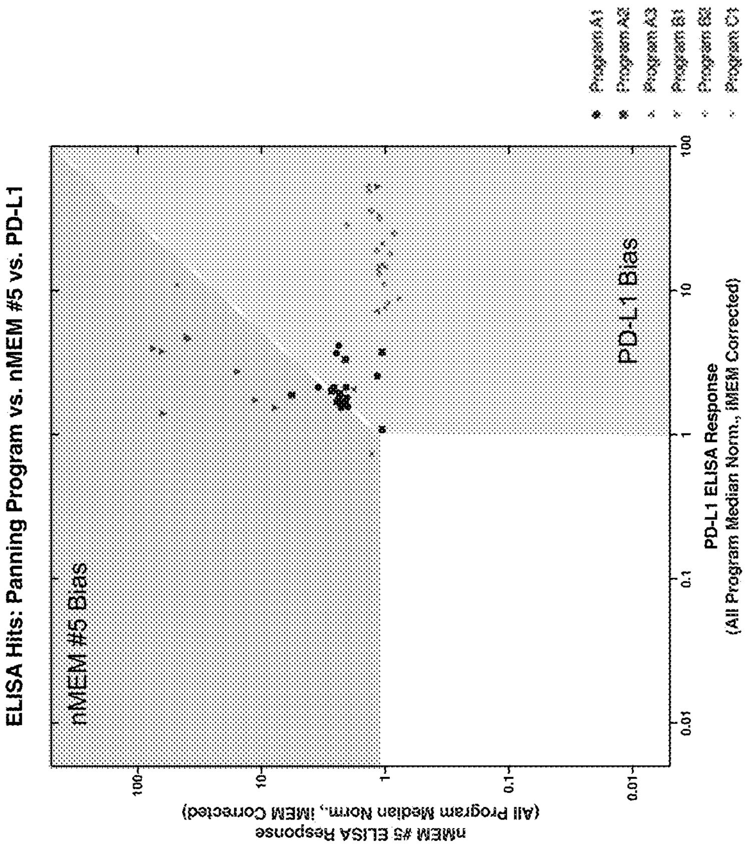
Figure 42D:
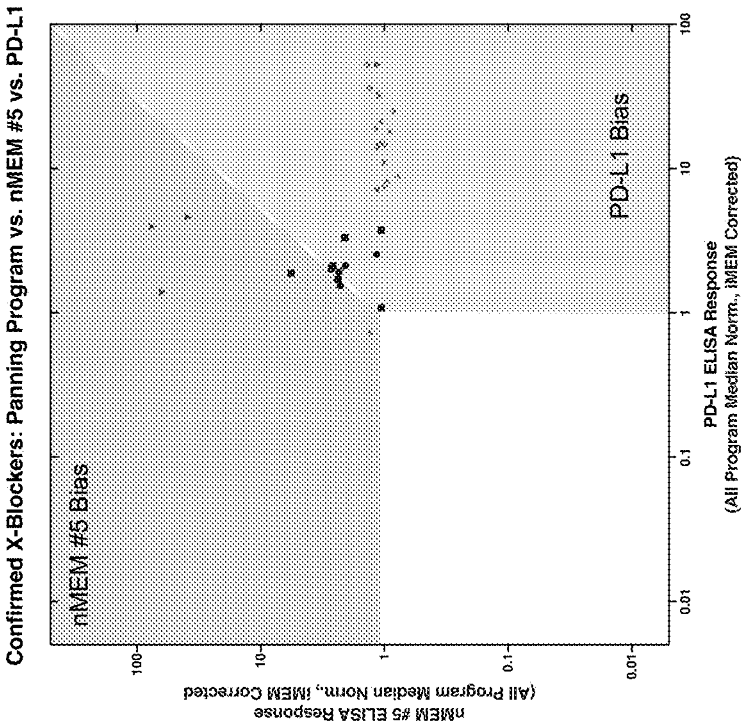
Figure 42F:
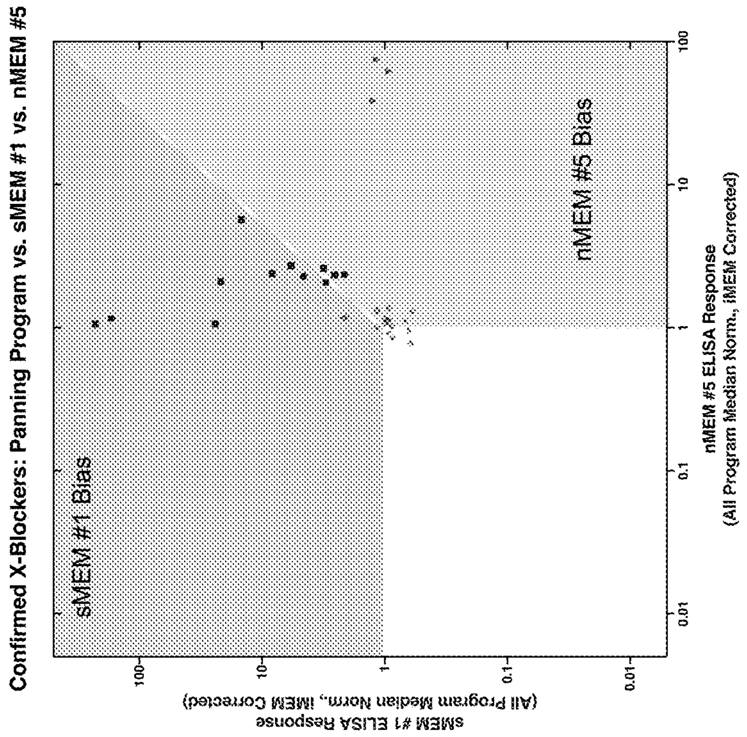
Figure 42E:
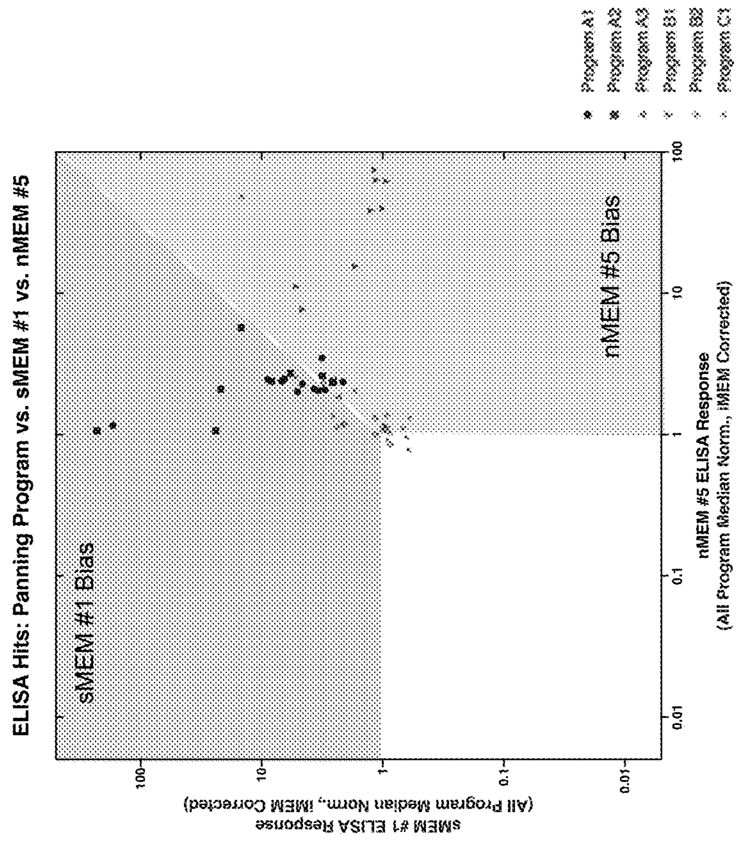

The ELISA response of the resulting pools selected using each program to PD-L1 and the different engineered peptides are summarized in FIGS. 34-38, with the full ELISA responses comparing different programs provided in FIGS. 39A-39U. The selected pools were also analyzed using different selection filter criteria with different combinations of desired binding behavior, as summarized in FIG. 40. A summary of the different clones selected from ELISA results, which were taken further through cross-blocking assays, is provided in Tables 2A and 2B below.

TABLE 2A

Anti-PD-L1 Panning Clones Selected from ELISA Results for Cross-blocking assay (full list: includes ELISA hits and controls)

| Selection Filter | Clone ID | Selected for Fab production (As hit or control) | PD-L1/ iMEM ELISA | sMEM #1/ iMEM ELISA | nMEM #5/ iMEM ELISA | In Vitro Program |
|---|---|---|---|---|---|---|
| 1 | YU349-B03 | N | 19.4 | 36.8 | 119.7 | S5 |
| 1 | YU349-E03 | N | 18.1 | 124.6 | 69.7 | S5 |
| 1 | YU349-B05 | Y | 15.3 | 57.1 | 38.3 | S2 |
| 1 | YU349-B12 | N | 11.7 | 35.6 | 8.8 | S1 |
| 1 | YU349-H11 | N | 11.2 | 29.9 | 6.5 | S1 |
| 1 | YU349-A12 | Y | 9.4 | 41.0 | 43.8 | S1 |
| 1 | YU349-C05 | N | 9.3 | 71.0 | 60.0 | S3 |
| 1 | YU349-G11 | N | 8.9 | 61.2 | 23.7 | S1 |
| 1 | YU349-A01 | Y | 7.2 | 95.4 | 4.6 | S2 |
| 1 | YU350-A01 | N | 6.8 | 23.9 | 25.1 | S1 |
| 1 | YU349-A04 | N | 6.4 | 42.6 | 14.3 | S5 |
| 1 | YU349-E11 | N | 5.8 | 61.1 | 22.4 | S1 |
| 1 | YU349-C01 | N | 5.6 | 36.0 | 26.7 | S2 |
| 1 | YU349-C11 | N | 4.6 | 60.3 | 136.9 | S4 |
| 1 | YU349-F01 | Y | 4.2 | 13.6 | 10.7 | S2 |
| 1 | YU349-A02 | Y | 4.2 | 126.8 | 40.2 | S2 |
| 1 | YU349-D10 | N | 4.1 | 96.5 | 167.0 | S4 |
| 1 | YU349-A05 | Y | 4.1 | 35.1 | 11.5 | S2 |
| 1 | YU349-G01 | Y | 4.1 | 99.8 | 17.1 | S2 |
| 1 | YU349-C12 | Y | 3.8 | 11.5 | 5.5 | S1 |
| 1 | YU349-F12 | N | 2.6 | 65.3 | 10.9 | S1 |
| 1 | YU349-F11 | Y | 2.4 | 48.8 | 15.6 | S1 |
| 1 | YU349-E12 | N | 1.7 | 30.8 | 6.9 | S1 |
| 3 | YU349-D04 | N | 35.7 | 1.2 | 1.8 | S5 |
| 3 | YU349-B03 | N | 19.4 | 36.8 | 119.7 | S5 |
| 3 | YU349-B05 | Y | 15.3 | 57.1 | 38.3 | S2 |
| 3 | YU349-B12 | N | 11.7 | 35.6 | 8.8 | S1 |
| 3 | YU349-H11 | N | 11.2 | 29.9 | 6.5 | S1 |
| 3 | YU349-A01 | Y | 7.2 | 95.4 | 4.6 | S2 |
| 3 | YU350-A01 | N | 6.8 | 23.9 | 25.1 | S1 |
| 3 | YU349-A04 | N | 6.4 | 42.6 | 14.3 | S5 |
| 3 | YU349-E09 | N | 4.9 | 2.8 | 57.2 | S4 |
| 3 | YU349-A05 | Y | 4.1 | 35.1 | 11.5 | S2 |
| 3 | YU349-C12 | Y | 3.8 | 11.5 | 5.5 | S1 |
| 4 | YU349-D02 | N | 71.8 | 3.2 | 0.7 | S5 |
| 4 | YU349-F05 | Y | 33.7 | 2.7 | 0.4 | S5 |
| 4 | YU349-G05 | N | 21.5 | 3.4 | 0.3 | S5 |
| 4 | YU349-B03 | N | 19.4 | 36.8 | 119.7 | S5 |
| 4 | YU349-D05 | N | 16.2 | 40.1 | 21.9 | S3 |
| 4 | YU349-B05 | Y | 15.3 | 57.1 | 38.3 | S2 |
| 4 | YU349-B12 | N | 11.7 | 35.6 | 8.8 | S1 |
| 4 | YU349-E05 | Y | 11.5 | 3.1 | 0.4 | S3 |
| 4 | YU349-H11 | N | 11.2 | 29.9 | 6.5 | S1 |
| 4 | YU349-A01 | Y | 7.2 | 95.4 | 4.6 | S2 |
| 4 | YU350-A01 | N | 6.8 | 23.9 | 25.1 | S1 |
| 4 | YU349-A04 | N | 6.4 | 42.6 | 14.3 | S5 |
| 4 | YU349-A05 | Y | 4.1 | 35.1 | 11.5 | S2 |
| 4 | YU349-C12 | Y | 3.8 | 11.5 | 5.5 | S1 |
| 5 | YU349-B03 | N | 19.4 | 36.8 | 119.7 | S5 |
| 5 | YU349-A10 | N | 4.6 | 0.0 | 59.4 | S4 |
| 5 | YU349-B11 | Y | 4.5 | 0.4 | 57.3 | S4 |
| 5 | YU349-C10 | N | 4.4 | 0.3 | 126.4 | S4 |
| 6 | YU349-B03 | N | 19.4 | 36.8 | 119.7 | S5 |
| 6 | YU349-B12 | N | 11.7 | 35.6 | 8.8 | S1 |
| 6 | YU349-H11 | N | 11.2 | 29.9 | 6.5 | S1 |
| 6 | YU349-A01 | Y | 7.2 | 95.4 | 4.6 | S2 |
| 6 | YU349-B01 | Y | 4.1 | 46.7 | 0.1 | S2 |
| 10 | YU349-C10 | N | 4.4 | 0.3 | 126.4 | S4 |
| 10 | YU349-G09 | Y | 3.7 | 0.3 | 112.5 | S4 |
| 10 | YU349-G10 | N | 0.8 | 0.1 | 81.7 | S4 |
| 10 | YU349-A11 | Y | 0.7 | −0.1 | 108.7 | S4 |
| 10 | YU349-F10 | N | 0.6 | 0.3 | 90.9 | S4 |
| 2 | YU349-G08 | N | 11.7 | 35.6 | 8.8 | S6 |
| 2 | YU349-E06 | N | 11.2 | 29.9 | 6.5 | S6 |
| 2 | YU349-D07 | N | 3.7 | 0.3 | 112.5 | S6 |
| 7 | YU349-B07 | N | 35.7 | 1.2 | 1.8 | S6 |
| 7 | YU349-A06 | N | 19.4 | 36.8 | 119.7 | S6 |
| 7 | YU349-A09 | Y | 19.4 | 36.8 | 119.7 | S6 |
| 7 | YU349-B06 | N | 18.1 | 124.6 | 69.7 | S6 |
| 7 | YU349-E08 | Y | 15.3 | 57.1 | 38.3 | S6 |
| 7 | YU349-H08 | N | 15.3 | 57.1 | 38.3 | S6 |

TABLE 2A-continued

Anti-PD-L1 Panning Clones Selected from ELISA Results for Cross-blocking assay (full list: includes ELISA hits and controls)

| Selection Filter | Clone ID | Selected for Fab production (As hit or control) | PD-L1/ iMEM ELISA | sMEM #1/ iMEM ELISA | nMEM #5/ iMEM ELISA | In Vitro Program |
|---|---|---|---|---|---|---|
| 7 | YU349-G07 | N | 11.7 | 35.6 | 8.8 | S6 |
| 7 | YU349-D06 | N | 11.7 | 35.6 | 8.8 | S6 |
| 7 | YU349-E06 | N | 11.2 | 29.9 | 6.5 | S6 |
| 7 | YU349-C09 | N | 9.4 | 41.0 | 43.8 | S6 |
| 7 | YU349-F07 | N | 9.3 | 71.0 | 60.0 | S6 |
| 7 | YU349-A08 | Y | 8.9 | 61.2 | 23.7 | S6 |
| 7 | YU349-E07 | N | 7.2 | 95.4 | 4.6 | S6 |
| 7 | YU349-C08 | Y | 6.8 | 23.9 | 25.1 | S6 |
| 7 | YU349-D08 | Y | 6.4 | 42.6 | 14.3 | S6 |
| 7 | YU349-D07 | N | 5.8 | 61.1 | 22.4 | S6 |
| 7 | YU349-F06 | N | 5.6 | 36.0 | 26.7 | S6 |
| 7 | YU349-A07 | N | 4.6 | 60.3 | 136.9 | S6 |
| 7 | YU349-H07 | Y | 4.2 | 13.6 | 10.7 | S6 |
| 7 | YU349-D09 | Y | 4.2 | 126.8 | 40.2 | S6 |
| 7 | YU349-C07 | N | 4.1 | 96.5 | 167.0 | S6 |
| 7 | YU349-B09 | Y | 4.1 | 35.1 | 11.5 | S6 |
| 7 | YU349-B08 | N | 4.1 | 99.8 | 17.1 | S6 |
| 7 | YU349-G06 | N | 3.8 | 11.5 | 5.5 | S6 |
| 7 | YU349-F08 | Y | 2.6 | 65.3 | 10.9 | S6 |
| 7 | YU349-H06 | Y | 2.4 | 48.8 | 15.6 | S6 |
| 7 | YU349-C06 | N | 1.7 | 30.8 | 6.9 | S6 |
| 8 | YU349-F04 | N | 71.8 | 3.2 | 0.7 | S5 |
| 8 | YU349-A03 | Y | 33.7 | 2.7 | 0.4 | S5 |
| 8 | YU349-H02 | Y | 21.5 | 3.4 | 0.3 | S5 |
| 8 | YU349-E02 | N | 19.4 | 36.8 | 119.7 | S5 |
| 8 | YU349-B02 | N | 19.4 | 36.8 | 119.7 | S5 |
| 8 | YU349-H03 | Y | 19.4 | 36.8 | 119.7 | S5 |
| 8 | YU349-B10 | N | 16.2 | 40.1 | 21.9 | S4 |
| 8 | YU349-G04 | N | 15.3 | 57.1 | 38.3 | S5 |
| 8 | YU349-F02 | Y | 11.7 | 35.6 | 8.8 | S5 |
| 8 | YU349-G03 | N | 11.5 | 3.1 | 0.4 | S5 |
| 8 | YU349-G12 | N | 11.2 | 29.9 | 6.5 | S1 |
| 8 | YU349-B04 | N | 11.2 | 29.9 | 6.5 | S5 |
| 8 | YU349-H09 | N | 7.2 | 95.4 | 4.6 | S4 |
| 8 | YU349-H10 | N | 7.2 | 95.4 | 4.6 | S4 |
| 8 | YU349-H04 | N | 7.2 | 95.4 | 4.6 | S5 |
| 8 | YU349-G02 | N | 6.8 | 23.9 | 25.1 | S5 |
| 8 | YU349-E10 | N | 6.8 | 23.9 | 25.1 | S4 |
| 8 | YU349-C04 | N | 6.4 | 42.6 | 14.3 | S5 |
| 8 | YU349-C02 | Y | 6.4 | 42.6 | 14.3 | S5 |
| 8 | YU349-D02 | N | 4.9 | 2.8 | 57.2 | S5 |
| 8 | YU349-D03 | N | 4.6 | 0.0 | 59.4 | S5 |
| 8 | YU349-F03 | N | 4.5 | 0.4 | 57.3 | S5 |
| 8 | YU349-D04 | N | 4.4 | 0.3 | 126.4 | S5 |
| 8 | YU349-H05 | N | 4.1 | 46.7 | 0.1 | S5 |
| 8 | YU349-C03 | Y | 4.1 | 35.1 | 11.5 | S5 |
| 8 | YU349-E04 | N | 4.1 | 35.1 | 11.5 | S5 |
| 8 | YU349-F09 | Y | 3.8 | 11.5 | 5.5 | S4 |
| 8 | YU349-D11 | N | 3.8 | 11.5 | 5.5 | S4 |
| 9 | YU349-E01 | N | 4.4 | 0.3 | 126.4 | S2 |
| 9 | YU349-H01 | N | 0.8 | 0.1 | 81.7 | S2 |
| 9 | YU349-D12 | Y | 0.7 | −0.1 | 108.7 | S1 |
| 9 | YU349-D01 | Y | 0.6 | 0.3 | 90.9 | S2 |

These ELISA hits were analyzed with a dose-responsive PD-L1 competition with avelumab or durvalumab, at 0 nM, 67 pM, 670 pM, and 6.7 nM to identify 34 putative cross-blocking clone hits. Blocking propensity was calculated as follows: ELISA Z-Score(sMEM1+sMEM5+PD-L1−iMEM)+MAX(Avelumab Blocking Z-score, Durvalumab Blocking Z-score). A summary of the results is provided in Table 3 below.

TABLE 3

Summary of cross-blocking ELISA response and blocking propensity

| | | | Robust Z-Score | | | | | |
|---|---|---|---|---|---|---|---|---|
| Notes | Clone ID | Panning Program | PD-L1 ELISA Response | sMEM #1 ELISA Response | nMEM #5 ELISA Response | Durvalumab Blocking Response | Avelumab Blocking Response | Blocking Propensity |
| ELISA & X-Block Hit | YU349-C03 | B2 | 72.15 | −0.13 | 0.67 | 114.13 | −228.58 | 186.01 |
| ELISA & X-Block Hit | YU349-F09 | B1 | 71.90 | −0.13 | 0.27 | 173.12 | 29.49 | 244.34 |
| ELISA & X-Block Hit | YU349-C02 | B2 | 66.61 | −0.94 | 0.27 | 216.72 | −33.18 | 284.00 |
| ELISA & X-Block Hit | YU349-F02 | B2 | 50.89 | 0.00 | 0.27 | 34.62 | 3.69 | 85.51 |
| ELISA & X-Block Hit | YU349-H02 | B2 | 48.29 | 0.27 | 0.54 | 178.25 | −132.72 | 226.54 |
| ELISA & X-Block Hit | YU349-A03 | B2 | 41.90 | 0.27 | 0.54 | 119.26 | −66.36 | 160.62 |
| ELISA & X-Block Hit | YU349-H03 | B2 | 35.85 | −0.27 | −0.27 | −14.11 | 66.36 | 101.13 |
| ELISA & X-Block Hit | YU349-E08 | C1 | 34.25 | −2.43 | −0.54 | 103.87 | −11.06 | 144.05 |
| ELISA & X-Block Hit | YU349-F05 | B2 | 33.71 | 2.70 | 0.40 | 142.34 | 110.60 | 179.69 |
| ELISA & X-Block Hit | YU349-C08 | C1 | 26.17 | 0.00 | 0.13 | 260.32 | 457.16 | 482.39 |
| ELISA & X-Block Hit | YU349-H06 | C1 | 23.67 | −0.13 | −0.13 | 106.44 | 117.98 | 140.57 |
| ELISA & X-Block Hit | YU349-D08 | C1 | 23.59 | −0.40 | 0.00 | 191.07 | 33.18 | 216.15 |
| ELISA & X-Block Hit | YU349-D09 | C1 | 22.39 | −0.13 | 0.13 | 29.49 | 7.37 | 51.62 |
| ELISA & X-Block Hit | YU349-B09 | C1 | 20.42 | 0.00 | 0.27 | 34.62 | 33.18 | 54.77 |
| ELISA & X-Block Hit | YU349-F08 | C1 | 20.17 | 0.27 | 0.00 | 126.95 | 247.01 | 266.91 |
| ELISA & X-Block Hit | YU349-H07 | C1 | 19.70 | −1.35 | −0.81 | 242.36 | 368.68 | 388.64 |
| ELISA & X-Block Hit | YU349-A09 | C1 | 16.73 | 0.00 | 0.27 | 319.31 | 545.64 | 561.56 |
| ELISA & X-Block Hit | YU349-B05 | A2 | 15.28 | 57.06 | 38.31 | 47.45 | −3.69 | 206.12 |
| ELISA & X-Block Hit | YU349-E05 | A3 | 11.53 | 3.10 | 0.40 | 83.35 | −95.86 | 98.93 |
| ELISA & X-Block Hit | YU349-A12 | A1 | 9.36 | 41.01 | 43.84 | 37.19 | 40.55 | 202.22 |
| ELISA & X-Block Hit | YU349-A01 | A2 | 7.23 | 95.37 | 4.59 | 19.24 | 40.55 | 152.34 |
| ELISA & X-Block Hit | YU349-B11 | B1 | 4.47 | 0.40 | 57.33 | 11.54 | 22.12 | 82.98 |
| ELISA & X-Block Hit | YU349-F01 | A2 | 4.23 | 13.62 | 10.66 | 16.67 | 29.49 | 70.96 |
| ELISA & X-Block Hit | YU349-A02 | A2 | 4.17 | 126.81 | 40.20 | 73.09 | 40.55 | 258.03 |
| ELISA & X-Block Hit | YU349-B01 | A2 | 4.15 | 46.68 | 0.13 | 26.93 | −3.69 | 77.35 |
| ELISA & X-Block Hit | YU349-A05 | A2 | 4.11 | 35.07 | 11.47 | 14.11 | −40.55 | 74.74 |

TABLE 3-continued

Summary of cross-blocking ELISA response and blocking propensity

| Notes | Clone ID | Panning Program | Robust Z-Score PD-L1 ELISA Response | sMEM #1 ELISA Response | nMEM #5 ELISA Response | Durvalumab Blocking Response | Avelumab Blocking Response | Blocking Propensity |
|---|---|---|---|---|---|---|---|---|
| ELISA & X-Block Hit | YU349-G01 | A2 | 4.10 | 99.83 | 17.13 | 26.93 | 22.12 | 170.65 |
| ELISA & X-Block Hit | YU349-C12 | A1 | 3.79 | 11.47 | 5.53 | 21.80 | 3.69 | 49.34 |
| ELISA & X-Block Hit | YU349-G09 | B1 | 3.71 | 0.27 | 112.51 | −32.06 | 110.60 | 225.74 |
| ELISA & X-Block Hit | YU349-F11 | A1 | 2.38 | 48.83 | 15.65 | 24.36 | 7.37 | 113.62 |
| ELISA & X-Block Hit | YU349-D12 | A1 | 1.91 | 250.78 | 0.27 | 21.80 | 3.69 | 273.14 |
| ELISA & X-Block Hit | YU349-A11 | B1 | 0.66 | −0.13 | 108.73 | 34.62 | −11.06 | 143.07 |
| ELISA & X-Block Hit | YU349-D01 | A2 | 0.30 | 339.68 | 0.13 | 44.88 | 18.43 | 383.38 |
| ELISA & X-Block Hit | YU349-A08 | C1 | −30.29 | −26.85 | 15.11 | 503.97 | −92.17 | 590.64 |

Figure 44:
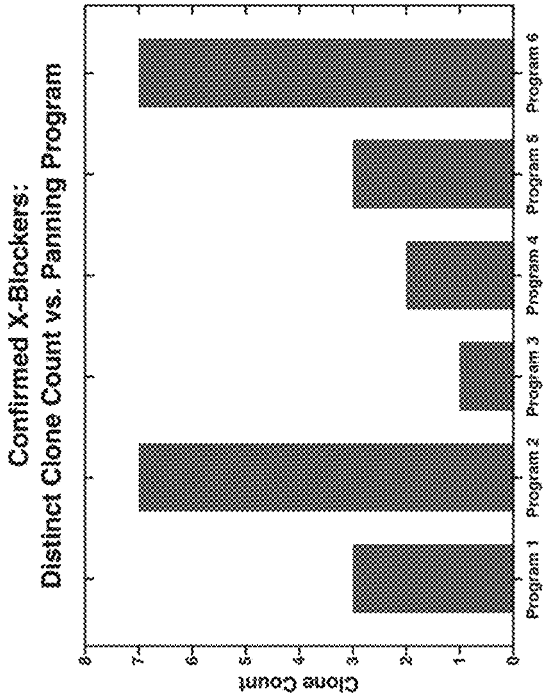
FIG. 44 is a chart of the confirmed cross-blocking distinct clones obtained from each of the programs described in FIG. 33.

The ELISA responses are provided in FIGS. 42A-42F. The 23 distinct clones identified from the cross-blocking hits were sequenced (via Sanger sequencing), and are listed in FIG. 43. A summary of the distinct clone count of cross-blocking hits across panning programs is provided in FIG. 44.

Figure 45A:
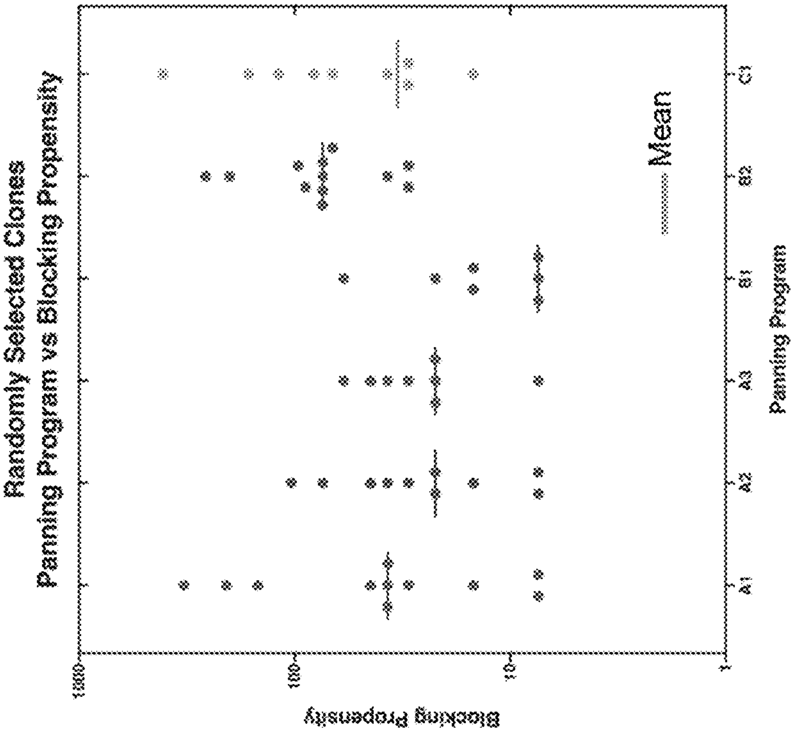
FIG. 45A is a graph of the blocking propensity of randomly selected clones obtained from each of the programs described in FIG. 33. Blocking was evaluated as blocking by clones of binding of PD-L1 to Avelumab or Durvalumab. The blocking propensity was evaluated as ELISA Z-Score (sMEM1+sMEM5+PD-L1−iMEM)+MAX(Avelumab Blocking Z-score, Durvalumab Blocking Z-score).

These results were analyzed to determine if any of the in vitro selection programs produce a random-selection enrichment of clones that cross-block PD-L1:avelumab/durvalumab. Based on the ELISA and cross-blocking data using clones from a uniform, random sampling of all in vitro selection programs as compared to the conventional program (using just PD-L1 and BSA as selection molecules), at least two of the programs using engineered peptides showed enrichment. The results and summary of clones are shown in FIGS. 45A-46 (shaded entries in FIG. 45C are from conventional panning). The following rationale was used in the analysis: Scoring rationale: If a blocking response is observed, through a significant (by robust z-score) negative slope, then blocking propensity is a combination of z-scores for PD-L1, MEM binding and X-blocking slope, where the X-blocking z-score used is the maximum z-score of avelumab vs. durvalumab since these Tx mAbs have slightly different epitopes on the surface.

Example 5: Machine-Learning Model for Selection of Engineered Peptides

Figure 61:
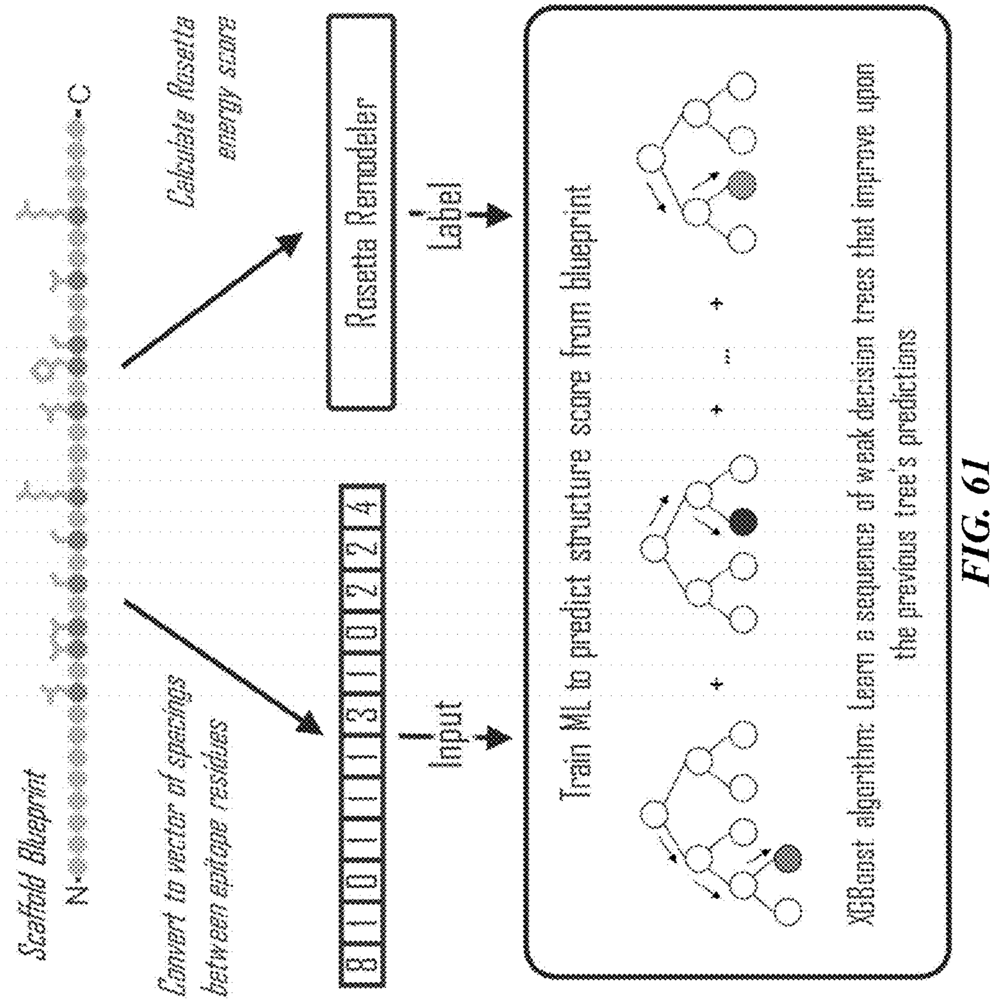
FIG. 61 is a schematic description of an exemplary method of engineered polypeptide design.

Using a reference target, a topological characteristic of the reference target (sequence) is identified and encoded in a scaffold blueprint (FIG. 61, top). The scaffold blueprint may constrain the sequence of the amino acids in the engineered polypeptide to match the order of the amino acids in the reference target. The sequence homology may be constrained to 100% (each amino acid in the reference target corresponds to one amino acid in the blueprint) or the sequence homology may be permitted to be lower, e.g., 10 to 90% homology. The scaffold blueprints may be converted into a vector representation (FIG. 61, left) and used to generate candidate polypeptides for which spatially-associated topological characteristics overlap with the combination of spatially-associated topological constraints derived from the reference target to produce the engineered peptide, with each scaffold blueprint assigned a label based on scoring of the overlap (FIG. 61, right).

A machine-learning (ML) model may be trained on training data that includes representations of the scaffold blueprints and the corresponding scores. The representations may be, for example, one-dimensional vector of numbers, two dimensional matrices of alphanumerical data, three-dimensional tensor of normalized numbers. More specifically, in some instances, the representations are vectors including an ordered list of numbers of intervening scaffold residue positions. Such representations may be used because the order of target-residues can be inferred from target structures, therefore the representations do not need to identify the amino acid identity of target-residue positions. The scores of the scaffold blueprints can be generated using computational protein modeling (e.g., Rosetta remodeler) that determines an energy term for each scaffold blueprint. The scores can be then calculated based on the energy terms generated by the computational protein modeling.

Figure 62:
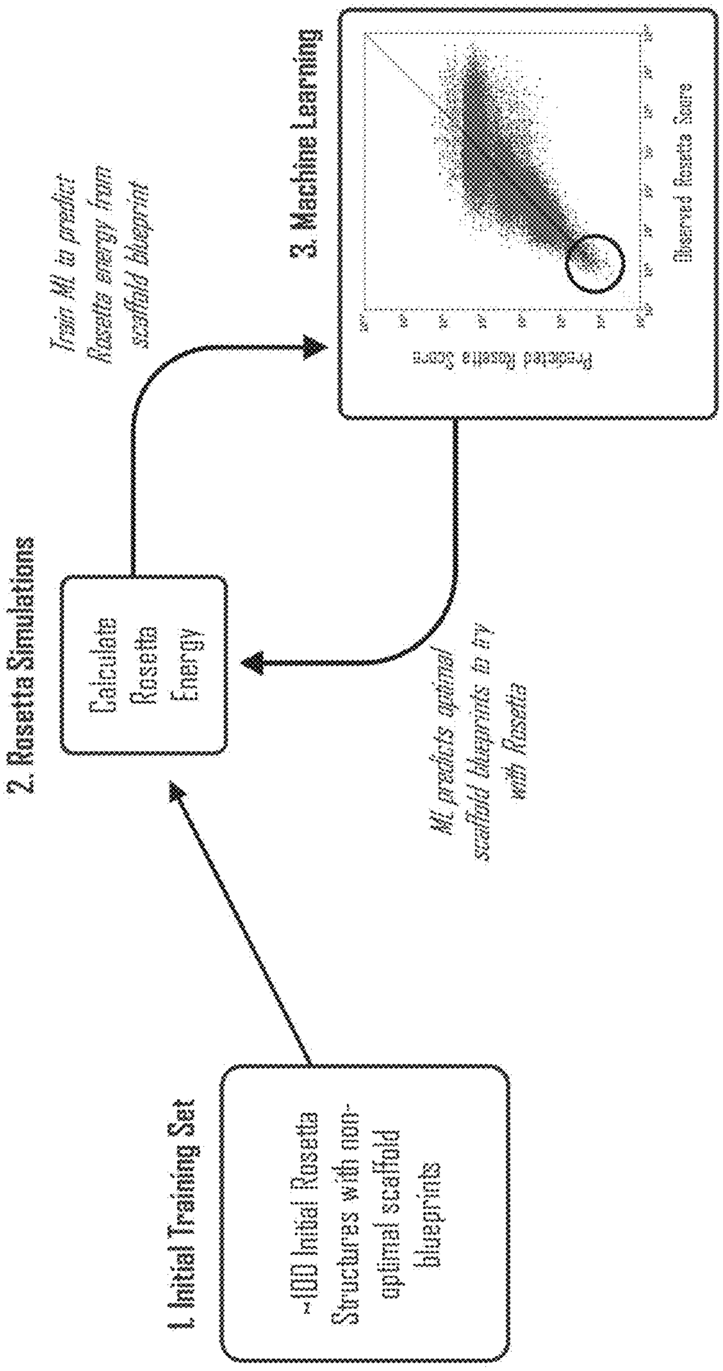
FIG. 62 is a schematic description of an exemplary method of using a machine learning model for engineered polypeptide design.

The ML model can be, for example, a boosted decision tree algorithm, an ensemble of decision trees, an extreme gradient boosting (XGBoost) model, a random forest, a support vector machine (SVM), and/or the like. Once trained, the ML model is then executed to generate a set of predicted scores from a set of scaffold blueprints. If a predicted score is above a desired score, a scaffold blueprint corresponding to the predicted score can be simulated by computational protein modeling to generate a ground-truth score. The ground-truth score and the predicted score can be compared to determine retraining of the ML model. In some implantations, the training and executing steps may be iterated as shown in FIG. 62 until optimal/improved scaffold blueprints having the desired score are predicted. The optimal/improved scaffold blueprints are then converted into engineered peptides.

What is claimed is:

1. An engineered peptide, wherein the engineered peptide has a molecular mass of between 1 kDa and 10 kDa and comprises up to 50 amino acids, and wherein the engineered peptide comprises:

a combination of spatially-associated topological constraints, wherein one or more of the spatially-associated topological constraints is a reference target-derived constraint, wherein between 10% to 98% of the amino acids of the engineered peptide meet the one or more reference target-derived constraints, and wherein the amino acids that meet the one or more reference target-derived constraints have less than 8.0 Å backbone root-mean-square deviation (RSMD) structural homology with the reference target.

2. The engineered peptide of claim 1, wherein the amino acids that meet the one or more reference target-derived constraints have between 10% and 90% sequence homology with the reference target.

3. The engineered peptide of claim 1, wherein the amino acids that meet the one or more reference target-derived constraints have a van der Waals surface area overlap with the reference target of between 30 $Å^2$ to 3000 $Å^2$.

4. The engineered peptide of claim 1, wherein the combination comprises one or more non-reference target-derived constraints that are not derived from the reference target.

5. The engineered peptide of claim 4, wherein the one or more non-reference target-derived constraints comprise a structural, dynamic, chemical, or functional characteristic, or any combinations thereof.

6. The engineered peptide of claim 1, wherein the one or more spatially-associated topological constraints are independently selected from the group consisting of:

atomic distances;
atomic fluctuations;
atomic energies;
chemical features;
solvent exposures;
amino acid sequence similarity;
bioinformatic features;
non-covalent bonding propensity;
phi angles;
psi angles;
van der Waals radii;
secondary structure propensity;
amino acid adjacency; and
amino acid contact.

7. The engineered peptide of claim 1, wherein one or more of the spatially-associated topological constraints is independently associated with a biological response or biological function selected from the group consisting of gene expression, metabolic activity, protein expression, cell proliferation, cell death, cytokine secretion, kinase activity, epigenetic modification, cell killing activity, inflammatory signals, chemotaxis, tissue infiltration, immune cell lineage commitment, tissue microenvironment modification, immune synapse formation, IL-2 secretion, IL-10 secretion, growth factor secretion, interferon gamma secretion, transforming growth factor beta secretion, immunoreceptor tyrosine-based activation motif activity, immunoreceptor tyrosine-based inhibition motif activity, antibody directed cell cytotoxicity, complement directed cytotoxicity, biological pathway agonism, biological pathway antagonism, biological pathway redirection, kinase cascade modification, proteolytic pathway modification, proteostasis pathway modification, protein folding/pathways, post-translational modification pathways, metabolic pathways, gene transcription/translation, mRNA degradation pathways, gene methylation/acetylation pathways, histone modification pathways, epigenetic pathways, immune directed clearance, opsonization, hormone signaling, integrin pathways, membrane protein signal transduction, ion channel flux, and g-protein coupled receptor response.

8. The engineered peptide of claim 1, comprising one or more atoms associated with a biological response or biological function.

9. The engineered peptide of claim 8, wherein the reference target comprises one or more atoms associated with a biological response or biological function, and wherein atomic fluctuations of the one or more atoms in the engineered peptide associated with the biological response or biological function overlap with atomic fluctuations of the one or more atoms in the reference target associated with the biological response or biological function.

10. The engineered peptide of claim 9, wherein at least a portion of the one or more atoms in the engineered peptide associated with the biological response or biological function are topologically constrained to a secondary structural element in the reference target.

11. The engineered peptide of claim 1, wherein at least one of the one or more reference target-derived constraints is selected from the group consisting of: a GPCR extracellular domain; an ion channel extracellular domain; and a protein-protein or peptide-protein interface junction.

12. The engineered peptide of claim 1, wherein at least one of the one or more reference target-derived constraints is derived from a polymorphic region of the target.

13. The engineered peptide of claim 1, wherein the engineered peptide has at least one structural difference when compared to the reference target.

14. The engineered peptide of claim 1, wherein between 10% to 90% of the amino acids meet one or more of the non-reference target-derived topological constraints.

15. A method of selecting an engineered peptide, comprising:

identifying one or more topological characteristics of a reference target;

designing spatially-associated constraints for each topological characteristic to produce a combination of spatially-associated topological constraints derived from the reference target;

comparing spatially-associated topological characteristics of candidate peptides with the combination of spatially-associated topological constraints derived from the reference target; and selecting a candidate peptide with spatially-associated topological characteristics that overlap with the combination of spatially-associated topological constraints derived from the reference target to produce the engineered peptide wherein:

overlap between each characteristic of the reference target is independently less than or equal to 75% Mean Percentage Error (MPE) as determined by one or more of Total Topological Constraint Distance (TCD), topological clustering coefficient (TCC), Euclidean distance, power distance, Soergel distance, Canberra distance, Sorensen distance, Jaccard distance, Mahalanobis distance, Hamming distance, Quantitative Estimate of Likeness (QEL), or Chain Topology Parameter (CTP); or one or more amino acids meeting the one or more reference target-derived spatially-associated topological constraints have a van der Waals surface area overlap with the reference of between 30 Å$^2$ to 3000 Å$^2$; or one or more spatially-associated topological constraints is independently associated with a biological response or biological function selected from the group consisting of gene expression, metabolic activity, protein expression, cell proliferation, cell death, cytokine secretion, kinase activity, epigenetic modification, cell killing activity, inflammatory signals, chemotaxis, tissue infiltration, immune cell lineage commitment, tissue microenvironment modification, immune synapse formation, IL-2 secretion, IL-10 secretion, growth factor secretion, interferon gamma secretion, transforming growth factor beta secretion, immunoreceptor tyrosine-based activation motif activity, immunoreceptor tyrosine-based inhibition motif activity, antibody directed cell cytotoxicity, complement directed cytotoxicity, biological pathway agonism, biological pathway antagonism, biological pathway redirection, kinase cascade modification, proteolytic pathway modification, proteostasis pathway modification, protein folding/pathways, post-translational modification pathways, metabolic pathways, gene transcription/translation, mRNA degradation pathways, gene methylation/acetylation pathways, histone modification pathways, epigenetic pathways, immune directed clearance, opsonization, hormone signaling, integrin pathways, membrane protein signal transduction, ion channel flux, and g-protein coupled receptor response and further wherein the reference target comprises one or more atoms associated with a biological response or biological function, and wherein atomic fluctuations of the one or more atoms in the engineered peptide associated with a biological response or biological function overlap with the atomic fluctuations of the one or more atoms in the reference target associated with a biological response or biological function.

16. The method of claim 15, wherein one or more amino acids meeting the one or more reference target-derived spatially-associated topological constraints have between 10% and 90% sequence homology with the reference target.

17. The method of claim 15, wherein the combination of spatially-associated topological constraints comprises one or more topological constraints not derived from a reference target.

18. The method of claim 17, wherein the one or more non-reference target-derived topological constraints comprise a structural, dynamic, chemical, or functional characteristic, or any combinations thereof.

19. The method of claim 15, wherein the spatially-associated topological constraints are independently selected from the group consisting of:

atomic distances;
atomic fluctuations;
atomic energies;
chemical features;
solvent exposures;
amino acid sequence similarity;
bioinformatic features;
non-covalent bonding propensity;
phi angles;
psi angles;
van der Waals radii;
secondary structure propensity;
amino acid adjacency; and
amino acid contact.

20. The method of claim 15, wherein the engineered peptide comprises one or more atoms associated with a biological response or biological function.

21. The method of claim 20, wherein at least a portion of the atoms in the engineered peptide associated with a biological response or biological function are topologically constrained to a secondary structural element in the reference target.

22. The method of claim 15, wherein at least one of the one or more reference target-derived spatially-associated topological constraints is selected from the group consisting of: a GPCR extracellular domain; an ion channel extracellular domain; and a protein-protein or protein-peptide interface junction.

23. The method of claim 15, wherein at least one of the one or more reference target-derived spatially-associated topological constraints is derived from a polymorphic region of the target.

24. The method of claim 15, wherein the engineered peptide has at least one structural difference when compared to the reference target.

25. The method of claim 15, wherein between 10% to 90% of the amino acids of the engineered peptide meet one or more non-reference target-derived topological constraints.

26. A composition comprising two or more selection steering polypeptides, wherein each polypeptide is independently a positive selection molecule comprising one or more positive steering characteristics, or a negative selection molecule comprising one or more negative steering characteristics, wherein each characteristic type is independently selected from the group consisting of:

amino acid sequence,
polypeptide secondary structure,
molecular dynamics,
chemical features,
biological function,
immunogenicity,
reference target(s) multi-specificity,
cross-species reference target reactivity,
selectivity of desired reference target(s) over undesired reference target(s), selectivity of reference target(s) within a sequence and/or structurally homologous family, selectivity of reference target(s) with similar protein function, selectivity of distinct desired reference target(s) from a larger family of undesired targets with high sequence and/or structurally homology, selectivity for distinct reference target alleles or mutations, selectivity for distinct reference target residue level chemical modifications, selectivity for cell type, selectivity for tissue type, selectivity for tissue environment, tolerance to reference target(s) structural diversity, tolerance to reference target(s) sequence diversity, and tolerance to reference target(s) dynamics diversity;

and wherein at least one of the two or more polypeptides is an engineered peptide according to claim 1.

* * * * *